(12) United States Patent
McConnel et al.

(10) Patent No.: US 7,714,010 B2
(45) Date of Patent: May 11, 2010

(54) PYRROLOBENZIMIDAZOLONES AND THEIR USE AS ANTI-PROLIFERATIVE AGENTS

(75) Inventors: Darryl McConnel, Vienna (AT); Steffen Steurer, Vienna (AT); Bernd Krist, Vienna (AT); Ulrike Weyer-Czernilofsky, Baden (AT); Maria Impagnatiello, Vienna (AT); Matthias Treu, Vienna (AT); Iris Kauffmann-Hefner, Attenweiler (DE); Pilar Garin-Chesa, Vienna (AT); Andreas Schnapp, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 212 days.

(21) Appl. No.: 11/130,542

(22) Filed: May 17, 2005

(65) Prior Publication Data
US 2005/0261350 A1 Nov. 24, 2005

(30) Foreign Application Priority Data
May 17, 2004 (EP) .................................. 04011703

(51) Int. Cl.
*A61K 31/4184* (2006.01)
*A61K 31/4188* (2006.01)
*C07D 235/02* (2006.01)

(52) U.S. Cl. .................................. 514/394; 548/302.1
(58) Field of Classification Search .............. 548/302.1; 514/394
See application file for complete search history.

(56) References Cited

U.S. PATENT DOCUMENTS 4,730,003 A * 3/1988 von der Saal et al. ....... 514/387
5,929,099 A 7/1999 Camden
6,407,131 B1 6/2002 Camden et al.
2003/0153611 A1 8/2003 Mailliet et al.

FOREIGN PATENT DOCUMENTS

DE 3639466 A1 * 5/1988
EP 268178 A1 * 5/1988
WO WO 03048106 12/2003

OTHER PUBLICATIONS

Freshney, Culture of Animal Cells, A Manual of Basic Technique, Alan R. Liss, Inc., 1983, New York.*
Dermer, Bio/Technology, 1994, 12:320.*
Wolfgang, Von der Saal. Nonsteroidal cardiotonics. 2. The inotropic activity of linear, tricyclic 5-6-6-fused heterocycles. Journal of Medicinal Chemistry. 32(7) 1989, 1481-1491.*

* cited by examiner

*Primary Examiner*—Kamal A Saeed
*Assistant Examiner*—Samantha L Shterengarts
(74) *Attorney, Agent, or Firm*—Michael P. Morris; Mary-Ellen M. Devlin; David L. Kershner

(57) ABSTRACT

The invention relates to pyrrolobenzimidazolone compounds of formula (I),

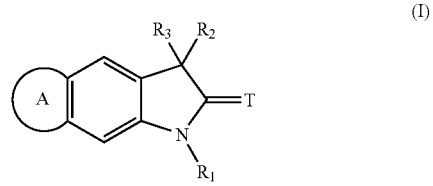

wherein A, T and $R_1$ to $R_3$ are defined as in claim 1, which are suitable for the treatment of diseases characterized by excessive or abnormal cell proliferation and the use thereof for preparing a pharmaceutical composition.

5 Claims, No Drawings

PYRROLOBENZIMIDAZOLONES AND THEIR USE AS ANTI-PROLIFERATIVE AGENTS

RELATED APPLICATION

This application claims priority to EP 04 011703.8 filed May 17, 2004 and the contents of which are incorporated herein.

SUMMARY OF THE INVENTION

The invention relates to pyrrolobenzimidazolone compounds of formula (I),

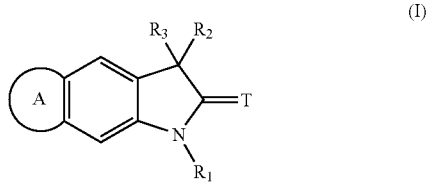

which possess tubulin inhibitory activity, pharmaceutically acceptable salts thereof and their use as antiproliferative agents.

BACKGROUND OF THE INVENTION

Microtubules are cytoskeletal structures assembled from α/β tubulin heterodimers that play an essential role in many cellular processes, such as cell motility, organelle transport, maintenance of cell polarity and cell division. Interference with microtubule dynamics by stabilization or destabilization in dividing cells leads to cell division arrest in the $G_2$/M phase and cell death.

A variety of clinically promising compounds which demonstrate potent cytotoxicity and antitumor activity are known to effect their primary mode of action through an efficient inhibition of tubulin. Several natural products and their derivatives disrupt microtubule dynamics, e.g., Taxol®, Taxotere®, Navelbine® and show a clinically useful therapeutic window between anticancer effects and dose-limiting toxicity in normal proliferating tissues, notably bone marrow and gastrointestinal mucosa in addition to neurotoxicity. Unfortunately the clinical success of these agents can be severely hindered by the emergence of drug resistant tumor cells. Although membrane P-glycoprotein mediated multi-drug resistance (MDR) has been known to occur with the taxanes and the *Vinca* alkaloids, differential expression of altered tubulin isotypes has also been implicated in resistance to the taxanes and other antimitotic agents.

Renewed interest in tubulin polymerisation inhibitors has been generated by the hope that non-MDR substrates that interact with tubulin at sites near to, overlapping with or different from those of the taxanes or the *Vinca* alkaloids can be discovered.

Novel tubulin-binding molecules which, upon binding to tubulin, interfere with tubulin polymerization can provide novel agents for the treatment of proliferative diseases.

Pyrrolobenzimidazolones are known in the state of the art as agents with an antithrombotic and cardiovascular effect. DE3639466A1, DE3642315A1 and DE4027592A1 describe the use of pyrrolobenzimidazolones for the treatment of heart and circulatory diseases.

DETAILED DESCRIPTION OF THE INVENTION

Surprisingly it was found that compounds of the formula (I), wherein the residues A, T, $R_1$, $R_2$ and $R_3$ have the meanings as defined herein, act as tubulin polymerisation inhibitors.

The invention therefore relates to the use of compounds of formula (I)

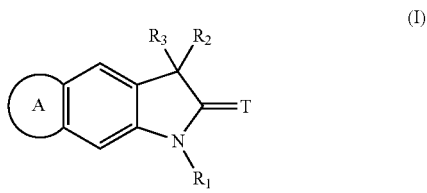

its salts or pharmaceutically acceptable derivatives thereof for the manufacture of a medicament for the treatment of antiproliferative diseases, wherein $R^1$ is selected from an optionally substituted group consisting of $C_{1-12}$alkyl, carbocyclic aryl-$(CH_2)_x$—, heteroaryl-$(CH_2)_x$—, biaryl-$(CH_2)_x$—, heteroalicyclo-$(CH_2)_x$—, cycloalkyl-$(CH_2)_x$—, —$(CH_2)_xOR_a$, —$(CH_2)_xC(=O)R_a$, —$(CH_2)_xS(=O)_2R_a$, —$(CH_2)_xS(=O)R_a$, —$(CH_2)_xSR_a$, —$(CH_2)_xOC(=O)R_a$, —$(CH_2)_xC(=O)OR_a$, —$(CH_2)_xS(=O)_2 NR_aR'_a$, —$(CH_2)_xNR_aS(=O)R'_a$, —$(CH_2)_xC(=O)NR_aR'_a$, —$(CH_2)_xNR_aC(=O)R'_a$, —$(CH_2)_x(R_a)C=NR_d$, —$(CH_2)_xC=N$; —$(CH_2)_xOC(=O)NR_aR'_a$, —$(CH_2)_xNR_aC(=O)OR'_a$ and —$(CH_2)_xNR''_aC(=O)NR_aR'_a$; and T is selected from O, S or two hydrogen atoms; and $R_2$ and $R_3$ are independently selected from hydrogen or from an optionally substituted group consisting of $C_{1-4}$alkyl and cycloalkyl; and wherein $R_2$ and $R_3$ may also combine to form a spiroalkyl group; and A is selected from formula (c-1) or (c-2)

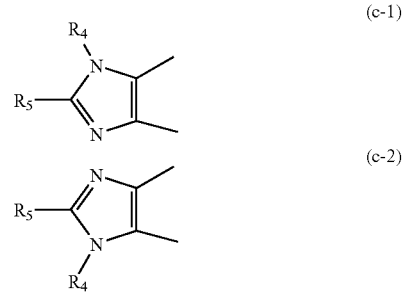

wherein $R_4$ is hydrogen or optionally substituted alkyl;

$R_5$ is selected from the group consisting of hydrogen, halo, hydroxy, thiol and cyano or from an optionally substituted group consisting of $C_{1-12}$alkyl, carbocyclic aryl-$(CH_2)_x$—, heteroaryl-$(CH_2)_x$—, biaryl-$(CH_2)_x$—, heteroalicyclo-$(CH_2)_x$—, cycloalkyl-$(CH_2)_x$—, —$(CH_2)_xS(=O)_2R_a$, —$(CH_2)_xS(=O)R_a$, —$(CH_2)_xSR_a$, —$(CH_2)_xOC(=O)R_a$, —$(CH_2)_xC(=O)OR_a$, —$(CH_2)_xS(=O)_2NR_aR'_a$, —$(CH_2)_xNR_aS(=O)_2R'_a$, —$(CH_2)_xC(=O)NR_aR'_a$, —$(CH_2)_xNR_aC(=O)R'_a$, —$(CH_2)_xOR_a$, —$(CH_2)_xC(=O)R_a$, —$(CH_2)_xS(=O)_2OR_a$, —$(CH_2)_xOS(=O)_2R_a$, —$(CH_2)_xNR''_aS(=O)_2NR_aR'_a$, —$(CH_2)_xOC(=O)NR_aR'_a$, —(CH₂)ₓNR_aC(=O)OR'_a, —(CH₂)ₓNR"_aC(=O)NR_aR'_a
and —(CH₂)ₓ(R_a)C=N_d; and x is 0, 1, 2, 3 or 4; and one or more hydrogens of the —(CH₂)ₓ group may be replaced by a group selected from hydroxy, halo, cyano, alkoxy, thiol and alkylthio or from an optionally substituted group consisting of alkyl and amino; and R_a, R'_a and R"_a are independently selected from hydrogen or from an optionally substituted group consisting of alkyl, cycloalkyl, heteroalicyclo and aryl; and wherein R_a and R'_a may also combine to form a heteroalicyclic ring; and R_d is selected from the group consisting of hydrogen and hydroxy or from an optionally substituted group consisting of amino, alkyl, cycloalkyl, heteroalicyclo, carbocyclic aryl, heteroaryl, alkoxy, aryloxy, N-amido, N-thioamido and urea.

A further aspect of the invention is a compound of formula (I)

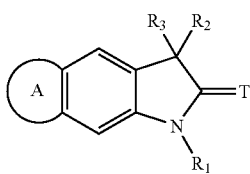

(I)

its salts or pharmaceutically acceptable derivatives thereof, wherein

R₁ is selected from an optionally substituted group consisting of C₁₋₁₂alkyl, carbocyclic aryl-(CH₂)ₓ—, heteroaryl-(CH₂)ₓ—, biaryl-(CH₂)ₓ—, heteroalicyclo-(CH₂)ₓ—, cycloalkyl-(CH₂)ₓ—, —(CH₂)ₓOR_a, —(CH₂)ₓC(=O)R_a, —(CH₂)ₓS(=O)₂R_a, —(CH₂)ₓS(=O)R_a, —(CH₂)ₓSR_a, —(CH₂)ₓOC(=O)R_a, —(CH₂)ₓC(=O)OR_a, —(CH₂)ₓS(=O)₂NR_aR'_a, —(CH₂)ₓNR_aS(=O)R'_a, —(CH₂)ₓC(=O)NR_aR'_a, —(CH₂)ₓNR_aC(=O)R'_a and —(CH₂)ₓ(R_a)C=NR_d, —(CH₂)ₓC≡N; —(CH₂)ₓOC(=O)NR_aR'_a, —(CH₂)ₓNR_aC(=O)OR'_a and —(CH₂)ₓNR"_aC(=O)NR_aR'_a; and T is selected from O, S or two hydrogen atoms; and R₂ and R₃ are independently selected from hydrogen or from an optionally substituted group consisting of C₁₋₄alkyl and cycloalkyl; R₂ and R₃ may also combine to form a spiroalkyl group; and A is selected from formula (c-1) or (c-2); and

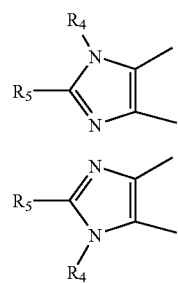

(c-1)

(c-2)

wherein

R₄ is hydrogen or optionally substituted alkyl;

R₅ is selected from the group consisting of hydrogen, halo, hydroxy, thiol and cyano or from an optionally substituted group consisting of C₁₋₁₂alkyl, carbocyclic aryl-(CH₂)ₓ—, heteroaryl-(CH₂)ₓ—, biaryl-(CH₂)ₓ—, heteroalicyclo-(CH₂)ₓ—, cycloalkyl-(CH₂)ₓ—, —(CH₂)ₓS(=O)₂R_a, —(CH₂)ₓS(=O)R_a, —(CH₂)ₓSR_a, —(CH₂)ₓOC(=O)R_a, —(CH₂)ₓC(=O)OR_a, —(CH₂)ₓS(=O)₂NR_aR'_a, —(CH₂)ₓNR_aS(=O)₂R'_a, —(CH₂)ₓC(=O)NR_aR'_a, —(CH₂)ₓNR_aC(=O)R'_a, —(CH₂)ₓOR_a, —(CH₂)ₓC(=O)R_a, —(CH₂)ₓS(=O)₂OR_a, —(CH₂)ₓOS(=O)₂R_a, —(CH₂)ₓNR"_aS(=O)₂NR_aR'_a, —(CH₂)ₓOC(=O)NR_aR'_a, —(CH₂)ₓNR_aC(=O)OR'_a, —(CH₂)ₓNR"_aC(=O)NR_aR'_a and —(CH₂)ₓ(R_a)C=N_d; and x is 0, 1, 2, 3 or 4; and one or more hydrogens of the —(CH₂)ₓ group may be replaced by a group selected from hydroxy, halo, cyano, alkoxy, thiol and alkylthio or from an optionally substituted group consisting of alkyl and amino; and R_a, R'_a and R"_a are independently selected from hydrogen or from an optionally substituted group consisting of alkyl, cycloalkyl, heteroalicyclo and aryl; and wherein R_a and R'_a may also combine to form a heteroalicyclic ring; and R_d is selected from the group consisting of hydrogen, hydroxy or from an optionally substituted group consisting of amino, alkyl, cycloalkyl, heteroalicyclo, carbocyclic aryl, heteroaryl, alkoxy, aryloxy, N-amido, N-thioamido and urea; with the proviso that if R₁ is methyl, ethyl, methoxyethyl or hydroxyethyl, then R₅ is not unsubstituted pyridyl, methoxyphenyl or hydroxyphenyl and further provided that the following compounds are excluded:

2-Cyanamino-6,7-dihydro-7,7-dimethyl-3H,5H-pyrrolo(2,3-f)benzimidazol-6-one 2-Cyanamino-5,7,7-trimethyl-6,7-dihydro-3H-pyrrolo(2,3-f)benzimidazol-6-one 2-Cyanamino-6,7-dihydro-7,7-cyclopropyl-3H,5H-pyrrolo(2,3-f) benzimidazol-6-one 2-Nitromethyl-6,7-dihydro-7,7-dimethyl-3H,5H-pyrrolo(2,3-f)benzimidazol-6-one 2-((4-Difluoromethoxy)-3-pyridyl)-6,7-dihydro-7,7-dimethyl-3H,5H-pyrrolo(2,3-f)-benzimidazol-6-one 2-(3-Quinolinyl) 7,7-dimethyl-6,7-dihydro-3H,5H-pyrrolo-[2,3-f]benzimidazol-6-one 2-(4-Quinolinyl) 7,7-dimethyl-6,7-dihydro-3H,5H-pyrrolo-[2,3-f]benzimidazol-6-one 7,7-Dimethyl-2-(2-indolyl)-6,7-dihydro-3H,5H-pyrrolo-[2,3-f]benzimidazol-6-one 7,7-Dimethyl-2-(3-pyridyl-amino)-6,7-dihydro-3H,5H-pyrrolo-[2,3-f]benzimidazol-6-one.

Another aspect of the invention is a compound of formula (I), wherein

R₁ is selected from an optionally substituted group consisting of C₁₋₈alkyl, carbocyclic aryl-(CH₂)ₓ—, heteroaryl-(CH₂)ₓ—, biaryl-(CH₂)ₓ—, cycloalkyl-(CH₂)ₓ—, —(CH₂)ₓOR_a, —(CH₂)ₓC(=O)R_a, —(CH₂)ₓC(=O)OR_a, —(CH₂)ₓC(=O)NR_aR'_a, —(CH₂)ₓNR_aC(=O)R'_a, —(CH₂)ₓ(R_a)C=NR_d, —(CH₂)ₓC≡N; —(CH₂)ₓOC(=O)NR_aR'_a, —(CH₂)ₓNR_aC(=O)OR'_a and —(CH₂)ₓNR"_aC(=O)NR_aR'_a.

An additional aspect of the invention is a compound of formula (I), wherein

R₅ is selected from an optionally substituted group consisting of C₁₋₁₂alkyl, carbocyclic aryl-(CH₂)ₓ—, heteroaryl-(CH₂)ₓ—, biaryl-(CH₂)ₓ—, —(CH₂)ₓS(=O)₂R_a, —(CH₂)ₓS(=O)R_a, —(CH₂)ₓSR_a, —(CH₂)ₓC(=O)NR_aR'_a, —(CH₂)ₓNR_aC(=O)R'_a, —(CH₂)ₓNR_aR'_a, —(CH₂)ₓOR_a, —(CH₂)ₓOC(=O)NR_aR'_a, —(CH₂)ₓNR_aC(=O)OR'_a and —(CH₂)ₓNR"_aC(=O)NR_aR'_a.

A further aspect of the invention is a compound of formula (I), wherein T is oxygen.

One aspect of the invention is a compound of formula (I), wherein R₂ and R₃ are methyl.

An additional aspect of the invention is a compound of formula (I), wherein R₄ is hydrogen.

Another aspect of the invention is a compound of formula (I), wherein $R_1$ is selected from an optionally substituted group consisting of $C_{1-8}$alkyl, carbocyclic aryl-$(CH_2)_x$—, heteroaryl-$(CH_2)_x$—, cycloalkyl-$(CH_2)_x$—, —$(CH_2)_xOR_a$, —$(CH_2)_xC(=O)R_a$, —$(CH_2)_xC(=O)OR_a$, —$(CH_2)_xC(=O)NR_aR'_a$, —$(CH_2)_x(R_a)C=NR_d$, —$(CH_2)_xC\equiv N$; —$(CH_2)_xOC(=O)NR_aR'_a$, —$(CH_2)_xNR_aC(=O)OR'_a$ and —$(CH_2)_xNR''_aC(=O)NR_aR'_a$; and $R_5$ is selected from an optionally substituted group consisting of $C_{1-12}$alkyl, carbocyclic aryl-$(CH_2)_x$—, heteroaryl-$(CH_2)_x$—, —$(CH_2)_xS(=O)_2R_a$, —$(CH_2)_xS(=O)R_a$, —$(CH_2)_xSR_a$, —$(CH_2)_xC(=O)NR_aR'_a$, —$(CH_2)_xNR_aC(=O)R'_a$, —$(CH_2)_xNR_aR'_a$, —$(CH_2)_xOR_a$, —$(CH_2)_xOC(=O)NR_aR'_a$, —$(CH_2)_xNR_aC(=O)OR'_a$ and —$(CH_2)_xNR''_aC(=O)NR_aR'_a$.

An additional aspect of the invention is a compound of formula (I) as a medicament.

A further aspect of the invention is a compound of formula (I) as an antiproliferative medicament.

One aspect of the invention is also the use of a compound of formula (I) for the manufacture of a medicament for the treatment of antiproliferative diseases. Another aspect of the invention is the use of a compound of formula (I) for the manufacture of a medicament for the treatment of cancer.

A further aspect of the invention is a pharmaceutical composition containing as active ingredient one or more compounds of formula (I) or their physiologically acceptable salts in combination with an usual adjuvants and/or carrier.

An additional aspect of the invention is a pharmaceutical composition comprising a compound of formula (I)

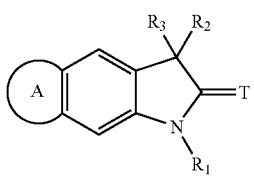

wherein $R^1$ is selected from an optionally substituted group consisting of $C_{1-12}$alkyl, carbocyclic aryl-$(CH_2)_x$—, heteroaryl-$(CH_2)_x$—, biaryl-$(CH_2)_x$—, heteroalicyclo-$(CH_2)_x$—, cycloalkyl-$(CH_2)_x$—, —$(CH_2)_xOR_a$, —$(CH_2)_xC(=O)R_a$, —$(CH_2)_xS(=O)_2R_a$, —$(CH_2)_xS(=O)R_a$, —$(CH_2)_xSR_a$, —$(CH_2)_xOC(=O)R_a$, —$(CH_2)_xC(=O)OR_a$, —$(CH_2)_xS(=O)_2NR_aR'_a$, —$(CH_2)_xNR_aS(=O)R'_a$, —$(CH_2)_xC(=O)NR_aR'_a$, —$(CH_2)_xNR_aC(=O)R'_a$, —$(CH_2)_x(R_a)C=NR_d$, —$(CH_2)_xC\equiv N$; —$(CH_2)_xOC(=O)NR_aR'_a$, —$(CH_2)_xNR_aC(=O)OR'_a$ and —$(CH_2)_xNR''_aC(=O)NR_aR'_a$; and T is selected from O, S or two hydrogen atoms; and $R_2$ and $R_3$ are independently selected from hydrogen or from an optionally substituted group consisting of $C_{1-4}$alkyl and cycloalkyl; and wherein $R_2$ and $R_3$ may also combine to form a spiroalkyl group; and A is selected from formula (c-1) or (c-2)

wherein $R_4$ is hydrogen or optionally substituted alkyl; and $R_5$ is selected from the group consisting of hydrogen, halo, hydroxy, thiol and cyano or from an optionally substituted group consisting of $C_{1-12}$alkyl, carbocyclic aryl-$(CH_2)_x$—, heteroaryl-$(CH_2)_x$—, biaryl-$(CH_2)_x$—, heteroalicyclo-$(CH_2)_x$—, cycloalkyl-$(CH_2)_x$—, —$(CH_2)_xS(=O)_2R_a$, —$(CH_2)_xS(=O)R_a$, —$(CH_2)_xSR_a$, —$(CH_2)_xOC(=O)R_a$, —$(CH_2)_xC(=O)OR_a$, —$(CH_2)_xS(=O)_2NR_aR'_a$, —$(CH_2)_xNR_aS(=O)_2R'_a$, —$(CH_2)_xC(=O)NR_aR'_a$, —$(CH_2)_xNR_aC(=O)R'_a$, —$(CH_2)_xNR_aR'_a$, —$(CH_2)_xOR_a$, —$(CH_2)_xC(=O)R_a$, —$(CH_2)_xS(=O)_2OR_a$, —$(CH_2)_xOS(=O)_2R_a$, —$(CH_2)_xNR''_aS(=O)_2NR_aR'_a$, —$(CH_2)_xOC(=O)NR_aR'_a$, —$(CH_2)_xNR_aC(=O)OR'_a$, —$(CH_2)_xNR''_aC(=O)NR_aR'_a$ and —$(CH_2)_x(R_a)C=NR_d$; and x is 0, 1, 2, 3 or 4; and wherein one or more hydrogens of the —$(CH_2)_x$ group may be replaced by a group selected from hydroxy, halo, cyano, alkoxy, thiol and alkylthio or from an optionally substituted group consisting of alkyl and amino; and $R_a$, $R'_a$ and $R''_a$ are independently selected from hydrogen or from an optionally substituted group consisting of alkyl, cycloalkyl, heteroalicyclo and aryl; and wherein $R_a$ and $R'_a$, may also combine to form a heteroalicyclic ring; and $R_d$ is selected from the group consisting of hydrogen and hydroxy or from an optionally substituted group consisting of amino, alkyl, cycloalkyl, heteroalicyclo, carbocyclic aryl, heteroaryl, alkoxy, aryloxy, N-amido, N-thioamido and urea, or a tautomer, a pharmaceutically acceptable salt, solvate, or physiologically functional derivative thereof, and at least one different cytostatic and/or cytotoxic active ingredient or a pharmaceutically acceptable salt, solvate, or physiologically functional derivative thereof, and a pharmaceutically acceptable carrier or excipient.

A further aspect of the invention is a compound of formula (IA)

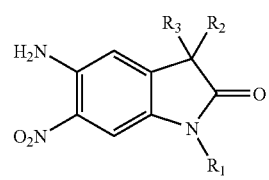

wherein $R_1$, $R_2$ and $R_3$ have the meanings as defined above with the provisio that $R_1$ is not methyl.

A further aspect of the invention is a compound of formula (IB)

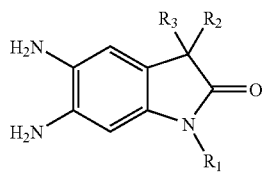

wherein
$R_1$, $R_2$ and $R_3$ have the meanings as defined above.

DEFINITIONS

As used herein, the following definitions shall apply unless otherwise indicated.

The term "optionally substituted" is used interchangeably with the phrase "substituted or unsubstituted" and means that a group may be substituted by one or more substituents which may be the same or different. When otherwise not specified these substituents are selected from alkyl, cycloalkyl, biaryl, carbocyclic aryl, heteroalicyclic, heteroaryl, acyl, amidino, amido, amino, alkoxyamino, carbamoyl, carboxy, cyano, ether, guanidine, hydroxamoyl, hydroxyl, imino, isocyanato, isothiocyanato, halo, nitro, silyl, sulfonyl, sulfinyl, sulfenyl, sulfonato, sulfamoyl, sulfonamido, thiocarbonyl, thiol, thiocyanato, thiocarbamoyl, thioamido or urea as those terms are define herein.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond. An "alkyne" moiety refers to a group consisting of at least two carbon atoms and at least one carbon-carbon triple bond. The alkyl moiety, whether saturated or unsaturated, may be branched or non-branched. Branched means that the alkyl moiety is substituted by one or more lower alkyl groups such as for example methyl, ethyl or propyl The alkyl group may have the number of carbon atoms as explicitly defined (e.g. $C_{1-12}$alkyl) or may also be undefined. Whenever it appears herein a numerical range such as "1 to 12" it refers to each integer in the given range. For example, "1 to 12 carbon atoms" means that the alkyl group may consist of 1 carbon atom, 2 carbon atoms, 3 carbon atoms, etc., up to and including 12 carbon atoms. When the number of carbon atoms is undefined the alkyl group has 1 to 12 carbon atoms. A medium sized alkyl refers to an alkyl group having 1 to 8 carbon atoms. A lower alkyl group refers to an alkyl group having 1 to 5 carbon atoms. The alkyl group, whether termed an alkyl, saturated alkyl, unsaturated alkyl, alkene or alkyne, may be unsubstituted or substituted as defined herein.

The term "carbocyclic" refers to a compound which contains one or more covalently closed ring structures and the atoms forming the backbone of the ring(s) are all carbon atoms. The term thus distinguishes carbocyclic from "heterocyclic" rings. Carbocyclic groups include both, a "cycloalkyl" group, which means a non-aromatic carbocycle, and a "carbocyclic aryl" group, which means an aromatic carbocycle. The carbocyclic group may be optionally substituted as defined herein.

The term "cycloalkyl" as used herein refers to mono-, bi- or tricyclic rings or ring systems. The ring system may be a "saturated ring", which means that the ring does not contain any alkene or alkyne moieties. The cycloalkyl group may also be an "unsaturated ring" which means that it contains at least one alkene or alkyne moiety and provided that the ring system is not aromatic. The cycloalkyl group may be unsubstituted or substituted as defined herein and the substituents, when positioned adjacent to one another, may combine to form carbocyclic or heterocyclic ring systems for example methylendioxy or difluoro-methylendioxy. In addition to the above mentioned substituents one or more ring carbon atoms may also be bonded via a double bond to a heteroatom selected from N, S and O and wherein N may optionally be substituted by $R_a$.

The term "aryl" as used herein refers to a mono-, bi- or tricyclic ring or ring systems which have at least one aromatic ring. Aryl groups include both, "carbocyclic aryl" and "heteroaryl" groups. The aryl moiety may be unsubstituted or substituted as defined herein and the substituents, when positioned adjacent to one another, may combine to form cycloalkyl or heteroalicyclic ring systems for example methylendioxy or difluoromethylendioxy.

The term "biaryl" as used herein refers to two aryl groups, as defined herein, joined together via a single bond. The biaryl moiety may be unsubstituted or substituted as defined herein and the substituents, when positioned adjacent to one another, may combine to form cycloalkyl or heteroalicyclic ring systems for example methylendioxy or difluoromethylendioxy.

The term "carbocyclic aryl" as used herein refers to mono-, bi- or tricyclic rings or ring systems which have at least one aromatic ring and all atoms forming the backbone are carbon atoms. Examples of carbocyclic aryl groups include but are not limited to phenyl, naphthyl and anthracyl. The carbocyclic aryl moiety may be unsubstituted or substituted as defined herein and the substituents, when positioned adjacent to one another, may combine to form cycloalkyl or heteroalicyclic ring systems for example methylendioxy or difluoromethylendioxy.

The term "heterocyclic" or "heterocyclo" as used herein refers to mono-, bi- or tricyclic rings or ring systems which include one or more heteroatoms selected from N, S and O. The rings or ring systems include 1 to 13 carbon atoms in addition to the heteroatom(s). The term heterocyclic group include both, a "heteroalicyclic" group, which means a non-aromatic heterocycle and a "heteroaryl" group, which means an aromatic heterocycle. The heterocyclic moiety may be unsubstituted or substituted as defined herein and the substituents, when positioned adjacent to one another, may combine to form cycloalkyl or heteroalicyclic ring systems for example methylendioxy or difluoromethylendioxy. The heterocyclic group may be bonded via a carbon atom or a heteroatom. The heterocyclic group may also include the oxides of nitrogen and sulfur if nitrogen or sulfur are present in the ring.

The term "heteroalicyclic" or "heteroalicyclo" as used herein refers to mono-, bi- or tricyclic ring or ring systems in which at least one of the atoms forming the backbone of the ring is a heteroatom. The ring system may be a "saturated ring", which means that the ring does not contain any alkene or alkyne moieties, or it may also be an "unsaturated ring" which means that it contains at least one alkene or alkyne moiety provided that the ring system is not aromatic. The heteroalicyclic group may be unsubstituted or substituted as defined herein. The substituents, when positioned adjacent to one another, may combine to form carbocyclic or heterocyclic ring systems for example methylendioxy or difluoromethylendioxy. The heteroalicyclic group may be bonded via a carbon atom or a heteroatom. In addition to the above mentioned substituents one or more ring carbon atoms may also be bonded via a double bond to a heteroatom selected from N, S and O and wherein N may optionally be substituted by $R_a$. The heteroalicyclic group may also include the oxides of nitrogen and sulfur if nitrogen or sulfur are present in the ring.

The term "heteroaryl", "heterocyclic aryl" or "heteroaromatic radical" as used herein refers to a mono-, bi- or tricyclic rings or ring systems which include one or more heteroatoms selected from N, S and O. The rings or ring systems include 1 to 13 carbon atoms in addition to the heteroatom(s) and contains at least one aromatic ring with a heteroatom. The heteroaryl group may also include the oxides of nitrogen and sulfur if nitrogen or sulfur are present, respectively. Examples of monocyclic heteroaryl groups include but are not limited to furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heterocycles include but are not limited to indolyl, benzofuranyl, benzothienyl, benzoxazolyl, benzothiazolyl, benzisoxazolyl, benzisothiazolyl, indazolyl, isoquinolinyl, quinolinyl, quinoxalinyl, cinnolinyl, phthalazinyl, quinazolinyl, benzotriazinyl and the like. Examples of tricyclic heterocycles include but are not limited to thianthrenyl, xanthenyl, phenoxathiinyl, carbazolyl, carbolinyl, phenanthridinyl, acridinyl, perimidinyl, phenanthrolinyl, phenazinyl, phenothiazinyl, phenoxazinyl. The heteroaryl group may be unsubstituted or substituted as defined herein. The substituents, when positioned adjacent to one another, may combine to form a cycloalkyl or heteroalicyclic ring for example methylendioxy and difluoromethylendioxy. The heteroaryl radical may be bonded via a carbon atom or a heteroatom.

The term "heteroarylalkyl", as used herein, refers to a chemical moiety of formula heteroaryl-$(CH_2)_x$— as those terms are defined herein.

The term "carbocyclic arylalkyl", as used herein, refers to a chemical moiety of formula carbocyclic aryl-$(CH_2)_x$— as those terms are defined herein.

The term "biarylalkyl", as used herein, refers to a chemical moiety of formula biaryl-$(CH_2)_x$— as those terms are defined herein.

The term "heteroarylalkyl", as used herein, refers to a chemical moiety of formula heteroaryl-$(CH_2)_x$— as those terms are defined herein.

The term "heteroalicycloalkyl", as used herein, refers to a chemical moiety of formula heteroalicyclo-$(CH_2)_x$— as those terms are defined herein.

The term "cycloalkylalkyl", as used herein, refers to a chemical moiety of formula cycloalkyl-$(CH_2)_x$— as those terms are defined herein.

The term "acyl", as used herein, refers to a chemical moiety of formula —$(CH_2)_xC(=O)R_a$.

The term "amidino" refers to a chemical moiety with the formula —$(CH_2)_xC(=NH)NR_aR'_a$.

The term "amido" refers to both, a "C-amido" group which means a chemical moiety with the formula —$(CH_2)_xC(=O)NR_aR'_a$ and a "N-amido" group which means a chemical moiety with the formula —$(CH_2)_xNC(=O)R'_a$.

The term "amine" or "amino" refers to a chemical moiety of formula —$(CH_2)_xN_aR'_a$. The definition of an amine is also understood to include their N-oxides.

The term "alkoxyamino", refers to both, an "N-alkoxyamino" group which means a chemical moiety with the formula —$(CH_2)_xNR_aOR'_a$ and an "O-alkoxyamino" group which means a chemical moiety with the formula —$(CH_2)_xONR_aR'_a$.

The term "carbamoyl" refers to both, an "O-carbamoyl" group which means a chemical moiety with the formula —$(CH_2)_xOC(=O)NR_aR'_a$ and a "N-carbamoyl" group which means a chemical moiety with the formula —$(CH_2)_xNR_aC(=O)OR'_a$.

The term "carboxy" refers to both, an "O-carboxy" group which means a chemical moiety with the formula-$(CH_2)_xOC(=O)R_a$ and a "C-carboxy" group which means a chemical moiety with the formula —$(CH_2)_xC(=O)OR_a$.

A "cyano" group refers to a —$(CH_2)_xC\equiv N$.

The term "ether" refers to a chemical moiety of formula —$(CH_2)_xOR_a$.

The term "guanidino" refers to a chemical moiety with the formula —$(CH_2)_xNHC(=NH)NHR_f$.

The term "hydroxamoyl" refers to a chemical moiety with the formula —$(CH_2)_xC(=O)NOR_a$.

The term "hydroxy" or "hydroxyl" as used herein, refers to a chemical moiety of formula —OH.

The term "imine" or "imino", as used herein, refers to a chemical moiety of formula —$(CH_2)_x(R_a)C=NR_a$.

An "isocyanato" group refers to a —NCO group.

An "isothiocyanato" group refers to a —NCS group.

The term "halogen" or "halo" refers to an atom selected from the group consisting of fluorine, chlorine, bromine and iodine.

The term "silyl", as used herein, refers to a chemical moiety with the formula —$Si(R_e)_3$.

The term "sulfone" or "sulfonyl" refers to a chemical moiety with the formula —$(CH_2)_xS(=O)_2R_a$.

The term "sulfinyl" refers to a chemical moiety with the formula —$(CH_2)_xS(=O)R_a$.

The term "sulfenyl" refers to a chemical moiety with the formula —$(CH_2)_xSR_a$.

The term "sulfonato" refers to both, an "S-sulfonato" group which means a chemical moiety with the formula —$(CH_2)_xS(=O)_2OR_a$ and an "O-sulfonato" group which means a chemical moiety with the formula —$(CH_2)_xOS(=O)_2R_a$.

A "sulfamoyl" group refers to a chemical moiety with the formula —$(CH_2)_xNR''_aS(=O)_2NR_aR'_a$.

The term "sulfonamido" refers to both, an "S-sulfonamido" group which means a chemical moiety with the formula —$(CH_2)_xS(=O)_2NR_aR'_a$ and an "N-sulfonamido" group which means a chemical moiety with the formula —$(CH_2)_xNR_aS(=O)_2R'_a$.

The term "thiocarbonyl" refers to a chemical moiety with the formula —$(CH_2)_xC(=S)R_a$.

The term "Thio" or "thiol", as used herein, refers to a chemical moiety of formula —SH.

A "thiocyanato" group refers to a —CNS group.

The term "thiocarbamoyl" refers to both, an "O-thiocarbamoyl" group which means a chemical moiety with the formula —$(CH_2)_xOC(=S)NR_aR'_a$ and a "N-thiocarbamoyl" group which means a chemical moiety with the formula —$(CH_2)_xNR_aC(=S)OR'_a$.

The term "thioamide" refers to both, a "C-thioamido" group which means a chemical moiety with the formula —$(CH_2)_xC(=S)NR_aR'_a$ and a "N-thioamido" group which means a chemical moiety with the formula —$(CH_2)_xNR_aC(=S)R'_a$.

An "urea" group refers to a —$(CH_2)_xNR''_aC(=O)NR_aR'_a$.

The term "alkoxy", as used herein, refers to a chemical moiety of formula —$OR_b$.

The term "alkylthio", as used herein, refers to a chemical moiety of formula —$SR_b$ including the S-oxides thereof.

The term "aryloxy", as used herein, refers to a chemical moiety of formula —$OR_c$.

The term "arylthio", as used herein, refers to a chemical moiety of formula —$SR_c$ including the S-oxides thereof.

The term "formyl", as used herein, refers to a chemical moiety of formula —C(=O)H.

The term "oxime ether" as used herein, refers to a chemical moiety of formula —$(CH_2)_x(R_a)C=NOR_a$.

By "combined", when referring to two adjacent "R" groups herein, is meant that the two "R" groups are covalently bonded to each other so as to form a ring system. The ring system may be cycloalkyl, carbocyclic aryl, heteroaryl or heteroalicyclic.

The term "spiroalkyl", as used herein, refers to an optionally substituted alkyl group where the linkage between the aforementioned alkyl group and a second ring system consists of a single atom common to both groups. The second ring system can be a cycloalkyl or heteroalicyclic group.

x is an integer selected from 0, 1, 2, 3 or 4. One or more hydrogens of a -($CH_2$), group may be replaced by a group selected from hydroxy, halo, cyano, alkoxy, thiol, alkylthio and optionally substituted alkyl and amino. The —$(CH_2)_x$ group may also contain double or triple bonds. In such cases, where a double or triple bond exists, the number of hydrogen atoms or substituents is such that the total number of bonds to any one carbon does not exceed 4.

$R_a$, $R'_a$ and $R''_a$ are independently selected from hydrogen or from an optionally substituted group consisting of alkyl, cycloalkyl, heteroalicyclo and aryl. $R_a$ and $R'_a$, $R_a$ and $R''_a$ and $R'_a$ and $R''_a$, when present, may also combine to form a heteroalicyclic ring.

$R_b$ is selected from an optionally substituted group consisting of alkyl, cycloalkyl and heteroalicyclo.

$R_c$ is an optionally substituted aryl group.

$R_d$ is selected from hydrogen or from an optionally substituted group consisting of amino, alkyl, cycloalkyl, heteroalicyclo, carbocyclic aryl, heteroaryl, hydroxy, alkoxy, aryloxy, N-amido, N-thioamido and urea.

$R_e$ is selected from the group consisting of hydrogen and hydroxy or from an optionally substituted group consisting of alkyl, alkoxy, aryloxy, cycloalkyl, heteroalicyclic, carbocyclic aryl and heterocyclic aryl, as those terms are defined herein.

$R_f$ is selected from the group consisting of hydrogen and cyano or from an optionally substituted group consisting of alkyl, cycloalkyl, heteroalicyclic (bonded through a ring carbon), carbocyclic aryl and heterocyclic aryl (bonded through a ring carbon), as those terms are defined herein.

In order that this invention be more fully understood, the following examples are set forth. These examples are for the purpose of illustrating embodiments of this invention and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

DESCRIPTION OF THE EXAMPLES

General Experimental Description of Examples

HPLC retention times and mass spectra are recorded according to methods AM1 to AM5. 1H NMR spectra are recorded with either NMR Avance 400 (400, 1330810 MHz) or NMR Avance 500 (500, 1300038 MHz). Microwave heating is performed with either a Personal Chemistry Smith Synthesizer or a CEM Explorer.

When otherwise not mentioned "aqueous workup" refers to following procedure: After completion of the reaction and removal of solvents the residue is taken up in $H_2O$ and EtOAc. The aqueous phase is extracted with EtOAc (up to 3 times). The combined organic layer is washed with saturated NaCl solution, dried over $MgSO_4$ and evaporated.

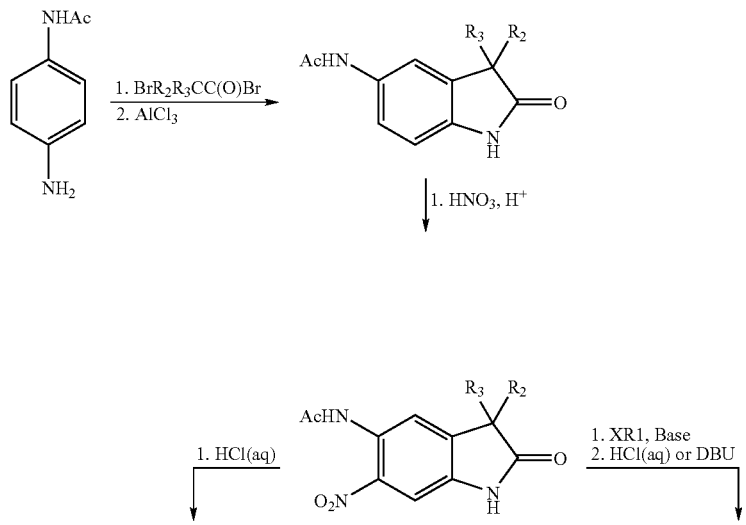

Scheme I for Preparing Building Blocks A and C

-continued
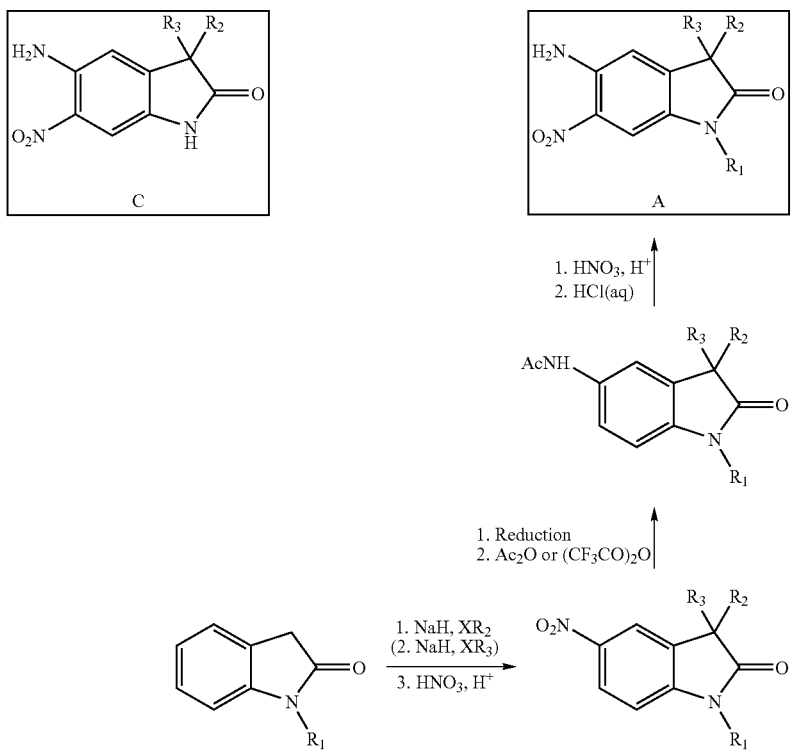
Scheme II for Preparing Building Blocks B, D, E, F, G and H
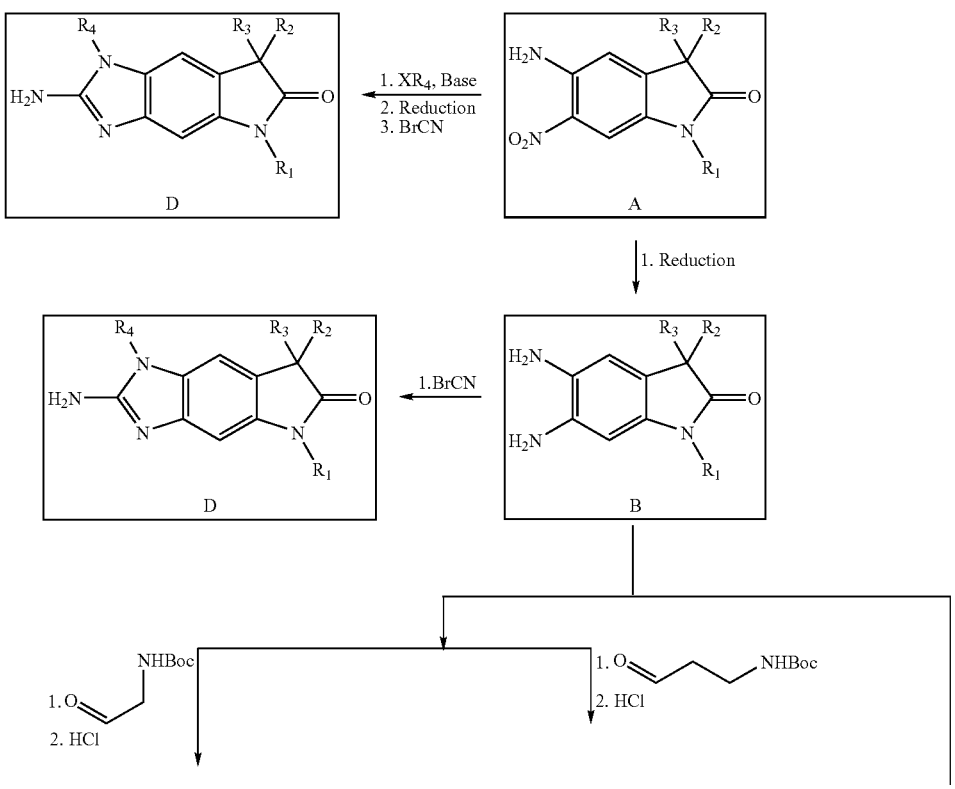

-continued

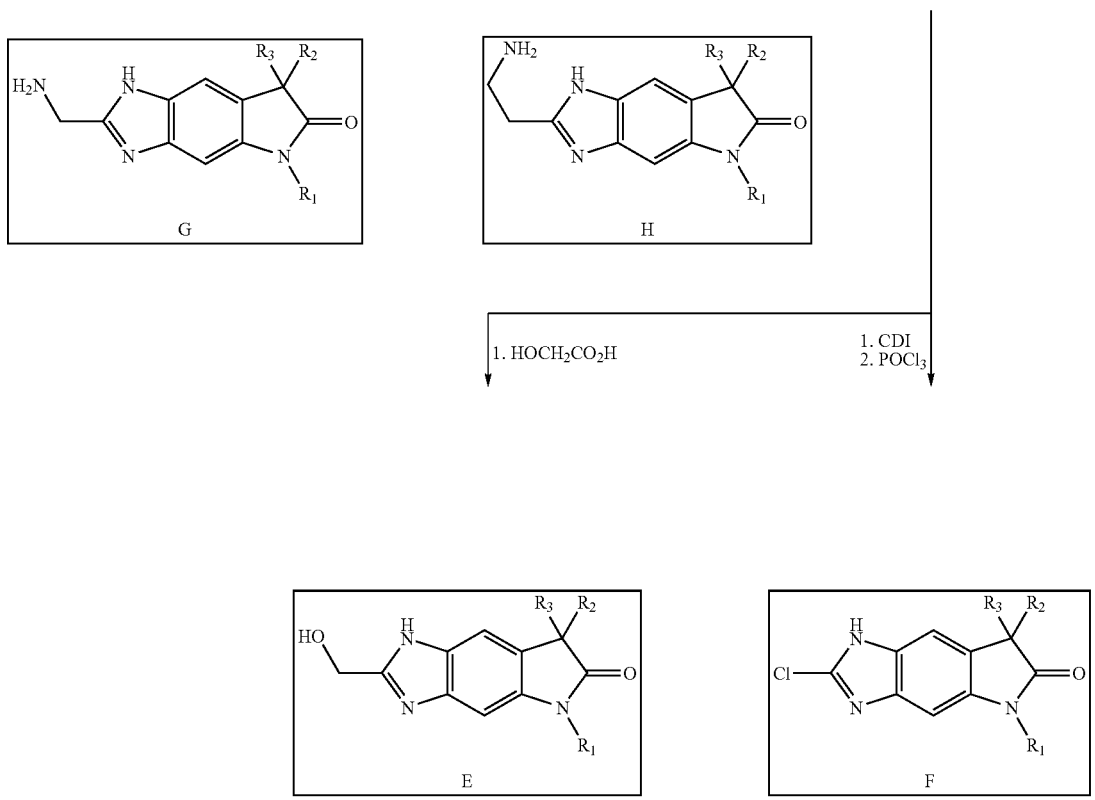

General Procedure (1) for the Synthesis of Building Blocks A

N-(3,3-dimethyl-6-nitro-2-oxo-2,3-dihydro-1H-indol-5-yl)-acetamide is synthesized according to J. Med. Chem. 1989, 32, 1481-1491. To a solution of N-(3,3-dimethyl-6-nitro-2-oxo-2,3-dihydro-1H-indol-5-yl)-acetamide (0.1 mol) in acetone/N,N-dimethylformamide mixtures (750 ml) or in pure N,N-dimethylformamide, the alkylhalide (0.2 mol) and freshly ground $K_2CO_3$ (0.2 mol) or KOtBu (0.2 mol) are successively added. The mixture is stirred at temperatures between RT and 65° C. for 1 to 7 days. If necessary, additional alkylhalide and base is added. After completion of the reaction the solvents are removed by evaporation and the residue is taken up in $H_2O$ and EtOAc. The aqueous phase is extracted with EtOAc (up to 3 times). The combined organic layer is washed with saturated NaCl solution, dried over $MgSO_4$ and evaporated to give the corresponding N-(1-alkyl-3,3-dimethyl-6-nitro-2-oxo-2,3-dihydro-1H-indol-5-yl)-acetamide. For removal of the acetyl group the purified or crude material is dissolved in alcohol (MeOH or 2-propanol; 250 ml) and hydrochloric acid (6 N, 150 ml) and heated under reflux for 0.5-4 h. After completion of the reaction the alcohol is removed by evaporation. The aqueous phase is neutralized with $NaHCO_3$ and extracted up to 4 times with EtOAc. The combined organic layer is washed with brine, dried over $MgSO_4$ and evaporated. Instead of an aqueous work-up, in some cases the product can be isolated by pouring the reaction mixture into ice-water and collecting the precipitate by filtration. Purification of the crude material is obtained either by re-crystallization or by flash chromatography on silica gel.

Synthesis of Building Blocks A1-A54

(A1) 5-Amino-1 3,3-trimethyl-6-nitro-1,3-dihydro-indol-2-one

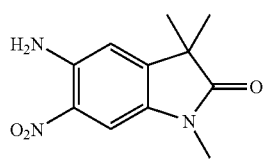

The building block 5-amino-1,3,3-trimethyl-6-nitro-1,3-dihydro-indol-2-one is prepared as described in literature (J. Med. Chem. 1989, 32, 1481-1491).

(A2) 5-Amino-1-ethyl-3,3-dimethyl-6-nitro-1.3-dihydro-indol-2-one

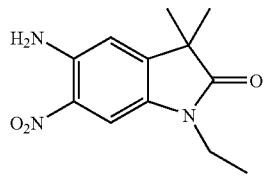

Analogously to general procedure (I) N-(3,3-dimethyl-6-nitro-2-oxo-2,3-dihydro-1H-indol-5-yl)-acetamide (0.75 g) is alkylated using ethyl iodide (0.5 ml; 5.7 mmol) and K₂CO₃ (1.6 g; 11.6 mmol) at 55° C. for 7 h. After aqueous work-up the crude alkylated acetamide (0.8 g; 2.74 mmol) is de-acetylated under reflux conditions in 2-propanol (3 ml) and hydrochloric acid (5 ml). After aqueous work-up the crude 5-amino-1-ethyl-3,3-dimethyl-6-nitro-1,3-dihydro-indol-2-one (0.6 g) is used without further purification.

(A3) 5-Amino-3,3-dimethyl-6-nitro-1-propyl-13-dihydro-indol-2-one

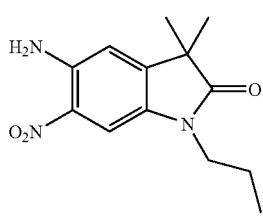

Analogously to general procedure (I) N-(3,3-dimethyl-6-nitro-2-oxo-2,3-dihydro-1H-indol-5-yl)-acetamide (4 g) is alkylated using propyl iodide (6 ml) and K₂CO₃ (8.4 g; 60.8 mmol) at RT for 2 days. After aqueous work-up and flash chromatography on silica gel eluting with CH₂Cl₂/MeOH (50:1) the pure alkylated acetamide (4.14 g) is de-acetylated under reflux conditions in 2-propanol (14 ml) and hydrochloric acid (49 ml). Pure 5-amino-3,3-dimethyl-6-nitro-1-propyl-1,3-dihydro-indol-2-one (3.2 g) is precipitated by pouring the reaction mixture into ice-water and is collected by filtration.

(A4) 5-Amino-1-butyl-3,3-dimethyl-6-nitro-1,3-dihydro-indol-2-one

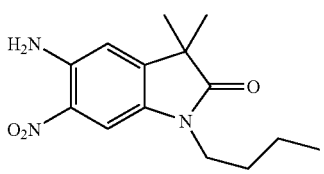

Analogously to general procedure (I) N-(3,3-dimethyl-6-nitro-2-oxo-2,3-dihydro-1H-indol-5-yl)-acetamide (1 g) is alkylated using butyl iodide (1.8 ml; 15.4 mmol) and K₂CO₃ (2.1 g; 15.2 mmol) at RT for 20 h. After aqueous work-up and flash chromatography on silica gel eluting with CH₂Cl₂/MeOH (30:1) the alkylated acetamide (0.94 g; 2.93 mmol) is de-acetylated under reflux conditions in 2-propanol (3 ml) and hydrochloric acid (6 N; 11 ml). Pure 5-amino-1-butyl-3,3-dimethyl-6-nitro-1,3-dihydro-indol-2-one (0.64 g) is obtained by flash chromatography on silica gel eluted with CH₂Cl₂/MeOH (50:1).

(A5) (E)-5-Amino-3,3-dimethyl-6-nitro-1-(pent-2-enyl)-1,3-dihydro-indol-2-one

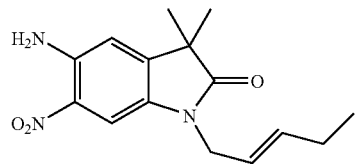

Analogously to general procedure (I) N-(3,3-dimethyl-6-nitro-2-oxo-2,3-dihydro-1H-indol-5-yl)-acetamide (1.47 g) is alkylated using (E)-1-bromo-2-pentene (1 g; 6.71 mmol) and KOtBu (0.75 g; 6.71 mmol) at RT for 20 h. After aqueous work-up and flash chromatography on silica gel eluting with light petroleum/EtOAc (2.5:1) the pure alkylated acetamide (0.85 g; 2.58 mmol) is de-acetylated under reflux conditions using DBU (0.6 ml) in MeOH (60 ml). (E)-5-amino-3,3-dimethyl-6-nitro-1-(pent-2-enyl)-1,3-dihydro-indol-2-one (0.6 g) is obtained after an aqueous work-up.

(A6) (Z)-5-Amino-3,3-dimethyl-6-nitro-1-(pent-2-enyl)-1,3-dihydro-indol-2-one

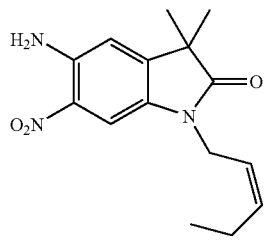

Analogously to general procedure (I) N-(3,3-dimethyl-6-nitro-2-oxo-2,3-dihydro-1H-indol-5-yl)-acetamide (1.47 g) is alkylated using (Z)-1-bromo-2-pentene (1 g; 6.71 mmol) and KOtBu (0.75 g; 6.71 mmol) at RT for 20 h. After aqueous work-up and flash chromatography on silica gel eluting with light petroleum/EtOAc (2.5:1) the pure alkylated acetamide (0.85 g; 2.56 mmol) is de-acetylated under reflux conditions using DBU (0.7 ml) in MeOH (60 ml). (Z)-5-amino-3,3-dimethyl-6-nitro-1-(pent-2-enyl)-1,3-dihydro-indol-2-one (0.62 g) is obtained after aqueous work-up.

(A7) 5-Amino-3,3-dimethyl-6-nitro-1-(pent-2-ynyl)-1,3-dihydro-indol-2-one

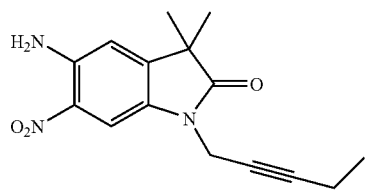

Analogously to general procedure (I) N-(3,3-dimethyl-6-nitro-2-oxo-2,3-dihydro-1H-indol-5-yl)-acetamide (4 g) is alkylated using 1-bromo-2-pentyne (3.1 ml; 30.4 mmol) and K₂CO₃ (4.2 g; 30.4 mmol) at 40° C. for 20 h. After aqueous work-up only a part of the crude material (1 g; 3.04 mmol) is de-acetylated under reflux using DBU (0.9 ml) in MeOH (80 ml). After aqueous work-up the crude 5-amino-3,3-dimethyl-6-nitro-1-(pent-2-ynyl)-1,3-dihydro-indol-2-one (0.87 g) is used without further purification.

(A8) 5-Amino-3,3-dimethyl-6-nitro-1-pentyl-1,3-dihydro-indol-2-one

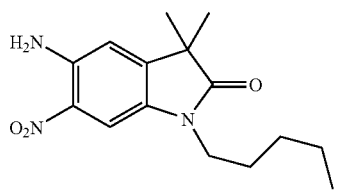

Analogously to general procedure (I) N-(3,3-dimethyl-6-nitro-2-oxo-2,3-dihydro-1H-indol-5-yl)-acetamide (50 g) is alkylated using pentyliodide (76.8 g; 0.38 mol) and $K_2CO_3$ (53.6 g; 0.38 mol) at 60° C. for 24 h. After aqueous work-up the crude material is de-acetylated under reflux in 2-propanol (500 ml) and hydrochloric acid (6 N; 300 ml). After aqueous work-up pure 5-amino-3,3-dimethyl-6-nitro-1-pentyl-1,3-dihydro-indol-2-one (40.7 g) is obtained by re-crystallization from MeCN.

(A9) 5-Amino-3,3-dimethyl-1-(3-methyl-butyl)-6-nitro-1,3-dihydro-indol-2-one

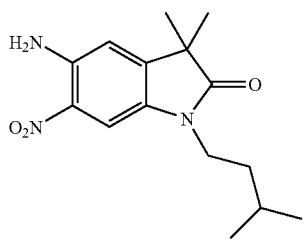

Analogously to general procedure (I) N-(3,3-dimethyl-6-nitro-2-oxo-2,3-dihydro-1H-indol-5-yl)-acetamide (1 g) is alkylated using 1-bromo-3-methylbutane (1.9 ml; 15.4 mmol) and $K_2CO_3$ (2.1 g; 15.2 mmol) at RT for 24 h. After aqueous work-up and flash chromatography the pure material (0.62 g; 1.86 mmol) is de-acetylated under reflux in 2-propanol (2 ml) and hydrochloric acid (6 N; 7 ml). Pure 5-amino-3,3-dimethyl-1-(3-methyl-butyl)-6-nitro-1,3-dihydro-indol-2-one (419 mg) is obtained by flash chromatography on silica gel eluting with $CH_2Cl_2$/MeOH (50:1).

(A10) 5'-Amino-6'-nitro-1'-pentyl-spiro[cyclopropane-1,3'-indoline]-2'-one

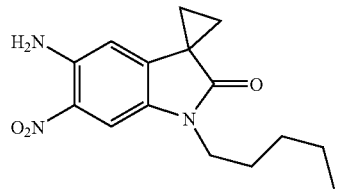

a) 1'-Pentyl-spiro[cyclopropane-1,3'-indoline]-2'-one

To a solution of 1-pentyl-1,3-dihydro-indol-2-one (Farmaco, Ed. Sci. 1977, 32, 703-712) (22 g) and 1,2-dibromoethane (14.1 ml; 162 mmol) in dry N,N-dimethylformamide (180 ml) is added sodium hydride (60% in mineral oil, 13 g; 325 mmol) in small portions over a period of 15 min. The resulting mixture is stirred at 15° C. for 1 h. MeOH (50 ml) and saturated $NH_4Cl$ solution (200 ml) is added and the aqueous phase is extracted with $Et_2O$. The combined organic layer is washed with water, brine and dried over $MgSO_4$. The compound (24.8 g) is obtained after evaporation.

b) 5'-Nitro-1'-pentyl-spiro[cyclopropane-1,3'-indoline]-2'-one

1'-Pentyl-spiro[cyclopropane-1,3'-indoline]-2'-one (24.8 g) is suspended in acetic acid (250 ml) and nitric acid (fuming, 11.9 ml) is added over a period of 15 min at 15° C. The mixture is stirred for 3 h, diluted with water and extracted with $Et_2O$ (3×300 ml). The combined organic layer is washed with water, saturated $K_2CO_3$ solution and brine, dried over $MgSO_4$ and evaporated to give the compound (29.3 g).

c) 5'-Amino-1'-pentyl-spiro[cyclopropane-1,3'-indoline]-2'-one

5'-Nitro-1'-pentyl-spiro[cyclopropane-1,3'-indoline]-2'-one (29.3 g) is dissolved in EtOAc (266 ml) and $SnCl_2.2 H_2O$ (96.0 g; 427 mmol) is added. The reaction mixture is refluxed overnight, cooled and filtered over $Al_2O_3$. After an aqueous work-up of the filtrate the compound (2.9 g) is obtained.

d) 2,2,2-Trifluoro-N-(2'-oxo-1'-pentyl-spiro[cyclopropane-1,3'-indole]-5'-yl)-acetamide 5'-Amino-1'-pentyl-spiro[cyclopropane-1,3'-indoline]-2'-one (1.8 g) and trifluoro acetic anhydride (4.54 g; 21.6 mmol) are dissolved in dry $CH_2Cl_2$ (5 ml). After addition of $NEt_3$ (2.19 g; 21.6 mmol) the mixture is stirred at RT for 25 min. After dilution with 0.1 N hydrochloric acid the mixture is extracted with $CH_2Cl_2$. The combined organic layer is washed with saturated $NaHCO_3$ solution and brine, dried over $MgSO_4$ and concentrated in vacuo to give the title compound (2.4 g).

e) 2,2,2-Trifluoro-N-(6'-nitro-2'-oxo-1'-pentyl-spiro[cyclopropane-1,3-indole]-5'-yl)-acetamide To a solution of 2,2,2-trifluoro-N-(2'-oxo-1'-pentyl-spiro[cyclopropane-1,3'-indole]-5'-yl)-acetamide (2.4 g) in acetic acid (20 ml) is added nitric acid (fuming, 0.9 ml) at 15° C. over a period of 3 min. The mixture is stirred at this temperature for 1 h and then diluted with water. The aqueous layer is extracted with $Et_2O$ (2×50 ml) The combined organic layer is washed with water, saturated K$_2$CO$_3$ solution and brine, dried over MgSO$_4$ and evaporated. The compound (2.6 g) is obtained as brownish oil.

f) 5'-Amino-6'-nitro-1'-pentyl-spiro[cyclopropane-13'-indoline]-2'-one (A10)

2,2,2-Trifluoro-N-(6'-nitro-2'-oxo-1'-pentyl-spiro[cyclopropane-1,3'-indole]-5'-yl)-acetamide (2.6 g) is dissolved in MeOH (20 ml) and water (8 ml). Freshly powdered K$_2$CO$_3$ (3.7 g; 26.8 mmol) is added and the reaction mixture is stirred at 50° C. for 12 h. After completion of the reaction the mixture is concentrated. Water and EtOAc are added. The aqueous phase is extracted with EtOAc. The combined organic phase is washed with water and brine and dried over MgSO$_4$. After evaporation the title compound (0.5 g) is obtained.

(A11) 5-Amino-1-benzyl-3,3-dimethyl-6-nitro-1,3-dihydro-indol-2-one

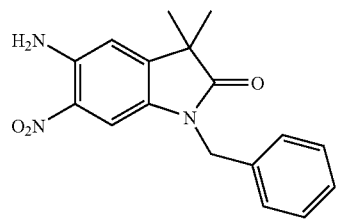

Analogously to general procedure (I) N-(3,3-dimethyl-6-nitro-2-oxo-2,3-dihydro-1H-indol-5-yl)-acetamide (1 g) is alkylated using benzyl bromide (0.46 ml; 3.9 mmol) and K$_2$CO$_3$ (1.5 g; 10.9 mmol) at RT for 20 h. After filtration and evaporation of the solvent the crude material is de-acetylated under reflux conditions in 2-propanol (10 ml) and hydrochloric acid (6 N, 30 ml). Pure 5-amino-1-benzyl-3,3-dimethyl-6-nitro-1,3-dihydro-indol-2-one (1.04 g) precipitates by pouring the reaction mixture into ice-water.

(A12) 5-Amino-3,3-dimethyl-1-(4-methyl-benzyl)-6-nitro-1,3-dihydro-indol-2-one

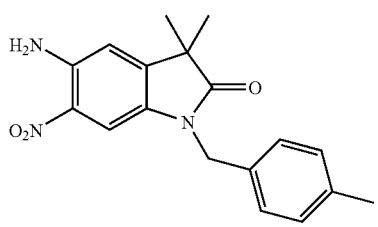

Analogously to general procedure (I) N-(3,3-dimethyl-6-nitro-2-oxo-2,3-dihydro-1H-indol-5-yl)-acetamide (1 g) is alkylated using 4-methylbenzyl bromide (0.71 g; 3.85 mmol) and K$_2$CO$_3$ (1.5 g; 10.9 mmol) at RT for 20 h. After filtration and evaporation of the solvent the crude material is de-acetylated under reflux conditions in 2-propanol (10 ml) and hydrochloric acid (6 N; 30 ml). Pure 5-amino-3,3-dimethyl-1-(4-methyl-benzyl)-6-nitro-1,3-dihydro-indol-2-one (1.18 g) precipitates by pouring the reaction mixture in ice-water.

(A13) 5-Amino-1-(4-methoxy-benzyl)-3,3-dimethyl-6-nitro-1,3-dihydro-indol-2-one

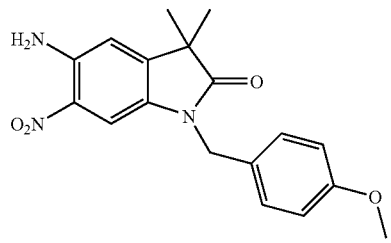

Analogously to general procedure (I) N-(3,3-dimethyl-6-nitro-2-oxo-2,3-dihydro-1H-indol-5-yl)-acetamide (1.5 g) is synthesized according to the general procedure using 4-methoxybenzyl chloride (0.92 g; 5.86 mmol) and K$_2$CO$_3$ (2.3 g; 16.6 mmol) at RT for 20 h. After filtration and evaporation of the solvent the crude material is de-acetylated under reflux conditions in 2-propanol (15 ml) and hydrochloric acid (6 N; 45 ml). Pure 5-amino-1-(4-methoxy-benzyl)-3,3-dimethyl-6-nitro-1,3-dihydro-indol-2-one (1.71 g) precipitates by pouring the reaction mixture into ice-water.

(A14) 5-Amino-1-(3-methoxy-benzyl)-3,3-dimethyl-6-nitro-1,3-dihydro-indol-2-one

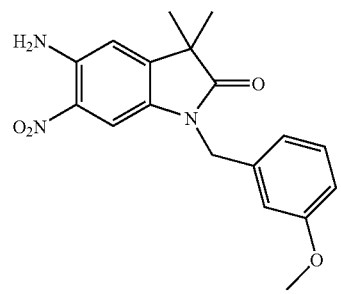

Analogously to general procedure (I) N-(3,3-dimethyl-6-nitro-2-oxo-2,3-dihydro-1H-indol-5-yl)-acetamide (1 g) is alkylated using 3-methoxybenzyl chloride (0.6 g; 3.85 mmol) and K$_2$CO$_3$ (1.5 g; 10.9 mmol) at RT for 20 h. After filtration and evaporation of the solvent the crude material is de-acetylated under reflux conditions in 2-propanol (10 ml) and hydrochloric acid (6 N; 30 ml). Pure 5-amino-1-(3-methoxy-benzyl)-3,3-dimethyl-6-nitro-1,3-dihydro-indol-2-one (1.06 g) precipitates by pouring the reaction mixture into ice-water.

(A15) 5-Amino-1-[2-(2-methoxy-phenyl)-2-oxo-ethyl]-3,3-dimethyl-6-nitro-1,3-dihydro-indol-2-one

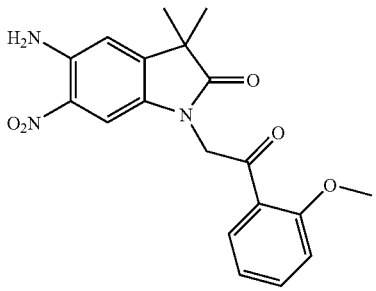

Analogously to general procedure (I) N-(3,3-dimethyl-6-nitro-2-oxo-2,3-dihydro-1H-indol-5-yl)-acetamide (1 g) is alkylated using 2-methoxyphenacyl bromide (9.6 g; 41.9 mmol) and K$_2$CO$_3$ (14.2 g; 102.7 mmol) at RT for 3 days. After filtration and evaporation of the solvent the crude material is de-acetylated under reflux in 2-propanol (150 ml) and hydrochloric acid (6 N; 100 ml). Pure 5-amino-1-[2-(2-methoxy-phenyl)-2-oxo-ethyl]-3,3-dimethyl-6-nitro-1,3-dihydro-indol-2-one (8.5 g) is obtained by aqueous work-up and re-crystallization.

(A16) 5-Amino-3,3-dimethyl-6-nitro-1-(2-oxo-2-phenyl-ethyl)-1,3-dihydro-indol-2-one

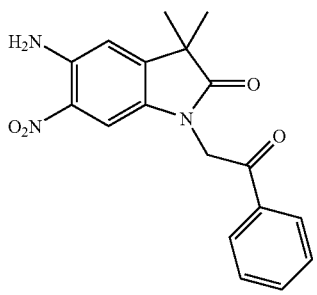

Analogously to general procedure (I) N-(3,3-dimethyl-6-nitro-2-oxo-2,3-dihydro-1H-indol-5-yl)-acetamide (8 g) is alkylated using 3-bromoacetophenone (6.8 g; 33.4 mmol) and K$_2$CO$_3$ (11.3 g; 82 mmol) at RT for 3 h. After filtration and evaporation of the solvent the crude material is de-acetylated under reflux conditions in 2-propanol (111 ml) and hydrochloric acid (6 N; 75 ml). Pure 5-amino-3,3-dimethyl-6-nitro-1-(2-oxo-2-phenyl-ethyl)-1,3-dihydro-indol-2-one (8.5 g) is obtained by aqueous work-up and re-crystallization.

(A17) 5-Amino-3,3-dimethyl-6-nitro-1-(3-pyridin-3-yl-propyl)-1,3-dihydro-indol-2-one

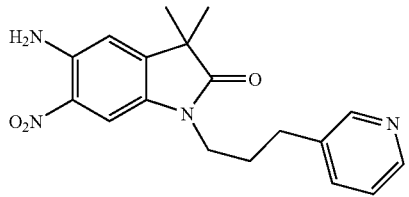

Analogously to general procedure (I) N-(3,3-dimethyl-6-nitro-2-oxo-2,3-dihydro-1H-indol-5-yl)-acetamide (1 g) is alkylated using 3-(3-bromo-propyl)-pyridine (3.04 g; 15.2 mmol) and K$_2$CO$_3$ (2.1 g; 15.2 mmol) at RT for 4 days. After aqueous work-up and flash chromatography on silica gel eluting with CH$_2$Cl$_2$/MeOH (30:1), the pure alkylated acetamide (425 mg; 1.11 mmol) is de-acetylated under reflux conditions in 2-propanol (1.2 ml) and hydrochloric acid (6 N; 3.7 ml). 5-Amino-3,3-dimethyl-6-nitro-1-(3-pyridin-3-yl-propyl)-1,3-dihydro-indol-2-one (319 mg) is obtained by aqueous work-up and used without further purification.

(A18) 5-Amino-1-[2-(2-methoxy-ethoxy)-ethyl]-3,3-dimethyl-6-nitro-1,3-dihydro-indol-2-one

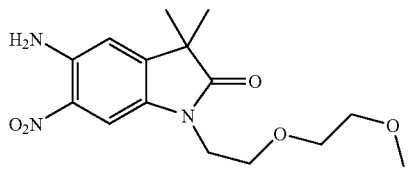

Analogously to general procedure (I) N-(3,3-dimethyl-6-nitro-2-oxo-2,3-dihydro-1H-indol-5-yl)-acetamide (3 g) is alkylated using 1-chloro-2-(2-methoxy-ethoxy)-ethane (1.7 ml; 12.2 mmol) and KOtBu (1.53 g; 13.7 mmol) at 50° C. for 10 h. After aqueous work-up and flash chromatography on silica gel eluting with light petroleum/EtOAc (2:1) pure alkylated acetamide (1.84 g; 5.03 mmol) is obtained. A part of the pure material (0.77 g; 2.11 mmol) is de-acetylated under reflux conditions in 2-propanol (5 ml) and hydrochloric acid (6 N; 3 ml). After aqueous work-up and flash chromatography 5-amino-1-[2-(2-methoxy-ethoxy)-ethyl]-3,3-dimethyl-6-nitro-1,3-dihydro-indol-2-one (0.62 g) is obtained.

(A19) 5-(5-Amino-3,3-dimethyl-6-nitro-2-oxo-2,3-dihydro-indol-1-yl)-pentanoic acid ethyl ester

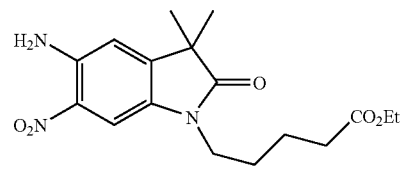

Analogously to general procedure (I) N-(3,3-dimethyl-6-nitro-2-oxo-2,3-dihydro-1H-indol-5-yl)-acetamide (2 g) is alkylated using 5-bromo-pentanoic acid ethyl ester (1.4 ml;

8.91 mmol) and KOtBu (1 g; 8.91 mmol) at RT for 20 h. After aqueous work-up and flash chromatography on silica gel eluting with light petroleum/EtOAc (1:1) the pure alkylated acetamide (1.14 g; 2.91 mmol) is obtained. A part of the pure material (0.6 g; 1.53 mmol) is de-acetylated under reflux conditions in saturated HCl in EtOH (10 ml). After aqueous work-up crude 5-(5-amino-3,3-dimethyl-6-nitro-2-oxo-2,3-dihydro-indol-1-yl)-pentanoic acid ethyl ester (0.51 g) is obtained.

(A20) 5-Amino-1-(4-imidazol-1-yl-butyl)-3,3-dimethyl-6-nitro-1,3-dihydro-indol-2-one

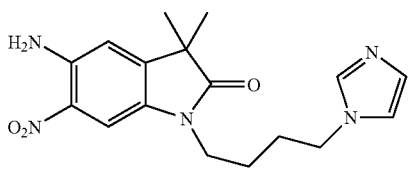

a) 1-(4-Chloro-butyl)-1H-imidazole acetate

To a suspension of NaH (1.11 g; 46.3 mmol) in dry THF, imidazole (3 g; 44.1 mmol) dissolved in 15 ml dry THF is added drop-wise at RT. After completion of the addition the mixture is refluxed for 1 h. After cooling to RT 1-bromo-4-chloro-butane (15.2 ml; 132 mmol) is added and the reaction is stirred for 16 h at RT. The mixture is acidified with acetic acid, filtered and evaporated. The residue is taken-up in hydrochloric acid (10%, 80 ml) and extracted with EtOAc (2×20 ml). The aqueous layer is adjusted to pH 8 with carbonate buffer and the product is extracted with $Et_2O$. After addition of 1 eq AcOH the organic layer is dried over $MgSO_4$ and concentrated in vacuo to give the compound (6.78 g).

b) 5-Amino-1-(4-imidazol-1-yl-butyl)-3,3-dimethyl-6-nitro-13-dihydro-indol-2-one (A20)

Analogously to general procedure (I) N-(3,3-dimethyl-6-nitro-2-oxo-2,3-dihydro-1H-indol-5-yl)-acetamide (1.29 g; 4.9 mmol) is alkylated using 1-(4-chloro-butyl)-1H-imidazole acetate (2.14 g; 9.8 mmol), $Cs_2CO_3$ (6.39 g; 19.6 mmol) and a catalytic amount of $nBu_4NI$ at 70° C. for 3 h. After aqueous work-up and flash chromatography on silica gel eluting with $CH_2Cl_2$/MeOH (18:1) the pure alkylated acetamide is de-acetylated in hydrochloric acid (6 N, 10 ml) at 80° C. in 1 h. The pure compound (1.1 g) is precipitated by neutralizing the reaction mixture with $NaHCO_3$.

(A21) 5-Amino-1-isopropyl-3,3-dimethyl-6-nitro-1,3-dihydro-indol-2-one

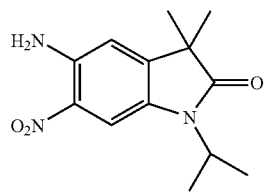

Analogously to general procedure (I) N-(3,3-dimethyl-6-nitro-2-oxo-2,3-dihydro-1H-indol-5-yl)-acetamide (1 g) is alkylated using isopropyl iodide (1.6 ml; 15.5 mmol) and $K_2CO_3$ (2.1 g; 15.2 mmol) at RT for 7 days. After aqueous work-up and flash chromatography on silica gel eluting with $CH_2Cl_2$/MeOH (30:1) the pure alkylated acetamide (0.45 g; 1.46 mmol) is de-acetylated under reflux in 2-propanol (1.5 ml) and hydrochloric acid (6 N; 5.5 ml). After completion of the reaction the mixture is poured into ice-water and the precipitate is collected to give pure 5-amino-1-isopropyl-3,3-dimethyl-6-nitro-1,3-dihydro-indol-2-one (0.3 g).

(A22) 5-Amino-3,3-dimethyl-1-(3-morpholin-4-yl-propyl)-6-nitro-1,3-dihydro-indol-2-one

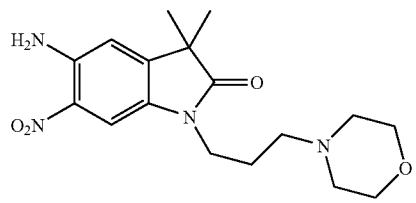

Analogously to general procedure (I) N-(3,3-dimethyl-6-nitro-2-oxo-2,3-dihydro-1H-indol-5-yl)-acetamide (0.5 g) is alkylated using 4-(3-chloro-propyl)-morpholine hydrocloride (0.57 g; 2.85 mmol), $Cs_2CO_3$ (1.55 g; 4.75 mmol) and a catalytic amount of $nBu_4NI$ at 70° C. for 4 days. After aqueous work-up the crude material is de-acetylated in hydrochloric acid (6 N, 20 ml) at 80° C. in 4 h. After aqueous work-up 5-amino-3,3-dimethyl-1-(3-morpholin-4-yl-propyl)-6-nitro-1,3-dihydro-indol-2-one (0.67 g) is obtained.

(A23) (rac)-5-Amino-3-isopropyl-1-methyl-6-nitro-1,3-dihydro-indol-2-one

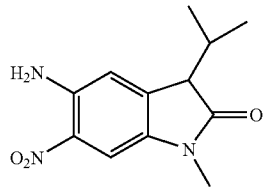

a) (rac)-3-Isopropyl-1-methyl-5-nitro-1,3-dihydro-indol-2-one

To a solution of (rac)-3-isopropyl-1-methyl-1,3-dihydro-indol-2-one (4.5 g) (J. Chem. Soc. Chem. Commun. 1986, 115-116) in concentrated sulfuric acid (7 ml) is added drop-wise a mixture of nitric acid (65%, 1.7 ml) and concentrated sulfuric acid (2.8 ml) at 0° C. over a period of 30 min. The reaction mixture is stirred at this temperature for 30 min and then poured into ice-water. The precipitate is collected by filtration and washed with water to give the title compound (3.4 g).

b) (rac)-N-(3-Isopropyl-1-methyl-2-oxo-2,3-dihydro-1H-indol-5-yl)-acetamide (rac)-3-Isopropyl-1-methyl-5-nitro-1,3-dihydro-indol-2-one (3.40 g) is dissolved in acetic acid (30 ml) and subjected to a catalytic hydrogenation with Raney-nickel (0.5 g) at 3 bar. After completion of the hydrogenation the mixture is filtered and evaporated. The residue is treated with acetic anhydride (10 ml) for 2 h at RT. The mixture is concentrated in vacuo to give the crude acetamide.

c) (rac)-N-(3-Isopropyl-1-methyl-6-nitro-2-oxo-2,3-dihydro-1H-indol-5-yl)-acetamide (rac)-N-(3-Isopropyl-1-methyl-2-oxo-2,3-dihydro-1H-indol-5-yl)-acetamide is dissolved in acetic acid (3 ml) and cooled to 0° C. Then nitric acid (fuming, 1.5 ml) is added drop-wise and the reaction mixture is stirred for 30 min at this temperature. After completion of the reaction the mixture is poured into ice-water and extracted with $CH_2Cl_2$. The combined organic layer is washed with water, dried over $MgSO_4$ and evaporated. The residue is subjected to flash chromatography on silica gel eluting with light petroleum/EtOAc to give the pure compound (1.7 g).

d) (rac)-5-Amino-3-isopropyl-1-methyl-6-nitro-1,3-dihydro-indol-2-one (A23)

(rac)-N-(3-Isopropyl-1-methyl-6-nitro-2-oxo-2,3-dihydro-1H-indol-5-yl)-acetamide (686 mg) is dissolved in 2-propanol (4 ml) and hydrochloric acid (6 N; 6 ml) and heated for 1 h at 100° C. After a typical aqueous work-up the crude material is purified by flash chromatography on silica gel eluting with light petroleum/EtOAc (1:1) to give the title compound (429 mg).

(A24) 5-Amino-3,3-diethyl-1-methyl-6-nitro-1 3-dihydro-indol-2-one

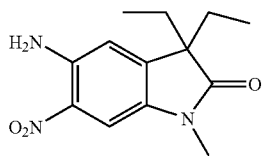

a) 3,3-Diethyl-1-methyl-5-nitro-1,3-dihydro-indol-2-one

To a solution of 3,3-diethyl-1-methyl-1,3-dihydro-indol-2-one (J. Chem. Soc., 1971, 1375) (7.6 g) in concentrated sulfuric acid (12 ml) is added a mixture of nitric acid (65%, 2.7 ml) and concentrated sulfuric acid (4.4 ml) at 0° C. over a period of 30 min. The reaction mixture is stirred at this temperature for 30 min and then poured into ice water. The precipitate is collected by filtration and washed with water to give the respective compound (9.3 g).

b) N-(3,3-Diethyl-1-methyl-2-oxo-2,3-dihydro-1H-indol-5-yl)-acetamide 3,3-Diethyl-1-methyl-5-nitro-1,3-dihydro-indol-2-one (9.3 g) is dissolved in acetic acid (100 ml) and subjected to a catalytic hydrogenation with Raney-nickel (1 g) at 3 bar. After completion of the hydrogenation the mixture is filtered and evaporated. The residue is treated with acetic anhydride (10 ml) for 3 h at RT. The mixture is concentrated in vacuo and purified by flash chromatography on silica gel eluting with light petroleum/EtOAc. After re-crystallization from diisopropyl ether the compound (7.1 g) is obtained as a white solid.

c) N-(3,3-Diethyl-1-methyl-6-nitro-2-oxo-2,3-dihydro-1H-indol-5-yl)-acetamide To a suspension of N-(3,3-diethyl-1-methyl-2-oxo-2,3-dihydro-1H-indol-5-yl)-acetamide (1.2 g) in acetic acid (5 ml) at 0° C. is added nitric acid (fuming, 0.5 ml) drop-wise. The mixture is stirred at RT for 30 min and then poured into ice-water. The precipitate is collected by filtration and washed with water to give N-(3,3-diethyl-1-methyl-6-nitro-2-oxo-2,3-dihydro-1H-indol-5-yl)-acetamide (1,38 g).

d) 5-Amino-3,3-diethyl-1-methyl-6-nitro-1,3-dihydro-indol-2-one (A24)

A suspension of N-(3,3-diethyl-1-methyl-6-nitro-2-oxo-2,3-dihydro-1H-indol-5-yl)-acetamide (1,38 g) in 2-propanol (5 ml) and hydrochloric acid (6 N; 20 ml) is stirred at 100° C. for 2 h. After cooling the mixture is diluted with water and extracted with $CH_2Cl_2$. The organic layer is washed with brine, dried over $MgSO_4$ and concentrated in vacuo to give the desired compound (1.12 g).

(A25) 5-Amino-3,3-dimethyl-6-nitro-1-pent-3-ynyl-1,3-dihydro-indol-2-one

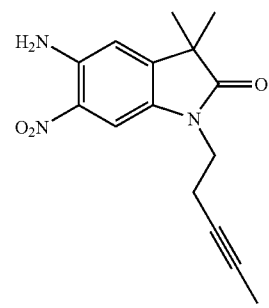

Analogously to general procedure (I) N-(3,3-dimethyl-6-nitro-2-oxo-2,3-dihydro-1H-indol-5-yl)-acetamide (3 g) is alkylated using 1-iodo-3-pentyne (4.42 g; 22.8 mmol) and $K_2CO_3$ (4.29 g; 30.4 mmol) at 40° C. for 5 d. After aqueous work-up and purification by RP chromatography a part of the material (0.4 g) is de-acetylated in MeOH (30 ml) using DBU (0.4 ml) at reflux. After aqueous work-up 5-amino-3,3-dimethyl-6-nitro-1-pent-3-ynyl-1,3-dihydro-indol-2-one (0.35 g) is obtained and used without further purification.

(A26) 5-Amino-3,3-dimethyl-6-nitro-1-(4,4,4-trifluoro-butyl)-1,3-dihydro-indol-2-one

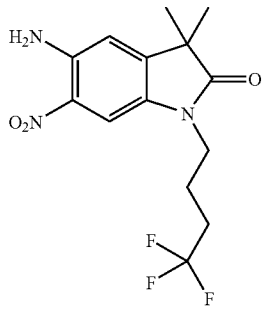

Analogously to general procedure (I) N-(3,3-dimethyl-6-nitro-2-oxo-2,3-dihydro-1H-indol-5-yl)-acetamide (2 g) is alkylated in a high pressure reaction vessel using 1-iodo-4,4,4-trifluoro-butane (3.62 g; 15.2 mmol) and $K_2CO_3$ (2.1 g; 15.2 mmol) at 60° C. for 3 days. After aqueous work-up and purification by RP chromatography the pure material (1.92 g) is de-acetylated in MeOH (200 ml) using DBU (1.6 ml) at reflux. After aqueous work-up 5-amino-3,3-dimethyl-6-nitro-1-(4,4,4-trifluoro-butyl)-1,3-dihydro-indol-2-one (1.65 g) is obtained and used without further purification.

(A27) 5-Amino-3,3-dimethyl-6-nitro-1-(333-trifluoro-propyl)-1,3-dihydro-indol-2-one

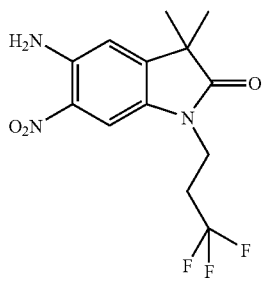

Analogously to general procedure (I) N-(3,3-dimethyl-6-nitro-2-oxo-2,3-dihydro-1H-indol-5-yl)-acetamide (2 g) is alkylated in a high pressure reaction vessel using 1-iodo-3,3,3-trifluoro-propane (1.8 ml; 15.2 mmol) and $K_2CO_3$ (2.1 g; 15.2 mmol) at 60° C. for 14 days After aqueous work-up and purification by RP chromatography the pure material (0.38 g; 1.07 mmol) is de-acetylated in MeOH (80 ml) using DBU (0.3 ml) at reflux. After aqueous work-up 5-amino-3,3-dimethyl-6-nitro-1-(3,3,3-trifluoro-propyl)-1,3-dihydro-indol-2-one (0.34 g) is obtained and used without further purification.

(A28) 5-Amino-3,3-dimethyl-6-nitro-1-(2.2.2-trifluoro-ethyl)-1,3-dihydro-indol-2-one

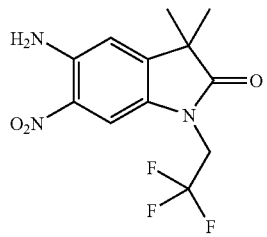

Analogously to general procedure (I) N-(3,3-dimethyl-6-nitro-2-oxo-2,3-dihydro-1H-indol-5-yl)-acetamide (5 g) is alkylated in a high pressure reaction vessel using 2-iodo-1,1,1-trifluoro-ethane (5.7 ml; 38 mmol) and $K_2CO_3$ (5.25 g; 38 mmol) at 50° C. for 14 days. After aqueous work-up and purification by RP chromatography the pure material (4 g) is de-acetylated in MeOH (150 ml) using DBU (3.6 ml) at reflux. After aqueous work-up 5-amino-3,3-dimethyl-6-nitro-1-(2,2,2-trifluoro-ethyl)-1,3-dihydro-indol-2-one (3,34 g) is obtained and used without further purification.

(A29) 5-Amino-3,3-dimethyl-6-nitro-1-(2-oxo-butyl)-1,3-dihydro-indol-2-one

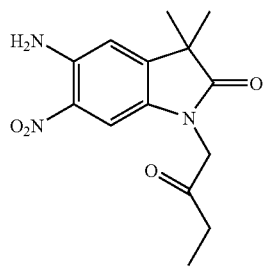

Analogously to the general procedure (I) N-(3,3-dimethyl-6-nitro-2-oxo-2,3-dihydro-1H-indol-5-yl)-acetamide (2 g) is alkylated using 1-bromo-2-butanone (1.7 ml; 15.2 mmol) and $K_2CO_3$ (2.1 g; 15.2 mmol) at 30° C. for 24 h. After aqueous work-up and purification by RP chromatography the pure material (0.65 g) is de-acetylated in MeOH (70 ml) using DBU (0.6 ml) at reflux. After aqueous work-up 5-amino-3,3-dimethyl-6-nitro-1-(2-oxo-butyl)-1,3-dihydro-indol-2-one (0.57 g) is obtained and used without further purification.

(A30) 5-Amino-1-(3,3-dimethyl-2-oxo-butyl)-3,3-dimethyl-6-nitro-1,3-dihydro-indol-2-one

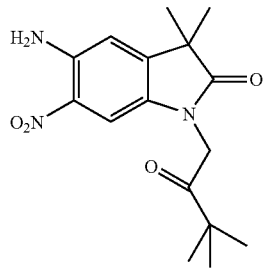

Analogously to general procedure (I) N-(3,3-dimethyl-6-nitro-2-oxo-2,3-dihydro-1H-indol-5-yl)-acetamide (2 g) is alkylated using 1-bromo-3,3-dimethyl-butan-2-one (2.72 g; 15.2 mmol) and K$_2$CO$_3$ (2.1 g; 15.2 mmol) at 40° C. for 16 h. After aqueous work-up and purification by RP chromatography the pure material (1.65 g) is de-acetylated in hydrochloric acid (6 N, 10 ml) at reflux. After aqueous work-up 5-amino-1-(3,3-dimethyl-2-oxo-butyl)-3,3-dimethyl-6-nitro-1,3-dihydro-indol-2-one (1.42 g) is obtained and used without further purification.

(A31) 5-Amino-1-(3-benzyloxy-propyl)-3,3-dimethyl-6-nitro-1,3-dihydro-indol-2-one

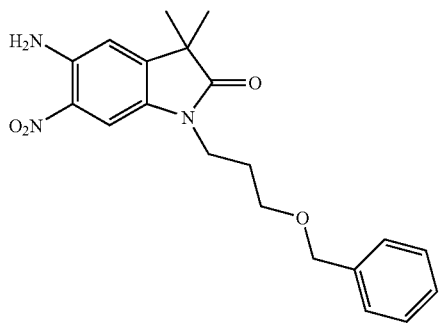

Analogously to general procedure (I) N-(3,3-dimethyl-6-nitro-2-oxo-2,3-dihydro-1H-indol-5-yl)-acetamide (1.49 g) is alkylated using (3-bromo-propoxymethyl)-benzene (1,36 g; 5.95 mmol) and K$_2$CO$_3$ (2.07 g; 15.0 mmol) at RT for 16 h. After aqueous work-up the crude material is de-acetylated in hydrochloric acid (6 N, 60 ml) at reflux. After aqueous work-up 5-amino-1-(3-benzyloxy-propyl)-3,3-dimethyl-6-nitro-1,3-dihydro-indol-2-one (2.1 g) is obtained and used without further purification.

(A32) 5-Amino-1-(4,4-dimethyl-pent-2-ynyl)-3,3-dimethyl-6-nitro-1,3-dihydro-indol-2-one

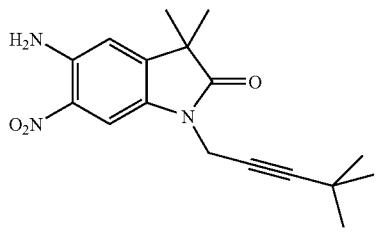

Analogously to general procedure (I) N-(3,3-dimethyl-6-nitro-2-oxo-2,3-dihydro-1H-indol-5-yl)-acetamide (10.5 g) is alkylated using 1-bromo-4,4-dimethyl-pent-2-yne (7 g; 40 mmol) and K$_2$CO$_3$ (5.52 g; 40 mmol) at 40° C. for 16 h. After aqueous work-up and purification by RP chromatography the pure material (3.9 g) is de-acetylated in MeOH (250 ml) using DBU (3.58 g) at reflux. After aqueous work-up 5-amino-1-(4,4-dimethyl-pent-2-ynyl)-3,3-dimethyl-6-nitro-1,3-dihydro-indol-2-one (2.9 g) is obtained and used without further purification.

(A33) 5-Amino-1-(3-cyclopropyl-prop-2-ynyl)-3,3-dimethyl-6-nitro-1,3-dihydro-indol-2-one

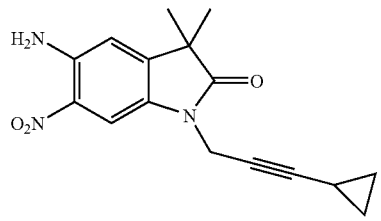

a) (3-Bromo-prop-1-ynyl)-cyclopropane

To a solution of 3-cyclopropyl-prop-2-yn-1-ol (2.95 g) (Synlett 2002, 923-926) in CH$_2$Cl$_2$ (60 ml) under argon is added CBr$_4$ (10.2 g; 30.7 mmol) at RT. After 30 min PPh$_3$ (8.05 g; 30.7 mmol) is added and the mixture is stirred overnight at RT. After careful evaporation of the solvens the crude material is directly used without further purification.

b) 5-Amino-1-(3-cyclopropyl-prop-2-ynyl)-3,3-dimethyl-6-nitro-1,3-dihydro-indol-2-one Analogously to general procedure (I) N-(3,3-dimethyl-6-nitro-2-oxo-2,3-dihydro-1H-indol-5-yl)-acetamide (1.6 g) is alkylated using (3-bromo-prop-1-ynyl)-cyclopropane (1.93 g; 12.2 mmol) and K$_2$CO$_3$ (1.71 g; 12.2 mmol) at 30° C. for 16 h. After aqueous work-up the crude material (2.1 g) is de-acetylated in MeOH (200 ml) using DBU (0.5 ml) at reflux.

After aqueous work-up 5-amino-1-(3-cyclopropyl-prop-2-ynyl)-3,3-dimethyl-6-nitro-1,3-dihydro-indol-2-one (1.80 g) is obtained and used without further purification.

(A34) 5-Amino-1-(2-cyclopropyl-ethyl)-3,3-dimethyl-6-nitro-1,3-dihydro-indol-2-one

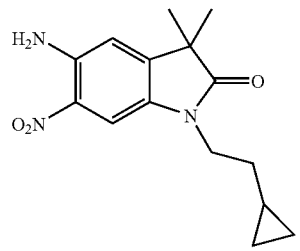

a) (2-Iodo-ethyl)-cyclopropane

To a solution of iodine (24.3 g; 95.8 mmol), imidazole (5.38 g; 76.6 mmol) and PPh$_3$ (15.5 g; 58.1 mmol) in CH$_2$Cl$_2$ (350 ml) is added 2-cyclopropyl-ethanol (5 g; 49.3 mmol) at RT and the mixture is stirred for 12 h. After aqueous work-up the organic layer is evaporated and treated with n-pentane (50 ml). The resulting precipitate (P(O)Ph$_3$) is removed by filtration and the filtrate is again evaporated to give (2-iodo-ethyl)-cyclopropane (6.13 g).

b) 5-Amino-1-(2-cyclopropyl-ethyl)-3,3-dimethyl-6-nitro-1,3-dihydro-indol-2-one Analogously to general procedure (I) N-(3,3-dimethyl-6-nitro-2-oxo-2,3-dihydro-1H-indol-5-yl)-acetamide (4 g) is alkylated using (2-iodo-ethyl)-cyclopropane (5.36 g; 27.3 mmol) and K$_2$CO$_3$ (6.30 g; 45.6 mmol) at 55° C. for 12 h. After aqueous work-up the crude material (4.21 g) is de-acetylated in hydrochloric acid (6 N, 30 ml) at reflux. After aqueous work-up 5-amino-1-(2-cyclopropyl-ethyl)-3,3-dimethyl-6-nitro-1,3-dihydro-indol-2-one (3.75 g) is obtained and used without further purification.

(A35) 4-(5-Amino-3,3-dimethyl-6-nitro-2-oxo-2,3-dihydro-indol-1-yl)-butyronitrile

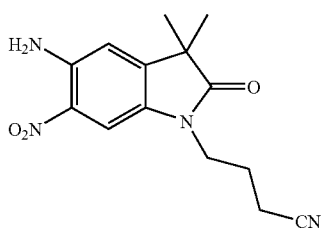

Analogously to general procedure (I) N-(3,3-dimethyl-6-nitro-2-oxo-2,3-dihydro-1H-indol-5-yl)-acetamide (0.24 g) is alkylated using 4-bromobutyronitrile (0.1 ml; 1 mmol) and K$_2$CO$_3$ (0.28 g; 2 mmol) at 50° C. for 3 days. After aqueous work-up the crude material (0.4 g) is de-acetylated in MeOH (10 ml) using DBU (0.1 ml) at RT in 3 h. After aqueous work-up 4-(5-amino-3,3-dimethyl-6-nitro-2-oxo-2,3-dihydro-indol-1-yl)-butyronitrile (0.33 g) is obtained and used without further purification.

(A36) 5-Amino-1-(2-ethylsulfanyl-ethyl)-3,3-dimethyl-6-nitro-1,3-dihydro-indol-2-one

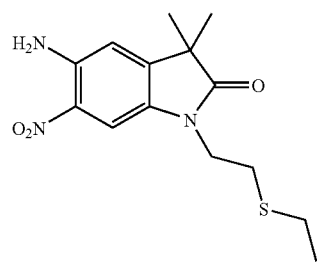

Analogously to general procedure (I) N-(3,3-dimethyl-6-nitro-2-oxo-2,3-dihydro-1H-indol-5-yl)-acetamide (1 g) is alkylated using 1-chloro-2-ethylsulfanyl-ethane (0.5 ml; 3.83 mmol) and K$_2$CO$_3$ (0.54 g; 3.83 mmol) at 40° C. for 4 d. After aqueous work-up and purification by RP chromatography the pure material (0.77 g) is de-acetylated in MeOH (35 ml) using DBU (0.3 ml) at reflux. After aqueous work-up 5-amino-1-(2-ethylsulfanyl-ethyl)-3,3-dimethyl-6-nitro-1,3-dihydro-indol-2-one (0.65 g) is obtained and used without further purification.

(A37) 5-Amino-1-(2-cyclopropoxy-ethyl)-3,3-dimethyl-6-nitro-1,3-dihydro-indol-2-one

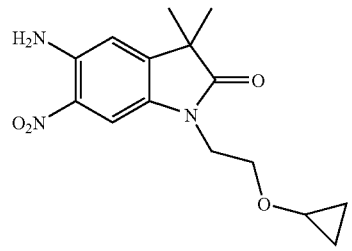

Analogously to the general procedure (I) N-(3,3-dimethyl-6-nitro-2-oxo-2,3-dihydro-1H-indol-5-yl)-acetamide (1.01 g) is alkylated using (2-chloro-ethoxy)-cyclopropane (0.5 g; 3.99 mmol), K$_2$CO$_3$ (1.06 g; 7.68 mmol) and KI (100 mg) as catalyst at 40° C. for 5 days. After aqueous work-up the crude material (1,33 g) is de-acetylated in MeOH (50 ml) using DBU (0.3 ml) at reflux. After aqueous work-up 5-amino-1-(2-cyclopropoxy-ethyl)-3,3-dimethyl-6-nitro-1,3-dihydro-indol-2-one (0.56 g) is obtained and used without further purification.

(A38) 5-Amino-3,3-dimethyl-6-nitro-1-(tetrahydro-furan-2-ylmethyl)-1,3-dihydro-indol-2-one

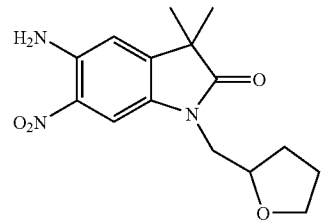

Analogously to general procedure (I) N-(3,3-dimethyl-6-nitro-2-oxo-2,3-dihydro-1H-indol-5-yl)-acetamide (2 g) is alkylated using 2-bromomethyl-tetrahydro-furan (1.7 ml; 15.2 mmol) and K$_2$CO$_3$ (2.1 g; 15.2 mmol) at 30° C. for 3 days. After aqueous work-up the crude material is de-acetylated in MeOH (150 ml) using DBU (2,3 ml) at reflux. After aqueous work-up and purification by RP chromatography 5-amino-3,3-dimethyl-6-nitro-1-(tetrahydro-furan-2-ylmethyl)-1,3-dihydro-indol-2-one (1.88 g) is obtained.

(A39) 5-Amino-3,3-dimethyl-6-nitro-1-prop-2-ynyl-1,3-dihydro-indol-2-one

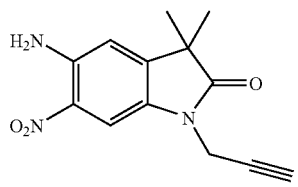

Analogously to general procedure (I) N-(3,3-dimethyl-6-nitro-2-oxo-2,3-dihydro-1H-indol-5-yl)-acetamide is alkylated using 3-bromo-propyne and $K_2CO_3$. After aqueous work-up the crude material (5.11 g) is de-acetylated in MeOH (180 ml) using DBU (1,3 ml) at reflux. After aqueous work-up 5-amino-3,3-dimethyl-6-nitro-1-prop-2-ynyl-1,3-dihydro-indol-2-one (4.32 g) is obtained and used without further purification.

(A40) (rac)-5-Amino-3,3-dimethyl-1-(1-methyl-prop-2-ynyl)-6-nitro-1,3-dihydro-indl-2-one

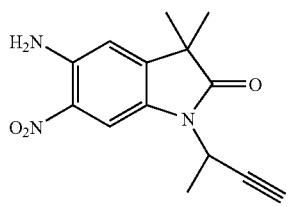

Analogously to general procedure (I) N-(3,3-dimethyl-6-nitro-2-oxo-2,3-dihydro-1H-indol-5-yl)-acetamide (2.5 g) is alkylated using (rac)-3-chloro-but-1-yne (0.86 g; 9.5 mmol) and $K_2CO_3$ (3.28 g; 23.7 mmol) at 50° C. for 14 days. After aqueous work-up the crude material (1.51 g) is de-acetylated in MeOH (40 ml) using DBU (0.3 ml) at reflux. After aqueous work-up (rac)-5-amino-3,3-dimethyl-1-(1-methyl-prop-2-ynyl)-6-nitro-1,3-dihydro-indol-2-one (1,3 g) is obtained and used without further purification.

(A41) 5-Amino-3,3-dimethyl-6-nitro-1-phenyl-13-dihydro-indol-2-one

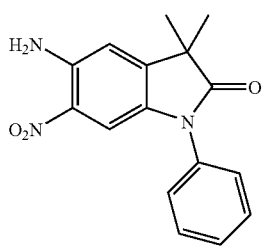

To a solution of phenyl bronic acid (0.47 g; 3.9 mmol), N-(3,3-dimethyl-6-nitro-2-oxo-2,3-dihydro-1H-indol-5-yl)-acetamide (0.5 g; 1.9 mmol) and $NEt_3$ (0.5 µl; 3.9 mmol) in $CH_2Cl_2$ (15 ml) is added molsieves (150 mg; 4 Å), $Cu(OAc)_2$ (70 mg; 385 µmol) and finally TEMPO (0.33 g; 2.11 mmol). The reaction mixture is stirred in an open flask at RT for 7 days. After completion MeOH (20 ml) is added and the mixture is adsorbed on silica gel. Purification by chromatography gives N-(3,3-dimethyl-6-nitro-2-oxo-1-phenyl-2,3-dihydro-1H-indol-5-yl)-acetamide (0.35 g). The material is de-acetylated in MeOH (10 ml) using DBU (80 µl) at reflux. After aqueous work-up 5-amino-3,3-dimethyl-6-nitro-1-phenyl-1,3-dihydro-indol-2-one (0.3 g) is obtained and used without further purification.

(A42) 5-Amino-1-(4-chloro-benzyl)-3,3-dimethyl-6-nitro-1,3-dihydro-indol-2-one

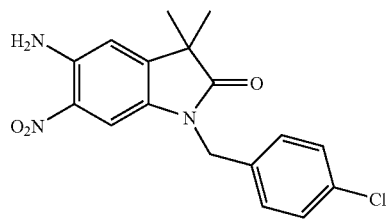

Analogously to general procedure (I) N-(3,3-dimethyl-6-nitro-2-oxo-2,3-dihydro-1H-indol-5-yl)-acetamide (1.2 g) is alkylated using 1-bromomethyl-4-chloro-benzene (0.98 g; 4.77 mmol) and $K_2CO_3$ (1.8 g; 13 mmol) at RT for 18 h. After aqueous work-up the crude material is de-acetylated using hydrochloric acid (60 ml; 6 N) at reflux. After aqueous work-up 5-amino-1-(4-chloro-benzyl)-3,3-dimethyl-6-nitro-1,3-dihydro-indol-2-one (1.44 g) is obtained and used without further purification.

(A43) 5-Amino-1-(4-fluoro-benzyl)-3,3-dimethyl-6-nitro-1,3-dihydro-indol-2-one

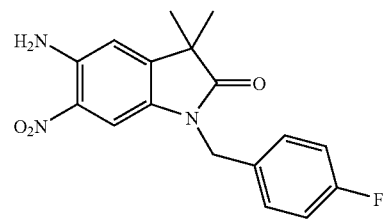

Analogously to general procedure (I) N-(3,3-dimethyl-6-nitro-2-oxo-2,3-dihydro-1H-indol-5-yl)-acetamide (1.2 g) is alkylated using 1-bromomethyl-4-fluoro-benzene (0.88 g; 4.66 mmol) and $K_2CO_3$ (1.8 g; 13 mmol) at RT for 18 h. After aqueous work-up the crude material is de-acetylated using hydrochloric acid (60 ml; 6 N) at reflux. After aqueous work-up 5-amino-1-(4-fluoro-benzyl)-3,3-dimethyl-6-nitro-1,3-dihydro-indol-2-one (1.29 g) is obtained and used without further purification.

(A44) 5-Amino-1-(2,4-difluoro-benzyl)-3,3-dimethyl-6-nitro-1,3-dihydro-indol-2-one

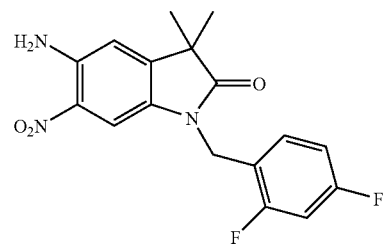

Analogously to general procedure (I) N-(3,3-dimethyl-6-nitro-2-oxo-2,3-dihydro-1H-indol-5-yl)-acetamide (1.2 g) is alkylated using 1-bromomethyl-2,4-difluoro-benzene (0.6 ml; 4.6 mmol) and K$_2$CO$_3$ (1.8 g; 13 mmol) at RT for 18 h. After aqueous work-up the crude material is de-acetylated using hydrochloric acid (60 ml; 6 N) at reflux. After aqueous work-up 5-amino-1-(2,4-difluoro-benzyl)-3,3-dimethyl-6-nitro-1,3-dihydro-indol-2-one (0.95 g) is obtained and used without further purification.

(A45) 5-Amino-1-(4-fluoro-2-methoxy-benzyl)-3,3-dimethyl-6-nitro-1,3-dihydro-indol-2-one

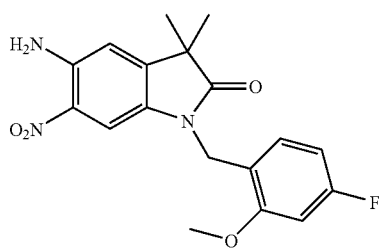

Analogously to general procedure (I) N-(3,3-dimethyl-6-nitro-2-oxo-2,3-dihydro-1H-indol-5-yl)-acetamide (5.28 g) is alkylated using 1-chloromethyl-4-fluoro-2-methoxy-benzene (3.5 g; 20 mmol) and K$_2$CO$_3$ (8.31 g; 60.2 mmol) at RT for 18 h. After aqueous work-up the crude material is de-acetylated in MeOH (35 ml) using DBU (1.52 g) at RT. After aqueous work-up 5-amino-i-(4-fluoro-2-methoxy-benzyl)-3,3-dimethyl-6-nitro-1,3-dihydro-indol-2-one (6.95 g) is obtained and used without further purification.

(A46) [2-(5-Amino-3,3-dimethyl-6-nitro-2-oxo-2,3-dihydro-indol-1-ylmethyl)-phenyl]-carbamic acid tert-butyl ester

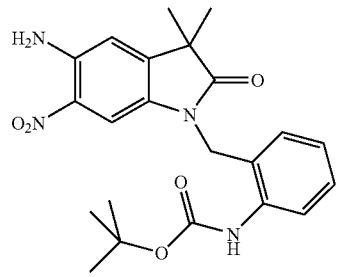

a) Methanesulfonic acid 2-tert-butoxycarbonylamino-benzyl ester

To a solution of (2-hydroxymethyl-phenyl)-carbamic acid tert-butyl ester (0.8 g; 3.6 mmol) in EtOAc (15 ml) at 0° C. is added NEt$_3$ (610 µl) and methanesulfonyl chloride (340 µl). After addition the mixture is warmed to RT and stirred for 3 days. After completion the reaction mixture is acidified with diluted hydrochloric acid and extracted twice with EtOAc. The organic phase is washed with brine, dried over MgSO$_4$ and evaporated to give methanesulfonic acid 2-tert-butoxycarbonylamino-benzyl ester (0.73 g).

b) [2-(5-Amino-3,3-dimethyl-6-nitro-2-oxo-2,3-dihydro-indol-1-ylmethyl)-phenyl]-carbamic acid tert-butyl ester Analogously to general procedure (I) N-(3,3-dimethyl-6-nitro-2-oxo-2,3-dihydro-1H-indol-5-yl)-acetamide (0.55 g) is alkylated using methanesulfonic acid 2-tert-butoxycarbonylamino-benzyl ester (0.69 g; 2.09 mmol) and K$_2$CO$_3$ (0.99 g; 7.19 mmol) at RT for 18 h. After aqueous work-up the crude material is de-acetylated in MeOH (50 ml) using DBU (0.3 ml) at reflux. After aqueous work-up [2-(5-amino-3,3-dimethyl-6-nitro-2-oxo-2,3-dihydro-indol-1-ylmethyl)-phenyl]-carbamic acid tert-butyl ester (1.03 g) is obtained and used without further purification.

(A47) 5-Amino-1-(3-fluoro-4-methoxy-benzyl)-3,3-dimethyl-6-nitro-1,3-dihydro-indol-2-one

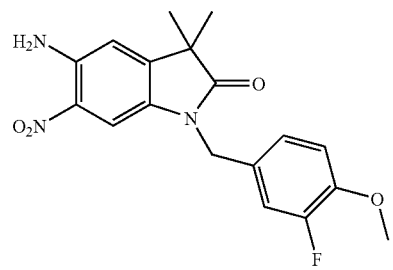

Analogously to general procedure (I) N-(3,3-dimethyl-6-nitro-2-oxo-2,3-dihydro-1H-indol-5-yl)-acetamide (0.57 g) is alkylated using 4-bromomethyl-2-fluoro-1-methoxy-benzene (0.5 g; 2.28 mmol) and K$_2$CO$_3$ (0.9 g; 6.52 mmol) at RT for 18 h. After aqueous work-up the crude material is de-acetylated in hydrochloric acid (20 ml; 6 N) at reflux. After aqueous work-up 5-amino-1-(3-fluoro-4-methoxy-benzyl)-3,3-dimethyl-6-nitro-1,3-dihydro-indol-2-one (0.68 g) is obtained and used without further purification.

(A48) 5-Amino-1-(3,5-difluoro-4-isopropoxy-benzyl)-3,3-dimethyl-6-nitro-1,3-dihydro-indol-2-one

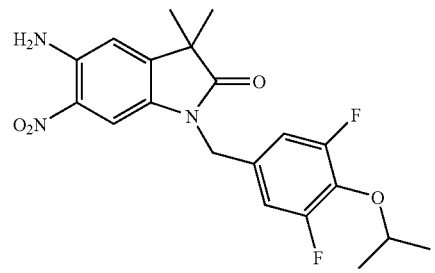

a) 3,5-Difluoro-4-hydroxy-benzaldehyde

To a solution of 2,6-difluoro phenol (1 g; 7.69 mmol) in CF$_3$COOH (10 ml) is added hexamethylene tetramine (1.08 g; 7.69 mmol) and the mixture is heated in a microwave apparatus at 130° C. for 15 min. After evaporation to dryness the residue is taken-up in CH$_2$Cl$_2$ and saturated K$_2$CO$_3$ solution. After acidification with hydrochloric acid the aqueous layer is extracted with CH$_2$Cl$_2$ (3×100 ml). The combined organic layer is washed with brine, dried over MgSO$_4$ and evaporated to dryness to give 3,5-difluoro-4-hydroxy-benzaldehyde as a colourless solid (0.82 g).

b) 3,5-Difluoro-4-isopropoxy-benzaldehyde

To a suspension of 3,5-difluoro-4-hydroxy-benzaldehyde as a colourless solid (0.81 g) and $K_2CO_3$ (2.14 g; 15.4 mmol) in MeCN (15 ml) is added 2-bromopropane (1.45 ml) dropwise. The mixture is stirred at 65° C. for 24 h. After evaporation of the solvent the residue is taken-up in $Et_2O$ and water. The organic layer is separated and extracted with brine, dried over $MgSO_4$ and evaporated to give 3,5-difluoro-4-isopropoxy-benzaldehyde (0.14 g).

c) 5-Chloromethyl-1,3-difluoro-2-isopropoxy-benzene

To a suspension of 3,5-difluoro-4-isopropoxy-benzaldehyde (0.14 g) in EtOH (10 ml) is added $NaBH_4$ (60.7 mg; 1.61 mmol) at 10° C. in 5 portions. The mixture is slowly warmed to RT and stirred for 3 h. After aqueous work-up (3,5-difluoro-4-isopropoxy-phenyl)-methanol is obtained which is directly chlorinated using $SOCl_2$ (1 ml; 13.8 mmol) in $CH_2Cl_2$ (10 ml) at RT for 3 h. After aqueous work-up 5-chloromethyl-1,3-difluoro-2-isopropoxy-benzene (0.14 g) is obtained as a yellow oil which is used without further purification.

d) 5-Amino-1-(3,5-difluoro-4-isopropoxy-benzyl)-3,3-dimethyl-6-nitro-1,3-dihydro-indol-2-one Analogously to general procedure (I) N-(3,3-dimethyl-6-nitro-2-oxo-2,3-dihydro-1H-indol-5-yl)-acetamide (0.17 g) is alkylated using 5-chloromethyl-1,3-difluoro-2-isopropoxy-benzene (0.15 g; 0.68 mmol) and $K_2CO_3$ (0.3 g; 2.16 mmol) at RT for 18 h. After aqueous work-up the crude material (0.27 g) is de-acetylated in hydrochloric acid (30 ml; 6 N) at reflux. After aqueous work-up 5-amino-1-(3,5-difluoro-4-isopropoxy-benzyl)-3,3-dimethyl-6-nitro-1,3-dihydro-indol-2-one (0.20 g) is obtained and used without further purification.

(A49) 5-Amino-1-(5-fluoro-pyridin-2-ylmethyl)-3,3-dimethyl-6-nitro-1,3-dihydro-indol-2-one

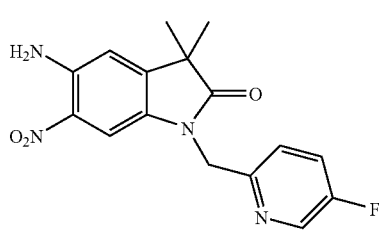

a) 2-Bromomethyl-5-fluoro-pyridine

To a solution of 5-fluoro-2-methyl-pyridine (0.75 g) (J. Med. Chem. 1989, 32, 1970) in $CCl_4$ (25 ml) is added N-bromosuccinimide (0.96 g; 5.4 mmol) and benzoyl peroxide (200 mg; 0.8 mmol). The mixture is heated at reflux for 3 h, cooled to RT and stirred for additional 12 h. The suspension is filtered through celite and the filtrate is washed with $Na_2SO_4$, dried over $MgSO_4$ and evaporated. The crude material (0.22 g) containing approximately 50% of the dibrominated species is used without further purification.

b) 5-Amino-1-(5-fluoro-pyridin-2-ylmethyl)-3,3-dimethyl-6-nitro-1,3-dihydro-indol-2-one Analogously to general procedure (I) N-(3,3-dimethyl-6-nitro-2-oxo-2,3-dihydro-1H-indol-5-yl)-acetamide (0.3 g; 1.14 mmol) is alkylated using 2-bromomethyl-5-fluoro-pyridine (0.22 g; 0.46 mmol) and $K_2CO_3$ (0.4 g; 0.23 mmol) at 35° C. for 18 h. After aqueous work-up and purification by RP chromatography the pure material (87 mg) is de-acetylated in MeOH (6 ml) using DBU (16 µl) at reflux. After aqueous work-up 5-amino-1-(5-fluoro-pyridin-2-ylmethyl)-3,3-dimethyl-6-nitro-1,3-dihydro-indol-2-one (75.0 mg) is obtained and used without further purification.

(A50) 5-Amino-3,3-dimethyl-6-nitro-1-oxazol-2-ylmethyl-1,3-dihydro-indol-2-one

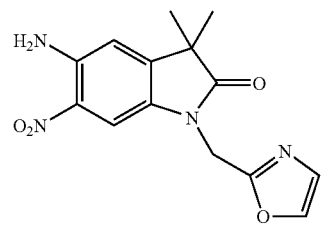

Analogously to general procedure (I) N-(3,3-dimethyl-6-nitro-2-oxo-2,3-dihydro-1H-indol-5-yl)-acetamide (1 g) is alkylated using 2-chloromethyl-oxazole (0.47 g; 4 mmol) and $K_2CO_3$ (1.1 g; 7.96 mmol) at RT for 18 h. After aqueous work-up the crude material (1.30 g) is de-acetylated in MeOH (30 ml) using DBU (280 µl) at reflux. After aqueous work-up 5-amino-3,3-dimethyl-6-nitro-1-oxazol-2-ylmethyl-1,3-dihydro-indol-2-one (1.09 g) is obtained and used without further purification.

(A51) 5-Amino-3,3-dimethyl-6-nitro-1-thiazol-4-ylmethly-1,3-dihydro-indol-2-one

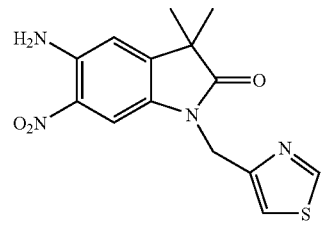

Analogously to general procedure (I) N-(3,3-dimethyl-6-nitro-2-oxo-2,3-dihydro-1H-indol-5-yl)-acetamide (3.62 g) is alkylated using 4-chloromethyl-thiazole hydrochloride (2.62 g; 15.4 mmol) and $K_2CO_3$ (4.41 g; 31.2 mmol) at 50° C. for 3 days. After aqueous work-up and purification by chromatography ($SiO_2$; cyclohexan/EtOAc gradient) the pure material (3.80 g) is de-acetylated in MeOH (100 ml) using DBU (1.6 ml) at 70° C. in 1.5 h. After aqueous work-up 5-amino-3,3-dimethyl-6-nitro-1-thiazol-4-ylmethyl-1,3-dihydro-indol-2-one (3,37 g) is obtained and used without further purification.

(A52) 5-Amino-1-(2,4-dimethyl-thiazol-5-ylmethyl)-3,3-dimethyl-6-nitro-1,3-dihydro-indol-2-one

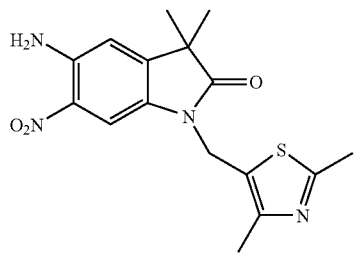

Analogously to general procedure (I) N-(3,3-dimethyl-6-nitro-2-oxo-2,3-dihydro-1H-indol-5-yl)-acetamide (1.77 g) is alkylated using 5-chloromethyl-2,4-dimethyl-thiazole (1.09 g; 6.74 mmol) (Zh. Obshch. Khim. 1956, engl. transl. 3835) and $K_2CO_3$ (1.05 g; 7.41 mmol) at 60° C. for 3 days. After aqueous work-up the crude material is de-acetylated in MeOH (70 ml) using DBU (2.2 ml) at reflux. After aqueous work-up 5-amino-1-(2,4-dimethyl-thiazol-5-ylmethyl)-3,3-dimethyl-6-nitro-1,3-dihydro-indol-2-one (1.44 g) is obtained and used without further purification.

(A53) 5-Amino-3,3-dimethyl-1-(3-methyl-isoxazol-5-ylmethyl)-6-nitro-1,3-dihydro-indol-2-one

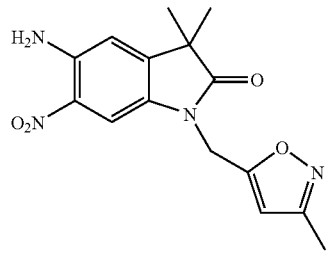

a) 5-Chloromethyl-3-methyl-isoxazole

To a cooled solution (10° C.) of acetaldehyde oxime (2 g; 33.9 mmol) and 3-chloro-propyne (1.9 ml; 37 mmol) in $CH_2Cl_2$ (15 ml) is added aqueous sodium hypochlorite solution (22.6 ml; 38 mmol) within 30 min. The mixture is stirred for 1 h at RT. After extraction with $CH_2Cl_2$ the combined organic layer is washed with brine, dried over $MgSO_4$ and evaporated to give 5-chloromethyl-3-methyl-isoxazole (1.65 g).

b) 5-Amino-3,3-dimethyl-1-(3-methyl-isoxazol-5-ylmethyl)-6-nitro-1,3-dihydro-indol-2-one Analogously to general procedure (I) N-(3,3-dimethyl-6-nitro-2-oxo-2,3-dihydro-1H-indol-5-yl)-acetamide (3 g) is alkylated using 5-chloromethyl-3-methyl-isoxazole (1.65 g; 12.5 mmol) and $K_2CO_3$ (3,3 g; 23.9 mmol) at RT for 3 days. After aqueous work-up and purification by RP chromatography the pure material (1.07 g) is de-acetylated in MeOH (50 ml) using DBU (220 µl) at 60° C. in 18 h. After aqueous work-up 5-amino-3,3-dimethyl-1-(3-methyl-isoxazol-5-ylmethyl)-6-nitro-1,3-dihydro-indol-2-one (0.93 g) is obtained and used without further purification.

(A54) 5-Amino-3,3-dimethyl-6-nitro-1-(3-phenyl-isoxazol-5-ylmethyl)-1,3-dihydro-2-one

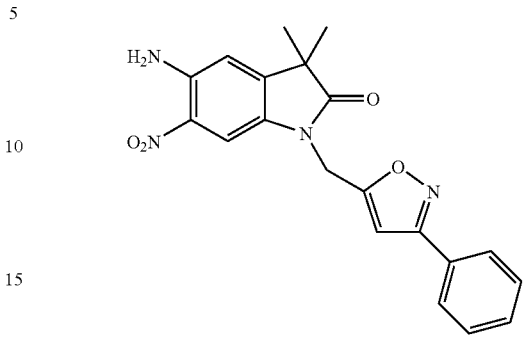

The compound (1.94 g) is obtained as described for building block A53 starting from benzaldehyde oxime (2.16 g), 3-chloro-propyne (2 ml; 18.1 mmol) and N-(3,3-dimethyl-6-nitro-2-oxo-2,3-dihydro-1H-indol-5-yl)-acetamide (2,33 g).

Examples Starting from Building Blocks A

Example 1 a) 3-Phenyl-N-(1,3,3-trimethyl-6-nitro-2-oxo-2,3-dihydro-1H-indol-5-yl)-propionamide To a solution of A1 (330 mg) in dry pyridine (1.9 ml) is added drop-wise a solution of 3-p-tolyl-propionyl chloride in $CH_2Cl_2$ (2 ml). The mixture is stirred at RT for 20 h. Hydrochloric acid (2 M; 5 ml) is added, the layers are separated and the aqueous layer is extracted with $CH_2Cl_2$ (2×10 ml) The combined organic layer is washed with water, dried over $MgSO_4$ and concentrated in vacuo to give the desired compound (532 mg).

b) 5,7,7-Trimethyl-2-(2-p-tolyl-ethyl)-5,7-dihydro-1H-imidazo[4,5-f]indol-6-one A solution of 3-phenyl-N-(1,3,3-trimethyl-6-nitro-2-oxo-2,3-dihydro-1H-indol-5-yl)-propionamide (532 mg) in acetic acid (8 ml) is hydrogenated at 2-4 bar at RT using Pd/C (10%, 80 mg), where upon ring closure occurs. After evaporation of the solvent the residue is taken-up in NaOH solution (2 N) and extracted with EtOAc (2×20 ml). The combined organic layer is washed with brine, dried over $Na_2SO_4$ and evaporated. The residual material is triturated with acetone to give the desired compound (466 mg).

Example 2 a) 3-(2,4-Dichloro-phenyl)-N-(1,33-trimethyl-6-nitro-2-oxo-2,3-dihydro-1H-indol-5-yl)-propionamide is prepared from A1 (300 mg) and 3-(2,4-dichloro-phenyl)-propionyl chloride (606 mg; 2.55 mmol) as described in Example 1a). The crude material is purified by flash chromatography on silica gel eluting with $CH_2Cl_2$/MeOH (30:1) (558 mg).

b) 2-[2-(2,4-Dichloro-phenyl)-ethyl]-5,7,7-trimethyl-5,7-dihydro-1H-imidazo[4,5-f]indol-6-one is prepared from 3-(2,4-dichloro-phenyl)-N-(1,3,3-trimethyl-6-nitro-2-oxo-2,3-dihydro-1H-indol-5-yl)-propionamide as described in Example 1b using Raney-nickel (71 mg) instead of Pd/C (497 mg).

Example 3 a) 3-Phenyl-N-(1,3,3-trimethyl-6-nitro-2-oxo-2,3-dihydro-1H-indol-5-yl)-propionamide is prepared from A1 (235 mg) and 3-(2,4-dichloro-phenyl)-propionyl chloride (172 mg; 1 mmol) as described in Example 1a (380 mg).

b) 5,7,7-Trimethyl-2-phenethyl-5,7-dihydro-3H-imidazo[4,5-f]indol-6-one

To a solution of 3-phenyl-N-(1,3,3-trimethyl-6-nitro-2-oxo-2,3-dihydro-1H-indol-5-yl)-propionamide (125 mg; 248 μmol) in acetic acid (3 ml) is added iron powder (403 mg; 7 mmol). The mixture is heated and irradiated in a microwave apparatus (150° C.; 900 s). After re-cooling the mixture is filtered and evaporated. The residue is taken-up in water (40 ml) and saturated $K_2CO_3$ solution (10 ml) and extracted with $CH_2Cl_2$ (4×50 ml). The combined organic layer is dried over $MgSO_4$ and concentrated in vacuo. The desired compound (55.0 mg) is obtained by preparative RP-HPLC eluting with a water/MeCN gradient.

Examples 4-9 are prepared analogously from A1 as described in Example 3.

Example 10 a) 2-Chloro-N-(1-ethyl-3,3-dimethyl-6-nitro-2-oxo-2,3-dihydro-1H-indol-5-yl)-isonicotinamide (602 mg) is prepared from A2 (500 mg) as described in Example 1a.

b) 2-(2-Chloro-pyridin-4-yl)-5-ethyl-7,7-dimethyl-5,7-dihydro-1H-imidazo[4,5-f]indol-6-one is prepared from 2-chloro-N-(1-ethyl-3,3-dimethyl-6-nitro-2-oxo-2,3-dihydro-1H-indol-5-yl)-isonicotinamide (230 mg) as described in Example 1b using Raney-nickel (50 mg) instead of Pd/C. After filtration the filtrate is poured into ice-water and the precipitate is collected by filtration to give the desired compound (140 mg).

Examples 11-13 are prepared analogously from A2 as described in Example 10.

Example 14 a) N-(3,3-Dimethyl-6-nitro-2-oxo-1-propyl-2,3-dihydro-1H-indol-5-yl)-4-trifluoromethyl-benzamide A solution of A3 (300 mg) and freshly prepared 4-trifluoromethyl-benzoyl chloride (476 mg; 2.28 mmol) in chlorobenzene (8 ml) is stirred at 150° C. for 3 h. After re-cooling, the mixture is poured into ice-water and extracted with EtOAc (3×50 ml). The combined organic layer is washed with saturated $NaHCO_3$ solution and brine dried over $Na_2SO_4$ and concentrated in vacuo. The compound (455 mg) is obtained by flash chromatography on silica gel eluting with light petroleum/EtOAc (2:1).

b) 7,7-Dimethyl-5-propyl-2-(4-trifluoromethyl-phenyl)-5,7-dihydro-1H-imidazo[4,5-f]indol-6-one (382 mg) is prepared from N-(3,3-dimethyl-6-nitro-2-oxo-1-propyl-2,3-dihydro-1H-indol-5-yl)-4-trifluoromethyl-benzamide (455 mg; 1.05 mmol) as described in Example 10.

Example 15 a) 4-Chloro-N-(3,3-dimethyl-6-nitro-2-oxo-1-propyl-2,3-dihydro-1H-indol-5-yl)-benzamide is prepared from A3 (300 mg) and 4-chlorobenzoyl chloride (357 mg; 2.28 mmol) as described in Example 14a. Purification by flash chromatography on silica gel eluting with light petroleum/EtOAc (3:1) give the desired compound (403 mg).

b) 2-(4-Chloro-phenyl)-7,7-dimethyl-5-propyl-5,7-dihydro-1H-imidazo[4,5-t]indol-6-one A solution of 4-chloro-N-(3,3-dimethyl-6-nitro-2-oxo-1-propyl-2,3-dihydro-1H-indol-5-yl)-benzamide (403 mg) in MeOH (6 ml) is hydrogenated as described in Example 1b using Raney-nickel (35 mg) as catalyst. After filtration and evaporation the crude material is dissolved in acetic acid (6 ml) and stirred at 80° C. for 1 h whereupon ring closure occurred. The mixture is concentrated in vacuo. The residue is taken-up in NaOH solution (2 M) and extracted with EtOAc (3×50 ml). The combined organic layer is washed with brine, dried over $Na_2SO_4$ and evaporated. The desired compound (280 mg) is obtained by flash chromatography on silica gel eluting with light petroleum/EtOAc (1:1).

Examples 16-17 are prepared analogously from A3 as described in Example 15.

Example 18 a) N-(1-Butyl-3,3-dimethyl-6-nitro-2-oxo-2,3-dihydro-1H-indol-5-yl)-3-(4-isopropoxy-phenyl)-propionamide is prepared from A4 (500 mg) and 3-(4-isopropoxy-phenyl)-propionyl chloride (1.01 g; 5.5 mmol) as described in Example 1a. The crude material is purified by flash chromatography eluting with light petroleum/EtOAc (6:1) to give the compound (791 mg).

b) 5-Butyl-2-(4-isopropoxy-phenyl)-7,7-dimethyl-5,7-dihydro-1H-imidazo[4,5-f]indol-6-one is prepared from N-(1-butyl-3,3-dimethyl-6-nitro-2-oxo-2,3-dihydro-1H-indol-5-yl)-3-(4-isopropoxy-phenyl)-propionamide (791 mg) as described in Example 1b using Raney-nickel (71 mg) instead of Pd/C. The desired compound (218 mg) is obtained by flash chromatography on silica gel eluting with light petroleum/EtOAc (2:1).

Examples 19-22 are prepared analogously from A4 by a two step procedure as described in Example 18.

Example 23

5-Butyl-2-(4-methoxy-phenyl)-7,7-dimethyl-5,7-dihydro-1H-imidazo[4,5-f]indole-6-thione To a solution of 5-butyl-2-(4-methoxy-phenyl)-7,7-dimethyl-5,7-dihydro-1H-imidazo[4,5-f]indol-6-one (82.9 mg) in 1,4-dioxane (1 ml) is added $PS_5$ (101 mg; 227 μmol). The mixture is stirred for 3 h at 140° C. After cooling to RT the reaction mixture is poured into ice-water. The resulting precipitate is filtered and washed with water. The desired compound (57.0 mg) is obtained by flash chromatography on silica gel eluting with light petroleum/EtOAc (1:2).

Example 24

5-Butyl-2-(4-methoxy-phenyl)-7,7-dimethyl-1,5,6,7-tetrahydro-imidazo[4,5-f]indole To a solution of 5-butyl-2-(4-methoxy-phenyl)-7,7-dimethyl-5,7-dihydro-1H-imidazo[4,5-f]indol-6-one (150 mg) in dry THF (10 ml) under an inert atmosphere (N2) is added $LiAlH_4$ (31.4 mg; 826 μmol). The reaction mixture is refluxed for 6 h and afterwards stirred at RT for another 15 h. Excess $LiAlH_4$ is carefully hydrolyzed with NaOH solution (1 M; 30 ml). The aqueous layer is extracted with $CH_2Cl_2$ (3×30 ml).

45

The combined organic layer is washed with brine, dried over MgSO$_4$ and concentrated in vacuo to give the desired compound (140 mg).

Example 25 a) N-[3,3-Dimethyl-6-nitro-2-oxo-1-((E)-pent-2-enyl)-2,3-dihydro-1H-indol-5-yl]-3-phenyl-propionamide Phenyl-propionic acid (360 mg) is treated with thionyl chloride (8 ml) and few drops of N,N-dimethylformamide under reflux for 45 min. Excess thionyl chloride is removed in vacuo and the resulting acid chloride is dissolved in chlorobenzene (10 ml). After addition of A5 (580 mg) the reaction mixture is heated under reflux for 2 h. Chlorobenzene is removed in vacuo and the residue is taken-up in EtOAc. The organic layer is washed with saturated NaHCO$_3$ solution and brine, dried over Na$_2$SO$_4$ and evaporated. The compound (685 mg) is obtained by flash chromatography on silica gel eluting with light petroleum/EtOAc (5:1).

b) 7,7-Dimethyl-5-((E)-pent-2-enyl)-2-phenethyl-5,7-dihydro-1H-imidazo[4,5-f]indol-6-one N-[3,3-Dimethyl-6-nitro-2-oxo-1-((E)-pent-2-enyl)-2,3-dihydro-1H-indol-5-yl]-3-phenyl-propionamide (470 mg) is dissolved in acetic acid (7 ml) and iron powder (470 mg; 8.42 mmol) is added. The mixture is heated and irradiated in a microwave apparatus (150° C., 15 min) and afterwards cooled to RT. Aqueous work-up as described in Example 3b gives the desired compound (344 mg).

Example 26

7,7-Dimethyl-5-((Z)-pent-2-enyl)-2-phenethyl-5,7-dihydro-1H-imidazo[4.5-f]indol-6-one The compound (549 mg) is prepared as described in Example 25a and b, starting from A6 (600 mg).

Example 27 a) N-(3,3-Dimethyl-6-nitro-2-oxo-1-pent-2-ynyl-2,3-dihydro-1H-indol-5-yl)-3-phenyl-propionamide is prepared as described in Example 25a starting from A7 (73 mg) using THF (3 ml) as solvent. The crude material (106 mg) is used without further purification.

b) 7,7-Dimethyl-5-pent-2-ynyl-2-phenethyl-5,7-dihydro-1H-imidazo [4.5-f]indol-6-one To a solution of N-(3,3-dimethyl-6-nitro-2-oxo-1-pent-2-ynyl-2,3-dihydro-1H-indol-5-yl)-3-phenyl-propionamide (50 mg) in THF (0.5 ml) is added a solution of SnCl$_2$.H$_2$O (107 mg; 476 µmol) in hydrochloric acid (1 M; 2 ml) at RT. The mixture is stirred 2 h at RT and subsequent 2 h at 40° C. The reaction mixture is adjusted to pH 12 and extracted with CH$_2$Cl$_2$ (3×15 ml). The combined organic layer is dried over MgSO$_4$ and concentrated in vacuo. The desired compound (19 mg) is obtained by flash chromatography on silica gel eluting with CH$_2$Cl$_2$/MeOH (99:1).

Example 28 a) (E)-N-(3,3-Dimethyl-6-nitro-2-oxo-1-pentyl-2,3-dihydro-1H-indol-5-yl)-3-(2-nitro-phenyl)-acrylamide To a solution of A8 (0.6 g) is added freshly prepared (E)-3-(2-nitro-phenyl)-acryloyl chloride (0.7 g; 3,31 mmol). The mixture is stirred for 2 h at RT in dry CH$_2$Cl$_2$ (15 ml). After an aqueous work-up the compound is obtained as a yellow solid.

b) (E)-N-(6-Amino-3,3-dimethyl-2-oxo-1-pentyl-2,3-dihydro-1H-indol-5-yl)-3-(2-amino-phenyl)-acrylamide (E)-N-(3,3-Dimethyl-6-nitro-2-oxo-1-pentyl-2,3-dihydro-1H-indol-5-yl)-3-(2-nitrophenyl)-acrylamide is dissolved in EtOAc (70 ml). SnCl$_2$.H$_2$O (5.44 g; 24.1 mmol) is added and the resulting mixture is heated under reflux for 20 h. After re-cooling the mixture is filtered over basic Al$_2$O$_3$ (120 g) and concentrated in vacuo. The residue is taken-up in EtOAc and saturated K$_2$CO$_3$ solution. After an aqueous work-up the compound (0.82 g) is obtained as a yellow solid.

c) 2-[(E)-2-(2-Amino-phenyl)-vinyl]-7,7-dimethyl-5-pentyl-5,7-dihydro-1H-imidazo[4,5-f]indol-6-one (E)-N-(6-Amino-3,3-dimethyl-2-oxo-1-pentyl-2,3-dihydro-1H-indol-5-yl)-3-(2-amino-phenyl)-acrylamide (0.82 g) is dissolved in water, 2-propanol and concentrated hydrochloric acid and heated for 3 h under reflux. After re-cooling the mixture is concentrated in vacuo. The residue is taken-up in EtOAc and saturated K$_2$CO$_3$ solution. After an aqueous work-up the desired compound (0.73 g) is obtained as a yellow solid. A small amount was treated with hydrochloric acid (2 N) to give the hydrochloric salt which precipitated in a pure form.

Examples 29-31 are prepared analogously from A8 as described in Example 1.

Examples 32-37 are prepared analogously from A8 as described in Example 14a.

Examples 38-53 are prepared in a two step procedure from A8 as described in Example 1a and 3b.

Example 54 a) 2-[(E)-2-(3-Amino-phenyl)-vinyl]-7,7-dimethyl-5-pentyl-5,7-dihydro-1H-imidazo[4,5-f]indol-6-one (177 mg) is prepared from A8 (251 mg) and (E)-3-(3-nitro-phenyl)-acryloyl chloride (200 mg; 1.01 mmol) as described in Example 28a and b.

b) 2-[(E)-2-(3-Dimethylamino-phenyl)-vinyl]-7,7-dimethyl-5-pentyl-5,7-dihydro-1H-imidazo[4,5-f]indol-6-one To a solution 2-[(E)-2-(3-amino-phenyl)-vinyl]-7,7-dimethyl-5-pentyl-5,7-dihydro-1H-imidazo[4,5-f]indol-6-one (170 mg) in dry THF (2.5 ml) and acetic acid (0.3 ml) is added p-formaldehyde (41.5 mg; 1,31 mmol) and resin-bound cyanoborohydride (MP-cyanoborohydride; Argonaut) (1.23 g; 2.50 mmol). The mixture is gently stirred under an inert atmosphere (Ar) at RT for 48 h. After completion of the reaction the mixture is filtered and concentrated in vacuo. The desired compound (43.0 mg) is obtained by preparative RP-HPLC.

Example 55 a) 3-(3-Amino-phenyl)-N-(3,3-dimethyl-6-nitro-2-oxo-1-pentyl-2,3-dihydro-1H-indol-5-yl)-propionamide The compound is synthesized from A8 (213 mg) and freshly prepared 3-(3-amino-phenyl)-propionyl chloride (223 mg; 1.21 mmol) as described in Example 1a.

b) N-{3-[2-(7,7-Dimethyl-6-oxo-5-pentyl-1,5,6,7-tetrahydro-imidazo[4,5-f]indol-2-yl)-ethyl]-phenyl}-acetamide is prepared from 3-(3-amino-phenyl)-N-(3,3-dimethyl-6-nitro-2-oxo-1-pentyl-2,3-dihydro-1H-indol-5-yl)-propionamide as described in Example 3b. Under the microwave conditions the acetylated product is formed. The desired N-{3-[2-(7,7-dimethyl-6-oxo-5-pentyl-1,5,6,7-tetrahydro-imidazo[4,5-f]indol-2-yl)-ethyl]-phenyl}-acetamide (229 mg) is obtained by flash chromatography on silica gel eluting with $CH_2Cl_2$/MeOH (99:1).

Example 56

2-[2-(3-Amino-phenyl)-ethyl]-7,7-dimethyl-5-pentyl-5,7-dihydro-1H-imidazo[4,5-f]indol-6-one A solution of N-{3-[2-(7,7-dimethyl-6-oxo-5-pentyl-1,5,6,7-tetrahydro-imidazo[4,5-f]indol-2-yl)-ethyl]-phenyl}-acetamide (70 mg) in 2-propanol (1 ml) and hydrochloric acid (6 M; 1 ml) is heated under reflux for 3.5 h. Afterwards the mixture is concentrated in vacuo and the residual aqueous layer is neutralized with saturated $NaHCO_3$ solution. The desired compound is obtained by an aqueous work-up (47 mg).

Example 57 a) N-(3,3-Dimethyl-6-nitro-2-oxo-1-pentyl-2,3-dihydro-1H-indol-5-yl)-3-phenyl-propionamide (1.17 g) is synthesized from A8 (807 mg) and freshly prepared 3-phenyl-propionyl chloride (0.5 ml; 3,3 mmol) as described in Example 1a.

b) N-(3,3-Dimethyl-6-nitro-2-oxo-1-pentyl-2,3-dihydro-1H-indol-5-yl)-N-methyl-3-phenyl-propionamide To a solution of N-(3,3-dimethyl-6-nitro-2-oxo-1-pentyl-2,3-dihydro-1H-indol-5-yl)-3-phenyl-propionamide (142 mg) in dry N,N-dimethylformamide (6 ml) is added $K_2CO_3$ (163 mg; 1.18 mmol) and methyl iodide (45 µl; 0.72 mmol). The mixture is stirred at 75° C. for 2 days. After an aqueous work-up the compound is obtained.

c) 1,7,7-Trimethyl-5-pentyl-2-phenethyl-5,7-dihydro-1H-imidazo[4,5-f]indol-6-one is prepared from crude N-(3,3-dimethyl-6-nitro-2-oxo-1-pentyl-2,3-dihydro-1H-indol-5-yl)-N-methyl-3-phenyl-propionamide as described in Example 3b. The desired compound (78 mg) is obtained by flash chromatography on silica gel eluting with $CH_2Cl_2$/MeOH (98:2).

Example 58 a) N-(3,3-Dimethyl-6-nitro-2-oxo-1-pentyl-2,3-dihydro-1H-indol-5-yl)-N-ethyl-3-phenyl-propionamide is prepared from N-(3,3-dimethyl-6-nitro-2-oxo-1-pentyl-2,3-dihydro-1H-indol-5-yl)-3-phenyl-propionamide (214 mg) and ethyl iodide (46 µl; 0.57 mmol) as described in Example 57b. The compound (55 mg) is obtained by flash chromatography on silica gel eluting with cyclohexane/EtOAc.

b) 1-Ethyl-7,7-dimethyl-5-pentyl-2-phenethyl-5,7-dihydro-1H-imidazo[4,5-f]indol-6-one (44 mg) is prepared from N-(3,3-dimethyl-6-nitro-2-oxo-1-pentyl-2,3-dihydro-1H-indol-5-yl)-N-ethyl-3-phenyl-propionamide (55 mg) as described in Example 3b.

Example 59

1-Ethyl-7,7-dimethyl-5-pentyl-2-(3-phenyl-propyl)-5,7-dihydro-1H-imidazo[4,5-f]indol-6-one (36 mg) is synthesized from A8 (200 mg), freshly prepared 4-phenyl-butyryl chloride (150 mg; 0.82 mmol) and ethyl iodide (70 µl; 0.87 mmol) as described in Example 57.

Example 60 a) N-[3,3-Dimethyl-1-(3-methyl-butyl)-6-nitro-2-oxo-2,3-dihydro-1H-indol-5-yl]-4-methoxy-benzamide is prepared from A9 (419 mg) and 4-methoxy-benzoyl chloride (491 mg; 2.88 mmol) as described in Example 1a. N-[3,3-dimethyl-1-(3-methyl-butyl)-6-nitro-2-oxo-2,3-dihydro-1H-indol-5-yl]-4-methoxy-benzamide (167 mg) is obtained by flash chromatography on silica gel eluting with $CH_2Cl_2$/MeOH (50:1)

b) 2-(4-Methoxy-phenyl)-7,7-dimethyl-5-(3-methyl-butyl)-5,7-dihydro-1H-imidazo[4,5-f]indol-6-one is prepared from N-[3,3-dimethyl-1-(3-methyl-butyl)-6-nitro-2-oxo-2,3-dihydro-1H-indol-5-yl]-4-methoxy-benzamide (167 mg) as described in Example 1b using Raney-nickel (25 mg). After aqueous work-up 2-(4-methoxy-phenyl)-7,7-dimethyl-5-(3-methyl-butyl)-5,7-dihydro-1H-imidazo[4,5-f]indol-6-one (120 mg) is obtained by flash chromatography on silica gel eluting with light petroleum/EtOAc (1:1).

Example 61 a) N-{[2',3'-Dihydro-6'-nitro-2'-oxo-1'-pentyl-spiro[cyclopropane-1,3'-[1H]indol]-5'yl}-4-methoxy-phenyl benzamide (178 mg) is synthesized from A10 (120 mg) and freshly prepared 4-methoxy-benzoyl chloride (170 mg; 1 mmol) as described in Example 1a.

b) N-{[6'-Amino-2',3'-dihydro-2'-oxo-1'-pentyl-spiro[cyclopropane-1,3'-[1H]indol]-5'yl}-4-methoxy-phenyl benzamide is prepared from the 6'-nitro compound (70 mg) as described in Example 28b using $SnCl_2.H_2O$ (149 mg; 0.66 mmol) in EtOAc (4 ml).

c) 2'-(4"-Methoxy-phenyl)-5'-methyl-5',6'-dihydro-1H-imidazo[4,5-f]-spiro[cyclo-propane-1,7'-indol]-6'-one is prepared from N-{[6'-amino-2',3'-dihydro-2'-oxo-1'-pentyl-spiro[cyclopropane-1,3'-[1H]indol]-5'-yl}-4-methoxy-phenyl benzamide as described in Example 3b. 2'-(4"-Methoxy-phenyl)-5'-methyl-5',6'-dihydro-1H-imidazo[4,5-f]-spiro[cyclo-propane-1,7'-indol]-6'-one (54 mg) is obtained by preparative RP-HPLC eluting with a water/MeCN gradient.

Example 62

2'-((E)-Styryl)-5'-methyl-5',6'-dihydro-1H-imidazo[4,5-f]-spiro[cyclo-propane-1,7'-indol]-6'-one The compound (66 mg; 0.18 mmol) is prepared from A10 (165 mg) as described in Example 61.

Example 63 a) (E)-N-(1-Benzyl-3,3-dimethyl-6-nitro-2-oxo-2,3-dihydro-1H-indol-5-yl)-3-phenyl-acrylamide is synthesized from A11 (93 mg) and freshly prepared (E)-3-phenyl-acryloyl chloride (67 mg; 0.4 mmol) analogously to Example 1a.

b) 5-Benzyl-7,7-dimethyl-2-((E)-styryl)-5,7-dihydro-1H-imidazo[4,5-f]indol-6-one (52 mg) is prepared from (E)-N-(1-benzyl-3,3-dimethyl-6-nitro-2-oxo-2,3-dihydro-1H-indol-5-yl)-3-phenyl-acrylamide as described in Example 3b. Purification is achieved by preparative RP-HPLC.

Examples 64-68 are prepared analogously from the corresponding building block A as described in Example 63.

Example 69 a) N-[3,3-Dimethyl-6-nitro-2-oxo-1-(3-pyridin-3-yl-propyl)-2,3-dihydro-1H-indol-5-yl]-3-phenyl-propionamide is prepared from A17 (319 mg) and freshly prepared 3-phenyl-propionyl chloride (236 mg; 1.4 mmol) as described in Example 1a. By adding hydrochloric acid (1 N) the title compound (367 mg) is precipitated and is collected by filtration.

b) 7,7-Dimethyl-2-phenethyl-5-(3-pyridin-3-yl-propyl)-5,7-dihydro-1H-imidazo[4,5-f]indol-6-one (330 mg) is prepared from N-[3,3-dimethyl-6-nitro-2-oxo-1-(3-pyridin-3-yl-propyl)-2,3-dihydro-1H-indol-5-yl]-3-phenyl-propionamide (367 mg; 0.78 mmol) as described in Example 1b. Purification is achieved by flash chromatography on silica gel eluting with $CH_2Cl_2$/MeOH (15:1).

Example 70 a) N-{1-[2-(2-Methoxy-ethoxy)-ethyl]-3,3-dimethyl-6-nitro-2-oxo-2,3-dihydro-1H-indol-5-yl}-3-phenyl-propionamide is prepared from A18 (621 mg) and freshly prepared 3-phenyl-propionyl chloride (817 mg; 4.85 mmol) as described in Example 1a. The desired compound (290 mg) is obtained by flash chromatography on silica gel eluting with light petroleum/EtOAc (1:1).

b) 5-[2-(2-Methoxy-ethoxy)-ethyl]-7,7-dimethyl-2-phenethyl-5,7-dihydro-1H-imidazo[4,5-f]indol-6-one is prepared from N-{1-[2-(2-methoxy-ethoxy)-ethyl]-3,3-dimethyl-6-nitro-2-oxo-2,3-dihydro-1H-indol-5-yl}-3-phenyl-propionamide (290 mg) as described in Example 1b. After aqueous work-up the desired compound (199 mg) is obtained.

Example 71 a) 5-[3,3-Dimethyl-6-nitro-2-oxo-5-(3-phenyl-propionylamino)-2,3-dihydro-indol-1-yl]-pentanoic acid ethyl ester is prepared from A19 (510 mg) and freshly prepared 3-phenyl-propionyl chloride (817 mg; 4.85 mmol) as described in Example 14a.

b) 5-(7,7-Dimethyl-6-oxo-2-phenethyl-6,7-dihydro-1H-imidazo[4,5-f]indol-5-yl)-pentanoic acid ethyl ester is obtained from 5-[3,3-dimethyl-6-nitro-2-oxo-5-(3-phenyl-propionylamino)-2,3-dihydro-indol-1-yl]-pentanoic acid ethyl ester (510 mg) as described in Example 15b using Pd/C (10%; 60 mg) as catalyst. Flash chromatography on silica gel eluting with $CH_2Cl_2$/MeOH (96:4) gives the desired compound (230 mg).

Example 72 a) N-[1-(4-Imidazol-1-yl-butyl)-3,3-dimethyl-6-nitro-2-oxo-2,3-dihydro-1H-indol-5yl]-4-methoxy-benzamide (1.11 g; 2,32 mmol) is prepared from A20 (1 g) and 4-methoxybenzoyl chloride (512 mg; 3 mmol) as described in Example 1a. Purification is achieved by flash chromatography on silica gel eluting with EtOAc/MeOH (90:10).

b) 5-(4-Imidazol-1-yl-butyl)-2-(4-methoxy-phenyl)-7,7-dimethyl-5,7-dihydro-1H-imidazo[4,5-f]indol-6-one is prepared from N-[1-(4-imidazol-1-yl-butyl)-3,3-dimethyl-6-nitro-2-oxo-2,3-dihydro-1H-indol-5-yl]-4-methoxy-benzamide (1.11 g) as described in Example 1b. Purification by flash chromatography on silica gel eluting with EtOAc/MeOH (85:15) gives the desired compound (654 mg).

Example 73 a). N-(1-Isopropyl-3,3-dimethyl-6-nitro-2-oxo-2,3-dihydro-1H-indol-5-yl)-4-methoxy-benzamide is prepared from A21 (296 mg) and 4-methoxybenzoyl chloride (384 mg; 2.25 mmol) as described in Example 1a. The crude material is purified by flash chromatography on silica gel eluting with $CH_2Cl_2$/MeOH (50:1) to give the compound (427 mg).

b) 5-Isopropyl-2-(4-methoxy-phenyl)-7,7-dimethyl-5,7-dihydro-1H-imidazo[4,5-]indol-6-one is prepared from N-(1-isopropyl-3,3-dimethyl-6-nitro-2-oxo-2,3-dihydro-1H-indol-5-yl)-4-methoxy-benzamide (427 mg) as described in Example 1b using Raney-nickel (70 mg) as catalyst. By pouring the reaction mixture into water the desired compound (358 mg) is precipitated and is collected by filtration.

Example 74 a) N-[3,3-Dimethyl-1-(3-morpholin-4-yl-propyl)-6-nitro-2-oxo-2,3-dihydro-1H-indol-5-yl]-4-methoxy-benzamide is prepared from A22 (665 mg) 4-methoxybenzoyl chloride (376 mg; 2.20 mmol) as described in Example 1a. By adding hydrochloric acid (1 N) the compound (575 mg) is precipitated and is collected by filtration.

b) 2-(4-Methoxy-phenyl)-7,7-dimethyl-5-(3-morpholin-4-yl-propyl)-5,7-dihydro-1H-imidazo[4,5-f]indol-6-one is prepared from N-[3,3-dimethyl-1-(3-morpholin-4-yl-propyl)-6-nitro-2-oxo-2,3-dihydro-1H-indol-5-yl]-4-methoxy-benzamide (575 mg) by hydrogenation at 70° C. as described in Example 1b using Raney-nickel (70 mg). The catalyst is filtered off and the filtrate is heated at 100° C. for 2 h. By adding concentrated ammonia the desired compound (360 mg) precipitates and is collected by filtration.

Example 75 a) (rac)-N-(3-Isopropyl-1-methyl-6-nitro-2-oxo-2,3-dihydro-1H-indol-5-yl)-4-methoxy-benzamide (443 mg; 1.16 mmol) is prepared from A23 (430 mg) and 4-methoxybenzoyl chloride (294 mg; 1.73 mmol) as described Example 14a.

b) (rac)-7-Isopropyl-2-(4-methoxy-phenyl)-5-methyl-5,7-dihydro-1H-imidazo [4,5-f]indol-6-one is prepared from (rac)-N-(3-Isopropyl-1-methyl-6-nitro-2-oxo-2,3-dihydro-1H-indol-5-yl)-4-methoxy-benzamide (443 mg) by hydrogenation at 70° C. as described in Example 1b) using Raney-nickel (70 mg). The catalyst is filtered off and the filtrate heated at 100° C. for 1 h. After a typical aqueous work-up the crude material is purified by flash chromatography on silica gel eluting with light petroleum/EtOAc (3:1) to give the desired compound (311 mg).

Example 76 a) N-(3,3-Diethyl-1-methyl-6-nitro-2-oxo-2,3-dihydro-1H-indol-5-yl)-4-methoxy-benzamide is prepared from A24 (419 mg) and 4-methoxybenzoyl chloride (273 mg; 1.6 mmol) as described in Example 14a. After evaporation of the solvent the residue is re-crystallized from $Et_2O$ to give the compound (260 mg).

b) 7,7-Diethyl-2-(4-methoxy-phenyl)-5-methyl-5,7-dihydro-1H-imidazo[4,5-f]indol-6-one is prepared from N-(3,3-diethyl-1-methyl-6-nitro-2-oxo-2,3-dihydro-1H-indol-5-yl)-4-methoxy-benzamide (250 mg) by hydrogenation at 70° C. as described in Example 1b using Raney nickel (70 mg) as catalyst. The crude material is purified by flash chromatography on silica gel eluted with light petroleum/EtOAc (1:2) to give the compound (95 mg).

Analytical HPLC Methods

Method 1

HPLC: Agilent 1100 Series; MS: 1100 Series LC/MSD Trap (ESI-Mode);

Column: Waters; Part No.186000594; Xterra MS C18 2.5 µm; 2.1×50 mm column

Solvent: A: $H_2O$ demineralised with 0,1% HCOOH;

Solvent B: MeCN HPLC grade

Detection: MS: scan range: 120-1000 m/z; scan resolution: normal (13000 m/z/min); threshold: 120; Trap: ICC; Target: 1000; Max. Accu. Time: 100 ms; Averages: 10

UV: UV 254 nm (bandwide 1, reference off); UV 230 nm (bandwide 1, reference off); peakwidth>0,05 min (1 s); 220-400 nm

| Injection: | 10 µl standard injection, needle wash | | |
|---|---|---|---|
| Separation: | Flow: | 0.6 ml/min | |
| | Column temp.: | 30° C. | |
| | Pump 1 : (binary) | 0.0 min | 10% solvent B |
| | | 0.0-2 min | 10% –> 90% solvent B |
| | | 4.0-4 min | 90% solvent B |
| | | 4.5-6.0 min | 90% –> 10% solvent B |
| | Pump 2 (quarternary): | | 10% solvent B |

Method 2

HPLC: Agilent 1100 Series; MS: 1100 Series LC/MSD Trap (ESI-Mode);

Column: Waters; Part No.186000594; Xterra MS C18 2.5 µm; 2.1×50 mm column

Solvent: A: $H_2O$ demineralised with 0,1% HCOOH;

Solvent B: MeCN HPLC grade

Detection: MS: scan range: 120-1000 m/z; scan resolution: normal (13000 m/z/min);

threshold: 120; Trap: ICC; Target: 1000; Max. Accu. Time: 100 ms; Averages: 10

UV: UV 254 nm (bandwide 1, reference off); UV 230 nm (bandwide 1, reference off); peakwidth>0,05 min (1 s); 220-400 nm

| Injection: | 10 µl standard injection, needle wash | | |
|---|---|---|---|
| Separation: | Flow: | 0.6 ml/min | |
| | Column temp.: | 30° C. | |
| | Pump 1 (binary): | 0.0 min | 5% solvent B |
| | | 0.0-3.5 min | 5% –> 95% solvent B |
| | | 3.5-4.0 min | 95% solvent B |
| | | 4.1-6.0 min | 95% –> 5% solvent B |
| | Pump 2 (quarternary): | | 5% solvent B |

Method 3

HPLC: Agilent 1100 Series; MS: 1100 Series LC/MSD (API-ES(+/−) 3000V, Quadrupol, G1946D); Mode: Scan pos 100-1000, neg 100-1000

Column: Waters; Part No.186000594; Xterra MS C18 2.5 µm; 2.1×50 mm column

Solvent: A: $H_2O$ demineralised with 0.1% HCOOH;

Solvent B: Acetonitril HPLC grade with 0.1% HCOOH

Detection: peakwide>0,1 min (2 s); 190-450 nm; UV 254 nm (bandwide 8, reference off);

UV 230 nm (bandwide 8, reference off)

| Injection: | 3 µl standard injection | | |
|---|---|---|---|
| Separation: | Flow: | 0.6 ml/min | |
| | Column temp.: | 35° C. | |
| | Pump gradient: | 0.0-0.5 min | 5% solvent B |
| | | 0.5-1.5 min | 5% –> 50% solvent B |
| | | 1.5-4.0 min | 50% –> 95% solvent B |
| | | 4.0-6.0 min | 95% solvent B |
| | | 6.0-6.5 min | 95% –> 5% solvent B |

Method 4

MS: Waters Micromass ZQ; pos. ESI, cone Voltage 50 V

HPLC Column: Xterra MS18, 3.5 µm; 4.6×50 mm

Flow: 1 ml/min

Solvent A: water/0.1% TFA

Solvent B: MeCN/0.1% TFA

| Pump gradient: | 0-5.0 min | 5% –> 98% solvent B |
|---|---|---|
| | 5.0-7.5 min | 98% solvent B |
| | 7.5-8.0 min | 98% –> 5% solvent B |

Method 5

MS: Waters Micromass ZQ; pos. ESI, cone Voltage 50 V

HPLC Column: Xterra MS18, 3.5 µm; 4.6×50 mm

Flow: 1 ml/min

Solvent A: water/0.1% HCOOH

Solvent B: MeCN/0.1% HCOOH

| Pump gradient: | 0-5.0 min | 5% –> 98% solvent B |
|---|---|---|
| | 5.0-7.5 min | 98% solvent B |
| | 7.5-8.0 min | 98% –> 5% solvent B |

Method 6

HPLC: Agilent 1100 Series; MS: 1100 Series LC/MSD Trap (ESI-Mode);

Column: Waters; Part No.186000592; Xterra MS C 18 2.5 µm; 2.1×30 mm column

Solvent A: $H_2O$ demineralised with 0.1% HCOOH;

Solvent B: MeCN HPLC grade with 0.1% HCOOH;

Detection: MS: scan range: 120-1000 m/z; scan resolution: normal (13000 m/z/min);

threshold: 120; Trap: ICC; Target: 1000; Max. Accu. Time: 100 ms; Averages: 10

UV: UV 254 nm (bandwide 1, reference off); UV 230 nm (bandwide 1, reference off); peakwidth<0.01 min (1 s); 220-400 nm

| Injection: | 5 μl standard injection, needle wash | |
|---|---|---|
| Separation: | Flow: | 1.10 ml/min |
| | Column temp.: | 40° C. |

-continued

| Pump 1 (binary): | 0.00 min | 5% solvent B |
|---|---|---|
| | 0.00-2.50 min | 5% -> 95% solvent B |
| | 2.50-2.80 min | 95% solvent B |
| | 2.80-2.81 min | 95% -> 5% solvent B |
| | 2.82-3.10 min | 5% solvent B |

Examples 1-76

| # | Structure | HPLC Rt [min] | MS [M + H]+ | NMR |
|---|---|---|---|---|
| 1 | 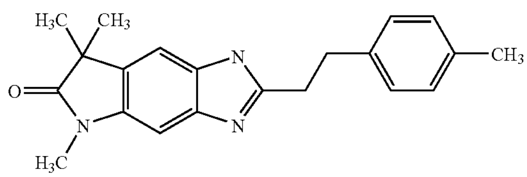 | 3.14 | 334 | (DMSO) d = 1.30 (s, 6H), 2.25 (s, 3H), 3.06 (s, 4H), 3.18 (s, 3H), 6.96/7.11 (2 s, 1H, tautomere), 7.08 (d, 2H), 7.11 (d, 2H), 7.38/7.48 (2 s, 1H, tautomere), 12.12 (br s, NH) |
| 2 | 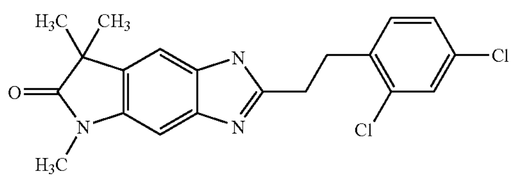 | | 388/90/92 | (DMSO) d = 1.30 (s, 6H), 3.10 (m, 2H), 3.20 (m, 5H), 6.98/7.11 (2 s, 1H, tautomere), 7.35 (m, 2H), 7.38/7.49 (2 s, 1H, tautomere), 7.59 (s, 1H), 12.18 (s, NH) |
| 3 | 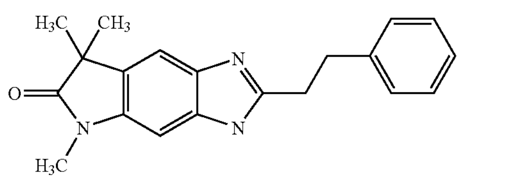 | 2.76 | 320 | (DMSO) d = 1.30 (s, 6H), 3.09 (s, 4H), 3.17 (s, 3H), 6.97-7.09 (2 br s, 1H), 7.15-7.19 (m, 1H), 7.23-7.29 (m, 4H), 7.38-7.46 (2 br s, 1H) |
| 4 | 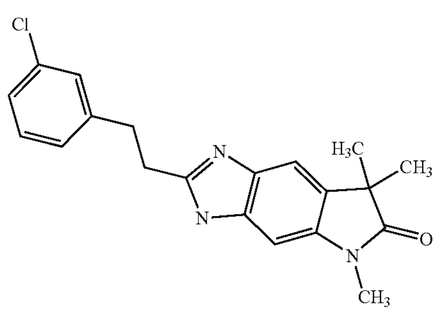 | 2.62 | 354 | (DMSO) d = 1.29 (s, 6H), 3.08-3.11 (m, 2H), 3.17 (s, 3H), 3.19-3.22 (m, 2H), 7.04 (1 br s, 1H), 7.22-7.27 (m, 2H), 7.32-7.38 (m, 1H), 7.41-7.48 (m, 2H) |
| 5 | 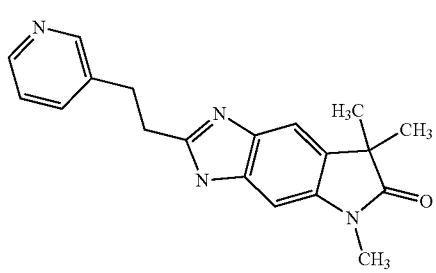 | | 321 | (DMSO) d = 1.29 (s, 6H), 3.12-3.16 (m, 7H), 7.01 (1 brs, 1H), 7.27-7.32 (m, 1H), 7.41 (1 br s, 1H), 7.62-7.67 (m, 1H), 8.36-8.38 (m, 1H), 8.45 (s, 1H) |

| # | Structure | HPLC Rt [min] | MS [M + H]+ | NMR |
|---|---|---|---|---|
| 6 | 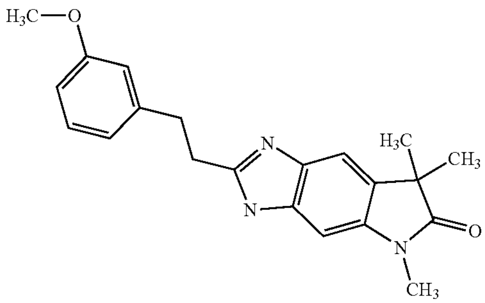 | 2.74 | 350 | (DMSO) d = 1.29 (s, 6H), 3.08 (s, 4H), 3.17 (s, 3H), 3.70 (s, 3H), 6.72-6.76 (m, 1H), 6.80-6.83 (m, 2H), 7.00 (1 br s, 1H), 7.14-7-20 (m, 1H), 7.43 (1 br s, 1H) |
| 7 | 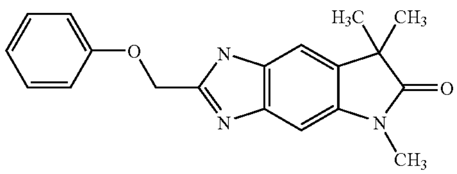 | 2.49 | 322 | (DMSO) d = 1.31 (s, 6H), 3.18 (s, 3H), 5.27 (s, 2H), 6.94-6.99 (m, 1H), 7.00/7.19 (2 br s, 1H, tautomer), 7.06-7.10 (m, 2H), 7.28-7.33 (m, 2H), 7.43/7.58 (2 br s, 1aH, tautomer), 12.62 (br s, 1H) |
| 8 | 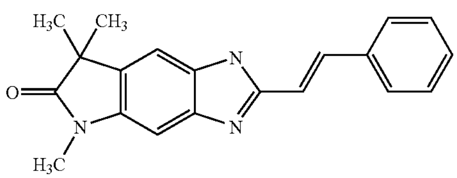 | 2.94 | 318 | (DMSO) d = 1.32 (s, 6H), 3.19-3.21 (m, 3H), 7.02 (s, 0.5H, tautomer), 7.16-7.18 (m, 1H), 7.21 (s, 0.5H, tautomer), 7.32-7.39 (m, 1H), 7.40-7.48 (m, 2H + 0.5H, tautomer), 7.53-7.63 (m, 1H + 0.5H, tautomer), 7.63-7.70 (m, 2H) |
| 9 | 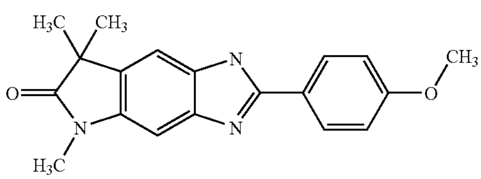 | 2.45 | 322 | |
| 10 | 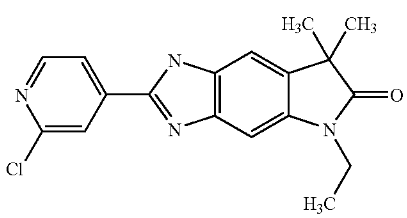 | | 341/343 | |
| 11 | 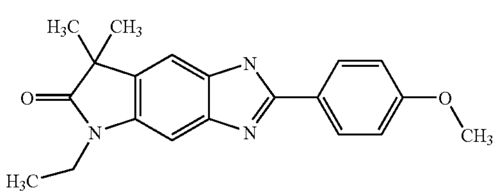 | | 336 | |
| 12 | 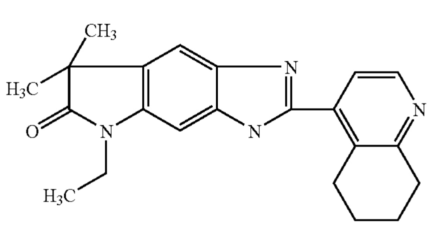 | 2.86 | 361 | (DMSO) d = 1.17-1.24 (m, 3H), 1.35 (s, 6H), 1.80-1.95 (m, 4H), 3.10-3.16 (m, 4H), 3.76-3.86 (m, 214), 7.28 (s, 1H), 7.76 (s, 1H), 8.17-8.19 (m, 114), 8.77-8.80 (m, 1H) |

-continued

| # | Structure | HPLC Rt [min] | MS [M + H]+ | NMR |
|---|---|---|---|---|
| 13 | 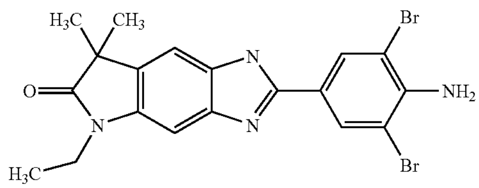 | 3.12 | 479 | (DMSO) d = 1.15-1.22 (m, 3H), 1.27-1.37 (m, 6H), 3.70-3.83 (m, 2H), 5.73-5.76 (m, 2H), 7.02 (s, 0.5H, tautomer), 7.21 (s, 0.5H, tautomer), 7.43 (s, 0.5H, tautomer), 7.57 (s, 0.514, tautomer), 8.15-8.25 (m, 2H), 12.66 (s, 1H) |
| 14 | 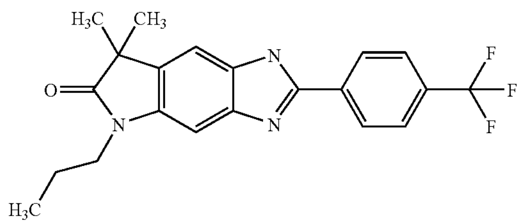 | | 388 | |
| 15 | 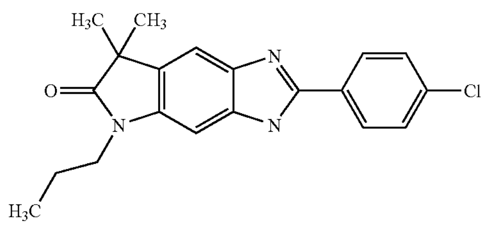 | | 354/356 | |
| 16 | 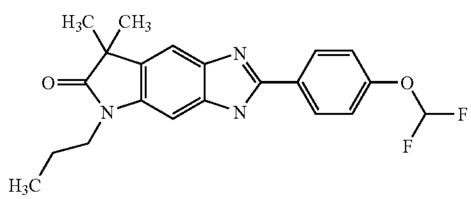 | | 386 | |
| 17 | 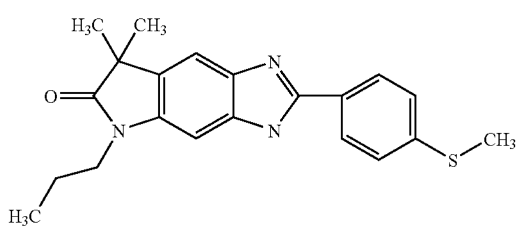 | 3.17 | 366 | (DMSO) d = 0.85-0.93 (m, 3H), 1.33 (s, 6H), 1.62-1.73 (m, 2H), 2.54 (s, 3H), 3.67-3.76 (m, 2H), 7.14(br s, 114), 7.38-7.44 (m, 2H), 7.54 (br s, 1H), 8.03-8.09 (m, 2H), 12.78 (br s, 1H) |
| 18 | 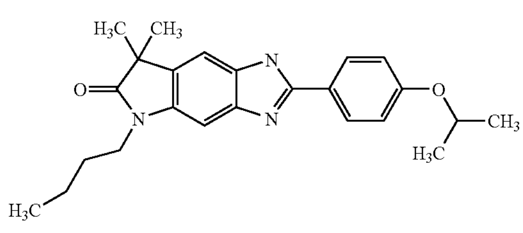 | 3.66 | 392 | (DMSO) d = 0.92 (t, 3H), 1.30 (m, 14H), 1.63 (m, 2H), 3.75 (t, 2H), 4.71 (m, 1H), 7.07 (br d, 3H), 7.51 (br s, 1H), 8.02 (d, 2H), 12.60 (br s, NH) |
| 19 | 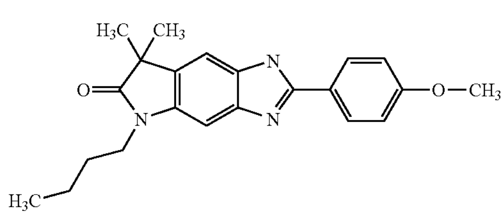 | 3.36 | 364 | (DMSO) d = 0.91 (t, 3H), 1.30 (m, 8H), 1.62 (m, 2H), 3.72 (t, 2H), 3.83 (s, 3H), 7.10 (d, 2H), 7.12 (br s, 1H),7.51 (br s, 1H), 8.09 (d, 1H) |

-continued

| # | Structure | HPLC Rt [min] | MS [M + H]+ | NMR |
|---|---|---|---|---|
| 20 | 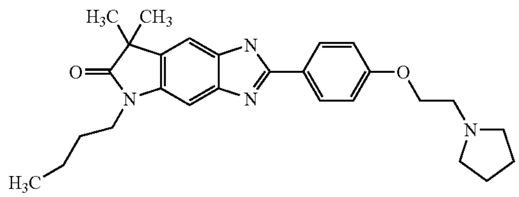 | 2.74 | 447 | (DMSO) d = 0.92 (t, 3H), 1.32 (m, 8H), 1.64 (m, 2H), 1.70 (m, 4H), 2.55 (m, 4H), 2.82 (t, 2H), 3.74 (t, 2H), 4.15 (t, 2H), 7.10 (br d, 3H), 7.51 (br s, 1H), 8.05 (d, 2H), 12.65 (br s, NH) |
| 21 | 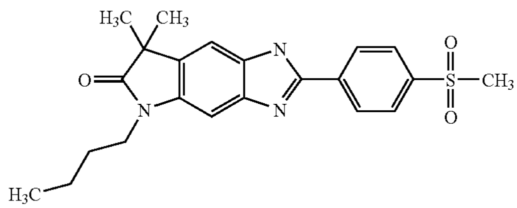 | | 412 | (DMSO) d = 0.92 (t, 3H), 1.33 (m, 8H), 1.65 (m, 2H), 3.29 (s, 3H), 3.78 (t, 2H), 7.19 (br s, 1H), 7.62 (br s, 1H), 8.09 (d, 2H), 8.38 (d, 2H) |
| 22 | 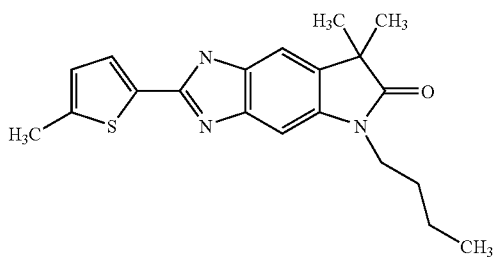 | 3.63 | 354 | (DMSO) d = 0.91 (t, 3H), 1.30 (m, 8H), 1.62 (m, 2H), 3.72 (t, 2H), 6.90 (d, 1H), 7.09 (br s, 1H), 7.50 (br s, 1H), 7.55 (d, 1H), 12.72 (br s, NH) |
| 23 | 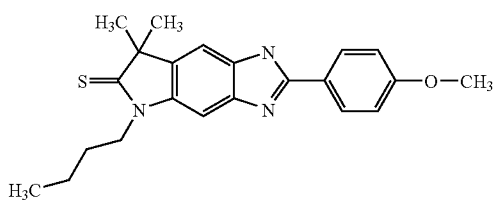 | | 380 | (DMSO) d = 0.95 (t, 3H), 1.40 (m, 4H), 1.45 (s, 6H), 1.72 (m, 2H), 3.90 (s, 3H), 4.35 (t, 2H), 7.29 (d, 2H), 7.59 (s, 1H), 7.90 (s, 1H), 8.30 (d, 2H) |
| 24 | 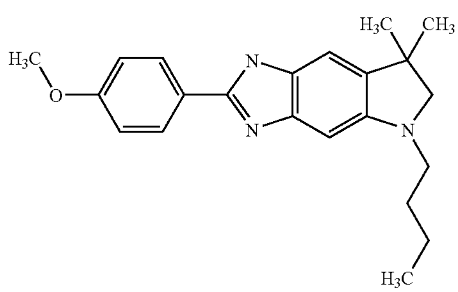 | 3.83 | 350 | (DMSO) d = 0.96 (t, 3H), 1.30 (s, 6H), 1.40 (m, 4H), 1.59 (m, 2H), 3.09 (m, 4H), 3.81 (s, 3H), 6.41/6.60(2 br s, 1H, tautomere), 6.89/7.20 (2 br s, 1H, tautomere), 7.06 (d, 2H), 7.99 (m, 2H), 12.20/12.28 (2 br s, NH, tautomere) |
| 25 | 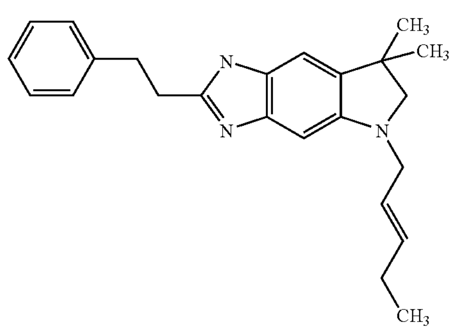 | 3.46 | 374 | (DMSO) d = 0.91 (t, 3H), 1.30 (s, 6H), 2.00 (m, 2H), 3.09 (s, 4H), 4.29 (d, 2H), 5.44 (m, 1H), 5.71 (m, 1H), 6.95 (br s, 1H), 7.19 (m, 1H), 7.28 (m, 4H), 7.45 (br s, 1H), 12.11 (br s, NH) |

-continued

| # | Structure | HPLC Rt [min] | MS [M + H]+ | NMR |
|---|---|---|---|---|
| 26 | 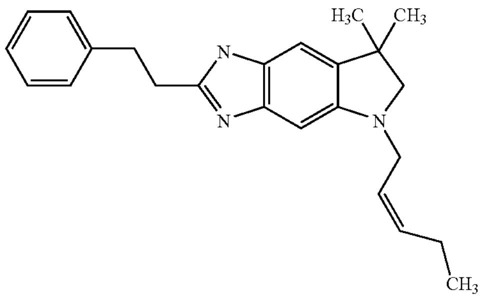 | 3.54 | 374 | (DMSO) d = 1.01 (t, 3H), 1.30 (s, 6H), 2.27 (m, 2H), 3.09 (s, 4H), 4.37 (d, 2H), 5.33 (m, 1H), 5.60 (m, 1H), 6.93 (br s, 1H), 7.19 (m, 1H), 7.28 (m, 4H), 7.45 (br s, 1H), 12.05 (br s, NH) |
| 27 | 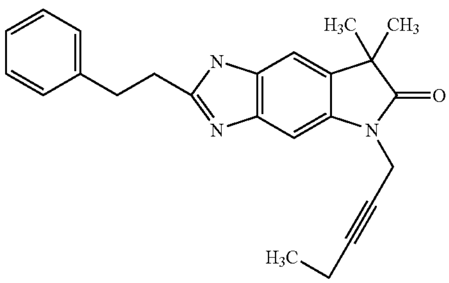 | 2.69 | 372 | (DMSO) d = 0.99-1.05 (m, 3H), 1.29 (s, 6H), 2.10-2.19 (m, 2H), 3.09 (s, 4H), 4.52 (s, 2H), 7.01-7.33 (m, 6H), 7.41/7.50 (2 br s, 1H), 12.18 (s, 1H) |
| 28 | 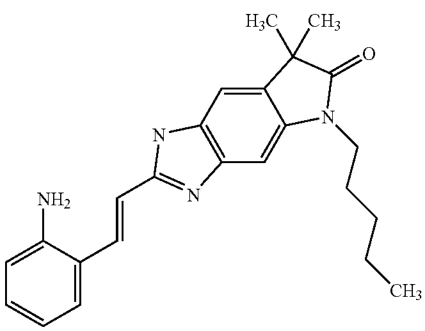 | 2.66 | 389 | (DMSO) d = 0.77-0.91 (m, 3H), 1.10-1.42 (m, 10H), 1.56-1.71 (m, 2H), 3.75-3.85 (m, 2H), 6.63-6.73 (m, 1H), 6.77-6.84 (m, 1H), 6.99-7.08 (m, 1H), 7.15-7.22 (m, 1H), 7.78 (s, 1H), 7.52-7.59 (m, 1H), 7.78 (s, 1H), 8.62-8.72 (m, 1H) |
| 29 | 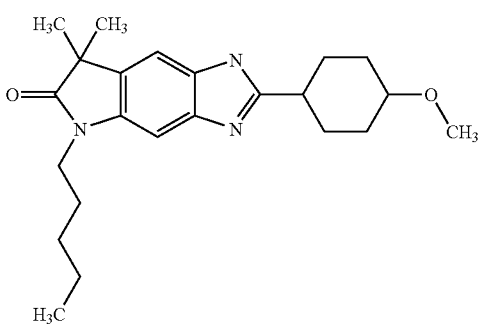 | 3.29 | 384 | (DMSO) d = 0.85 (t, 3H), 1.29 (m, 12H), 1.60 (m, 4H), 1.72 (m, 1H), 1.90 (m, 2H), 2.10 (m, 2H), 2.78/2.88 (2 m, 1H, tautomere), 3.25/3.28 (2 s, 3H, tautomere), 3.70 (m, 2H), 6.94/7.34 (2 br d, 1H, tautomere), 7.12/7.49 (2 br s, 1H, tautomere), 12.03/12.07 (2 br s, NH, tautomere) |
| 30 | 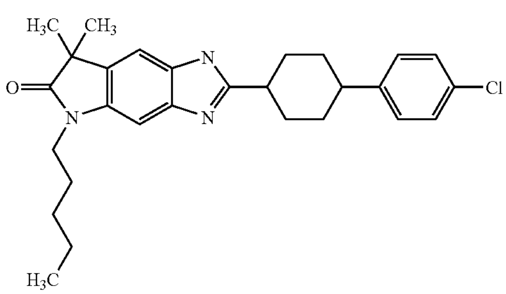 | 4.06 | 464/466 | (DMSO) d = 0.85 (t, 3H), 1.29 (m, 10H), 1.61 (m, 4H), 1.74 (m, 2H), 1.92 (m, 2H), 2.15 (m, 2H), 2.62 (m, 1H), 2.89 (m, 1H), 3.70 (m, 2H), 6.98/7.15 (2 br s, 1H, tautomere), 7.10-7.51 (m, 5H), 12.10/12.12 (2 br s, NH) |

-continued

| # | Structure | HPLC Rt [min] | MS [M + H]+ | NMR |
|---|---|---|---|---|
| 31 | 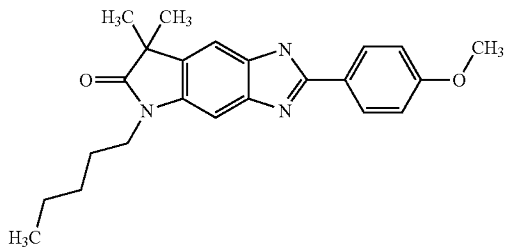 | 3.54 | 378 | (DMSO) d = 0.86 (t, 3H), 1.30(m, 10H), 1.66 (m, 2H), 3.72 (m, 2H), 3.83 (s, 3H), 7.01/7.22 (2s, 1H, tautomere), 7.10 (d, 2H), 7.43/7.60 (2s, 1H, tautomere), 8.08 (m, 2H), 12.69 (br s, NH) |
| 32 | 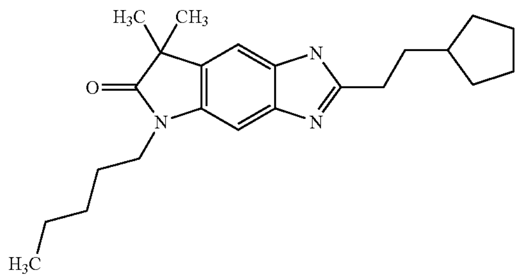 | 3.64 | 368 | (DMSO) d = 0.85 (t, 3H), 1.05-1.81 (m, 23H), 2.79 (m, 2H), 3.70 (br s, 2H), 6.96/7.10 (2 br s, 1H, tautomere), 7.35/7.46 (2 br s, 1H, tautomere), 12.01/12.08 (2 br s, NH, tautomere) |
| 33 | 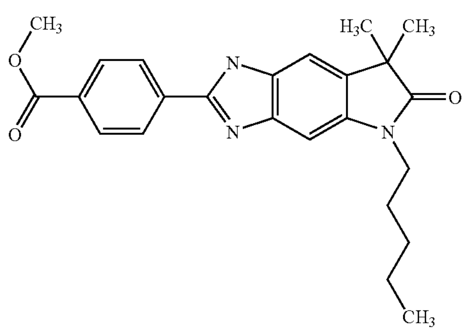 | 4.23 | 406 | (DMSO) d = 0.87 (t, 3H), 1.31 (m, 10H), 1.68 (m, 2H), 3.75 (t, 2H), 3.90 (s, 3H), 7.17 (br s, 1H), 7.61 (br s, 1H), 8.11 (d, 2H), 8.28 (d, 2H), 13.05 (br s, NH) |
| 34 | 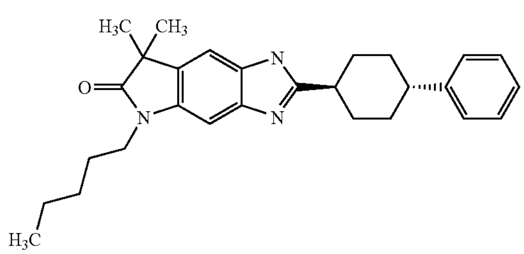 | 3.81 | 430 | (DMSO) d = 0.85 (t, 3H), 1.29 (m, 10H), 1.63 (m, 4H), 1.77 (br q, 2H), 1.96 (br d, 2H), 2.18 (brd, 2H), 2.61 (m, 1H), 2.90 (m, 1H), 6.98/7.15 (2 br s, 1H, tautomere), 7.20 (m, 1H), 7.30 (m, 4H), 7.38/7.50 (2 br s, 1H, tautomere), 12.04/12.08 (2 br s, NH, tautomere) |
| 35 | 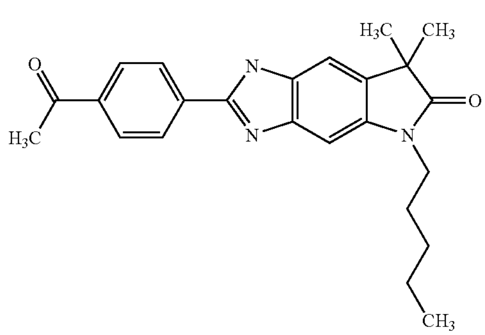 | 3.89 | 390 | (DMSO) d = 0.87 (t, 3H), 1.32 (m, 10H), 1.68 (m, 2H), 2.63 (s, 3H), 3.76 (t, 2H), 7.18 (br s, 1H), 7.61 (br s, 1H), 8.11 (d, 2H), 8.28 (d, 2H), 13.03 (br s, NH) |

-continued

| # | Structure | HPLC Rt [min] | MS [M + H]+ | NMR |
|---|---|---|---|---|
| 36 | 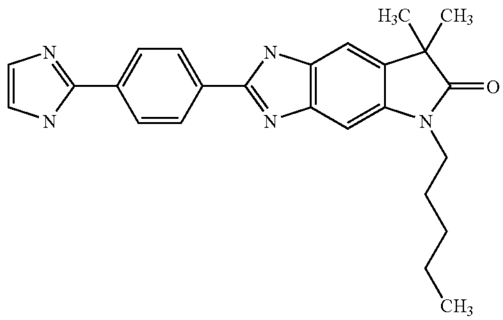 | 3.09 | 414 | (DMSO) d = 0.86 (t, 3H), 1.30 (m, 10H), 1.67 (m, 2H), 3.75 (m, 2H), 7.00-7.40 (m, 3H), 7.47-7.70 (m, 1H), 8.09 (d, 2H), 8.19 (d, 2H), 12.63 (br s, NH), 12.88 (br s, NH) |
| 37 | 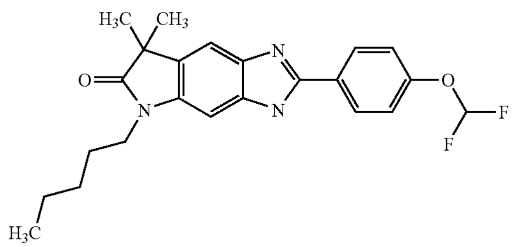 | 4.03 | 414 | (DMSO) d = 0.85 (t, 3H), 1.30 (m, 10H), 1.65 (m, 2H), 3.73 (t, 2H), 7.00-7.69 (m, 3H), 7.35 (d, 2H), 8.16 (d, 2H), 12.84 (br s, NH) |
| 38 | 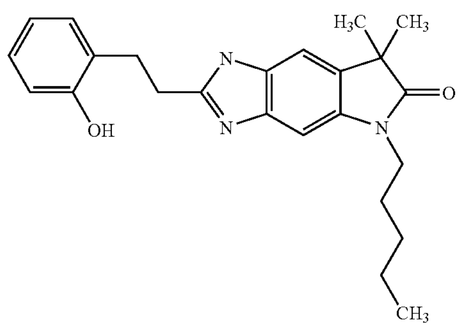 | 2.83 | 392 | (DMSO) d = 0.83-0.86 (m, 3H), 1.25-1.33 (m, 10H), 1.58-1.65 (m, 2H), 3.01-3.08 (m, 4H), 3.68-3.73 (m, 2H), 6.68-6.72 (m, 1H), 6.78-6.80 (m, 1H), 6.98-7.12 (m, 3H), 7.44 (s, 1H) |
| 39 | 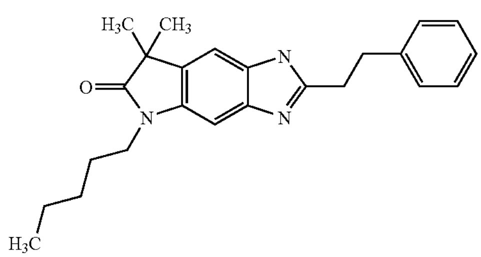 | 2.84 | 375 | (DMSO) d = 0.78-0.88 (m, 3H), 1.25-1.33 (m, 10H), 1.58-1.67 (m, 2H), 3.00-3.15 (m, 4H), 3.60-3.75 (m, 2H), 7.04 (br s, 1H), 7.13-7.20 (m, 1H), 7.22-7.32 (m, 4H), 7.42 (br s, 1H), |
| 40 | 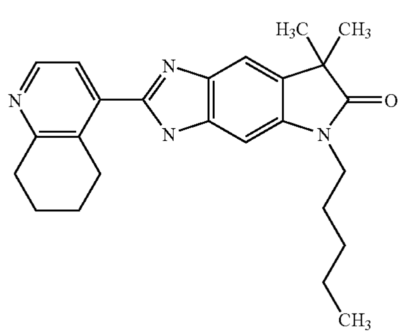 | 2.86 | 403 | (DMSO) d = 0.83-0.88 (m, 3H), 1.27-1.36 (m, 10H), 1.61-1.69 (m, 2H), 1.73-1.80 (m, 2H), 1.84-1.89 (m, 2H), 2.91-2.97 (m, 2H), 3.14-3.18 (m, 2H), 3.73-3.79 (m, 2H), 7.09/7.34 (2br s, 1H), 7.50/7.72 (2br s, 1H), 7.50-7.54 (m, 1H), 8.44-8.49 (m, 1H), 12.80 (br, 1H). |

-continued

| # | Structure | HPLC Rt [min] | MS [M + H]+ | NMR |
|---|---|---|---|---|
| 41 | 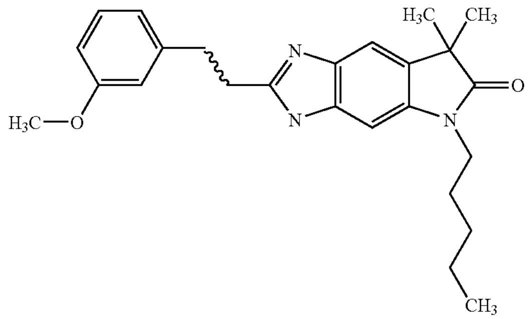 | 2.91 | 404 | |
| 42 | 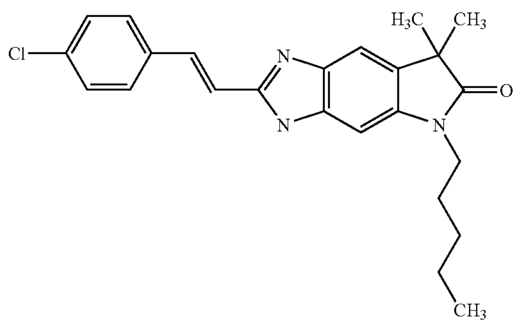 | 2.84 | 408 | |
| 43 | 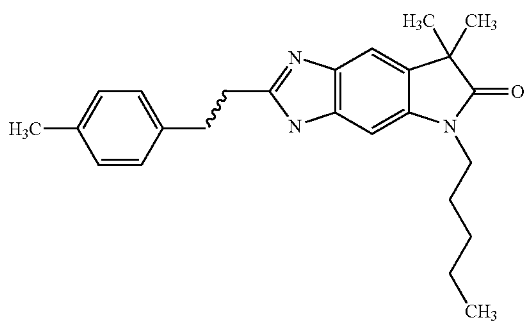 | 2.81 | 388 | |
| 44 | 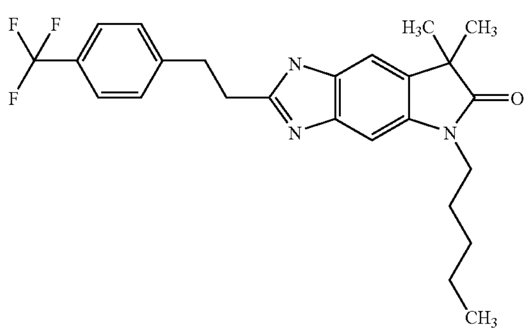 | 2.94 | 444/445 | (DMSO) d = 0.81-0.88 (m, 3H), 1.25-1.35 (m, 10H), 1.56-1.66 (m, 2H), 3.10-3.24 (m, 4H), 3.67-3.74 (m, 2H), 7.00 (br s, 0.5H, tautomer), 7.13 (br s, 0.5H, tautomer), 7.40 (br s, 0.5H, tautomer), 7.46-7.53 (m, 2H + 0.5H tautomer), 7.61-7.68 (m, 2H), 12.11-12.23 (m, 1H) |

-continued

| # | Structure | HPLC Rt [min] | MS [M + H]+ | NMR |
|---|---|---|---|---|
| 45 | 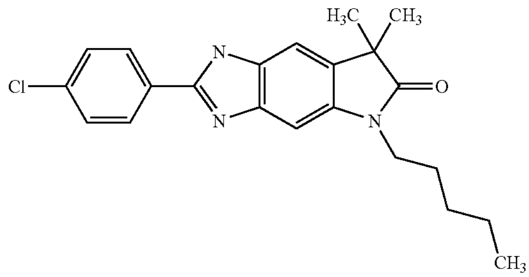 | 3.14 | 382 | (DMSO) d = 0.84-0.89 (m, 3H), 1.27-1.35 (m, 10H), 1.62-1.69 (m, 2H), 3.70-3.77 (m, 2H), 7.05/7.27 (2s, 1H), 7.49/7.65 (2s, 1H) 7.59-7.62 (m, 2H), 8.15 (m, 2H), 12.90 (br, 1H). |
| 46 | 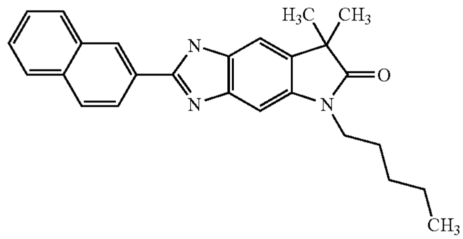 | 3.09 | 398 | (DMSO) d = 0.83-0.90 (m, 3H), 1.28-1.38 (m, 10H), 1.65-1.71 (m, 2H), 3.73-3.79 (m, 2H), 7.60-7.67 (m, 3H), 7.99-8.16 (m, 3H), 8.27-8.30 (m, 1H), 8.60 (s, 1H), 8.68 (s, 1H). |
| 47 | 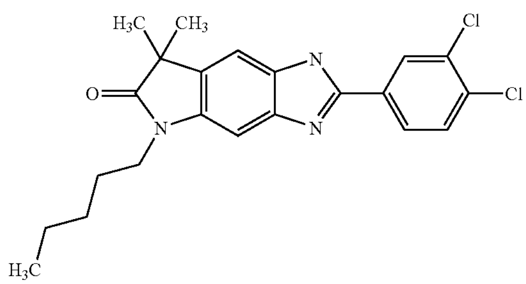 | 3.35 | 416/418 | (DMSO) d = 0.83-0.89 (m, 3H), 1.33 (br s, 10H), 1.63-1.69 (m, 2H), 3.71-3.78 (m, 2H), 7.10/7.30 (2br s, 1H), 7.53/7.69 (2br s, 1H), 7.60-7.62 (m, 1H), 7.81 (s, 1H), 7.90-7.93 (m, 1H), 12.64-12.75 (m, 1H). |
| 48 | 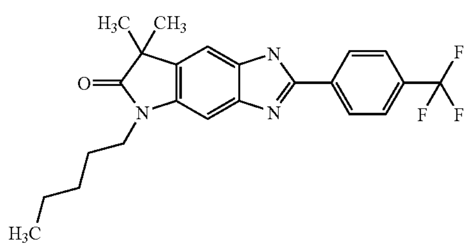 | 3.35 | 416/417 | (DMSO) d = 0.83-0.87 (m, 3H), 1.29-1.36 (m, 10H), 1.64-1.69 (m, 2H), 3.73-3.79 (m, 2H), 7.06/7.32 (2s, 1H), 7.57/7.70 (2s, 1H), 7.90-7.93 (m, 2H), 8.32-8.37 (m, 2H), 13.08-13.13 (m, 1H). |
| 49 | 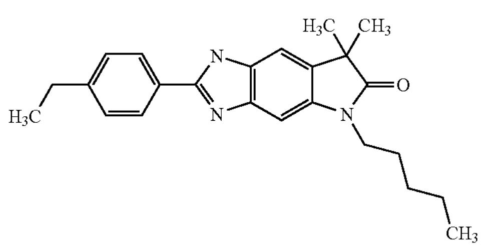 | 2.99 | 376 | (DMSO) d = 0.83-0.88 (m, 3H), 1.20-1.32 (m, 13H), 1.62-1.69 (m, 2H), 2.65-2.71 (m, 2H), 3.71-3.77 (m, 2H), 7.05/7.25 (2br s, 1H), 7.49/7.60 (2br s, 1H), 7.36-7.48 (m, 2H), 8.03-8.06 (m, 2H). |

-continued

| # | Structure | HPLC Rt [min] | MS [M + H]+ | NMR |
|---|---|---|---|---|
| 50 | 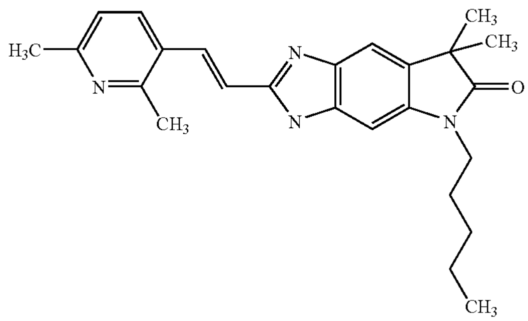 | 2.57 | 403 | (DMSO) d = 0.80-0.90 (m, 3H), 1.21-1.38 (m, 10H), 1.59-1.69 (m, 2H), 2.45 (s, 3H), 2.61 (s, 3H), 3.70-3.78 (m, 2H), 7.00-7.19 (m, 3H), 7.44-7.61 (br s, 1H), 7.69-7.79 (m, 1H), 7.99-8.04 (m, 1H) |
| 51 | 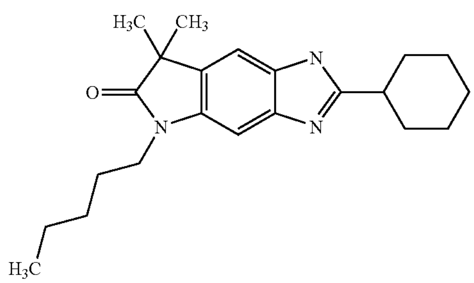 | 2.86 | 354 | (DMSO) d = 0.83-0.87 (m, 3H), 1.23-1.46 (m, 14H), 1.57-1.75 (m, 4H), 1.79-1.83 (m, 2H), 2.01-2.04 (m, 2H), 2.90-2.96 (m, 1H), 3.71-3.76 (m, 2H), 7.14 (s, 1H), 7.56 (s, 1H). |
| 52 | 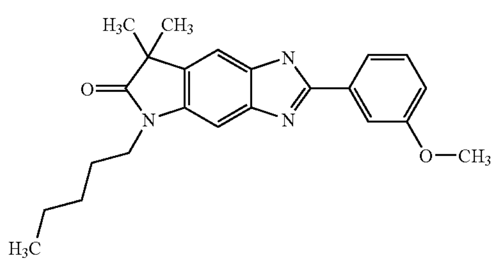 | 2.99 | 378 | (DMSO) d = 0.83-0.87 (m, 3H), 1.32 (br s, 10H), 1.61-1.69 (m, 2H), 3.70.3.77 (m, 2H), 3.86 (s, 3H), 7.03 (br s, 2H), 7.42-7.47 (m, 2H), 7.69-7.73 (m, 2H), 12.78-12.80 (m, 1H). |
| 53 | 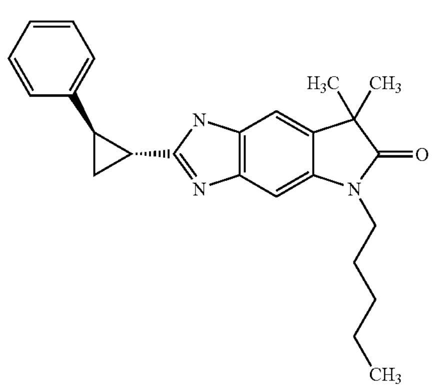 | 2.91 | 388 | (DMSO) d = 0.81-0.86 (m, 3H), 1.24-1.33 (m, 10H), 1.56-1.64 (m, 3H), 1.73-1.78 (m, 1H), 2.31-2.36 (m, 1H), 2.42-2.48 (m, 1H), 3.68-3.72 (m, 2H), 7.04 (br s, 1H), 7.18-7.23 (m, 3H), 7.29-7.33 (m, 2H), 7.41 (br s, 1H), 12.23 (br s, 1H), |

| # | Structure | HPLC Rt [min] | MS [M + H]+ | NMR |
|---|---|---|---|---|
| 54 | 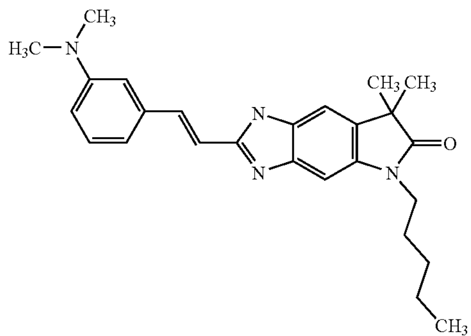 | 2.84 | 417 | (DMSO) d = 0.80-0.89 (m, 3H), 1.22-1.37 (m, 10H), 1.59-1.69 (m, 2H), 2.96 (s, 6H), 3.69-3.77 (m, 2H), 6.70-6.76 (m, 1H), 6.90-6.97 (m, 2H), 6.99-7.12 (br s, 1H), 7.11-7.17 (m, 1H), 7.20-7.26 (m, 1H), 7.45-7.57 (m, 2H). |
| 55 | 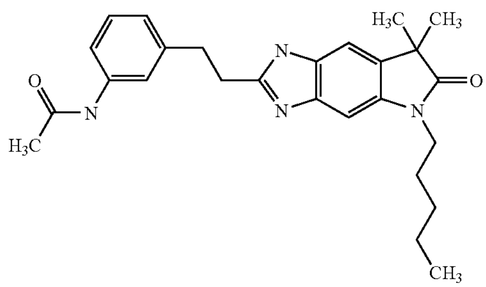 | 2.74 | 433 | (DMSO) d = 0.83-0.86 (m, 3H), 1.25-1.33 (m, 10H), 1.58-1.66 (m, 2H), 2.03 (s, 3H), 3.03-3.07 (m, 4H), 3.67-3.73 (m, 2H), 6.90-6.94 (m, 1H), 6.98/7.12 (2 br s, 1H, tautomer), 7.16-7.21 (m, 1H), 7.37-7.41 (m, 1H + 0.5H tautomer), 7.48 (br s, 0.5H, tautomer), 7.52 (s, 1H), 9.85 (s, 1H), 12.10-12.19 (m, 1H) |
| 56 | 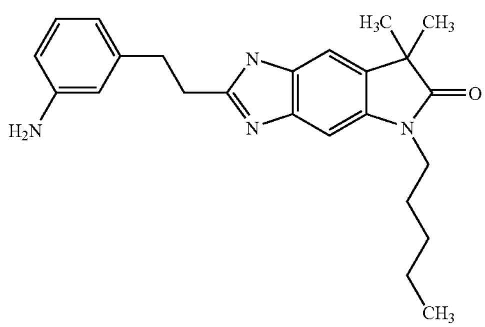 | 2.63 | 391 | (DMSO) d = 0.82-0.87 (m, 3H), 1.25-1.34 (m, 10H), 1.58-1.67 (m, 2H), 2.89-2.94 (m, 2H), 2.99-3.04 (m, 2H), 3.68-3.72 (m, 2H), 4.94 (s, 2H), 6.37-6.41 (m, 2H), 6.46 (s, 1H), 6.89-6.93 (m, 1H), 6.98/7.12 (2 br s, 1H, tautomer), 7.37/7.47 (2 br s, 1H, tautomer) |
| 57 | 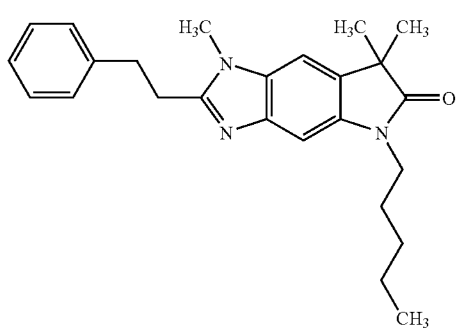 | 2.91 | 390 | (DMSO) d = 0.82-0.87 (m, 3H), 1.27-1.33 (m, 10H), 1.59-1.68 (m, 2H), 3.09-3.15 (m, 4H), 3.65-3.66 (m, 3H), 3.68-3.73 (m, 2 H), 7.16 (s, 1H), 7.18-7.23 (m, 1H), 7.27-7.31 (m, 4H), 7.51 (s, 1H) |

-continued
| # | Structure | HPLC Rt [min] | MS [M + H]+ | NMR |
|---|---|---|---|---|
| 58 | 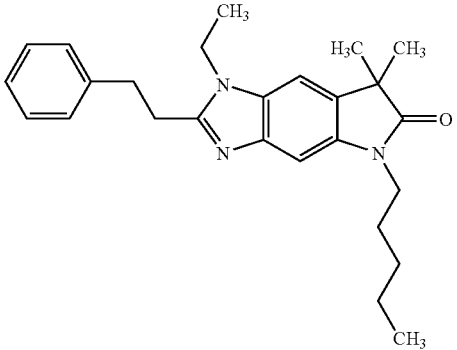 | 2.92 | 404 | (DMSO) d = 0.82-0.87 (m, 3H), 1.18-1.25 (m, 3H), 1.25-1.34 (m, 10H), 1.60-1.67 (m, 2H), 3.13-3.15 (m, 4H), 3.67-3.73 (m, 2H), 4.12-4.20 (m, 2H), 7.17 (s, 1H), 7.18-7.23 (m, 1H), 7.26-7.32 (m, 4H), 7.54 (s, 1H) |
| 59 | 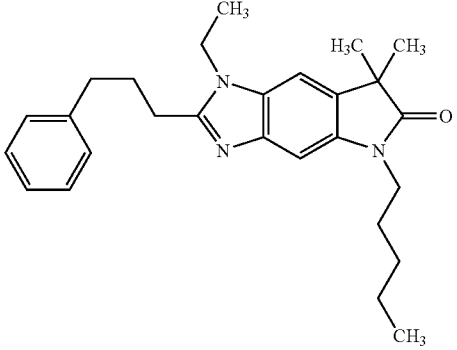 | 2.96 | 418 | (DMSO) d = 0.82-0.86 (m, 3H), 1.24-1.32 (m, 13H), 1.59-1.66 (m, 2H), 2.05-2.12 (m, 2H), 2.70-2.76 (m, 2H), 2.81-2.86 (m, 2H), 3.68-3.73 (m, 2H), 4.14-4.20 (m, 2H), 7.15-7.32 (m, 6H), 7.54 (s, 1H) |
| 60 | 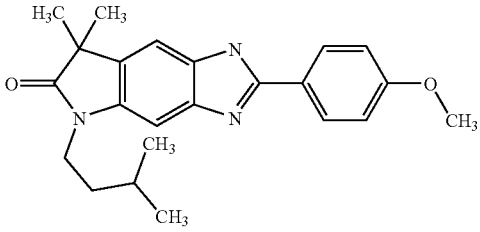 | 3.66 | 378 | (DMSO) d = 0.96 (s, 6H), 1.32 (s, 6H), 1.54 (m, 2H), 1.60 (m, 1H), 3.75 (t, 2H), 3.85 (s, 3H), 7.00/7.20 (2 br s, 1H, tautomere), 7.10 (d, 2H), 7.44/7.60 (2 br s, 1H, tautomere), 8.07 (m, 2H), 12.68 (br s, NH) |
| 61 | 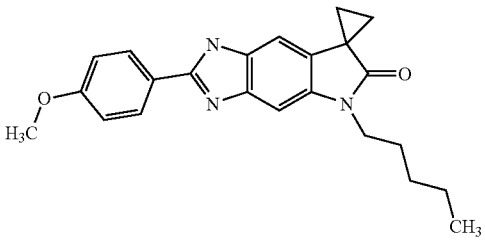 | 2.8 | 376 | (DMSO) d = 0.80-0.90 (m, 3H), 1.26-1.38 (m, 4H), 1.48-1.71 (m, 6H), 3.75-3.86 (m, 5H), 7.01-7.37 (m, 4H), 8.01-8.10 (m, 2H) |
| 62 | 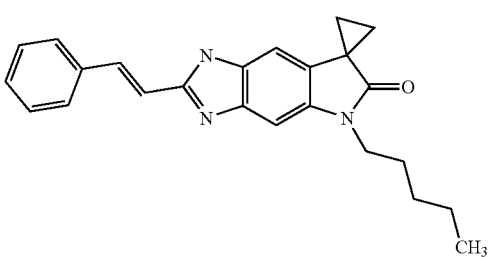 | 2.84 | 372 | (DMSO) d = 0.80-0.92 (m, 3H), 1.26-1.39 (m, 4H), 1.46-1.71 (m, 6H), 3.75-3.86 (m, 2H), 6.99-7.30 (m, 3H), 7.32-7.40 (m, 1H), 7.40-7.47 (m, 2H), 7.55/7.59 (2 br s, 1H), 7.61-7.67 (m, 2H) |

| # | Structure | HPLC Rt [min] | MS [M + H]+ | NMR |
|---|---|---|---|---|
| 63 | 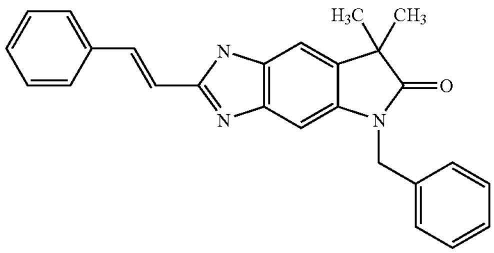 | 2.89 | 394 | (DMSO) d = 1.40 (s, 6H), 4.98 (s, 2H), 6.75-7.18 (m, 2H), 7.19-7.38 (m, 6H), 7.38-7.44 (m, 2H), 7.44-7.67 (m, 4H), 12.38-12.67 (m, 1H) |
| 64 | 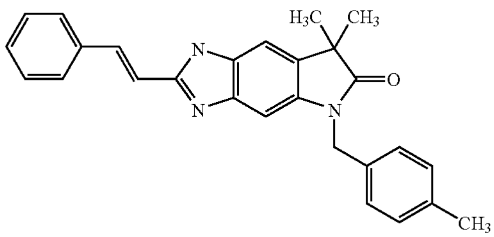 | 2.92 | 408 | (DMSO) d = 1.38 (s, 6H), 2.25 (s, 3H), 4.92 (s, 2H), 6.64-7.27 (m, 7H), 7.28-7.37 (m, 1H), 7.37-7.70 (m, 5H), 11.90-12.80 (m, 1H) |
| 65 | 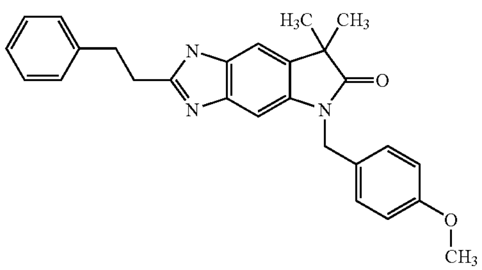 | 2.7 | 426 | (DMSO) d = 1.35 (s, 6H), 3.04 (s, 4H), 3.70 (s, 3H), 4.86 (s, 2H), 6.77-7.03 (m, 3H), 7.12-7.19 (m, 1H), 7.19-7.30 (m, 6H), 7.31-7.53 (2br s,1H), 11.96-12.20 (m, 1H) |
| 66 | 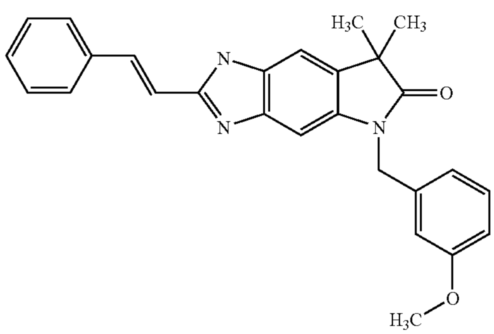 | 2.89 | 424 | (DMSO) d = 1.27-1.46 (m, 6H), 3.67-3.73 (m, 3H), 4.60-5.00 (m, 2H), 6.65-7.70 (m, 13H), 11.85-12.65 (m, 1H) |
| 67 | 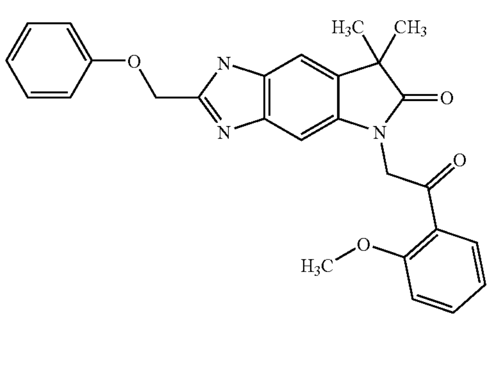 | 2.84 | 456 | (CDCl3) d = 1.42 (s, 6H), 3.86 (s, 3H), 5.10 (s, 2H), 5.24 (s, 2H), 6.78 (br s, 1H), 6.66-7.00 (m, 5H), 7.14-7.22 (m, 2H), 7.40 (br s, 1H), 7.44-7.48 (m, 1H), 7.72-7.78 (m ,1H) |

-continued
| # | Structure | HPLC Rt [min] | MS [M + H]+ | NMR |
|---|---|---|---|---|
| 68 | 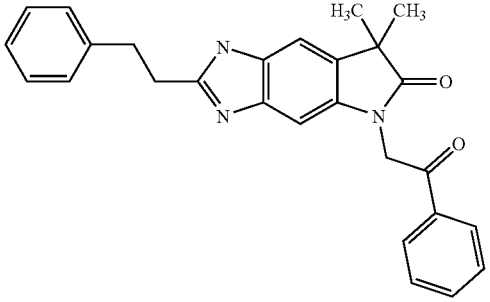 | 2.64 | 424 | (CDCl3) d = 1.34-1.43 (s, 6H), 3.01-3.15 (m, 4H), 5.09 (s, 2H), 6.79 (s, 1H), 6.98-7.05 (m, 2H), 7.06-7.18 (m, 3H), 7.30-7.41 (m, 3H), 7.47-7.56 (m ,1H), 7.84-7.91 (m, 2H) |
| 69 | 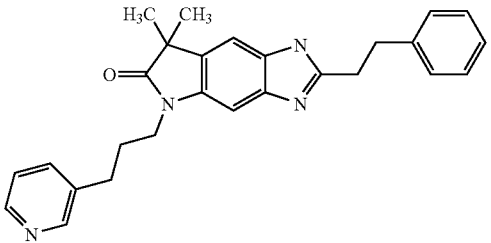 | 2.66 | 425 | (DMSO) d = 1.30 (s, 6H), 1.93 (m, 2H), 2.65 (t, 2H), 3.10 (s, 4H), 3.77 (t, 2H), 7.08 (br s, 1H), 7.19 (m, 1H), 7.22-7.31 (m, 5H), 7.45 (br s, 1H), 7.66 (d, 1H), 8.40 (m, 11-1), 8.45 (br s, 1H), 12.13 (br s, NH) |
| 70 | 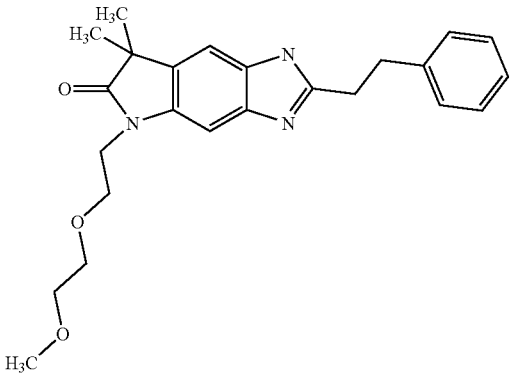 | | 408 | |
| 71 | 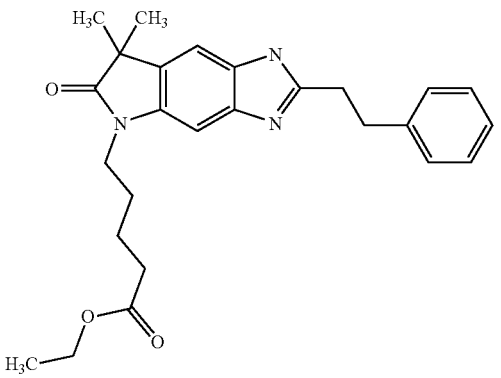 | 3.33 | 434 | (DMSO) d = 1.13 (t, 3H), 1.30 (s, 6H), 1.53 (m, 2H), 1.65 (m, 2H), 2.32 (t, 2H), 3.09 (s, 4H), 3.72 (m, 2H), 4.01 (q, 2H), 6.99/7.14 (2 br s, 1H, tautomere), 7.15-7.30 (m, 5H), 7.3 8/7.48 (2 br s, 1H, tautomere), 12.10/12.12(2 br s, NH, tautomere) |

-continued

| # | Structure | HPLC Rt [min] | MS [M + H]+ | NMR |
|---|---|---|---|---|
| 72 | 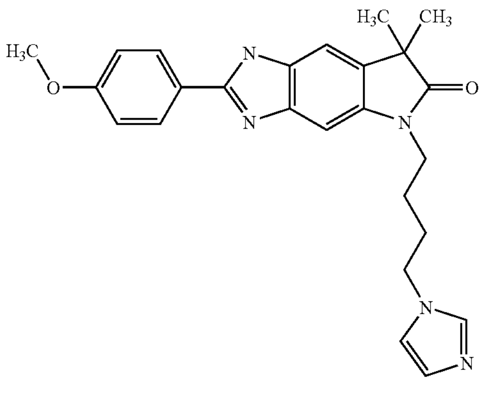 | 2.66 | 430 | (DMSO) d = 1.31 (s, 6H), 1.60 (m, 2H), 1.72 (m, 2H), 3.78 (m, 2H), 3.84 (s, 3H), 4.01 (m, 2H), 6.87 (s, 1H), 7.00/7.27 (2 s, 1H, tautomere), 7.10 (d, 2H), 7.13 (s, 1H), 7.42/7.60 (2 s, 1H, tautomere), 7.60 (s, 1H), 8.08 (m, 2H), 12.65 (s, NH) |
| 73 | 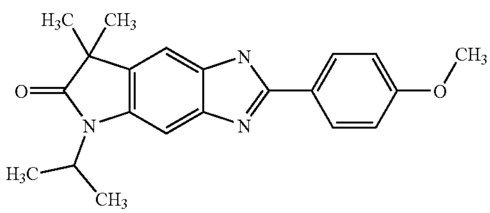 | | 350 | |
| 74 | 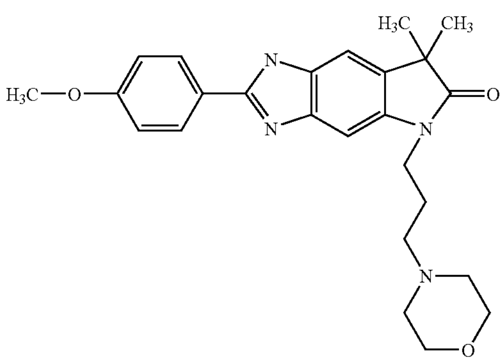 | 2.61 | 435 | (DMSO) d = 1.31 (s, 6H), 1.80 (m, 2H), 2.31 (m, 6H), 3.59 (m, 4H), 3.78 (m, 2H), 3.82 (s, 3H), 7.06/7.28 (2 br s, 1H, tautomere), 7.10 (d, 2H), 7.42/7.59 (2 br s, 1H, tautomere), 8.07 (d, 2H), 12.62 (br s, NH) |
| 75 | 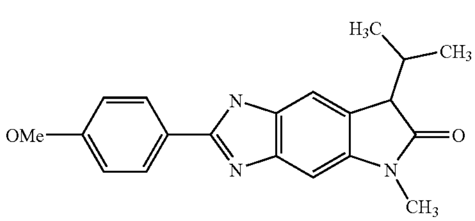 | | 336 | |
| 76 | 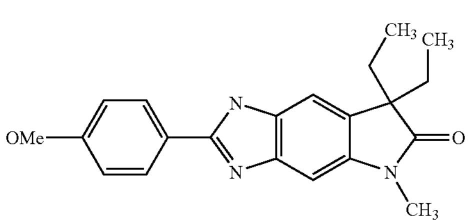 | | 350 | |

Synthesis of Building Blocks B (B1) 5-Amino-3,3-dimethyl-6-methylamino-1,3-dihydro-indol-2-one

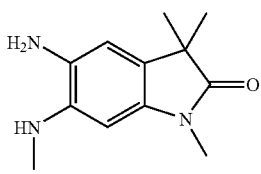

The synthesis of 5-amino-3,3-dimethyl-6-methylamino-1,3-dihydro-indol-2-one, starting from 3,3-dimethyl-6-nitro-1,3-dihydro-indol-2-one, is described in J. Med. Chem. 1989, 32, 1481-1491.

(B2) 6-Amino-3,3-dimethyl-5-methylamino-1,3-dihydro-indol-2-one

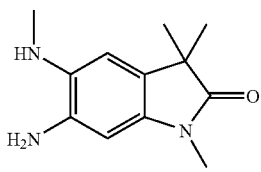

a) N-Methyl-N-(1,3,3-trimethyl-2-oxo-2,3-dihydro-1H-indol-5-yl-acetamide

To a solution of N-(1,3,3-trimethyl-2-oxo-2,3-dihydro-indol-5-yl)-acetamide (2 g) in N,N-dimethylformamide (53 ml) is added KOtBu (4.11 g; 36.7 mmol) and MeI (2,3 ml; 36.7 mmol) at RT. The mixture is stirred for 20 h, filtered and evaporated. After an aqueous work-up the crude material is purified by flash chromatography on silica gel eluted with $CH_2Cl_2$/MeOH (15:1) and giving the compound (1.04 g).

b) N-Methyl-N-(1,3,3-trimethyl-6-nitro-2-oxo-2,3-dihydro-1H-indol-5-yl)-acetamide To a cooled solution of the pure acetamide (1.04 g) in acetic acid (6 ml) is added drop-wise $HNO_3$ (fuming; 0.4 ml). The resulting mixture is warmed to RT and stirred for 30 min. The compound together with an isomeric side-product is precipitated by pouring the reaction mixture into ice-water and collected by filtration (0.61 g).

c) 1,3,3-Trimethyl-5-methylamino-6-nitro-1,3-dihydro-indol-2-one

The crude N-methyl-N-(1,3,3-trimethyl-6-nitro-2-oxo-2,3-dihydro-1H-indol-5-yl)-acetamide is dissolved in hydrochloric acid (6 N; 8 ml) and heated at reflux for 3 h. The mixture is poured into ice-water and the resulting precipitate collected by filtration. After drying the compound (176 mg) is obtained.

d) 6-Amino-3,3-dimethyl-5-methylamino-1,3-dihydro-indol-2-one (B2)

1,3,3-Trimethyl-5-methylamino-6-nitro-1,3-dihydro-indol-2-one (176 mg) is dissolved in MeOH (22 ml) and hydrogenated at 3 bar and 40° C. for 5 h using Pd/C (10%) (18 mg). After filtration and evaporation the crude material is purified by flash chromatography on silica gel eluting with $CH_2Cl_2$/MeOH (30:1) to give the title compound (128 mg).

General Procedure (II) for the Synthesis of Building Blocks B3-B28

To a solution of the corresponding building block A (1 g) in MeOH or THF (40-80 ml) is added Pd/C 10% (0.08-0.13 g). The reaction mixture is stirred in a hydrogenation reactor under a hydrogen pressure of 3-4 bar for 2-24 h at RT. After completion of the hydrogenation the mixture is filtered and evaporated to give the corresponding 5,6-diamino-1,3-dihydro-indol-2-one.

| # | Structure | Conditions | Yield |
|---|---|---|---|
| B3 | 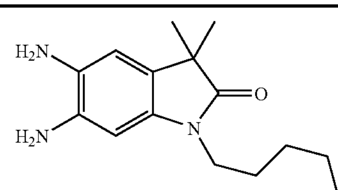 | A8 (11 g) Pd/C (1.1 g), MeOH (550 ml) | 9.75 g |
| B4 | 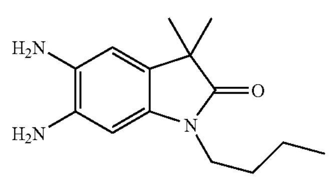 | A4 (2.95 g) Ra-Ni (0.5 g) MeOH (60 ml) | 2.52 g |
| B5 | 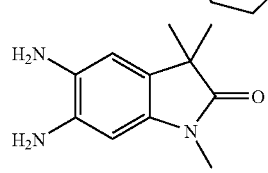 | A1 (3.9 g) Pd/C (0.4 g) MeOH (160 ml)h | 3.30 g |

| # | Structure | Conditions | Yield |
|---|---|---|---|
| B6 | 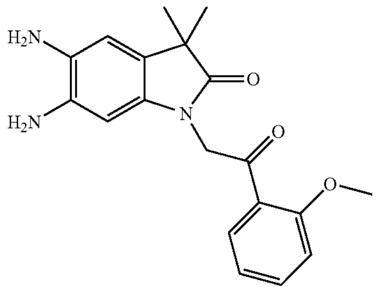 | A15 (3.5 g)<br>Pd/C (0.36 g)<br>MeOH (140 ml) | 3.13 |
| B7 | 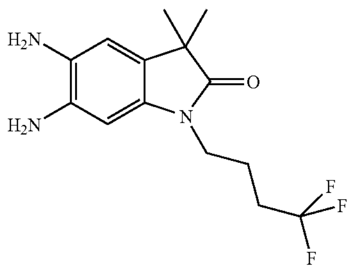 | A26 (0.3 g)<br>Pd/C (30 mg; 10%)<br>MeOH (30 ml) | 0.30 g |
| B8 | 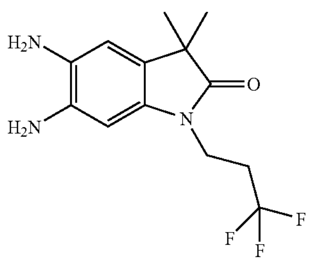 | A27 (0.34 g)<br>Pd/C (40 mg; 10%)<br>MeOH (40 ml) | 0.27 g |
| B9 | 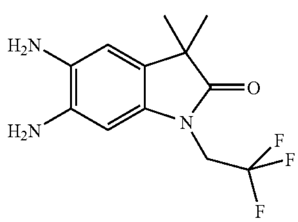 | A28 (0.5 g)<br>Pd/C (60 mg; 10%)<br>MeOH (60 ml) | 0.42 g |
| B10 | 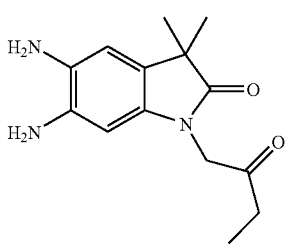 | A29 (0.27 g)<br>Pd/C (27 mg; 10%)<br>MeOH (27 ml) | 0.19 g |
| B11 | 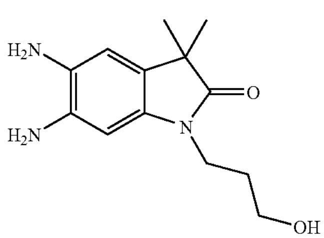 | A31 (2.1 g)<br>Pd/C (220 mg; 10%)<br>MeOH (60 ml)<br>HCl (3.0 ml, 1N) | 1.13 g |

-continued

| # | Structure | Conditions | Yield |
|---|---|---|---|
| B12 | ![structure] | A32 (0.45 g) Pd/C (100 mg; 10%) MeOH (100 ml) | 0.40 g |
| B13 | ![structure] | A38 (0.94 g) Pd/C (90 mg; 10%) MeOH (150 ml) HCl (15 ml; 1N) | 0.82 g |
| B14 | ![structure] | A41 (0.19 g) Pd/C (50 mg; 10%) MeOH (120 ml) | 0.18 g |
| B15 | ![structure] | A13 (0.25 g) Pd/C (40 mg; 10%) MeOH (5 ml) HCl (0.3 ml; 1N) | 0.14 g |
| B16 | ![structure] | A42 (0.15 g) Pd/C (15 mg; 10%) MeOH (5 ml) HCl (0.3 ml, 1N) | 0.14 g |
| B17 | ![structure] | A43 (0.15 g) Pd/C (15 mg; 10%) MeOH (5 ml) HCl (0.3 ml, 1N) | 0.12 g |

-continued

| # | Structure | Conditions | Yield |
|---|---|---|---|
| B18 | 5,6-diamino-3,3-dimethyl-1-(2,4-difluorobenzyl)indolin-2-one | A44 (0.15 g)<br>Pd/C (15 mg; 10%)<br>MeOH (5 ml)<br>HCl (0.3 ml; 1N) | 0.13 g |
| B19 | 5,6-diamino-3,3-dimethyl-1-(3-fluoro-4-methoxybenzyl)indolin-2-one | A47 (0.17 g)<br>Pd/C (30 mg; 10%)<br>MeOH (10 ml)<br>HCl (0.5 ml; 1N) | 0.15 gl |
| B20 | 5,6-diamino-3,3-dimethyl-1-(3,5-difluoro-4-isopropoxybenzyl)indolin-2-one | A48 (0.20 g)<br>Pd/C (20 mg; 10%)<br>MeOH (15 ml)<br>HCl (1 ml; 1N) | 0.18 g |
| B21 | 5,6-diamino-3,3-dimethyl-1-((5-fluoropyridin-2-yl)methyl)indolin-2-one | A49 (75.4 mg)<br>Pd/C (17 mg; 10%)<br>MeOH (65 ml) | 68.6 mg |
| B22 | 5,6-diamino-3,3-dimethyl-1-(oxazol-2-ylmethyl)indolin-2-one | A50 (1.05 g)<br>Pd/C (100 mg; 10%)<br>MeOH (100 ml) | 0.94 g |
| B23 | 5,6-diamino-3,3-dimethyl-1-(3,3-dimethyl-2-oxobutyl)indolin-2-one | A30 (1.42 g)<br>Pd/C (140 mg; 10%)<br>MeOH (200 ml)h | 1.03 g |

| # | Structure | Conditions | Yield |
|---|---|---|---|
| B24 | 5,6-diamino-3,3-dimethyl-1-(2-cyclopropylethyl)indolin-2-one | A34 (2.10 g)<br>Pd/C (200 mg, 10%)<br>MeOH (70 ml)<br>HCl (10 ml; 1N) | 1.83 g |
| B25 | 5,6-diamino-3,3-dimethyl-1-(4-fluoro-2-methoxybenzyl)indolin-2-one | A45 (1.70 g)<br>Pd/C (200 mg; 10%)<br>MeOH (30 ml)<br>HCl (4 ml; 1N) | 1.50 g |
| B26 | 5,6-diamino-3,3-dimethyl-1-((2,4-dimethylthiazol-5-yl)methyl)indolin-2-one | A52 (1.04 g)<br>Pd/C (104 mg; 10%)<br>MeOH (100 ml) | 0.90 g |
| B27 | 5,6-diamino-3,3-dimethyl-1-((3-methylisoxazol-5-yl)methyl)indolin-2-one | A53 (0.93 g)<br>Pd/C (100 mg; 10%)<br>MeOH (130 ml)<br>HCl (20 ml; 1N) | 0.85 g |
| B28 | 5,6-diamino-3,3-dimethyl-1-((3-phenylisoxazol-5-yl)methyl)indolin-2-one | A54 (1. g)<br>Pd/C (100 mg; 10%)<br>MeOH (130 ml)<br>HCl (20 ml; 1N) | 0.99 g |

(B29) 5,6-Diamino-1-(3-cyclopropyl-prop-2-ynyl)-3,3-dimethyl-1,3-dihydro-indol-2-one

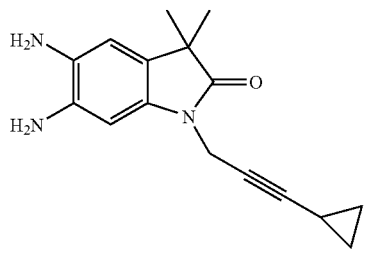

To a solution of A33 (1 g) in THF (15 ml) is added a solution of SnCl₂ dihydrate (3.01 g; 13.4 mmol) in hydrochloric acid (50 ml; 1 N) dropwise. The reaction mixture is stirred at 35° C. for 3 days. After completion 1 N NaOH (until pH 12) is added and the mixture is extracted with CH₂Cl₂ (2×75 ml). The combined organic layer is washed with brine, dried over MgSO₄ and evaporated to give 5,6-diamino-1-(3-cyclopropyl-prop-2-ynyl)-3,3-dimethyl-1,3-dihydro-indol-2-on (0.90 g) which is used without further purification.

(B30) 5,6-Diamino-1-(2-ethylsulfanyl-ethyl)-3,3-dimethyl-1,3-dihydro-indol-2-one

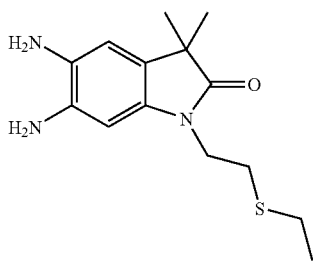

To a solution of A36 (0.78 g) in THF (15 ml) is added a solution of SnCl₂ dihydrate (2.23 g; 9.88 mmol) in hydrochloric acid (35 ml; 1 N) dropwise. The reaction mixture is stirred at RT for 4 days. After completion 1 N NaOH (until pH 12) is added and the mixture is extracted with CH₂Cl₂ (2×75 ml). The combined organic layer is washed with brine, dried over MgSO₄ and evaporated to give 5,6-diamino-1-(2-ethylsulfanyl-ethyl)-3,3-dimethyl-1,3-dihydro-indol-2-one (0.73 g) which is used without further purification.

(B31) 5,6-Diamino-1-(2-cyclopropoxy-ethyl)-3,3-dimethyl-1,3-dihydro-indol-2-one

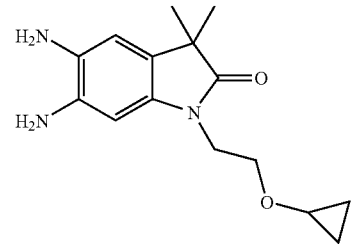

To a solution of A37 (0.55 g) in THF (50 ml) is added a solution of SnCl₂ dihydrate (1,35 g; 5.98 mmol) in hydrochloric acid (20 ml; 1 N) dropwise. The reaction mixture is stirred at RT for 14 days. After completion 1 N NaOH (until pH 12) is added and the mixture is extracted with CH₂Cl₂ (2×75 ml). The combined organic layer is washed with brine, dried over MgSO₄ and evaporated. Purification by RP chromatography gives 5,6-diamino-1-(2-cyclopropoxy-ethyl)-3,3-dimethyl-1,3-dihydro-indol-2-one (0.21 g).

(B32) 5,6-Diamino-3,3-dimethyl-1-pent-2-ynyl-1,3-dihydro-indol-2-one

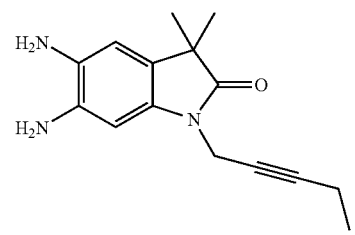

To a solution of A7 (0.87 g) in THF (17 ml) is added a solution of SnCl₂ dihydrate (2.73 g; 12.1 mmol) in hydrochloric acid (50 ml; 1 N) dropwise. The reaction mixture is stirred at RT for 3 h. After completion 1 N NaOH (until pH 12) is added and the mixture is extracted with CH₂Cl₂ (2×75 ml). The combined organic layer is washed with brine, dried over MgSO₄ and evaporated to give 5,6-diamino-3,3-dimethyl-1-pent-2-ynyl-1,3-dihydro-indol-2-one (0.51 g) which is used without further purification.

(B33) 5,6-Diamino-3,3-dimethyl-1-pent-3-ynyl-1,3-dihydro-indol-2-one

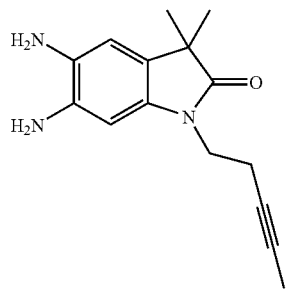

To a solution of A25 (0.35 g) in THF (7 ml) is added a solution of SnCl$_2$ dihydrate (1.1 g; 4.87 mmol) in hydrochloric acid (20 ml; 1 N) dropwise. The reaction mixture is stirred at RT for 18 h. After completion 1 N NaOH (until pH 12) is added and the mixture is extracted with CH$_2$Cl$_2$ (2×75 ml). The combined organic layer is washed with brine, dried over MgSO$_4$ and evaporated to give 5,6-diamino-3,3-dimethyl-1-pent-3-ynyl-1,3-dihydro-indol-2-one (0.31 g) which is used without further purification.

(B34) 5,6-Diamino-3,3-dimethyl-1-prop-2-ynyl-1,3-dihydro-indol-2-one

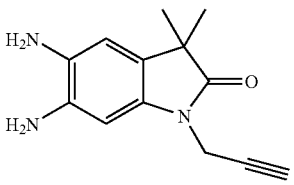

To a solution of A39 (4.32 g) in EtOAc (115 ml) is added SnCl$_2$ dihydrate (15 g; 66.7 mmol) in small portions. The reaction mixture is heated to 70° C. for 1 h. After cooling to RT concentrated NH$_3$ (20 ml) is added and the resulting precipitate is filtered. The filtrate is extracted with EtOAc (3×75 ml). The combined organic layer is washed with brine, dried over MgSO$_4$ and evaporated to give 5,6-diamino-3,3-dimethyl-1-prop-2-ynyl-1,3-dihydro-indol-2-one (3,32 g) which is used without further purification.

(B35) (rac)-5,6-Diamino-3,3-dimethyl-1-(1-methyl-prop-2-ynyl)-1,3-dihydro-indol-2-one

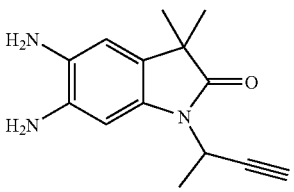

To a solution of A40 (1,3 g) in THF (25 ml) is added a solution of SnCl$_2$ dihydrate (4.29 g; 19.0 mmol) in hydrochloric acid (75 ml; 1 N) dropwise. The reaction mixture is stirred at 45° C. for 24 h. After completion 1 N NaOH (until pH 12) is added and the mixture is extracted with CH$_2$Cl$_2$ (2×75 ml). The combined organic layer is washed with brine, dried over MgSO$_4$ and evaporated to give (rac)-5,6-diamino-3,3-dimethyl-1-(1-methyl-prop-2-ynyl)-1,3-dihydro-indol-2-one (0.85 g) which is used without further purification.

(B36) 5,6-Diamino-3,3-dimethyl-1-thiazol4-ylmethyl-1,3-dihydro-indol-2-one

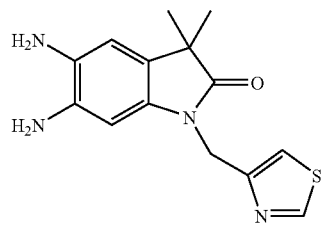

To a solution of A51 (1.54 g) in THF (30 ml) is added a solution of SnCl$_2$ dihydrate (4.42 g; 19.6 mmol) in hydrochloric acid (50 ml; 1 N) dropwise. The reaction mixture is stirred at 40° C. for 4 days. After completion 1 N NaOH (until pH 12) is added and the mixture is extracted with CH$_2$Cl$_2$ (2×75 ml). The combined organic layer is washed with brine, dried over MgSO$_4$ and evaporated to give 5,6-diamino-3,3-dimethyl-1-thiazol-4-ylmethyl-1,3-dihydro-indol-2-one (1,38 g) which is used without further purification.

(B37) 4-(5,6-Diamino-3,3-dimethyl-2-oxo-2,3-dihydro-indol-1-yl)-butyronitrile

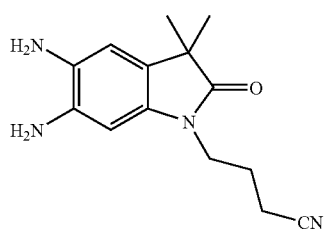

To a solution of A35 (0.33 g) in EtOH (20 ml) is added Pd/C (32 mg; 10%) and hydrazine monohydrate (150 µl; 3.03 mmol). The reaction mixture is stirred at RT for 18 h. After completion the reaction mixture is filtered and evaporated to give 4-(5,6-diamino-3,3-dimethyl-2-oxo-2,3-dihydro-indol-1-yl)-butyronitrile (0.23 g) which is used without further purification.

(B38) [2-(5,6-Diamino-3,3-dimethyl-2-oxo-2,3-dihydro-indol-1-ylmethyl)-phenyl]-carbamic acid tert-butyl ester

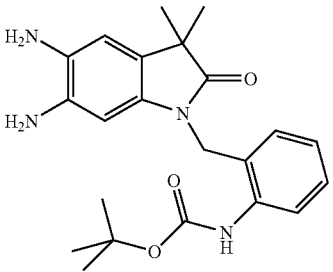

To a solution of A46 (0.93 g) in EtOH (150 ml) is added Pd/C (331 mg; 10%) and hydrazine monohydrate (1 ml; 20.2 mmol). The reaction mixture is stirred at RT for 18 h. After completion the reaction mixture is filtered and evaporated to give [2-(5,6-diamino-3,3-dimethyl-2-oxo-2,3-dihydro-indol-1-ylmethyl)-phenyl]-carbamic acid tert-butyl ester (0.85 g) which is used without further purification.

Examples Starting from Building Blocks B

Example 77 a) (E)-3-Phenyl-N-(1,3,3-trimethyl-6-methylamino-2-oxo-2,3-dihydro-1H-indol-5-yl)-acrylamide To a solution of B1 (200 mg) in N,N-dimethylformamide (1.5 ml) is added (E)-3-phenyl-acrylic acid (142 mg; 0.96 mmol), TBTU (308 mg; 0.96 mmol) and NEt$_3$ (97 mg; 0.96 mmol). The mixture is stirred at RT for 20 h. Saturated NaHCO$_3$ solution is added and the aqueous layer is extracted with EtOAc (3×20 ml). The combined organic layer is washed with brine, dried and concentrated in vacuo. The crude material is purified by flash chromatography on silica gel eluting with light petroleum/EtOAc (1:2) to give the compound (288 mg).

b) 3,5,7,7-Tetramethyl-2-((E)-styryl)-5,7-dihydro-3H-imidazo[4,5-f]indol-6-one

A solution of (E)-3-phenyl-N-(1,3,3-trimethyl-6-methylamino-2-oxo-2,3-dihydro-1H-indol-5-yl)-acrylamide (288 mg) in acetic acid (6 ml) is heated under reflux for 1 h. After recooling the mixture is poured into ice-water whereupon the desired compound (250 mg) is precipitated.

Example 78

5,7,7-Tetramethyl-2-((E)-styryl)-5,7-dihydro-1H-imidazo[4,5-f]indol-6-one (105 mg;) is Prepared from B2 (128 mg) as Described in Example 77.

Example 79

2-(6-Methoxy-pyridin-3-yl)-7,7-dimethyl-5-pentyl-5,7-dihydro-1H-imidazo[4,5-f]indol-6-one A solution of B3 (100 mg) and 6-methoxy-pyridine-3-carbaldehyde (53 mg; 0.38 mmol) in N,N-dimethylformamide (5 ml) is stirred at 35° C. for 48 h in an open flask. After completion of the reaction, the mixture is concentrated in vacuo and subjected to RP-MPLC eluted with a water/MeCN gradient. Product containing fractions are collected and lyophilized to give the desired compound (63 mg) as brownish powder.

Examples 80-91 are prepared analogously to Example 79 starting from B3 and B4 respectively.

Example 92 a) [(S)-1-(7,7-Dimethyl-6-oxo-5-pentyl-1,5,67-tetrahydro-imidazo[4,5-f]indol-2-yl)-2-phenyl-ethyl]-carbamic acid tert-butyl ester (125 mg) is prepared from B3 (110 mg) and N-(tert-butyloxycarbonyl)-L-phenylalaninal (112 mg) as described in Example 79.

b) 2-((S)-1-Amino-2-phenyl-ethyl)-7,7-dimethyl-5-pentyl-5 7-dihydro-1H-imidazo[4,5-f]indol-6-one

[(S)-1-(7,7-Dimethyl-6-oxo-5-pentyl-1,5,6,7-tetrahydro-imidazo[4,5-f]indol-2-yl)-2-phenyl-ethyl]-carbamic acid tert-butyl ester (50 mg) is treated with a mixture of 1,4-dioxane (5 ml) and hydrochloric acid (2 N; 5 ml) for 15 min at 50° C. The solvents are evaporated and the residue lyophilized. The desired compound (43 mg) is obtained as a hydrochloride (white solid).

Example 93

2-((R)-1-Amino-2-phenyl-ethyl)-7,7-dimethyl-5-pentyl-5,7-dihydro-1H-imidazo[4,5-f]indol-6-one (42 mg) is prepared from B3 (131 mg) and N-(tertbutyloxycarbonyl)-D-phenylalaninal (138 mg) as described in Example 92.

Example 94

(7,7-Dimethyl-6-oxo-5-pentyl-1,5,6,7-tetrahydro-imidazo[4,5-f]indol-2-yl)-carbamic acid methyl ester To a solution of B3 (2.7 g) in MeOH (70 ml) is added 1,3-bis(methoxycarbonyl)-2-methyl-2-thiopseudourea (2.25 g; 10.6 mmol) and the mixture is heated under reflux for 10 h. The reaction mixture is cooled to 0° C. and the resulting solid is filtered and washed with cold MeOH to give the desired compound (1.91 g). More precipitate if formed by concentrating the filtrate in vacuo to 20 ml (1.11 g).

Examples 95 and 96 are prepared from the corresponding diamino building block as described in Example 94.

Example 97

(7,7-Dimethyl-6-oxo-5-pentyl-1,5,6,7-tetrahydro-imidazo[4,5-f]indol-2-yl)-carbamic acid benzyl ester is prepared from B3 (200 mg) and 1,3-bis(benzyloxycarbonyl)-2-methyl-2-thiopseudourea (285 mg; 0.78 mmol) as described in Example 94. After completion of the reaction the mixture is concentrated in vacuo and the desired compound (118 mg) is obtained by flash chromatography eluted with CH$_2$Cl$_2$/MeOH (99:1).

Example 98

(7,7-Dimethyl-6-oxo-5-pentyl-1,5,6,7-tetrahydro-imidazo[4,5-f]indol-2-yl)-carbamic acid allyl ester A suspension of (7,7-dimethyl-6-oxo-5-pentyl-1,5,6,7-tetrahydro-imidazo[4,5-f]indol-2-yl)-carbamic acid methyl ester (150 mg) in allyl alcohol (2 ml) is heated in a microwave apparatus at 120° C. for 20 min. The mixture is evaporated to give the desired compound (161 mg).

Examples 99-102 are prepared analogously from (7,7-dimethyl-6-oxo-5-pentyl-1,5,6,7-tetrahydro-imidazo[4,5-f]indol-2-yl)-carbamic acid methyl ester as described in Example 98.

Example 103 a) N-(6-Amino-1,3,3-trimethyl-2-oxo-2,3-dihydro-1H-indol-5-yl)-3-(1H-benzoimidazol-2-yl)-propionamide To a solution of B5 (400 mg) and 3-(1H-benzoimidazol-2-yl)-propionic acid (346 mg; 1.82 mmol) in N,N-dimethylformamide (2.7 ml) is added TBTU (584 mg; 1.82 mmol) and $NEt_3$ (419 mg; 4.14 mmol). The resulting mixture is stirred at RT for 20 h, diluted with water and extracted with EtOAc (3×20 ml). The combined organic layer is washed with brine, dried over $Na_2SO_4$ and concentrated in vacuo. The compound (218 mg) is obtained by flash chromatography on silica gel eluted with $CH_2Cl_2$/MeOH (15:1).

b) 2-[2-(1H-Benzoimidazol-2-yl)-ethyl]-5,7,7-trimethyl-5,7-dihydro-1H-imidazo[4,5-f]indol-6-one A solution of N-(6-amino-1,3,3-trimethyl-2-oxo-2,3-dihydro-1H-indol-5-yl)-3-(1H-benzoimidazol-2-yl)-propionamide (218 mg) in acetic acid (6 ml) is heated under reflux for 3 h. After re-cooling, water is added and the mixture is extracted with EtOAc (3×30 ml). The combined organic layer is washed with saturated $NaHCO_3$ solution and brine, dried over $Na_2SO_4$ and concentrated in vacuo to give the desired compound (90 mg).

Examples 104-110 are prepared analogously from B3 and the corresponding carboxylic acid as described in Example 103.

Example 111 a) N-(6-Amino-1,3,3-trimethyl-2-oxo-2,3-dihydro-1H-indol-5-yl)-3-benzo[1,3]dioxol-5-yl-propionamide is prepared from B3 (96 mg) and 3-benzo[1,3]dioxol-5-yl-propionic acid (74 mg; 0.38 mmol) as described in Example 103a. Purification of the crude material is achieved by RP-MPLC eluting with a water/MeCN gradient.

b) 2-(2-Benzo[1,3]dioxol-5-yl-ethyl)-5,7,7-trimethyl-5,7-dihydro-1H-imidazo[4,5-f]indol-6-one A solution of N-(6-amino-1,3,3-trimethyl-2-oxo-2,3-dihydro-1H-indol-5-yl)-3-benzo[1,3]dioxol-5-yl-propionamide (60 mg) in acetic acid (1.6 ml) is heated in a microwave apparatus at 150° C. for 15 min. After dilution with water the mixture is extracted with EtOAc (3×15 ml). The organic layer is washed with brine, dried over $MgSO_4$ and concentrated in vacuo to give the desired compound (57 mg).

Example 112 a) (E)-3-(1-Methyl-1H-imidazol-2-yl)-acrylic acid methyl ester

To a solution of trimethyl phosphono acetate (0.86 ml) in dry THF (5 ml) is added NaH (0.14 g; 5,63 mmol) under an inert atmosphere ($N_2$). The mixture is stirred for 1 h at RT. 1-Methyl-1H-imidazole-2-carbaldehyde (0.58 g; 5.27 mmol) is added and the resulting solution is stirred for another 2 h. After evaporation of the solvent, the residue is taken-up in EtOAc and the organic layer is washed with brine, dried over $MgSO_4$ and concentrated in vacuo to give the compound (0.86 g).

b) 3-(1-Methyl-1H-imidazol-2-yl)-propionic acid methyl ester (E)-3-(1-Methyl-1H-imidazol-2-yl)-acrylic acid methyl ester (0.86 g) is dissolved in MeOH (10 ml) and hydrogenated at 3 bar at RT for 2 h using Pd/C (10%, 0.1 g) as catalyst. After filtration and evaporation of the solvent the compound (0.87 g) is obtained.

c) 3-(1-Methyl-1H-imidazol-2-yl)-propionic acid 3-(1-Methyl-1H-imidazol-2-yl)-propionic acid methyl ester (0.87 g) is treated with hydrochloric acid (6 N; 5 ml) at RT for 20 h. After evaporation of the solvent the compound (0.86 g) is obtained as hydrochloric salt.

d) N-(6-Amino-1-butyl-3,3-dimethyl-2-oxo-2,3-dihydro-1H-indol-5-yl)-3-(1-methyl-1H-imidazol-2-yl)-propionamide (0.70 g) is prepared from B4 (0.92 g) and 3-(1-methyl-1H-imidazol-2-yl)-propionic acid (0.74 g; hydrochloride) as described in Example 103a.

e) 5-Butyl-7,7-dimethyl-2-[2-(1-methyl-1H-imidazol-2-yl)-ethyl]-5,7-dihydro-1H-imidazo[4,5-f]indol-6-one (0.42 g) is prepared from N-(6-amino-1-butyl-3,3-dimethyl-2-oxo-2,3-dihydro-1H-indol-5-yl)-3-(1-methyl-1H-imidazol-2-yl)-propionamide (0.70 g; 1.83 mmol) as described in Example 103b, and purified by crystallization from $Et_2O$.

Example 113 a) (E)-3-(3-Dimethylaminomethyl-phenyl)-acrylic acid ethyl ester

A mixture of (3-bromo-benzyl)-dimethyl-amine (1.10 g), ethyl acrylate (0.8 ml; 7.7 mmol), tri-o-tolyl-phosphane (156 mg; 0.53 mmol), Pd(OAc)$_2$ (40 mg; 0.16 mmol) and $NEt_3$ (1.4 ml; 10 mmol) is heated under reflux for 8 h. The reaction mixture is evaporated and the residue is subjected to flash chromatography on silica gel eluting with $CH_2Cl_2$/MeOH (95:5) to give the compound (800 mg).

b) (E)-3-(3-Dimethylaminomethyl-phenyl)-acrylic acid

To a solution of (E)-3-(3-dimethylaminomethyl-phenyl)-acrylic acid ethyl ester (400 mg) in MeOH (3 ml) is added sodium hydroxide solution (2 N; 2.5 ml; 5 mmol). After stirring for 2 h at RT the mixture is neutralized with hydrochloric acid (1 N; 5 ml; 5 mmol) and evaporated to dryness to give the compound (together with 5 mmol NaCl).

c) 2-[(E)-2-(3-Dimethylaminomethyl-phenyl)-vinyl]-7,7-dimethyl-5-pentyl-5,7-dihydro-1H-imidazo[4,5-f]indol-6-one A mixture of B3 (340 mg) and polyphosphoric acid (800 mg) is heated at 150° C. for 4 h. After this the reaction mixture is diluted with water and ammonia and extracted with $CH_2Cl_2$. The combined organic layer is washed with water, dried over $Na_2SO_4$ and concentrated in vacuo. The desired compound (100 mg) is obtained by flash chromatography on silica gel eluting with CH2Cl₂/MeOH).

Example 114

7,7-Dimethyl-5-pentyl-2-((E)-2-pyridazin-3-yl-vinyl)-5,7-dihydro-1H-imidazo[4,5-f]indol-6-one The desired compound (150 mg) is prepared from B3 (471 mg) and (E)-3-pyridazin-3-yl-acrylic acid (300 mg; 2.00 mmol) as described Example 113c.

Example 115

7,7-Dimethyl-5-pentyl-2-(2-piperidin-1-yl-ethyl)-5,7-dihydro-1H-imidazo[4,5-f]indol-6-one HCl gas is bubbled through a solution of 2-cyanoethyl-piperidine (0.5 ml) in CH$_2$Cl$_2$ (10 ml) and EtOH (0.2 ml) for 5 min. The mixture is stirred for 20 h and evaporated to dryness. The residue is taken-up in CH$_2$Cl$_2$ (10 ml), B3 (900 mg) is added and the resulting solution is stirred at 45° C. for 20 h. After a typical aqueous work-up the crude material is purified by flash chromatography on silica gel eluted with CH$_2$Cl$_2$/MeOH. The pure material is treated with HCl (saturated in Et$_2$O) to give the desired compound (480 mg) as hydrochloride.

Example 116

7,7-Dimethyl-5-pentyl-5,7-dihydro-1H-imidazo[4,5-f]indol-6-one

A solution of B3 (3.5 g) in formic acid (0.5 ml; 13.4 mmol) and hydrochloric acid (4 N, 350 ml) is heated under reflux for 3 h. After re-cooling the mixture is neutralized with ammonia and extracted with CH$_2$Cl$_2$. The combined organic layer is washed with water, dried over MgSO$_4$ and evaporated in vacuo. The desired compound (634 mg) is obtained by RP-MPLC.

Example 117

7,7-Dimethyl-6-oxo-5-pentyl-1,5,6,7-tetrahydro-imidazo[4,5-f]indole-2-carboxylic acid phenylamide To a solution of B3 (440 mg) in N,N-dimethylformamide (3 ml) is added N-phenyl-oxalamic acid ethyl ester (328 mg; 1.7 mmol). The mixture is heated under reflux for 12 h. After completion of the reaction the solvent is evaporated and the residue is purified by flash chromatography on silica gel to give the desired compound (110 mg).

Example 118

N-{5-[2-(4-Methoxy-phenyl)-2-oxo-ethyl]-7,7-dimethyl-6-oxo-1,5,6,7-tetrahydro-imidazo[4,5-f]indol-2-yl}-benzamide A solution of B6 (150 mg) and N-(bis-methylsulfanyl-methylene)-benzamide (111 mg; 0.44 mmol) in dry N,N-dimethylformamide (3 ml) is stirred at 100° C. for 3 h. The mixture is evaporated to dryness and the residue is purified by flash chromatography on silica gel eluted with cyclohexane/EtOAc to give the desired compound (47 mg).

Example 119

N-[7,7-Dimethyl-6-oxo-5-(4,4,4-trifluoro-butyl)-3,5,6,7-tetrahydro-imidazo[4,5-f]indol-2-yl]-benzamide A solution of B7 (148 mg) and N-(bis-methylsulfanyl-methylene)-benzamide (123 mg; 0.49 mmol) in dry N,N-dimethylformamide (5 ml) is stirred at 100° C. for 3 h. The mixture is evaporated to dryness and the residue is purified by RP-MPLC eluted with MeCN/water to yield the desired compound (99 mg).

Example 120

N-[7,7-Dimethyl-6-oxo-5-(3,3,3-trifluoro-propyl)-3,5,6,7-tetrahydro-imidazo[4,5-f]indol-2-yl]-benzamide A solution of B8 (133 mg) and N-(bis-methylsulfanyl-methylene)-benzamide (115 mg; 0.51 mmol) in dry N,N-dimethylformamide (5.0 ml) is stirred at 100° C. for 3 h. The mixture is evaporated to dryness and the residue is purified by RP-MPLC eluted with MeCN/water to yield the desired compound (65 mg).

Example 121

N-[7,7-Dimethyl-6-oxo-5-(2,2,2-trifluoro-ethyl)-3,5,6,7-tetrahydro-imidazo[4,5-f]indol-2-yl]-benzamide A solution of B9 (200 mg) and N-(bis-methylsulfanyl-methylene)-benzamide (181 mg; 0.81 mmol) in dry N,N-dimethylformamide (5 ml) is stirred at 100° C. for 3 h. The mixture is evaporated to dryness and the residue is purified by RP-MPLC eluted with MeCN/water to yield the desired compound (198 mg).

Example 122

N-[7,7-Dimethyl-6-oxo-5-(2-oxo-butyl)-3,5,6,7-tetrahydro-imidazo[4,5-f]indol-2-yl]-benzamide A solution of B 10 (93 mg) and N-(bis-methylsulfanyl-methylene)-benzamide (89.1 mg; 0.36 mmol) in dry N,N-dimethylformamide (5 ml) is stirred at 100° C. for 3 h. The mixture is evaporated to dryness and the residue is purified by chromatography on RP-MPLC eluted with MeCN/water to yield the desired compound (15 mg).

Example 123

N-(5-{2-[(Z)-Methoxyimino]-butyl}-7,7-dimethyl-6-oxo-3,5,6,7-tetrahydro-imidazo[4,5-f]indol-2-yl)-benzamide To a solution of N-[7,7-dimethyl-6-oxo-5-(2-oxo-butyl)-3,5,6,7-tetrahydro-imidazo[4,5-f]indol-2-yl]-benzamide (80 mg) in MeOH (20 ml) is added O-methyl-hydroxylamine hydrochloride (20.5 mg; 0.25 mmol) and the mixture is stirred at RT for 18 h. After evaporation EtOAc is added and the organic phase is washed three times with saturated K$_2$CO$_3$ solution, dried over MgSO$_4$ and evaporated again. The residue is purified by RP-MPLC eluted with MeCN/water to yield the desired compound (57 mg).

Examples 124 and 125

(2R)-N-[5-(2-Hydroxy-butyl)-7,7-dimethyl-6-oxo-3, 5,6,7-tetrahydro-imidazo[4,5-f]indol-2-yl]-benzamide and (2S)-N-[5-(2-hydroxy-butyl)-7,7-dimethyl-6-oxo-3,5,6,7-tetrahydro-imidazo[4,5-f]indol-2-yl]-benzamide To a cooled solution (0° C.) of N-[7,7-dimethyl-6-oxo-5-(2-oxo-butyl)-3,5,6,7-tetrahydro-imidazo[4,5-f]indol-2-yl]-benzamide (150 mg) in $CH_2Cl_2$ (3.5 ml) and MeOH (1.5 ml) is added $NaBH_4$ (29.1 mg; 0.77 mmol). The mixture is stirred and warmed to RT overnight. After completion hydrochloric acid (5 ml; 1 N) is added and the mixture extracted with EtOAc. The organic phase is washed with brine, dried over $MgSO_4$ and evaporated to dryness to give N-[5-(2-hydroxy-butyl)-7,7-dimethyl-6-oxo-3,5,6,7-tetrahydro-imidazo[4,5-f]indol-2-yl]-benzamide (67 mg) as a racemic mixture.

The enantiomers are separated by HPLC on a ChiralpakADH column eluting with EtOH/MeOH=10:90 using 0.1% $NHEt_2$ as a modifier to yield 16 mg of the first eluted enantiomer and 19 mg (0.05 mmol) of the second eluted enantiomer.

Example 126 a) N-[5-(3-Hydroxy-propyl)-7,7-dimethyl-6-oxo-3,5, 6,7-tetrahydro-imidazo[4,5-f]indol-2-yl]-benzamide A solution of B11 (1.13 g) and N-(bis-methylsulfanyl-methylene)-benzamide (1.11 g; 4.91 mmol) in dry N,N-dimethylformamide (10 ml) is stirred at reflux for 2 h. The mixture is evaporated to dryness to give N-[5-(3-hydroxy-propyl)-7,7-dimethyl-6-oxo-3,5,6,7-tetrahydro-imidazo[4,5-f]indol-2-yl]-benzamide (1.12 g) which is used without further purification.

b) N-[7,7-Dimethyl-6-oxo-5-(3-oxo-propyl)-3,5,6,7-tetrahydro-imidazo[4,5-f]indol-2-yl]-benzamide To a solution of N-[5-(3-hydroxy-propyl)-7,7-dimethyl-6-oxo-3,5,6,7-tetrahydro-imidazo[4,5-f]indol-2-yl]-benzamide (1.12 g) in $CH_2Cl_2$ (10 ml) is added Dess Martin reagent (3.5 g; 8.25 mmol) and the mixture is stirred at RT for 4 h. After evaporation to dryness the crude material is purified by flash chromatography on Alox B eluting with $CH_2Cl_2$/MeOH gradient to give N-[7,7-dimethyl-6-oxo-5-(3-oxo-propyl)-3,5,6,7-tetrahydro-imidazo[4,5-f]indol-2-yl]-benzamide (0.42 g).

c) N-[5-(3-tert-Butoxyimino-propyl)-7,7-dimethyl-6-oxo-3,5,6,7-tetrahydro-imidazo[4,5-f]indol-2-yl]-benzamide A solution of N-[7,7-dimethyl-6-oxo-5-(3-oxo-propyl)-3,5,6,7-tetrahydro-imidazo[4,5-f]indol-2-yl]-benzamide (50 mg) and O-tert-butyl-hydroxylamine hydrochloride (117 mg; 0.93 mmol) in MeOH (10 ml) and water (1 ml) is stirred at RT for 18 h. After evaporating to dryness the crude material is purified by preparative RP-HPLC eluting with MeCN/water to give the desired compound (7 mg).

Example 127

N-[5-(4,4-Dimethyl-pentyl)-7,7-dimethyl-6-oxo-3 5,6,7-tetrahydro-imidazo[4,5-f]indol-2-yl]-benzamide A solution of B12 (0.33 g) and N-(bis-methylsulfanyl-methylene)-benzamide (0.26 g; 1.14 mmol) in dry N,N-dimethylformamide (10 ml) is stirred at 65° C. for 3 h. The mixture is evaporated to dryness and the residue is purified by flash chromatography on silica gel to yield the desired compound (0.15 g).

Example 128

N-[7,7-Dimethyl-6-oxo-5-(tetrahydro-furan-2-ylmethyl)-3,5,6,7-tetrahydro-imidazo[4,5-f]indol-2!-yl]-benzamide A solution of B13 (280 mg) and N-(bis-methylsulfanyl-methylene)-benzamide (229 mg; 1.07 mmol) in dry N,N-dimethylformamide (5 ml) is stirred at 100° C. for 5 h. The mixture is evaporated to dryness and the residue is purified by RP-MPLC eluted with $CH_3CN$/water to yield the desired compound (93 mg).

Example 129

N-(7,7-Dimethyl-6-oxo-5-phenyl-3,5,6,7-tetrahydro-imidazo[4,5-f]indol-2-yl)-benzamide A solution of B14 (175 mg) and N-(bis-methylsulfanyl-methylene)-benzamide (150 mg; 0.67 mmol) in dry N,N-dimethylformamide (20 ml) is stirred at 100° C. for 18 h. The mixture is evaporated to dryness and the residue is purified by RP-MPLC eluted with MeCN/water to yield the desired compound (185 mg).

Example 130

N-[5-(4-Methoxy-benzyl)-7,7-dimethyl-6-oxo-3,5,6, 7-tetrahydro-imidazo[4,5-f]indol-2-yl]-benzamide A solution of B15 (68 mg) and N-(bis-methylsulfanyl-methylene)-benzamide (49.6 mg; 0.22 mmol) in dry N,N-dimethylformamide (1 ml) is stirred at reflux for 2 h. The mixture is evaporated to dryness and the residue is purified by preparative RP, eluted with MeCN/water to yield the desired compound (32.5 mg).

Example 131

N-[5-(4-Hydroxy-benzyl)-7,7-dimethyl-6-oxo-3,5,6, 7-tetrahydro-imidazo[4,5-f]indol-2-yl]-benzamide N-[5-(4-Methoxy-benzyl)-7,7-dimethyl-6-oxo-3,5,6,7-tetrahydro-imidazo[4,5-f]indol-2-yl]-benzamide (10 mg; 0.02 mmol) is suspended in a $BBr_3$ solution in $CH_2Cl_2$ (1 M; 100 µl) and stirred at RT for 18 h. After addition of hydrochloric acid (200 µl; 1 N) the mixture is stirred at RT for another 1 h and then evaporated to dryness. The crude material is purified by preparative RP-HPLC, eluted with MeCN/water to yield the desired compound (5 mg).

Example 132

N-[5-(4-Chloro-benzyl)-7,7-dimethyl-6-oxo-3,5,6,7-tetrahydro-imidazo[4,5-f]indol-2-yl]-benzamide A solution of B16 (140 mg) and N-(bis-methylsulfanyl-methylene)-benzamide (105 mg; 0.47 mmol) in dry N,N-dimethylformamide (1 ml) is stirred at reflux for 2 h. The mixture is evaporated to dryness and the residue is purified by preparative RP-HPLC, eluted with MeCN/water to yield the desired compound (36 mg).

Example 133

N-[5-(4-Fluoro-benzyl)-7,7-dimethyl-6-oxo-3,5,6,7-tetrahydro-imidazo[4,5-f]indol-2-yl]-benzamide A solution of B17 (116 mg) and N-(bis-methylsulfanyl-methylene)-benzamide (95 mg; 0.42 mmol) in dry N,N-dimethylformamide (1 ml) is stirred at reflux for 2 h. The mixture is evaporated to dryness and the residue is purified by preparative RP-HPLC eluted with MeCN/water to yield the desired compound (59 mg).

Example 134

N-[5-(2,4-Difluoro-benzyl)-7,7-dimethyl-6-oxo-3,5,6,7-tetrahydro-imidazo[4,5-f]indol-2-yl]-benzamide A solution of B18 (131 mg) and N-(bis-methylsulfanyl-methylene)-benzamide (102 mg; 0.45 mmol) in dry N,N-dimethylformamide (1 ml) is stirred at reflux for 2 h. The mixture is evaporated to dryness and the residue is purified by preparative RP-HPLC eluted with MeCN/water to yield the desired compound (83 mg).

Example 135

N-[5-(3-Fluoro-4-methoxy-benzyl)-7,7-dimethyl-6-oxo-3,5,6,7-tetrahydro-imidazo [4,5-f]indol-2-yl]-benzamide A solution of B19 (152 mg) and N-(bis-methylsulfanyl-methylene)-benzamide (109 mg; 0.49 mmol) in dry N,N-dimethylformamide (2 ml) is stirred at reflux for 2 h. The mixture is evaporated to dryness to yield the desired compound (210 mg).

Example 136

N-[5-(3-Fluoro-4-hydroxy-benzyl)-7,7-dimethyl-6-oxo-3,5,6,7-tetrahydro-imidazo[4,5-f]indol-2-yl]-benzamide N-[5-(3-Fluoro-4-methoxy-benzyl)-7,7-dimethyl-6-oxo-3,5,6,7-tetrahydro-imidazo[4,5-f]indol-2-yl]-benzamide (105 mg) is suspended in a $BBr_3$ solution in $CH_2Cl_2$ (1 M; 700 µl) and stirred at RT for 18 h. After addition of hydrochloric acid (400 µl; 1 N) the mixture is stirred at RT for another 1 h and then evaporated to dryness. The crude material is purified by preparative RP-HPLC, eluted with MeCN/water to yield the desired compound (25 mg).

Example 137

N-[5-(3,5-Difluoro-4-isopropoxy-benzyl)-7,7-dimethyl-6-oxo-3,5,6,7-tetrahydro-imidazo[4,5-f]indol-2-yl]-benzamide A solution of B20 (98 mg) and N-(bis-methylsulfanyl-methylene)-benzamide (63.1 mg; 0.28 mmol) in dry N,N-dimethylformamide (2 ml) is stirred at reflux for 2 h. The mixture is evaporated to dryness to yield the desired compound (103 mg).

Example 138

N-[5-(3,5-Difluoro-4-hydroxy-benzyl)-7,7-dimethyl-6-oxo-3,5,6,7-tetrahydro-imidazo[4,5-f]indol-2-yl]-benzamide N-[5-(3,5-Difluoro-4-isopropoxy-benzyl)-7,7-dimethyl-6-oxo-3,5,6,7-tetrahydro-imidazo[4,5-f]indol-2-yl]-benzamide (90 mg; 0.18 mmol) is suspended in a $BBr_3$ solution in $CH_2Cl_2$ (1 M; 600 µl) and stirred at RT for 18 h. After addition of hydrochloric acid (300 µl; 1 N) the mixture is stirred at RT for another 1 h and then evaporated to dryness. The crude material is purified by preparative RP-HPLC, eluted with MeCN/water to yield the desired compound (27.7 mg).

Example 139

N-[5-(5-Fluoro-pyridin-2-ylmethyl)-7,7-dimethyl-6-oxo-3,5,6,7-tetrahydro-imidazo[4,5-f]indol-2-yl]-benzamide A solution of B21 (69 mg) and N-(bis-methylsulfanyl-methylene)-benzamide (57.5 mg; 0.23 mmol) in dry N,N-dimethylformamide (3 ml) is stirred at 80° C. for 18 h. The mixture is evaporated to dryness and the residue is purified by flash chromatography on silica gel eluted with cyclohexane/EtOAc to yield the desired compound (45.0 mg).

Example 140

N-(7,7-Dimethyl-5-oxazol-2-ylmethyl-6-oxo-3,5,6,7-tetrahydro-imidazo[4,5-f]indol-2-yl)-benzamide A solution of B22 (100 mg) and N-(bis-methylsulfanyl-methylene)-benzamide (85 mg; 0.38 mmol) in dry N,N-dimethylformamide (5 ml) is stirred at 45° C. for 18 h. The mixture is evaporated to dryness and the residue is purified by flash chromatography on silica gel eluted with cyclohexane/EtOAc to yield the desired compound (90 mg).

Example 141

N-[5-(3-Cyclopropyl-prop-2-ynyl)-7,7-dimethyl-6-oxo-3,5,6,7-tetrahydro-imidazo[4,5-f]indol-2-yl]-benzamide A solution of B29 (200 mg) and N-(bis-methylsulfanyl-methylene)-benzamide (184 mg; 0.82 mmol) in dry N,N-dimethylformamide (13 ml) is stirred at RT for 24 h. The mixture is evaporated to dryness and the residue is purified by flash chromatography on silica gel eluted with cyclohexane/EtOAc to yield the desired compound (10 mg).

Example 142

N-[5-(2-Ethylsulfanyl-ethyl)-7,7-dimethyl-6-oxo-3,5,6,7-tetrahydro-imidazo[4,5-f]indol-2-yl]-benzamide A solution of B30 (0.73 g) and N-(bis-methylsulfanyl-methylene)-benzamide (0.72 g; 2.70 mmol) in dry N,N-dimethylformamide (35 ml) is stirred at 80° C. for 18 h. The mixture is evaporated to dryness and the residue is purified by preparative RP-MPLC eluted with MeCN/water to yield the desired compound (0.76 g).

Example 143

N-[5-(2-Cyclopropoxy-ethyl)-7,7-dimethyl-6-oxo-3,5,6,7-tetrahydro-imidazo[4,5-f]indol-2-yl]-benzamide A solution of B31 (210 mg) and N-(bis-methylsulfanyl-methylene)-benzamide (165 mg; 0.73 mmol) in dry N,N-dimethylformamide (8 ml) is stirred at 40° C. for 24 h. The mixture is evaporated to dryness and the residue is purified by flash chromatography on silica gel eluted with cyclohexane/EtOAc to yield the desired compound (113 mg).

Example 144

N-[5-(3-Cyano-propyl)-7,7-dimethyl-6-oxo-3,5,6,7-tetrahydro-imidazo [4,5-f]indol-2-yl]-benzamide A solution of B37 (190 mg) and N-(bis-methylsulfanyl-methylene)-benzamide (150 mg; 0.67 mmol) in dry N,N-dimethylformamide (3 ml) is stirred at 150° C. for 24 h. The mixture is evaporated to dryness and the residue is purified by preparative RP-HPLC eluted with MeCN/water to yield the desired compound (84.2 mg).

Examples 77-144

| # | Structure | MP [° C.] | Rt [min] | MS | NMR |
|---|---|---|---|---|---|
| 77 | 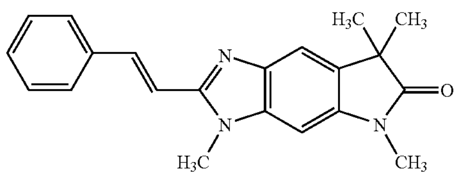 | | 3.18 | 332 | (DMSO) d = 1.32 (s, 6H), 3.22 (s, 3H), 3.95 (s, 3H), 7.20 (s, 1H), 7.35 (t, 1H), 7.44 (t, 2H), 7.49 (s, 1H), 7.58 (s, 1H), 7.71 (s, 1H), 7.78 (t, 2H) |
| 78 | 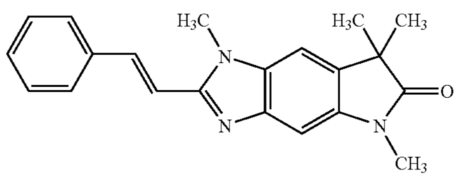 | | 3.21 | 332 | (DMSO) d = 1.35 (s, 6H), 3.20 (s, 3H), 3.94 (s, 3H), 7.18 (s, 1H), 7.37 (t, 1H), 7.45 (t, 2H), 7.49 (s, 1H), 7.61 (s, 1H), 7.75 (s, 1H), 7.80 (t, 2H) |
| 79 | 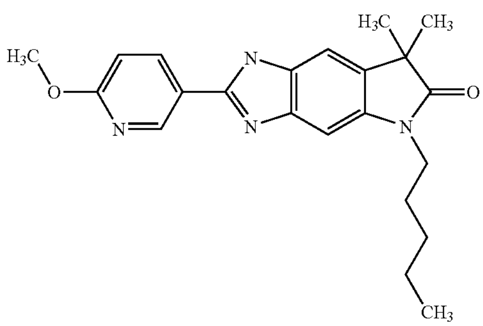 | 206-208 | 2.79 | 379 | (DMSO) d = 0.83-0.86 (m, 3H), 1.22-1.36 (m, 10H), 1.60-1.70 (m, 2H), 3.70-3.79 (m, 2H), 3.93 (s, 3H), 6.97-7.03 (m, 1H), 7.14/7.56 (2br s, 2H), 8.16 (s, 1H), 8.33-8.40 (m, 1H), 8.88-8.92 (m, 1H) |
| 80 | 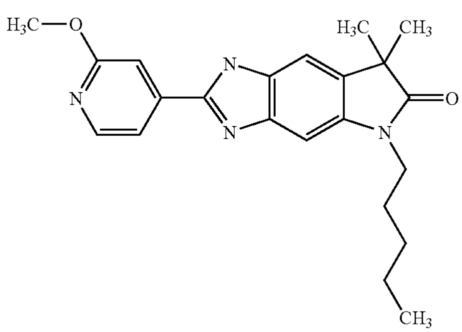 | Zers. ~78 | 3.04 | 379 | (DMSO) d = 0.80-0.89 (m, 3H), 1.22-1.39 (m, 10H), 1.59-1.70 (m, 2H), 3.70-3.79 (m, 2H), 3.92 (s, 3H), 6.95-7.3 7 (m, 1H), 7.47 (s, 1H), 7.49/7.80 (m, 2H), 8.27-8.37 (m, 1H) |

-continued
| # | Structure | MP [° C.] | Rt [min] | MS | NMR |
|---|---|---|---|---|---|
| 81 | 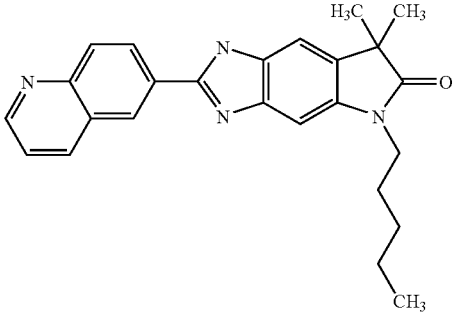 | Zers. ~102.5 | 2.89 | 399 | (DMSO) d = 0.81-0.90 (m, 3H), 1.20-1.39 (m, 10H), 1.59-2.26 (m, 2H), 3.72-3.8 1 (m, 2H), 7.19 (br s, 1H), 7.56-7.71 (m, 2H), 8.12-8.20 (m, 1H), 8.45-8.57 (m, 2H), 8.69-8.74 (m, 1H), 8.9 1-8.99 (m, 1H), 12.80-13.40 (br m, 1H, tautomere) |
| 82 | 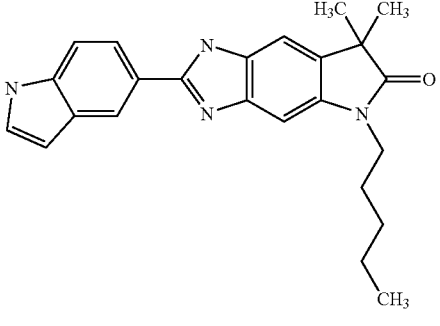 | Zers. ~149 | 2.81 | 387 | (DMSO) d = 0.80-0.91 (m, 3H), 1.24-1.27 (m, 10H), 1.60-1.70 (m, 2H), 3.69-3.79 (m, 2H), 6.53-6.58 (m, 1H), 7.10 (br s, 1H), 7.41-7.66 (m, 3H), 7.88-7.94 (m, 1H), 8.30-8.37 (m, 1H), 11.25-11.35 (m, 1H), 12.63 (br s, 1H, tautomere) |
| 83 | 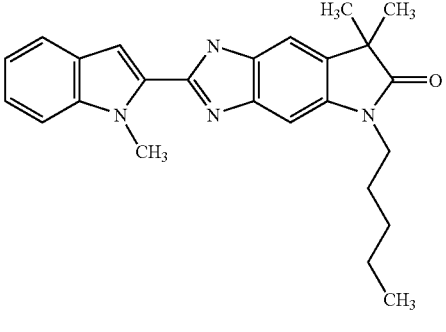 | Zers. ~103 | 3.34 | 401 | (DMSO) d = 0.81-0.89 (m, 3H), 1.25-1.40 (m, 10H), 1.60-1.70 (m, 2H), 3.68-3.79 (m 2H), 4.28 (s, 3H), 7.06/7.34/7.49/7.71 (4 br s, 2H), 7.09-7.15 (m, 1H), 7.19 (s, 1H), 7.24-7.30 (m, 1H), 7.52-7.59 (m, 1H), 7.63-7.68 (m, 1H), 12.85 (br s, 1 H, tautomere) |
| 84 | 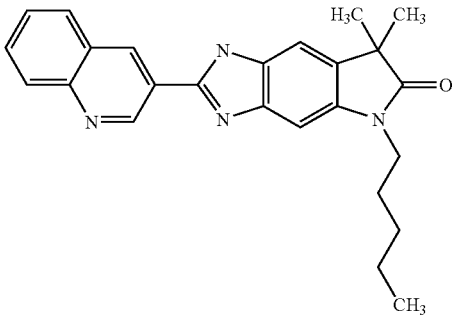 | 206-208 | 3.03 | 399 | (DMSO) d = 0.8 1-0.89 (m, 3H), 1.24-1.40 (m, 10H), 1.61-1.72 (m, 2H), 3.74-3.82 (m 2H), 7.15/7.32 (2 br s, 1H), 7.54-7.80 (m, 2H), 7.81-7.89 (m, 1W), 8.07-8.19 (m, 2H), 8.98 (s, 1H), 9.62-9.70 (m, 1H), 13.25 (br s, 1H, tautomere) |

| # | Structure | MP [° C.] | Rt [min] | MS | NMR |
|---|---|---|---|---|---|
| 85 | 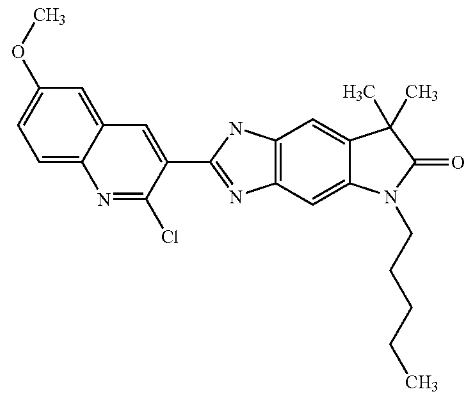 | Zers. ~115 | 3.31 | 463/65 | (DMSO) d = 0.81-0.90 (m, 3H), 1.22-1.39 (m, 10H), 1.62-1.71 (m, 2H), 3.71-3.81 (m 2H), 3.93 (s, 3H), 7.15/7.33 (2 br s, 1H), 7.50-7.76 (m, 3H), 7.93-7.99 (m, 1H), 8.79 (s, 1H), 12.77/12.86 (2br s, 1H, tautomere) |
| 86 | 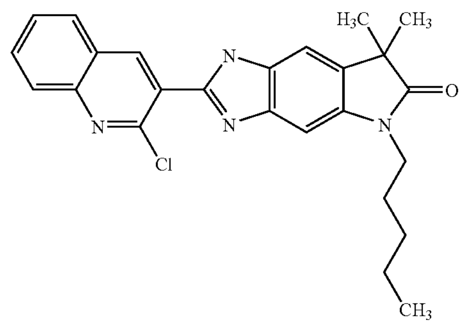 | Zers. ~121 | 3.28 | 433/35 | (DMSO) d = 0.78-0.93 (m, 3H), 1.16-1.45 (m, 10H), 1.58-1.74 (m, 2H), 3.67-3.85 (m 2H), 7.23 (s, 1H), 7.66 (s, 1H), 7.72-7.79 (m, 1H), 7.88-7.96 (m, 1H), 8.03-8.09 (m, 1H), 8.16-8.22 (m, 1H), 8.93 (s, 1H), 12.84(brs, 1H, tautomere) |
| 87 | 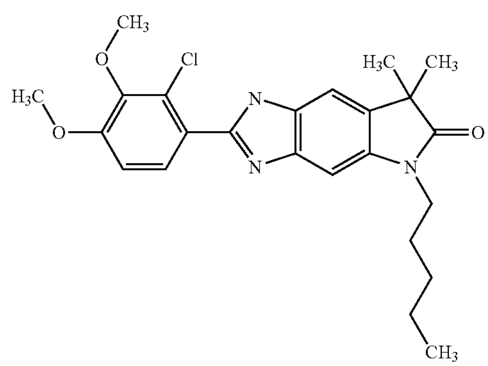 | Zers. ~92 | 2.98 | 442/44 | (DMSO) d = 0.79-0.90 (m, 3H), 1.22-1.39 (m, 10H), 1.59-1.71 (m, 2H), 3.69-3.77 (m 2H), 3.82 (s, 3H), 3.92 (s, 3H), 7.07/7.26/7.48/7.63 (3 br s, 2H), 7.19-7.24 (m, 1H), 7.56-7.62 (m, 1H), 12.44/12.51 (2 br s, 1H, tautomere) |
| 88 | 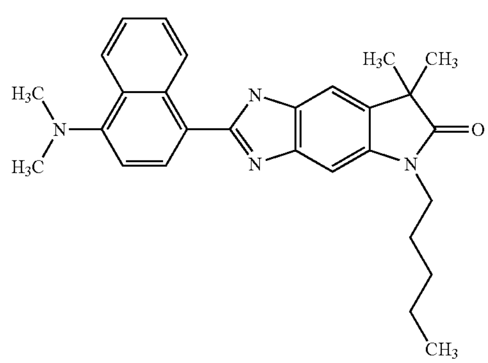 | Zers. ~124 | 3.02 | 441 | (DMSO) d = 0.81-0.89 (m, 3H), 1.24-1.39 (m, 10H), 1.62-1.72 (m, 2H), 2.91 (s, 6H), 3.72-3.79 (m 2H), 7.07/7.36/7.49/7.72 (4 br s, 2H), 7.20-7.25 (m, 1H), 7.55-7.62 (m, 2H), 7.84-7.91 (m, 1H), 8.22-8.27 (m, 1H), 12.66/12.70 (2 br s, 1 H, tautomere) |

-continued

| # | Structure | MP [° C.] | Rt [min] | MS | NMR |
|---|---|---|---|---|---|
| 89 | 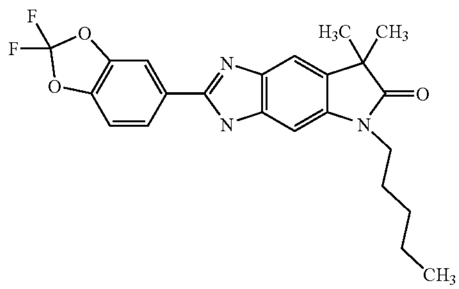 | | 3.2 | 428 | (DMSO) d = 0.80-0.91 (m, 3H), 1.23-1.40 (m, 10H), 1.60-1.71 (m, 2H), 3.68-3.82 (m 2H), 7.07/7.25 (2 br s, 1H), 7.45-7.71 (m, 2H), 7.95-8.03 (m, 1H), 8.07 (s, 1H), 12.90 (br s, 1H, tautomere) |
| 90 | 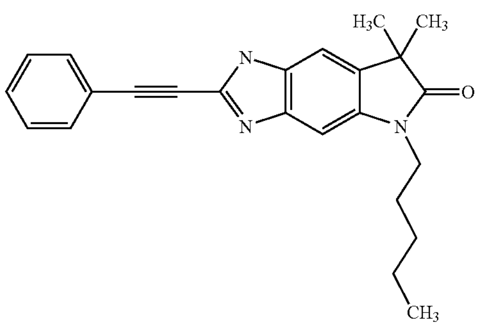 | | 3.35 | 372 | (CDCl3) d = 0.83-0.90 (m, 3H), 1.28-1.40 (m, 10H), 1.64-1.73 (m, 2H), 3.69-3.75 (m, 2H), 7.05 (br s, 1H), 7.28-7.40 (m, 3H), 7.46-7.51 (m ,3H) |
| 91 | 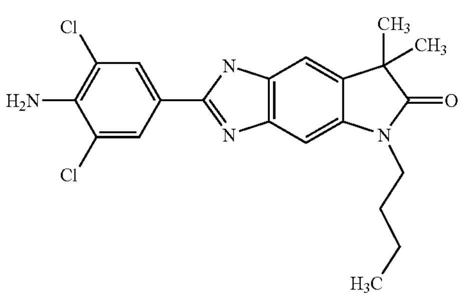 | | 3.66 | 417/ 19/ 21 | (DMSO) d = 0.91 (t, 3H), 1.30 (m, 8H), 1.61 (m, 2H), 3.73 (m, 2H), 5.95 (d, NH2), 7.00/7.20 (2 s, 1H, tautomere), 7.43/7.58 (2 s, 1H, tautomere), 8.00 (d, 2H), 12.65 (s, NH) |
| 92 | Chiral | Zers. ~158 | 2.74 | 391 | (DMSO) d = 0.78-0.88 (m, 3H), 1.20-1.36 (m, 10H), 1.56-1.66 (m, 2H), 2.66-4.82 (m, 4H), 4.88-4.98 (m, 1H), 7.15-7.27 (m, 6H), 7.69 (s, 1H), 9.11 (brs, 2H) |

-continued

| # | Structure | MP [° C.] | Rt [min] | MS | NMR |
|---|---|---|---|---|---|
| 93 | Chiral | Zers. ~158 | 2.73 | 391 | (DMSO) d = 0.79-0.86 (m, 3H), 1.18-1.35 (m, 10H), 1.56-1.65 (m, 2H), 2.70-4.70 (m, 4H), 4.84-4.93 (m, 1H), 7.14-7.28 (m, 6H), 7.66 (s, 1H), 9.04 (br s, 2H) |
| 94 | 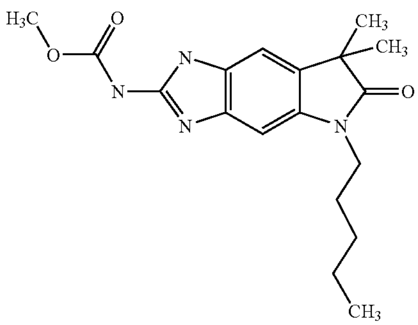 | 217.5-220.6 | 2.67 | 345 | (DMSO) = 0.80-0.90 (m, 3H), 1.22-1.37 (m, 10H), 1.57-1.69 (m, 2H), 3.63-3.73 (m, 2H), 3.76 (s, 3H), 7.03 (s, 1H), 7.36 (s, 1H), 11.57 (br s, 2H, tautomere) |
| 95 | 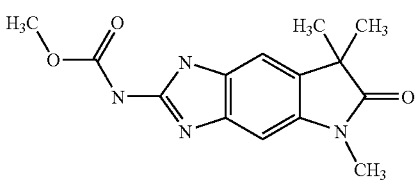 | | 3.1 | 289 | (DMSO) = 1.28 (s, 6H), 3.15 (s, 3H), 3.75 (s, 3H), 7.00 (s, 1H), 7.35 (s, 1H), 11.54 (br s, 2H, tautomere) |
| 96 | 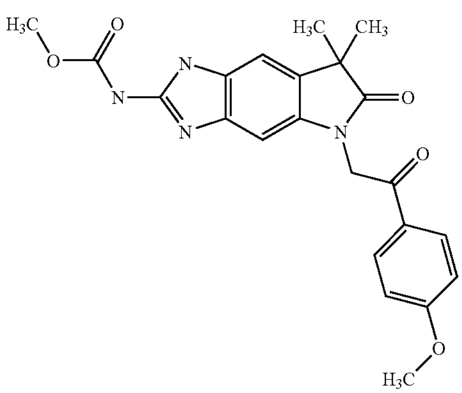 | | 2.55 | 423 | (DMSO) d = 1.35 (s, 6H), 3.71 (s, 3H), 3.87 (s, 3H), 5.25 (s, 2H), 6.87 (s, 1H), 7.09-7.13 (m, 2H), 7.38 (s, 1H), 8.05-8.10 (m, 2H) |

-continued

| # | Structure | MP [° C.] | Rt [min] | MS | NMR |
|---|---|---|---|---|---|
| 97 | 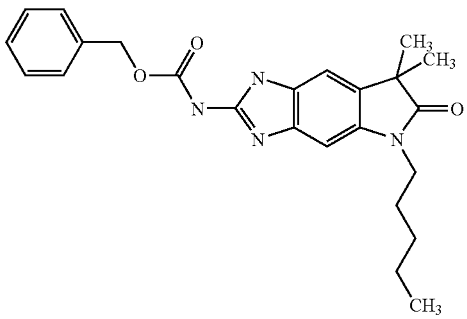 | 149.6-152.9 | 3.13 | 421 | (DMSO) = 0.81-0.88 (m, 3H), 1.22-.135 (m, 10H), 1.58-1.66 (m, 2H), 3.64-3.70 (m, 2H, 5.24 (s, 2H), 7.02 (s, 1H), 7.32-7.47 (m, 6H, 11.56 (br s, 2H, tautomere) |
| 98 | 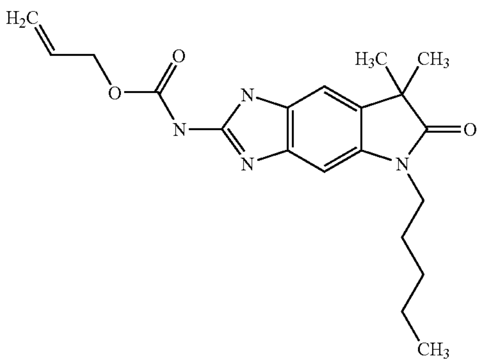 | Zers. ~180 | 2.93 | 371 | (DMSO) = 0.80-0.88 (m, 3H), 1.21-1.36(m, 10H), 1.57-1.67 (m, 2H, 3.64-3.71 (m, 2H, 4.65-4.73 (m, 2H), 5.23-5.30 (m, 1H), 5.35-5.43 (m, 1H), 5.95-6.06 (m, 1H), 7.03 (s, 1H, 7.36 (s, 11-1), 11.59 (br s, 2 H) |
| 99 | 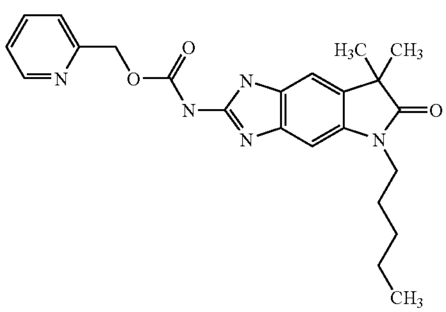 | 181.0-183.9 | 2.78 | 422 | (DMSO) = 0.81-0.88 (m, 3H), 1.21-1.34 (m, 10H), 1.57-1.67 (m, 2H), 3.63-3.71 (m, 2H), 5.29 (s, 2H), 7.02 (s, 1H), 7.32-7.38 (m, 2H), 7.46-7.50 (m, 1H), 7.81-7.89 (m, 1H), 8.54-8.60 (m, 1H), 11.64 (br s, 2H, tautomere) |
| 100 | 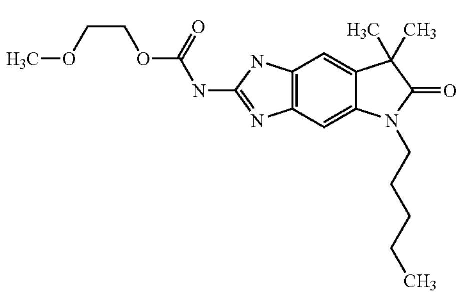 | 189.8-192.5 | 4.06 | 389 | (DMSO) = 0.81-0.89 (m, 3H), 1.20-1.37 (m, 10H), 1.57-1.67 (m, 2H), 3.57-3.62 (m, 2H), 3.64-3.71 (m, 2H), 4.26-4.33 (m, 2H, 7.02 (s, 1H), 7.35 (s, 1H), 11.51 (br s, 2H, tautomere) [one CH3-group hidden] |

-continued

| # | Structure | MP [° C.] | Rt [min] | MS | NMR |
|---|---|---|---|---|---|
| 101 | 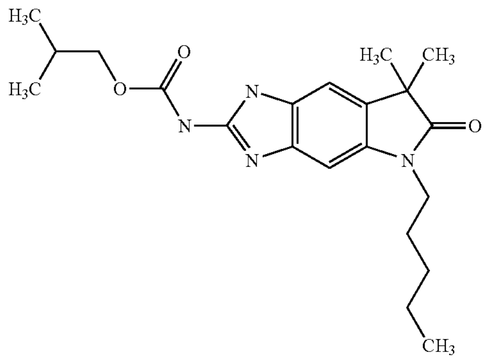 | 107.9-111.4 | 3.05 | 387 | (DMSO) 0.80-0.87 (m, 3H), 0.91-0.98 (m, 6H), 1.21-1.36 (m, 10H), 1.58-1.67 (m, 2H), 1.90-2.01 (m, 1H), 3.63-3.71 (m, 2H), 3.92-3.98 (m, 2H), 7.02 (s, 1H, 7.35 (s, 1H), 11.48 (br s, 2H, tautomere) |
| 102 | 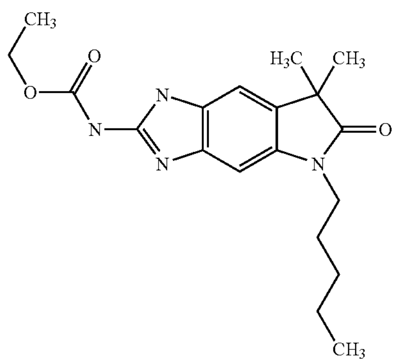 | 192.7-195.8 | 2.88 | 359 | (DMSO) = 0.81-0.88 (m, 3H), 1.22-1.36 (m, 13 H), 1.58-1.67 (m, 2H), 3.64-3.71 (m, 2H), 4.19-4.26 (m, 2H), 7.03 (s, 1H), 7.36 (s, 1H), 11.53 (br s, 2H, tautomere) |
| 103 | 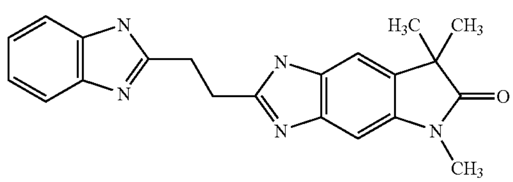 | | 2.51 | 360 | (DMSO) d = 1.29 (s, 6H), 3.16 (s, 3H), 3.35 (s, 4H), 6.95-7.56 (m, 6H), 12.30 (br s, NH) |
| 104 | 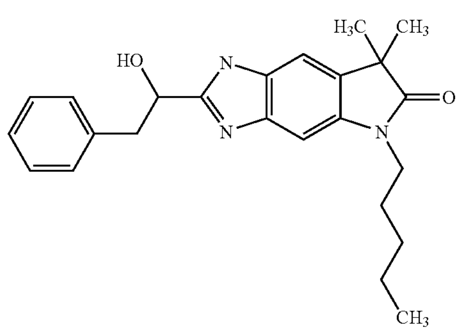 | | 3.39 | 392 | (DMSO) d = 0.86 (t, 3H), 1.21-1.39 (m, 10H), 1.59-1.69 (m, 2H), 3.15-3.45 (m, 2H), 3.71 (t, 2H), 4.95 (m, 1H), 7.05/7.44 (2 br s, 1H, tautomere), 7.13-7.30 (m, 5H), 7.97 (br s, 1H) |
| 105 | 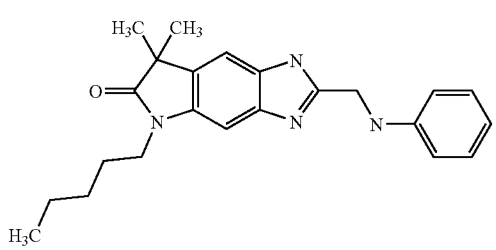 | | 3.51 | 377 | (DMSO) d = 0.85 (t, 3H), 1.20-1.38 (m, 10H), 1.61 (m, 2H), 3.70 (m, 2H), 4.44 (d, 2H), 6.21 (t, NH), 6.58 (t, 1H), 6.64 (d, 2H), 6.98/7.16 (2 br s, 1H, tautomere), 7.06 (t, 2H), 7.38/7.52 (2 br s, 1H, tautomere), 12.11/12.20 (2 br s, NH, tautomere) |

| # | Structure | MP [° C.] | Rt [min] | MS | NMR |
|---|---|---|---|---|---|
| 106 | 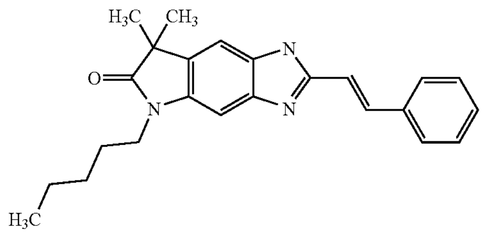 | | 3.73 | 374 | (DMSO) d = 0.85 (t, 3H), 1.30 (m, 10H), 1.65 (m, 2H), 3.74 (t, 2H), 7.10 (br s, 1H), 7.19 (d, 1H), 7.35 (t, 1H), 7.42 (t, 2H), 7.51 (br s, 1H), 7.59 (d, 1H), 7.66 (d, 2H) |
| 107 | 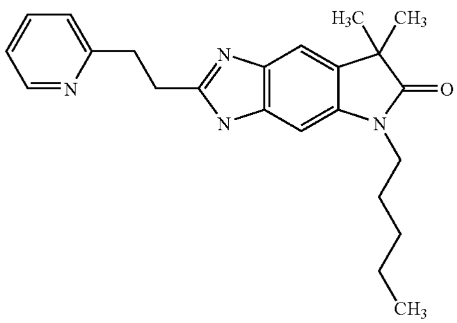 | | 2.98 | 377 | (DMSO) d = 0.85 (t, 3H), 1.30 (m, 10H), 1.62 (m, 2H), 3.22 (m, 2H), 3.70 (m, 2H), 6.98/7.11 (2 br s, 1H, tautomere), 7.20 (m, 1H), 7.30 (d, 1H), 7.38/7.49 (2 br s, 1H, tautomere), 7.69 (t, 1H), 8.50 (d, 1H), 12.10/12.15 (2 br s, NH, tautomere) |
| 108 | 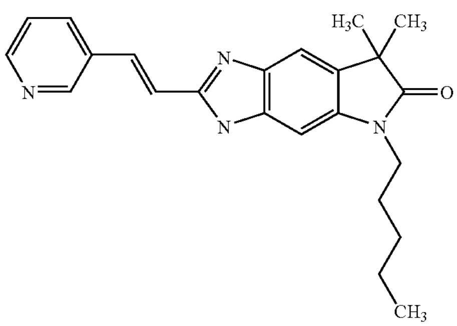 | | 3.26 | 375 | (DMSO) d = 0.86 (t, 3H), 1.30 (m, 10H), 1.65 (m, 2H), 3.74 (m, 2H), 7.00-7.70 (m, 5H), 8.12 (d, 1H), 8.53 (m, 1H), 8.82 (br s, 1H), 12.61 (br s, NH) |
| 109 | 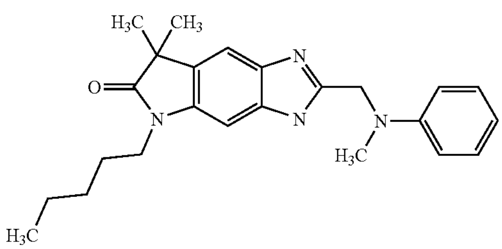 | | 4.09 | 391 | (DMSO) d = 0.84 (t, 3H), 1.29 (m, 10H), 1.62 (m, 2H), 3.10 (s, 3H), 3.69 (t, 2H), 4.68 (s, 2H), 6.64 (t, 1H), 6.80 (d, 2H), 7.05 (br s, 1H), 7.15 (m, 2H), 7.45 (br s, 1H), 12.19 (br s, NH) |
| 110 | 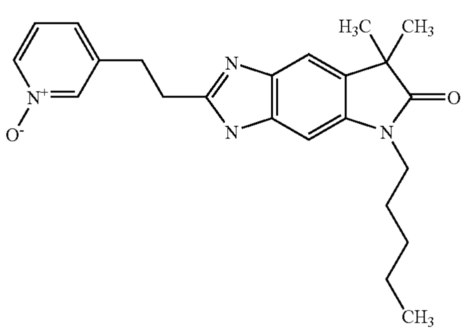 | | 3.47 | 393 | (DMSO) d = 0.85 (t, 3H), 1.29 (m, 10H), 3.10 (m, 4H), 3.70 (t, 2H), 7.07 (s, 1H), 7.23 (d, 1H), 7.30 (t, 1H), 7.45 (s, 1H), 8.04 (d, 1H), 8.17 (s, 1H), 11.95 (br s, NH) |

-continued

| # | Structure | MP [° C.] | Rt [min] | MS | NMR |
|---|---|---|---|---|---|
| 111 | 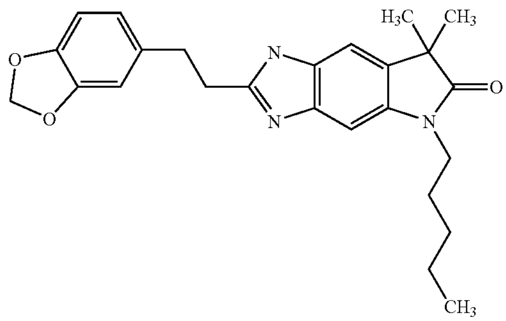 | | 2.68 | 420 | (DMSO) d = 0.80-0.89 (m, 3H), 1.20-1.35 (m, 10H), 1.56-1.67 (m, 2H), 2.96-3.07 (m, 4H), 3.64-3.77 (m, 2H), 5.95 (s, 2H), 6.66-6.73 (m, 1H), 6.76-6.81 (m, 1H), 6.84 (s, 1H), 7.04 (br s, 1H), 7.46 (br s, 1H), 12.13 (hr s, 1H) |
| 112 | 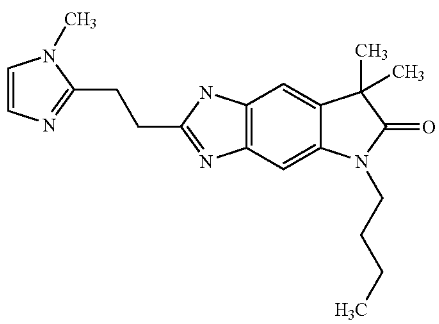 | | 1.44 | 366 | (DMSO) d = 0.90 (t, 3H, 1.30 (m, 8H), 1.61 (m, 2H), 3.11 (m, 2H), 3.20 (m, 2H), 3.59 (s, 3H), 3.71 (t, 2H), 6.75 (s, 1H), 7.00 (s, 1H), 7.06 (hr s, 1H), 7.43 (br s, 1H), 12.20 (br s, NH) |
| 113 | 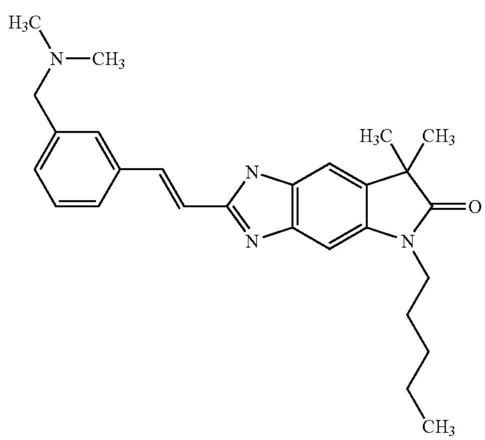 | | 2.91 | 431 | (DMSO) d = 0.86 (t, 3H), 1.30 (m, 10H), 1.65 (m, 2H), 2.19 (s, 6H), 3.45 (s, 2H), 3.72 (m, 2H), 7.02/7.17 (2 br s, 1H, tautomere), 7.19 (m, 1H), 7.28 (d, 1H), 7.39 (t, 1H), 7.47/7.61 (2 br s, 1H, tautomere), 7.55 (t, 1H), 12.49/12.51 (2 br s, NH, tautomere) |
| 114 | 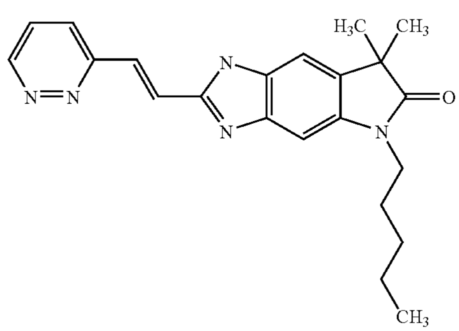 | | 3.76 | 376 | (DMSO) d = 0.86 (t, 3H), 1.30 (m, 10H), 1.64 (m, 2H), 3.73 (m, 2H), 7.54-7.85 (m, 5H), 8.10 (d, 1H), 9.15 (m, 1H), 12.83 (br s, NH) |

-continued

| # | Structure | MP [° C.] | Rt [min] | MS | NMR |
|---|---|---|---|---|---|
| 115 | 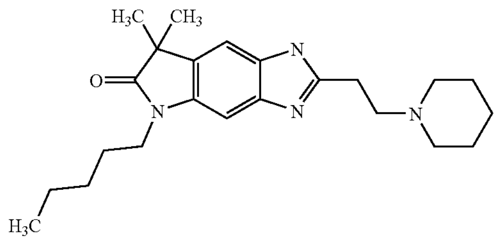 | | 2.81 | 383 | (DMSO) d = 0.85 (t, 3H), 1.29 (m, 4H), 1.35 (s, 6H), 1.52-1.68 (m, 4H), 1.82 (m, 4H), 3.25 (br s, 4H), 3.71 (s, 4H), 3.78 (t, 2H), 7.33 (s, 1H), 7.80 (s, 1H) |
| 116 | 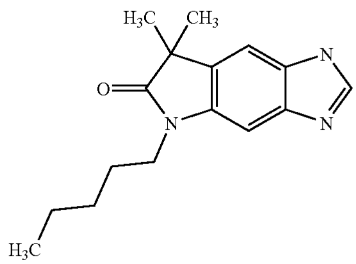 | | 2.42 | 272 | (DMSO) d = 0.77-0.91 (m, 3H), 1.19-1.41 (m, 10H), 1.56-1.68 (m, 2H), 3.65-3.79 (m, 2H), 7.10-7.21 (m, 1H), 7.55 (s, 1H), 8.07 (s, 1H), 12.36 (br s, 1H |
| 117 | 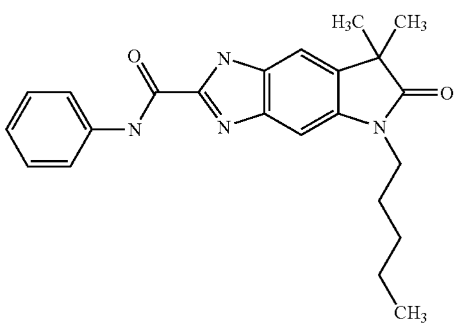 | | 5.09 | 391 | (DMSO) d = 0.86 (t, 3H), 1.21-1.39 (m, 10H), 1.66 (m, 2H), 3.76 (t, 2H), 7.03-7.16 (m, 2H), 7.29-7.40 (m, 3H), 7.90 (s, 1H), 7.93 (s, 1H), 10.68 (br s, NH), 13.38 (br s, NH) |
| 118 | 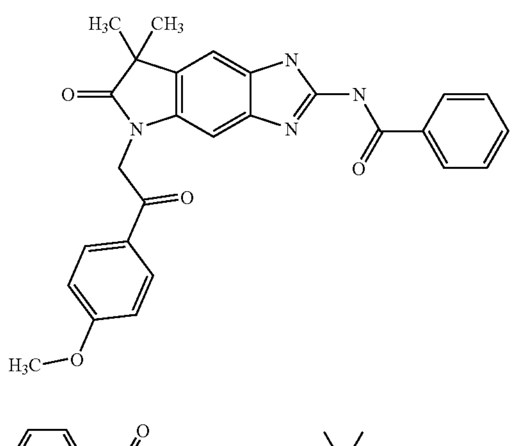 | | 2.85 | 469 | (DMSO) d = 1.38 (s, 6H), 3.88 (s, 3H), 5.29 (s, 2H), 6.97 (s, 1H), 7.09-7.16 (m, 2H), 7.46 (s, 1H), 7.49-7.56 (m, 2H), 7.57-7.65 (m, 1H), 8.06-8.15 (m, 4H), 12.16 (br s, 1H) |
| 119 | 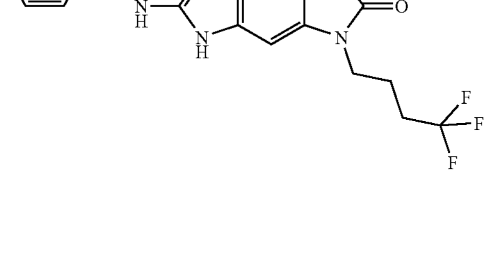 | | 3.67 | 431 | |

| # | Structure | MP [° C.] | Rt [min] | MS | NMR |
|---|---|---|---|---|---|
| 120 | 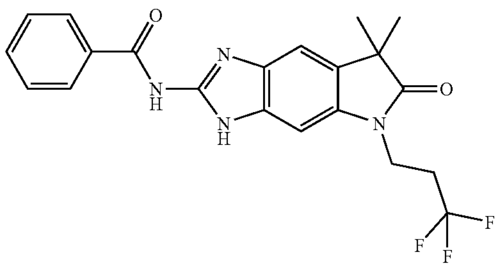 | | 3.57 | 417 | |
| 121 | 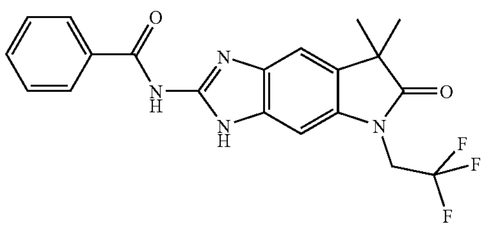 | | 3.59 | 403 | |
| 122 | 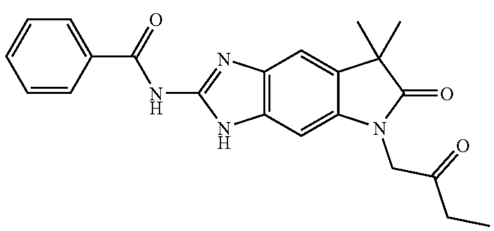 | | 3.35 | 391 | |
| 123 | 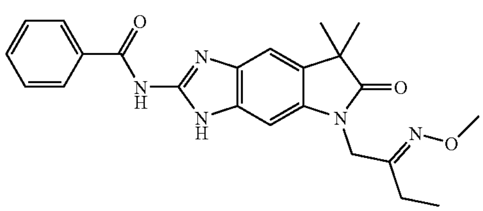 | | 3.55 | 420 | |
| 124 | Chiral | | 3.33 (18.23 min on Chiralpa kADH) | 393 | |
| 125 | Chiral | | 3.33 (26.85 min on Chiralpa kADH) | 393 | |

-continued

| # | Structure | MP [° C.] | Rt [min] | MS | NMR |
|---|---|---|---|---|---|
| 126 | 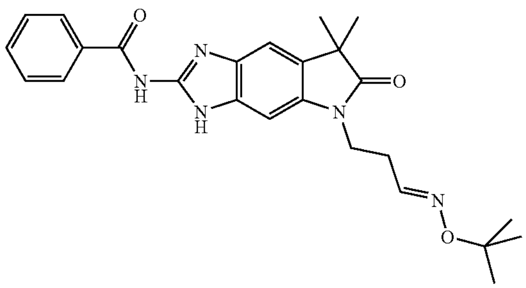 | | 3.62 | 448 | |
| 127 | 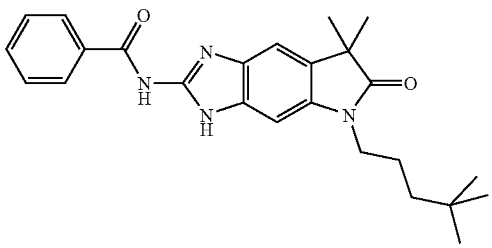 | | 3.85 | 419 | |
| 128 | 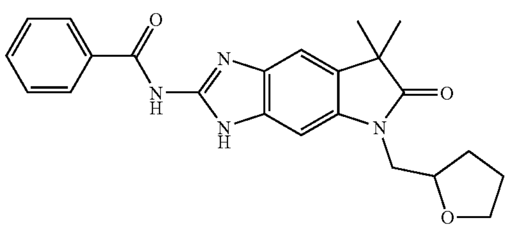 | | 3.21 | 405 | |
| 129 | 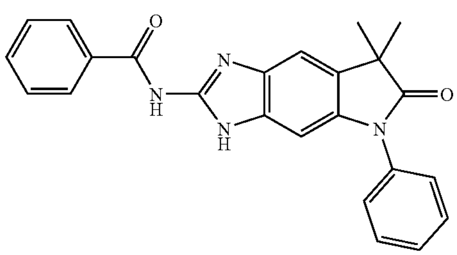 | | 3.63 | 397 | |
| 130 | 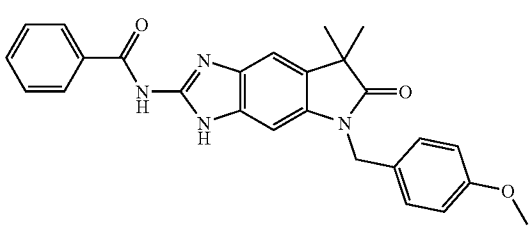 | | 3.60 | 441 | |
| 131 | 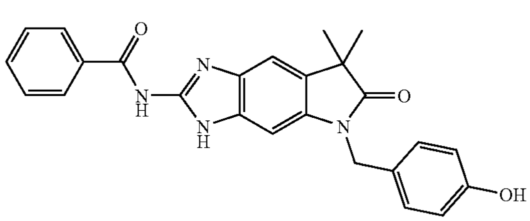 | | 3.35 | 427 | |

-continued

| # | Structure | MP [° C.] | Rt [min] | MS | NMR |
|---|---|---|---|---|---|
| 132 | 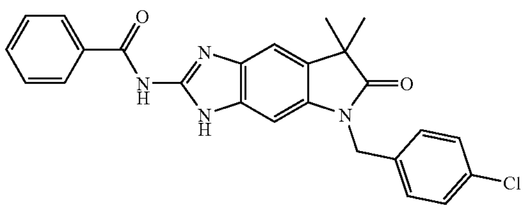 | | 3.80 | 445 | |
| 133 | 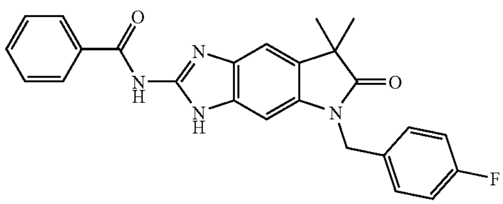 | | 3.61 | 429 | |
| 134 | 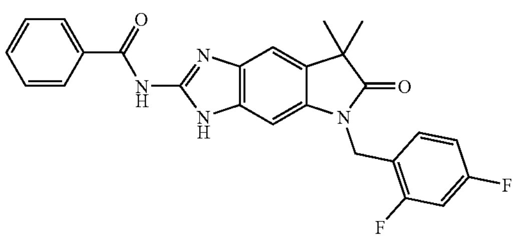 | | 3.70 | 447 | |
| 135 | 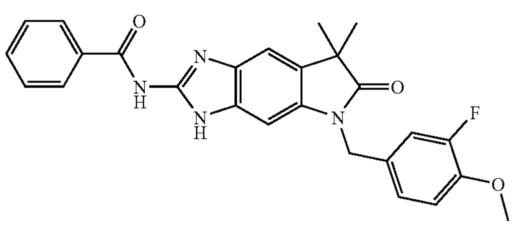 | | 3.40 | 459 | |
| 136 | 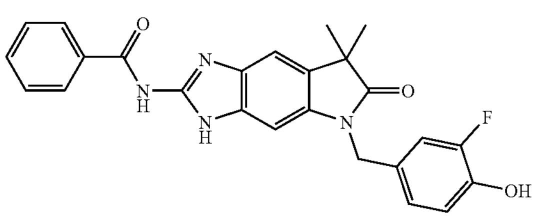 | | 3.23 | 445 | |
| 137 | 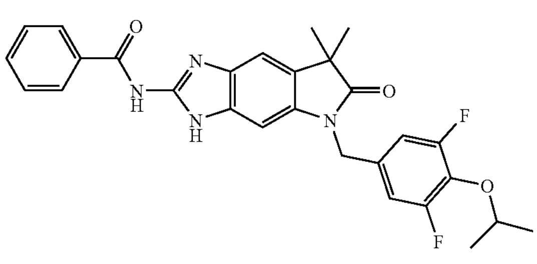 | | | 505 | |

-continued

| # | Structure | MP [° C.] | Rt [min] | MS | NMR |
|---|---|---|---|---|---|
| 138 | 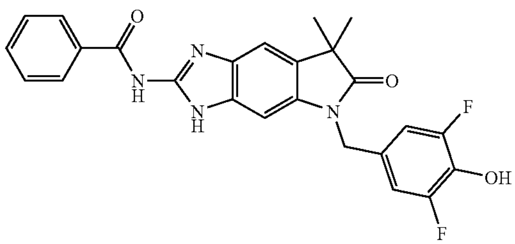 | | | 463 | |
| 139 | 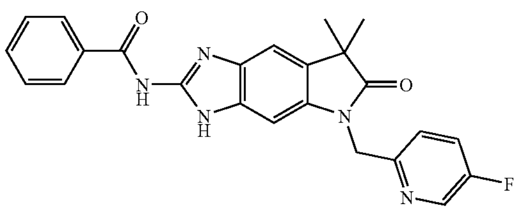 | | 3.36 | 430 | |
| 140 | 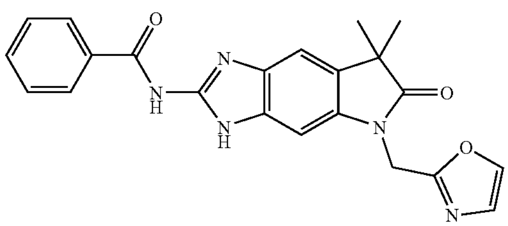 | | 3.15 | 402 | |
| 141 | 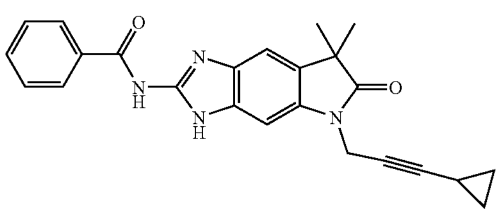 | | 3.62 | 399 | |
| 142 | 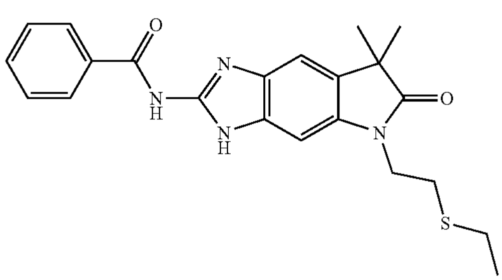 | | 3.37 | 409 | |
| 143 | 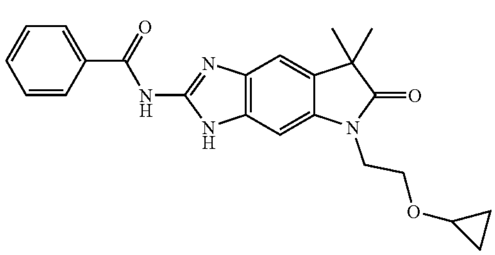 | | 3.37 | 405 | |

-continued

| # | Structure | MP [° C.] | Rt [min] | MS | NMR |
|---|---|---|---|---|---|
| 144 | 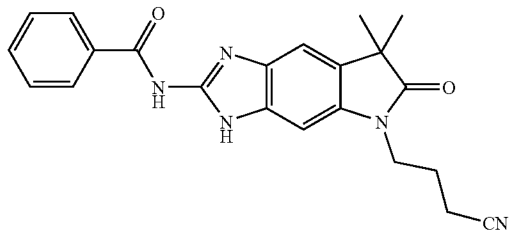 | | 3.23 | 388 | |

Synthesis of Building Blocks C

(C1) 5-Amino-3,3-dimethyl-6-nitro-1,3-dihydro-indol-2-one

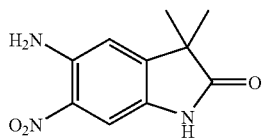

5-Amino-3,3-dimethyl-6-nitro-1,3-dihydro-indol-2-one (C1) is prepared from 4-aminoacetanilide as described in EP0161632A1.

Examples Starting from Building Block C

Example 145 a) N-(3,3-Dimethyl-6-nitro-2-oxo-2,3-dihydro-1H-indol-5-yl)-4-methoxy-benzamide

To a solution of C1 (3.1 g) and dry pyridine (3.5 ml; 42 mmol) in dry $CH_2Cl_2$ (75 ml) is added 4-methoxy-benzoyl chloride (2.63 g; 15.4 mmol) over a period of 2 min. After addition the mixture is stirred at RT for 20 h. $CHCl_3$ (200 ml) is added and the organic layer is washed with sodium hydroxide solution (0.5 N) and water, dried over $MgSO_4$ and concentrated in vacuo. The crude material is triturated with boiling EtOH and the precipitate is collected by filtration (3.73 g).

b) 5-Allyl-2-(4-methoxy-phenyl)-7,7-dimethyl-5,7-dihydro-1H-imidazo[4,5-f]indol-6-one A solution of N-(3,3-dimethyl-6-nitro-2-oxo-2,3-dihydro-1H-indol-5-yl)4-methoxy-benzamide (200 mg), allyl bromide (78 mg; 0.65 mmol) and $K_2CO_3$ (233 mg; 1.69 mmol) in acetone (3.2 ml) and N,N-dimethylformamide (1.6 ml) is stirred at 50° C. for 48 h. The mixture is filtered and concentrated in vacuo. The residue is suspended in acetic acid (3 ml), iron (150 mg; powder) is added and the resulting mixture is heated in a microwave apparatus at 150° C. for 900 s. After re-cooling the mixture is filtered and concentrated in vacuo. The desired compound is obtained by preparative RP-HPLC.

Examples 146-164 are prepared analogously from N-(3,3-dimethyl-6-nitro-2-oxo-2,3-dihydro-1H-indol-5-yl)-4-methoxy-benzamide and the corresponding alkyl halide as described in Example 145b.

Example 165

5-(2-Hydroxy-2-phenyl-ethyl)-2-(4-methoxy-phenyl)-7,7-dimethyl-5,7-dihydro-1H-imidazo[4,5-f]indol-6-one To a mixture of 2-(4-methoxy-phenyl)-7,7-dimethyl-5-(2-oxo-2-phenyl-ethyl)-5,7-dihydro-1H-imidazo[4,5-f]indol-6-one (33 mg) and trifluoroacetic acid (77 µl) is added dropwise $SiEt_3$ (30 µl) at RT for 48 h. The mixture is concentrated in vacuo and the residue is taken-up in MeOH (5 ml), $CH_2Cl_2$ (5 ml) and saturated $NaHCO_3$ solution. The resulting solution is stirred at RT for 30 min, neutralized with hydrochloric acid (1 N) and extracted with $CH_2Cl_2$. The organic layer is washed with water, dried over $MgSO_4$ and evaporated. The desired compound (15 mg) is obtained by preparative RP-HPLC, eluted with a water/MeCN gradient.

Example 166

2-(4-Methoxy-phenyl)-7,7-dimethyl-6-oxo-6,7-dihydro-1H-imidazo[4,5-f]indole-5-carboxylic acid propylamide A solution of N-(3,3-dimethyl-6-nitro-2-oxo-2,3-dihydro-1H-indol-5-yl)-4-methoxy-benzamide (200 mg) and propyl isocyanate (59 µl) in dry toluene (2 ml) is stirred in a microwave apparatus at 150° C. for 900 s. The resulting solid is collected by filtration, dissolved in acetic acid (3 ml) and iron (200 mg; powder) is added and the mixture is again stirred in a microwave apparatus at 150° C. for 900 s to achieve reduction of the nitro function and ring closure. The mixture is filtered and concentrated in vacuo. The desired compound (65 mg) is obtained by preparative RP-HPLC.

Example 167

2-(4-Methoxy-phenyl)-7,7-dimethyl-6-oxo-6,7-dihydro-1H-imidazo[4,5-f]indole-5-carboxylic acid phenylamide A solution of N-(3,3-dimethyl-6-nitro-2-oxo-2,3-dihydro-1H-indol-5-yl)-4-methoxy-benzamide (100 mg) and phenyl isocyanate (35 mg; 0.3 mmol) in dry toluene (2 ml) is stirred in a microwave apparatus at 150° C. for 900 s. The mixture is filtered and concentrated in vacuo. The residue is dissolved in acetic acid (2 ml), iron (115 mg; powder) is added and the mixture is again stirred in a microwave apparatus at 150° C. for 900 s to achieve reduction of the nitro function and ring closure. The mixture is filtered and concentrated in vacuo. The desired compound (26 mg) is obtained by preparative RP-HPLC.

Example 168

2-(4-Methoxy-phenyl)-7,7-dimethyl-6-oxo-6,7-dihydro-1H-imidazo [45-f]indole-5-carboxylic acid propyl ester A solution of N-(3,3-dimethyl-6-nitro-2-oxo-2,3-dihydro-1H-indol-5-yl)-4-methoxy-benzamide (50 mg), propyl chloroformate (18 µl) and NEt$_3$ (0.2 ml) in dry toluene (3 ml) is stirred in a microwave apparatus at 150° C. for 900 s. The mixture is filtered and concentrated in vacuo. The residue is dissolved in acetic acid (2.5 ml), iron (50 mg; powder) is added and the mixture is again stirred in a microwave apparatus at 150° C. for 900 s to achieve reduction of the nitro function and ring closure. The mixture is filtered and concentrated in vacuo. The desired compound (26 mg) is obtained by preparative RP-HPLC.

Example 169 a) 5-(4-Methoxy-benzoylamino)-3,3-dimethyl-6-nitro-2-oxo-2,3-dihydro-indole-1-carboxylic acid 4-nitro-phenyl ester A solution of N-(3,3-dimethyl-6-nitro-2-oxo-2,3-dihydro-1H-indol-5-yl)4-methoxy-benzamide (200 mg), 4-nitrophenyl chloroformate (166 mg; 0.83 mmol) and NEt$_3$ (0.2 ml) in dry toluene (3 ml) is stirred in a microwave apparatus at 150° C. for 800 s. The resulting precipitate is collected by filtration and washed with cold toluene. After drying under reduced pressure the compound (240 mg) is obtained.

b) 5-(4-Methoxy-benzoylamino)-3,3-dimethyl-6-nitro-2-oxo-2,3-dihydro-indole-1-carboxylic acid benzylamide To a solution of 5-(4-methoxy-benzoylamino)-3,3-dimethyl-6-nitro-2-oxo-2,3-dihydro-indole-1-carboxylic acid 4-nitro-phenyl ester (54 mg) in CH$_2$Cl$_2$ (10 ml) is added benzyl amine (44 µl) at RT. The reaction mixture is stirred at RT for 20 h. After an aqueous work-up and concentration in vacuo, the residue is dissolved in acetic acid (3 ml) and iron (60 mg; powder) is added. The mixture is stirred in a microwave apparatus at 150° C. for 900 s. After filtration and evaporation of the solvent the crude material is purified by preparative RP-HPLC.

Examples 145-169

| # | Structure | HPLC Rt [min] | MS | NMR |
|---|---|---|---|---|
| 145 | 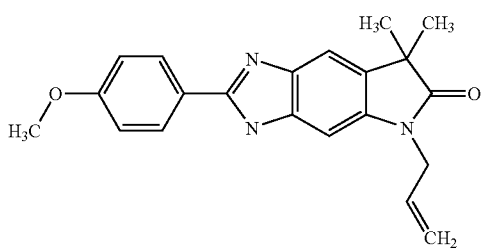 | 2.68 | 348 | (DMSO) d=1.37 (s, 6H), 3.83 (s, 3H), 4.37-4.39 (m, 2H), 5.15-5.22 (m, 2H), 5.85-5.94 (m, 1H), 6.99/7.02 (2s, 1H), 7.08-7.10 (m, 2H), 7.88/7.90 (2s, 1H), 8.05-8.07 (m, 2H), 12.66 (br, 1H). |
| 146 | 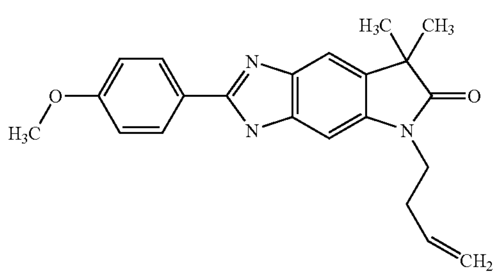 | 2.75 | 362 | (DMSO) d=1.32 (s, 6H), 2.40-2.45 (m, 2H), 3.80-3.85 (m, 5H), 4.95-5.02 (m, 2H), 5.75-5.86 (m, 1H), 7.09-7.11 (m, 2H), 7.22 (br, 1H), 7.50 (br, 1H), 8.05-8.08 (m, 2H), 12.66 (br, 1H). |
| 147 | 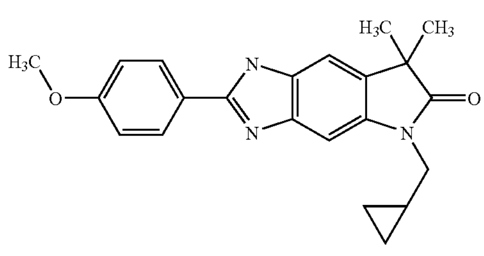 | 2.78 | 362 | (DMSO) d=0.34-0.38 (m, 2H), 0.46-0.50 (m, 2H), 1.16-1.25 (m, 1H), 1.33 (s, 6H), 3.64-3.69 (m, 2H), 3.85 (s, 3H), 7.09-7.13 (m, 2H), 7.22-7.69 (m, 2H), 8.06-8.11 (m, 2H). |

-continued

| # | Structure | HPLC Rt [min] | MS | NMR |
|---|---|---|---|---|
| 148 | 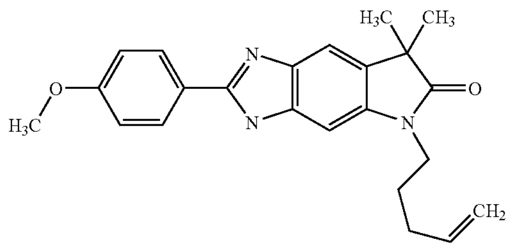 | 2.86 | 376 | (DMSO) d=1.33 (s, 6H, 1.70-1.80 (m, 2H), 2.05-2.11 (m, 2H) 3.73-3.78 (m, 2H), 3.84 (s, 3H), 4.90-5.67 (m, 2H) 5.81-5.92 (m, 1H), 7.02/7.24 (2br s, 1H), 7.09-7.11 (m, 2H, 7.43/7.59 (2br s, 1H), 8.05-8.08 (m, 2H), 12.65 (br, 1H). |
| 149 | 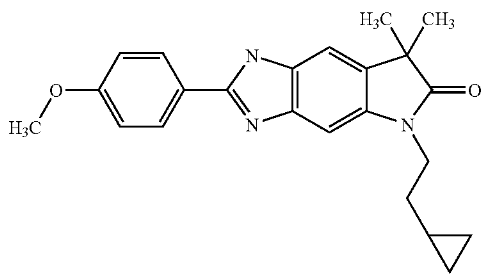 | 2.66 | 376 | (DMSO) d=0.00-0.04 (m, 2H), 0.31-0.40 (m, 2H), 0.65-0.76 (m, 1H), 1.32 (s, 6H), 1.50-1.60 (m, 2H), 3.75-3.89 (m, 5H), 6.92-7.35 (m, 3H), 7.35-7.69 (br s, 1H), 8.00-8.10 (m, 2H) |
| 150 | 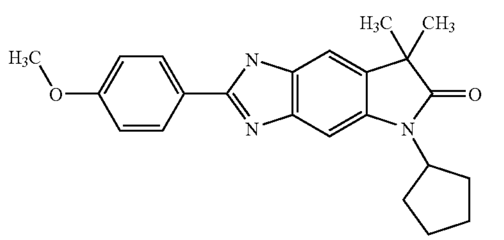 | 2.83 | 376 | n.d. |
| 151 | 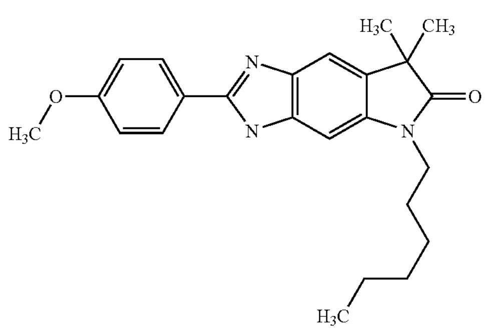 | 2.84 | 392 | (DMSO) d=0.79-0.88 (m, 3H), 1.21-1.37 (m, 12H), 1.59-1.70 (m, 2H), 3.69-3.78 (m, 2H), 3.85 (s, 3H), 7.08-7.18 (m, 3H), 7.54 (s, 1H), 8.04-8.10 (m, 2H) |
| 152 | 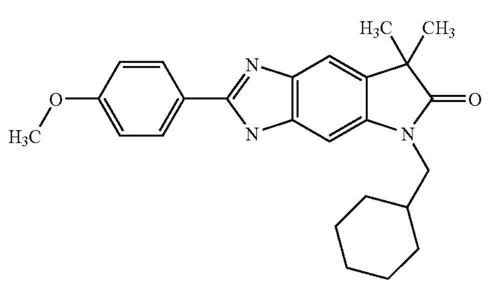 | 2.88 | 404 | (DMSO) d=1.08-1.10 (m, 2H), 1.10-1.21 (m, 3H), 1.32 (s, 6H), 1.54-1.72 (m, 5H), 1.78-1.90 (m, 1H), 3.53-3.61 (m, 2H), 3.81 (s, 3H), 6.93-7.31 (m, 3H), 7.35-7.67 (br s, 1H), 8.02-8.10 (m, 2H) |

-continued

| # | Structure | HPLC Rt [min] | MS | NMR |
|---|---|---|---|---|
| 153 | 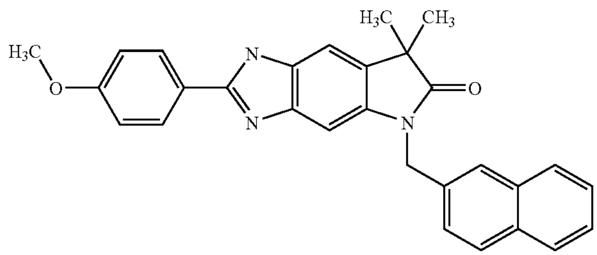 | 2.79 | 448 | (DMSO) d=1.43 (s, 6H), 3.81 (s, 3H), 5.15 (s, 2H), 6.79-7.14 (m, 3H), 7.39-7.45 (m, 1H), 7.45-7.66 (m, 3H), 7.82-7.94 (m, 4H), 7.95-8.02 (m, 2H), 12.31-12.82 (m, 1H) |
| 154 | 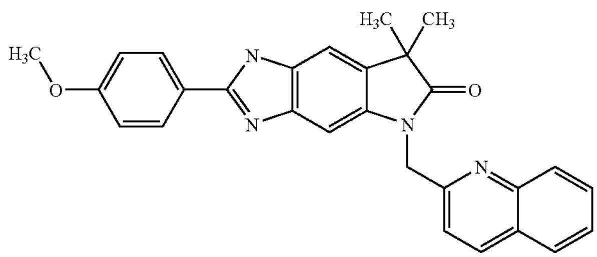 | 2.66 | 449 | (DMSO) d=1.46 (s, 6H), 3.80 (s, 3H), 5.25 (s, 2H), 6.79-7.10 (m, 3H), 7.33-7.40 (m, 1H), 7.43-7.68 (m, 2H), 7.72-7.80 (m, 1H), 7.91-8.04 (m, 4H), 8.21-8.37 (m, 1H), 12.41-12.71 (2br s, 1H) |
| 155 | 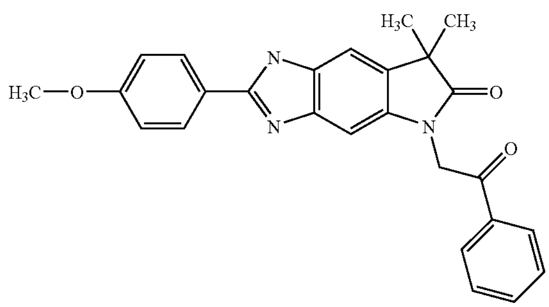 | 2.67 | 426 | |
| 156 | 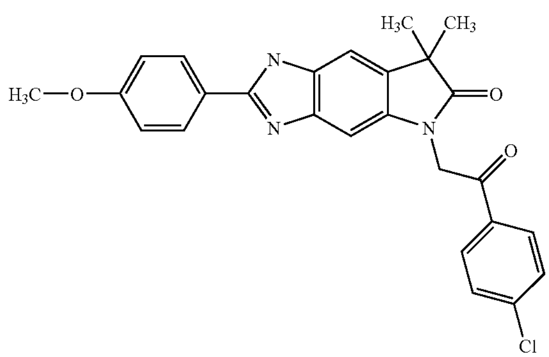 | 2.95 | 460 | (DMSO) d=1.39 (s, 6H), 3.82 (s, 3H), 5.38 (s, 2H), 6.94-7.20 (m, 3H), 7.47-7.62 (br s, 1H), 7.65-7.70 (m, 2H), 8.01-8.07(m, 2H), 8.00-8.14 (m, 2H) |
| 157 | 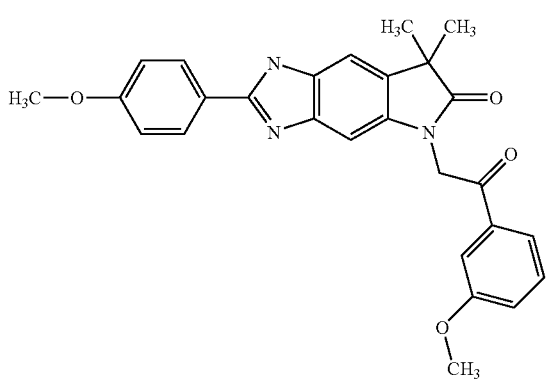 | 2.86 | 456 | (DMSO) d=1.39 (s, 6H), 3.83 (s, 3H), 3.85 (s, 3H), 5.37 (s, 2H), 6.90-7.20 (m, 3H), 7.27-7.32 (m, 1H), 7.41-7.66 (m, 3H), 7.68-7.74(m, 1H), 8.00-8,08 (m, 2H), 12.48-12.80 (2br s, 1H) |

-continued

| # | Structure | HPLC Rt [min] | MS | NMR |
|---|---|---|---|---|
| 158 | 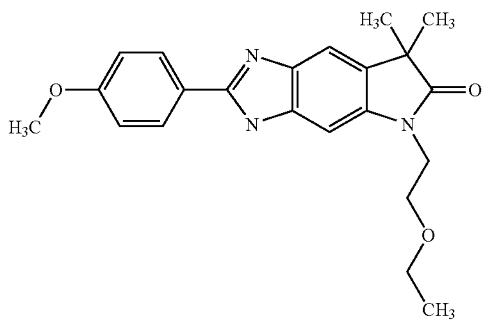 | 2.54 | 380 | |
| 159 | 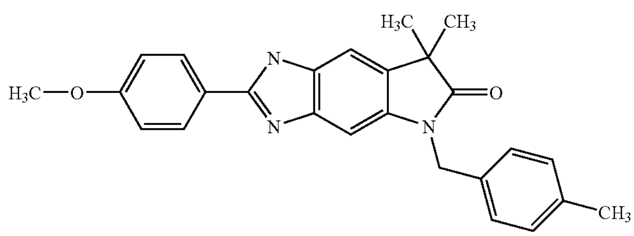 | 2.86 | 412 | |
| 160 | 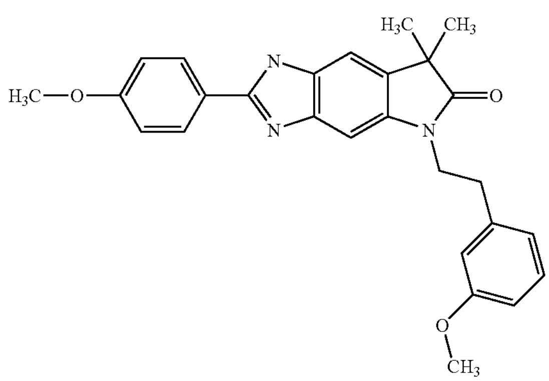 | 2.89 | 442 | |
| 161 | 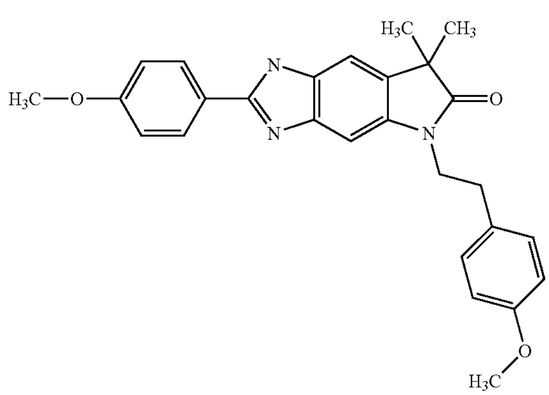 | 2.7 | 442 | |

-continued

| # | Structure | HPLC Rt [min] | MS | NMR |
|---|---|---|---|---|
| 162 | 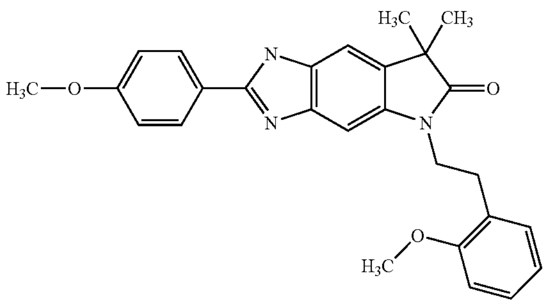 | 2.68 | 442 | |
| 163 | 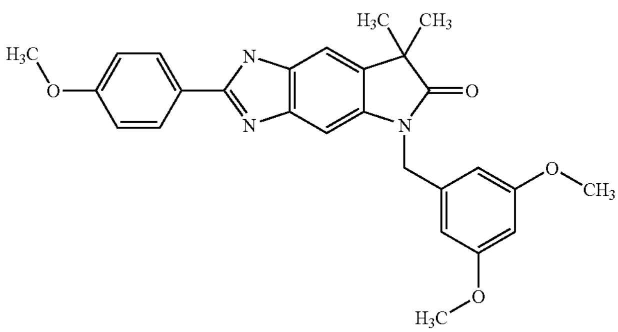 | 2.86 | 458 | |
| 164 | 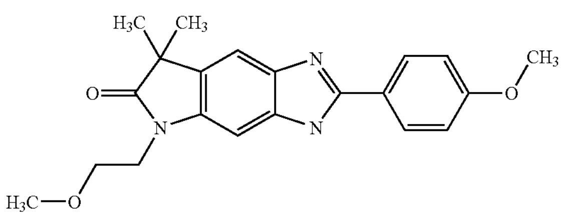 | 2.84 | 366 | (DMSO) d=1.32 (s, 6H), 3.25 (s, 3H), 3.57-3.63 (m, 2H), 3.84 (s, 3H), 3.88-3.95 (m, 2H), 7.08-7.10 (m, 2H), 7.15 (br s, 1H), 7.52 (br s, 1H), 8.03-8.10 (m, 2H), 12.65 (brs, 1H) |
| 165 | 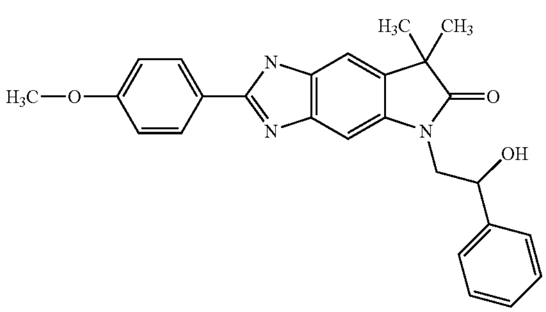 | 2.8 | 428 | |
| 166 | 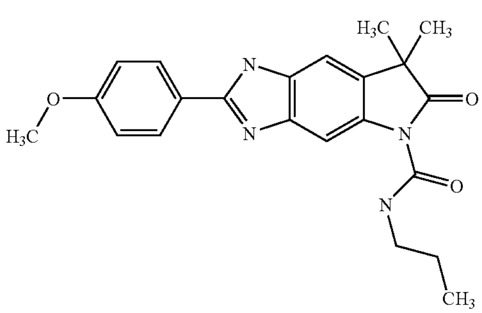 | 2.87 | 393 | (DMSO) d=0.88-0.99 (m, 3H), 1.43 (s, 6H), 1.51-1.66 (m, 2H), 3.24-3.34 (m, 2H), 3.84 (s, 3H), 7.05-7.16 (m, 2H), 7.43-7.74 (br s, 1H), 8.02-8.13 (m, 2H), 8.26 (s, 1H), 8.62-8.73 (m, 1H) |

| # | Structure | HPLC Rt [min] | MS | NMR |
|---|---|---|---|---|
| 167 | 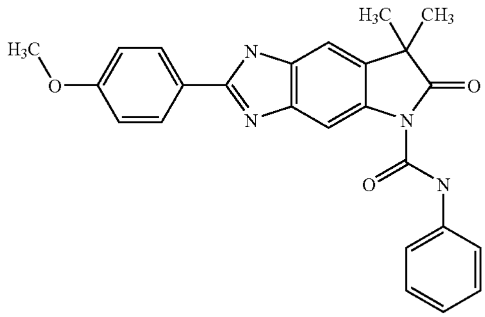 | 3.03 | 427 | (DMSO) d=1.50 (s, 6H), 3.84 (s, 3H), 7.08-7.14 (m, 2H), 7.14-7.19 (m, 1H), 7.38-7.44 (m, 2H), 7.53-7.76(m, 3H), 8.05-8.13 (m, 2H), 8.27 (s, 1H), 10.71 (s, 1H) |
| 168 | 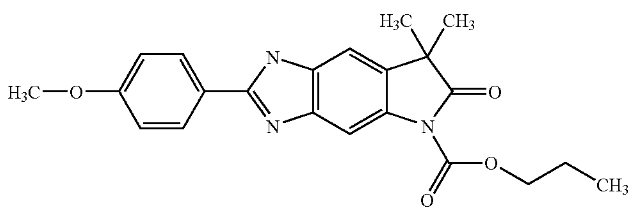 | 2.89 | 394 | (DMSO) d=0.99-1.05 (m, 3H), 1.42 (s, 6H), 1.72-1.81 (m, 2H), 3.84 (s, 3H), 4.29-4.35 (m, 2H), 7.08-7.13(m, 2H), 7.48-7.71 (br s, 1H), 7.95-8.03 (br s, 1H), 8.04-8.13(m, 2H), 12.55-12.95 (br s, 1H) |
| 169 | 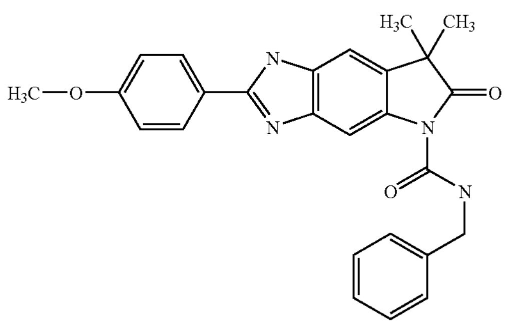 | 3 | 441 | (DMSO) d=1.44 (s, 6H), 3.84 (s, 3H), 4.51-4.57 (m, 2H), 7.08-7.13 (m, 2H), 7.25-7.30 (m, 1H), 7.34-7.43 (m, 4H), 7.51-7.69(br s, 1H), 8.05-8.10 (m, 2H), 8.27(s, 1H), 9.06-9.11 (m, 1H) |

General Procedure (III) for the Synthesis of Building Blocks D

To a solution of the corresponding building block B (1 mmol) in water (5-15 ml) and THF (2-10 ml) BrCN (3 M solution in CH$_2$Cl$_2$ or solid; 1.1-2.0 eq) is added at 0° C. The mixture is warmed to RT and stirred for 20 h. After completion the organic solvents are removed in vacuo, the residual aqueous phase is made alkaline (NaOH, K$_2$CO$_3$ or Na$_2$CO$_3$) and extracted three times with EtOAc (20 ml each). The combined organic phase is washed with saturated NaCl solution, dried over MgSO$_4$ and evaporated to give the 2-amino benzimidazole building block D. Purification is achieved by re-crystallization or by flash chromatography on silica gel eluting with a CH$_2$Cl$_2$/MeOH gradient.

(D1) 2-Amino-5,7,7-trimethyl-5,7-dihydro-1H-imidazo[4,5-f]indol-6-one

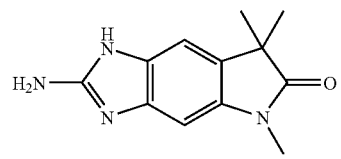

Analogously to general procedure (III) B5 (2.8 g) is cyclized using BrCN (1.5 g; 14.2 mmol) at RT in water (120 ml) and THF (60 ml). After aqueous work-up pure D1 (2.47 g) is obtained as a brownish solid.

(D2) 2'-Amino-5'-methyl-5,7-dihydro-1H-imidazo [4',5'-f]-spiro[cyclopropane-1,7'-indol]-6'-one

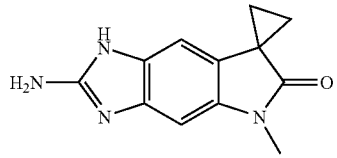

a) 1'-Methyl-5'-nitro-spiro[cyclopropane-1,3'-indoline]-2'-one

To a solution of 1'-methyl-spiro[cyclopropane-1,3'-indoline]-2'-one (8 g) in acetic acid (150 ml) is added nitric acid (fuming, 5.5 ml) over a period of 15 min at 15° C. The mixture is stirred at RT for 3 h and then poured into water. The precipitate is collected by filtration and washed with water, 2-propanol and tertbutyl-methyl-ether to give the title compound (8.80 g).

b) 5'-Amino-1'-methyl-spiro[cyclopropane-1,3'-indoline]-2'-one

1'-Methyl-5'-nitro-spiro[cyclopropane-1,3'-indoline]-2'-one (3 g) is dissolved in EtOAc (105 ml) and $SnCl_2 \cdot 2H_2O$ (9 g; 46.5 mmol) is added. The reaction mixture is refluxed overnight, cooled and filtered over $Al_2O_3$. After an aqueous work-up of the filtrate the compound (2.2 g) is obtained.

c) 2,2,2-Trifluoro-N-(1'-methyl-2'-oxo-spiro[cyclopropane-1,3'-indole]-5'-yl)-acetamide The crude 5'-amino-1'-methyl-spiro[cyclopropane-1,3'-indoline]-2'-one (2 g) and trifluoroacetic anhydride (2 g; 9.52 mmol) are dissolved in dry $CH_2Cl_2$ (30 ml). After addition of $NEt_3$ (2 g; 19.7 mmol) the mixture is stirred at RT for 25 min. After dilution with 0.1 N hydrochloric acid is the mixture extracted three times with $CH_2Cl_2$. The combined organic layer is washed subsequently with 0.1 N hydrochloric acid, water, saturated $K_2CO_3$ solution and brine, dried over $MgSO_4$ and evaporated to give the compound (3 g).

d) 2,2,2-Trifluoro-N-(1'-methyl-6'-nitro-2'-oxo-spiro [cyclopropane-1,3'-indole]-5'-yl)-acetamide To a solution of 2,2,2-trifluoro-N-(1'-methyl-2'-oxo-spiro [cyclopropane-1,3'-indole]-5'-yl)-acetamide (2 g) in acetic acid (20 ml) at 15° C. is added nitric acid (fuming, 0.8 ml) over a period of 3 min. The mixture is stirred at this temperature for 1 h and then diluted with water. The aqueous layer is extracted with EtOAc. The combined organic layer is washed with water, saturated $K_2CO_3$ solution and brine, dried over $MgSO_4$ and evaporated. The compound (2.25 g) is obtained as a brown semi-solid.

e) 5'-Amino-1'-methyl-6'-nitro-spiro[cyclopropane-1,3'-indoline]-2'-one 2,2,2-Trifluoro-N-(1'-methyl-6'-nitro-2'-oxo-spiro[cyclopropane-1,3'-indole]-5'-yl)-acetamide (2 g) is dissolved in MeOH (15 ml), DMF (10 ml) and water (6.1 ml). Freshly powdered $K_2CO_3$ (2.9 g; 21 mmol) is added and the reaction is stirred at 50° C. for 12 h. After completion of the reaction the mixture is poured into water and the precipitate is collected by filtration and washed with 2-propanol and tertbutylmethyl ether. The compound (1 g) is obtained as a red solid.

f) 5',6'-Diamino-1'-methyl-spiro[cyclopropane-1,3'-indol]-2'-one

Analogously to general procedure (II) the compound is prepared from 5'-amino-1'-methyl-6'-nitro-spiro[cyclopropane-1,3'-indoline]-2'-one (50 mg) in MeOH (10 ml) and hydrochloric acid (1 ml) using Pd/C (15.0 mg) as catalyst (3 h; 1 bar). After an aqueous work-up the compound is used without further purification.

g) 2'-Amino-5'-methyl-5,7-dihydro-1H-imidazo[4', 5'-f]-spiro[cyclo-propane-1,7'-indol]-6'-one (D2)

Analogously to general procedure (III) 5',6'-diamino-1'-methyl-spiro[cyclopropane-1,3'-indoline]-2'-one (28 mg) is cyclized using BrCN (16.1 mg; 152 μmol) at RT in water (1.5 ml) and THF (0.8 ml). After aqueous work-up the compound (27 mg; 118 μmol) is obtained as colorless foam.

(D3) 2-Amino-5-ethyl-7,7-dimethyl-5,7-dihydro-1H-imidazo[4,5-f]indol-6-one

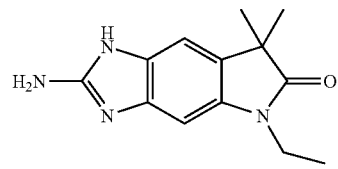

a) 5,6-Diamino-1-ethyl-3,3-dimethyl-1,3-dihydro-indol-2-one

Analogously to general procedure (II) the compound (1,3 g) is prepared from A2 (3.9 g) in MeOH (160 ml) using Pd/C (0.4 g) as a catalyst (12 h).

b) 2-Amino-5-ethyl-7,7-dimethyl-5,7-dihydro-1H-imidazo[4,5-f]indol-6-one (D3)

Analogously to general procedure (III) 5,6-diamino-1-ethyl-3,3-dimethyl-1,3-dihydro-indol-2-one (1.32 g) is cyclized using BrCN (3 M; 2.2 ml; 6.6 mmol) at RT in water (5 ml) and THF (13 ml). After aqueous work-up and recrystallization from EtOAc the desired compound (1.03 g) is obtained as a solid.

(D4) 2-Amino-7,7-dimethyl-5-propyl-5,7-dihydro-1H-imidazo[4,5-f]indol-6-one

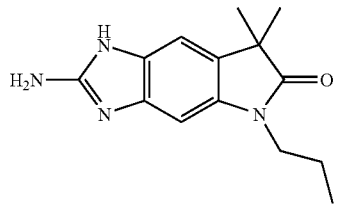

a) 5,6-Diamino-3,3-dimethyl-1-propyl-1,3-dihydro-indol-2-one

Analogously to general procedure (II) the compound (1.51 g) is prepared from A3 (1.7 g) in MeOH (40 ml) using Pd/C (0.20 g) as a catalyst (12 h).

b) 2-Amino-7,7-dimethyl-5-propyl-5,7-dihydro-1H-imidazo[4,5-f]indol-6-one (D4)

Analogously to general procedure (III) 5,6-diamino-3,3-dimethyl-1-propyl-1,3-dihydro-indol-2-one (1.52 g) is cyclized using BrCN (3 M; 2.4 ml; 7.2 mmol) at RT in water (5 ml) and THF (13 ml). After aqueous work-up and flash chromatography on silica gel eluting with $CH_2Cl_2$/MeOH (15:1) the desired compound (1.56 g) is obtained.

(D5) 2-Amino-7,7-dimethyl-5-pentyl-5,7-dihydro-1H-imidazo[4,5-f]indol-6-one

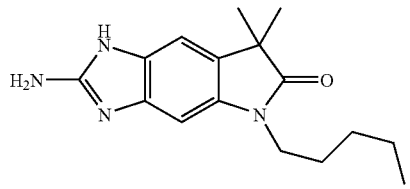

Analogously to general procedure (III) B3 (4.9 g) is cyclized using at RT BrCN (2.04 g; 19.2 mmol) in water (200 ml) and THF (100 ml). After aqueous work-up pure D5 (4,54 g) is obtained as a solid.

(D6) 2-Amino-1-isopropyl-7,7-dimethyl-5-pentyl-5,7-dihydro-1H-imidazo [4,5-f]indol-6-one

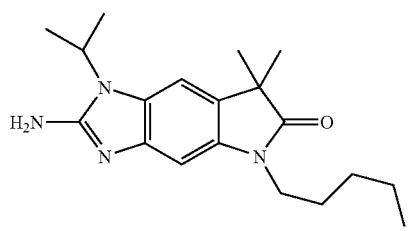

a) 5-Isopropylamino-3,3-dimethyl-6-nitro-1-pentyl-1,3-dihydro-indol-2-one

A8 (0.5 g) is alkylated using 2-iodopropane (0.5 ml; 5 mmol) and KOtBu (561 mg; 5 mmol) in N,N-dimethylformamide (7 ml) for 20 h at RT. After aqueous work-up and flash chromatography on silica gel eluting with $CH_2Cl_2$/MeOH (98:2) the compound (200 mg) is obtained.

b) 6-Amino-5-isopropylamino-3,3-dimethyl-1-pentyl-1,3-dihydro-indol-2-one

5-Isopropylamino-3,3-dimethyl-6-nitro-1-pentyl-1,3-dihydro-indol-2-one (200 mg) is dissolved in N,N-dimethylformamide (10 ml) and hydrogenated at RT at 3 bar for 12 h using Pd/C (10%; 0.1 g) as catalyst. After completion of the reaction the mixture is filtered and evaporated to give the compound (180 mg).

c) 2-Amino-1-isopropyl-7,7-dimethyl-5-pentyl-5,7-dihydro-1H-imidazo[4,5-f]indol-6-one Analogously to general procedure (III) 6-amino-5-isopropylamino-3,3-dimethyl-1-pentyl-1,3-dihydro-indol-2-one (180 mg) is cyclized using BrCN (3 M; 0.2 ml; 600 µmol) at RT in water (2.5 ml) and THF (1 ml). After aqueous work-up the desired compound (190 mg) is obtained.

(D7) 2-Amino-5-(3,3-dimethyl-2-oxo-butyl)-7,7-dimethyl-5,7-dihydro-3H-imidazo[4,5-f]indol-6-one

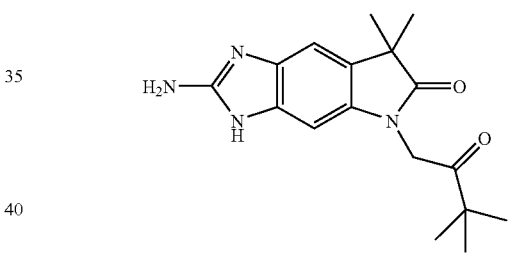

Analogously to the general procedure (III) B23 (0.63 g) is cyclized using at RT BrCN (0.24 g; 2.18 mmol) and THF/$H_2O$ (25/30 ml). After aqueous work-up D7 (0.61 g) is obtained and used without further purification.

(D8) 2-Amino-5-(2-cyclopropyl-ethyl)-7,7-dimethyl-5,7-dihydro-3H-imidazo[4,5-f]indol-6-one

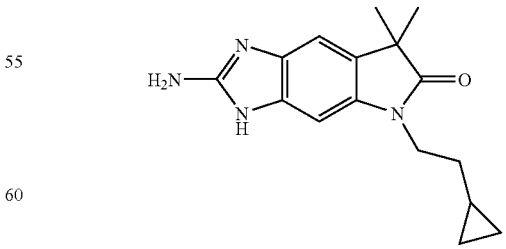

Analogously to general procedure (III) B24 (1.83 g) is cyclized using at RT BrCN (0.82 g; 7.76 mmol) and THF/$H_2O$ (30/60 ml). After aqueous work-up D8 (1.91 g) is obtained and used without further purification.

(D9) 2-Amino-5-(4-fluoro-2-methoxy-benzyl)-7,7-dimethyl-5,7-dihydro-3H-imidazo[4,5-f]indol-6-one

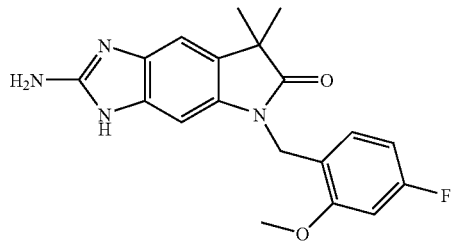

Analogously to the general procedure (III) B25 (1.53 g) is cyclized using at RT BrCN (0.50 g; 4.69 mmol) and THF/H$_2$O (10/20 ml). After aqueous work-up D9 (1,32 g) is obtained and used without further purification.

(D10) 2-Amino-5-(2,4-dimethyl-thiazol-5-ylmethyl)-7,7-dimethyl-5,7-dihydro-3H-imidazo[4,5-f]indol-6-one

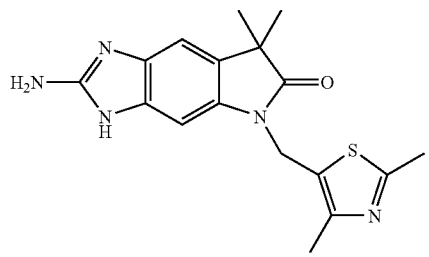

Analogously to general procedure (III) B26 (1.30 g) is cyclized using at RT BrCN )0.45 g; 4.10 mmol) and THF/H$_2$O (25/50 ml). After aqueous work-up D10 (0.93 g) is obtained and used without further purification.

(D11) 2-Amino-7,7-dimethyl-5-(3-methyl-isoxazol-5-ylmethyl)-5,7-dihydro-3H-imidazo[4,5-f]indol-6-one

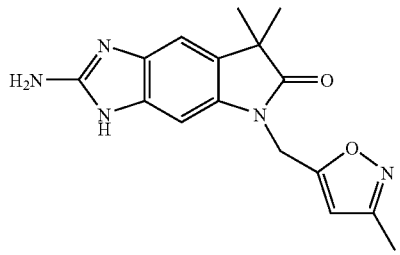

Analogously to general procedure (III) B27 (0.64 g) is cyclized using at RT BrCN (0.25 g; 2.29 mmol) and THF/H$_2$O (15/25 ml). After aqueous work-up D11 (0.75 g) is obtained and used without further purification.

(D12) 2-Amino-7,7-dimethyl-5-(3-phenyl-isoxazol-5-ylmethyl)-5,7-dihydro-3H-imidazo[4,5-f]indol-6-one

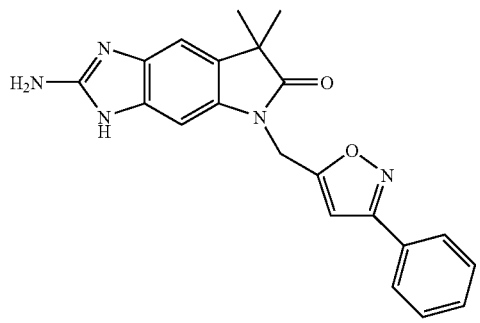

Analogously to general procedure (III) B28 (0.95 g) is cyclized using at RT BrCN (0.3 g; 2.75 mmol) and THF/H$_2$O (30/60 ml). After aqueous work-up D12 (1.05 g) is obtained and used without further purification.

(D13) 2-Amino-7,7-dimethyl-5-pent-2-ynyl-5,7-dihydro-3H-imidazo[4,5-f]indol-6-one

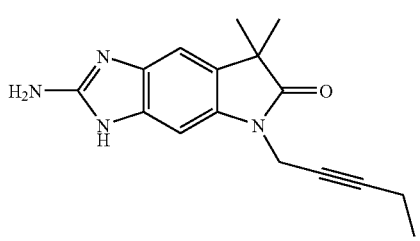

Analogously to the general procedure (III) B32 (0.45 g) is cyclized using at RT BrCN (0.19 g; 1.75 mmol) and THF/H$_2$O (30/20 ml). After aqueous work-up D13 (0.49 g) is obtained and used without further purification.

(D14) 2-Amino-7,7-dimethyl-5-pent-3-ynyl-5,7-dihydro-3H-imidazo[4,5-f]indol-6-one

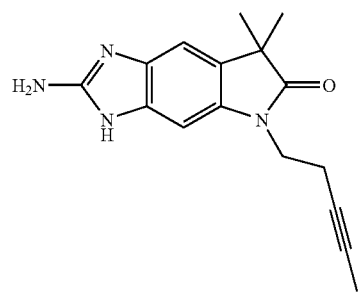

Analogously to general procedure (III) B33 (0.15 g) is cyclized using at RT BrCN (63.6 mg; 0.58 mmol) and THF/H$_2$O (6/9 ml). After aqueous work-up D14 (0.13 g) is obtained and used without further purification.

(D15) 2-Amino-7,7-dimethyl-5-prop-2-ynyl-5,7-dihydro-3H-imidazo[4,5-f]indol-6-one

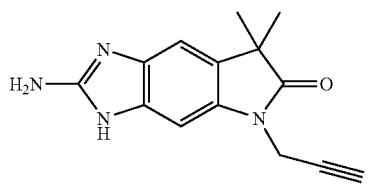

Analogously to the general procedure (III) B34 (3.31 g) is cyclized using at RT BrCN (1.73 g; 15.9 mmol) and THF/H$_2$O (70/140 ml). After aqueous work-up D15 (3.62 g) is obtained and used without further purification.

(D16) (rac)-2-Amino-7,7-dimethyl-5-(1-methyl-prop-2-ynyl)-5,7-dihydro-3H-imidazo[4,5-f]indol-6-one

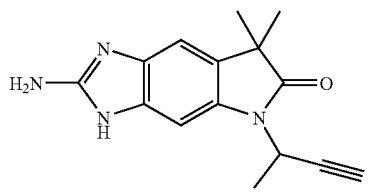

Analogously to general procedure (III) B35 (0.70 g) is cyclized using at RT BrCN (0.31 g; 2.73 mmol) and THF/H$_2$O (10/20 ml). After aqueous work-up D16 (0.57 g) is obtained and used without further purification.

(D17) 2-Amino-7,7-dimethyl-5-thiazol-4-ylmethyl-5,7-dihydro-3H-imidazo[4,5-f]indol-6-one

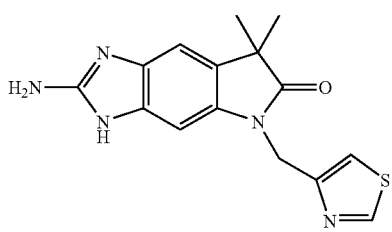

Analogously to general procedure (III) B36 (1.38 g) is cyclized using at RT BrCN (0.54 g; 4.95 mmol) and THF/H$_2$O (40/75 ml). After aqueous work-up D17 (1.42 g) is obtained and used without further purification.

(D18) [2-(2-Amino-7,7-dimethyl-6-oxo-6,7-dihydro-3H-imidazo[4,5-f]indol-5-ylmethyl)-phenyl]-carbamic acid tert-butyl ester

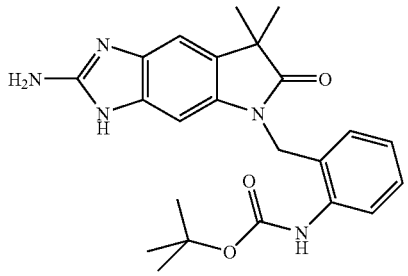

Analogously to general procedure (III) B38, 0.27 g) is cyclized using at RT BrCN (58 mg; 0.55 mmol), N,N-diisopropylethyl amine (90 µl; 0.51 mmol) and THF/H$_2$O (3/5 ml). After aqueous work-up and purification by RP chromatography D18 (26.5 mg) is obtained.

Examples Starting from Building Block D

Example 170

N-(5,7,7-Trimethyl-6-oxo-1,5,6,7-tetrahydro-imidazo[4,5-f]indol-2-yl)-benzamide

To a solution of D1 (210 mg) and DIPEA (4 ml; 23 mmol) in 1,4-dioxane (5.5 ml) is added benzoyl chloride (158 µl) at RT. The mixture is stirred for 20 h at RT and 2 h at 80° C. After completion of the reaction water is added and the aqueous layer is extracted with EtOAc. The combined organic layer is washed with saturated NaHCO$_3$ solution and brine, dried over MgSO$_4$ and concentrated in vacuo. Purification by flash chromatography on silica gel eluting with CH$_2$Cl$_2$/MeOH (98:2) afforded the desired compound (135 mg).

Examples 171-172 are Prepared Analogously from D1 as Described in Example 170

Example 173

N-(5'-methyl-6'-oxo-5,7-dihydro-1H-imidazo[4',5'-f]-spiro[cyclo-propane-1,7'-indol]-2-yl)-benzamide A solution of D2 (165 mg), benzoyl chloride (224 mg; 1.59 mmol) and NEt$_3$ (0.1 ml) in dry THF (1 ml) and dry CH$_2$Cl$_2$ (5 ml) is stirred under an inert atmosphere (Ar) at RT for 1 h. The mixture is concentrated in vacuo and the residue is dissolved in EtOAc (25 ml). The organic layer is washed with water, saturated NaHCO$_3$ and brine, dried over MgSO$_4$ and concentrated in vacuo. A product mixture is obtained containing the desired mono-acylated compound and the bis-acylated compound. Therefore the crude material is dissolved in EtOH (6 ml) and piperidine (2 ml) and stirred at RT for 2 h to cleave the labile benzoyl group of the undesired bis-acylated product. After an aqueous work-up the product is purified by preparative RP-HPLC to yield the desired compound (51 mg).

Example 174

N-(5-Ethyl-7,7-dimethyl-6-oxo-1,5,6,7-tetrahydro-imidazo[4,5-f]indol-2-yl)-benzamide A solution of D3 (500 mg) and benzoyl chloride (0.6 ml; 5.12 mmol) in pyridine (15 ml) is stirred at RT for 20 h. After completion, water is added and the aqueous layer is extracted with EtOAc. The combined organic layer is washed with hydrochloric acid (1 N), saturated NaHCO3 solution and brine, dried over $Na_2SO_4$ and concentrated in vacuo. Purification by flash chromatography on silica gel eluting with $CH_2Cl_2$/MeOH (30:1) afford the title compound (484 mg).

Example 175

N-(7,7-Dimethyl-6-oxo-5-propyl-1,5,6,7-tetrahydro-imidazo[4,5-f]indol-2-yl)-benzamide (399 mg) is prepared from D4 (500 mg) as described in Example 174.

Example 176

2-Bromo-N-(7,7-dimethyl-6-oxo-5-pentyl-1,5,6,7-tetrahydro-imidazo[4,5-f]indol-2-yl)-benzamide (136 mg) is prepared from D5 (211 mg) and 2-bromobenzoyl chloride (342 mg; 1.51 mmol) as described in Example 170.

Examples 179-180 are Prepared Analogously from D5 and the Freshly Prepared Corresponding Carboxylic Acid Chloride as Described in Example 170

Example 181

N-(7,7-Dimethyl-6-oxo-5-pentyl-1,5,6,7-tetrahydro-imidazo[4,5-f]indol-2-yl)-propionamide (37 mg) is prepared from D5 (100 mg) and propionyl chloride (71 mg; 0.77 mmol) as described in Example 173.

Example 182

N-(7,7-Dimethyl-6-oxo-5-pentyl-1,5,6,7-tetrahydro-imidazo[4,5-f]indol-2-yl)-benzamide A solution of D5 (100 mg) and benzoyl chloride (298 mg; 2.12 mmol) in pyridine (12 ml) is stirred at RT for 20 h and then at 80° C. for 2 h. After an aqueous work-up the desired compound is obtained by flash chromatography on silica gel eluted with EtOAc/MeOH (99.5:0.5).

Examples 183-186 are Prepared Analogously from D5 and the Corresponding Carboxylic Acid Chloride as Described in Example 182

Example 187

N-(7,7-Dimethyl-6-oxo-5-pentyl-1,5,6,7-tetrahydro-imidazo[4,5-f]indol-2-yl)-2-trifluoromethoxy-benzamide To a solution of D5 (849 mg), TBTU (987 mg; 3.07 mmol) and DIPEA (1 ml) in THF (25 ml) is added drop-wise a solution of 2-trifluoromethoxy-benzoic acid (737 mg; 3.58 mmol) in THF (5 ml) at 0° C. over a period of 15 min. The reaction mixture is warmed to RT and stirred for 20 h. After completion of the reaction the solution is filtered over Alox B and concentrated in vacuo. Purification by flash chromatography on silica gel eluting with cyclohexane/EtOAc yield the desired compound (736 mg).

Example 188 a) 7,7-Dimethyl-2-methylamino-5-pentyl-5,7-dihydro-1H-imidazo[4,5-f]indol-6-one

Freshly cut sodium (300 mg) is dissolved in dry MeOH (12 ml) and D5 (700 mg) is added and the mixture stirred for 5 min. Then p-formaldehyde (102 mg; 3.4 mmol) is added and the mixture stirred for 20 h at RT. After the addition of NaBH4 (93 mg; 2.46 mmol) the solution is heated under reflux for 2 h, cooled to RT and diluted with water. The aqueous layer is extracted with EtOAc. The combined organic layer is washed with brine, dried over $Na_2SO_4$ and concentrated in vacuo. The compound (700 mg) is obtained by flash chromatography on silica gel eluted with $CH_2Cl_2$/MeOH (95:5).

b) 7,7-Dimethyl-2-methylamino-5-pentyl-1-(toluene-4-sulfonyl)-5,7-dihydro-1H-imidazo[4,5-f]indol-6-one To a solution of 7,7-dimethyl-2-methylamino-5-pentyl-5,7-dihydro-1H-imidazo[4,5-f]indol-6-one (230 mg) in pyridine (6 ml) is added 4-methyl-benzenesulfonyl chloride (160 mg; 0.84 mmol) at 0° C. After addition the mixture is warmed to RT and stirred for 48 h. The reaction solution is dissolved with water and the aqueous layer is extracted with EtOAc. The combined organic layer is washed with hydrochloric acid (0.5 N) and brine, dried over $Na_2SO_4$ and concentrated in vacuo. The compound (135 mg) is obtained by flash chromatography on silica gel eluting with $CH_2Cl_2$/MeOH (40:1).

c) N-(7,7-Dimethyl-6-oxo-5-pentyl-1,5,6,7-tetrahydro-imidazo[4,5-f]indol-2-yl)-N-methyl-benzamide To a solution of 7,7-dimethyl-2-methylamino-5-pentyl-1-(toluene-4-sulfonyl)-5,7-dihydro-1H-imidazo[4,5-f]indol-6-one (120 mg) in pyridine (5 ml) is added drop-wise benzoyl chloride (0.1 ml; 0.79 mmol) at 0° C. After addition the mixture is heated at 130° C. for 5 h. An aqueous work-up and purification by flash chromatography on silica gel eluting with $CH_2Cl_2$/MeOH (40:1) yield the desired compound (38 mg).

Example 189

2-Amino-7,7-dimethyl-5-pentyl-1-(2-trifluoromethyl-benzoyl)-5,7-dihydro-1H-imidazo[4,5-f]indol-6-one (163 mg) is prepared from D5 (214 mg) as described in Example 170. After purification by flash chromatography on silica gel eluting with $CH_2Cl_2$/MeOH (99:1) the desired compound is obtained.

Example 190

1-(7,7-Dimethyl-6-oxo-5-pentyl-1,5,6,7-tetrahydro-imidazo[4,5-f]indol-2-yl)-3-phenyl-urea A solution of D5 (172 mg) and phenyl isocyanate (72 mg; 0.6 mmol) in acetone (3 ml) is stirred at RT for 3 days. Acetone is evaporated and the residue is purified by flash

Example 191

N-(1-Isopropyl-7,7-dimethyl-6-oxo-5-pentyl-1,5,6,7-tetrahydro-imidazo[4,5-f]indol-2-yl)-benzamide The compound (170 mg) is prepared from D6 (190 mg) and benzoyl chloride (0.2 ml; 1.60 mmol) as described in Example 174.

Example 192

N-[5-(3,3-Dimethyl-2-oxo-butyl)-7,7-dimethyl-6-oxo-3,5,6,7-tetrahydro-imidazo[4,5-f]indol-2-yl]-benzamide A solution of benzoic acid (85.5 mg), TBTU (225 mg; 0.70 mmol) and DIPEA (240 µl) in N,N-dimethylformamide (8 ml) is stirred at RT for 5 min. Afterwards D7 (210 mg) is added and the mixture is stirred at RT for 18 h. After evaporation of the solvent the crude material is purified by RP-MPLC eluted with MeCN/water to give the desired compound (186 mg).

Examples 193-201 are Prepared Similar to Example 192 Starting from the Suitable Building Block D and Benzoic Acid or A Substituted Benzoic Acid

Example 202 a) (2-{7,7-Dimethyl-6-oxo-2-[(pyridine-3-carbonyl)-amino]-6,7-dihydro-3H-imidazo[4,5-f]indol-5-ylmethyl}-phenyl)-carbamic acid tert-butyl ester A solution of nicotinic acid (11.8 mg; 0.09 mmol), TBTU (28.1 mg; 0.09 mmol) and DIPEA (33 µl) in N,N-dimethylformamide (600 µl) is stirred at RT for 5 min. Afterwards D18 (26.5 mg) is added and the mixture is stirred at RT for 18 h. After evaporation of the solvent the crude material is used without further purification.

b) N-[5-(2-Amino-benzyl)-7,7-dimethyl-6-oxo-3,5,6,7-tetrahydro-imidazo[4,5-f]indol-2-yl]-nicotinamide (2-{7,7-Dimethyl-6-oxo-2-[(pyridine-3-carbonyl)-amino]-6,7-dihydro-3H-imidazo[4,5-f]indol-5-ylmethyl}-phenyl)-carbamic acid tert-butyl ester (33.2 mg) is dissolved in $CH_2Cl_2$ (4 ml) and TFA (1.5 ml). The mixture is stirred at RT for 0.5 h. Saturated $K_2CO_3$ solution is added and the aqueous layer is extracted with $CH_2Cl_2$. The organic layer is dried over $MgSO_4$, evaporated to dryness and the residue is purified by RP-HPLC, eluted with MeCN/water to give the desired product (4,5 mg).

Example 203

N-[5-(2-Cyclopropyl-ethyl)-7,7-dimethyl-6-oxo-3,5,6,7-tetrahydro-imidazo[4,5-f]indol-2-yl]-benzamide A solution of D8 (120 mg), benzoic acid chloride (87 µl), $NEt_3$ (150 µl) in THF (1 ml) and $CH_2Cl_2$ (3 ml) is stirred at RT for 3 h. After evaporation EtOAc is added and the organic phase is washed with saturated $NaHCO_3$ solution and brine, dried over $MgSO_4$ and evaporated again. The residue is purified by preparative RP-HPLC to give the desired compound (13.4 mg).

Example 204 a) N-[5-(4-Fluoro-2-methoxy-benzyl)-7,7-dimethyl-6-oxo-3,5,6,7-tetrahydro-imidazo[4,5-f]indol-2-yl]-3-methyl-benzamide To a solution of 3-methyl-benzoyl chloride (62 mg) in THF (2 ml) is added D9 (35.4 mg) and DIPEA (30 µl). The reaction mixture is stirred at 50° C. for 12 h. Afterwards MeOH (1 ml) and piperidine (100 µl) are added. After shaking for 2 h the mixture is evaporated to dryness and purified by preparative RP-HPLC, eluted with MeCN/water to give the desired product (5 mg).

b) N-[5-(4-Fluoro-2-hyroxy-benzyl)-7,7-dimethyl-6-oxo-3,5,6,7-tetrahydro-imidazo[4,5-f]indol-2-yl]-3-methyl-benzamide N-[5-(4-Fluoro-2-methoxy-benzyl)-7,7-dimethyl-6-oxo-3,5,6,7-tetrahydro-imidazo[4,5-f]indol-2-yl]-3-methyl-benzamide (5 mg) is suspended in a $BBr_3$ solution in $CH_2Cl_2$ (1 M; 33 µl) and stirred at RT for 10 h. After addition of hydrochloric acid (200 µl; 1 N) the mixture is stirred at RT for another 1 h and then evaporated to dryness. The crude material is purified by preparative RP-HPLC eluted with MeCN/water to yield the desired compound (3.2 mg).

Examples 170-204

| # | Structure | HPLC Rt [min] | MS [M + H] | NMR |
|---|-----------|---------------|------------|-----|
| 170 | 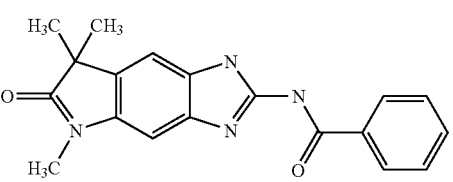 | 2.51 | 335 | (DMSO) d=1.31 (s, 6H), 3.18 (s, 3H) 7.06 (s, 1H), 7.42 (s, 1H), 7.52-7.55 (m, 2H), 7.59-7.63 (m, 1H), 8.13-8.15 (m, 2H), 12.20 (br s, 2H), |

| # | Structure | HPLC Rt [min] | MS [M + H] | NMR |
|---|---|---|---|---|
| 171 | 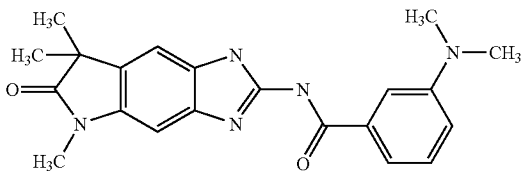 | 2.76 | 378 | (CDCl3) d=1.29 (s, 6H), 2.87 (s, 6H), 3.08 (br s, 3H), 5.94/6.29 (2 br s, 1H), 6.75/7.12 (2 br s, 1H, 6.90-6.93 (m, 1H), 7.28-7.33 (m, 1H), 7.41 (s, 1H), 7.44-7.47 (m, 1H), 11.68/13.77 (2 brs, 1H) |
| 172 | 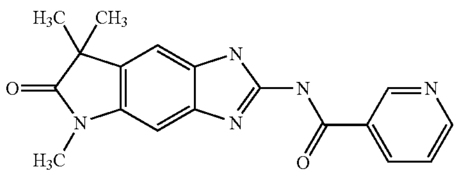 | 3.81 | 336 | (DMSO) d=1.31 (s, 6H), 3.18 (s, 3H), 7.07 (s, 1H), 7.43 (s, 1H), 7.54-7.58 (m, 1H), 8.44-8.47 (m, 1H), 8.73-8.76 (m, 1H), 9.26-9.28 (m, 1H), 11.64-12.50 (br s, 1H) [1 NH not visible] |
| 173 | 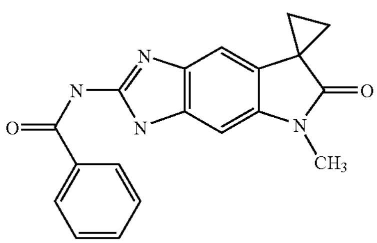 | 2.48 | 333 | (DMSO) d=1,48-1.61 (m, 4H), 3.25 (s, 3H), 7.07-7.16 (m, 2H), 7.49-7.66 (m, 3H), 8.09-8.17 (m, 2H) |
| 174 | 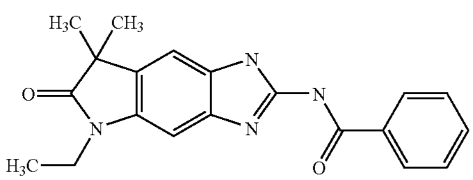 | 3.49 | 349 | (DMSO) d=1.19 (t, 3H), 1.30 (s, 6H), 3.73 (q, 2H), 7.10 (s, 1H), 7.42 (s, 1H), 7.52 (t, 2H), 7.61 (t, 1H), 8.14 (d, 2H), 12.19 (brs, NH) |
| 175 | 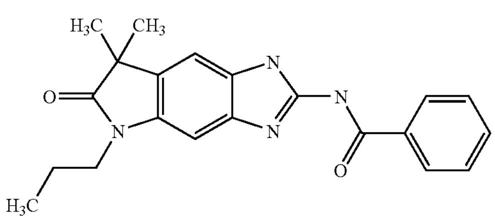 | 3.69 | 363 | (DMSO) d=0.89 (t, 3H), 1.30 (s, 6H), 1.68 (m, 2H), 3.69 (t, 2H), 7.10 (s, 1H), 7.42 (s, 1H), 7.53 (t, 2H), 7.61 (t, 1H), 8.13 (d, 2H), 12.18 (br s, NH) |
| 176 | 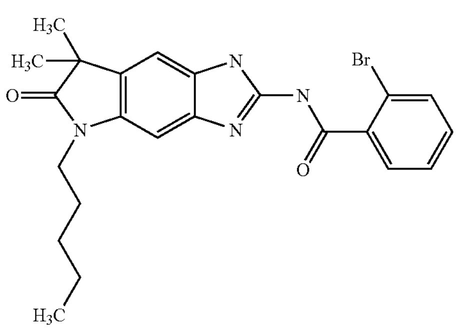 | 3.22 | 469/471 | (DMSO) d=0.83-0.88 (m, 3H), 1.26-1.35 (m, 10H), 1.59-1.68 (m, 2H), 3.67-3.72 (m, 2H), 7.11 (s, 1H), 7.43 (s, 1H), 7.44-7.53 (m, 2H), 7.60-7.64 (m, 1H), 7.70-7.75 (m, 1H), 12.17 (s, 1H) |

| # | Structure | HPLC Rt [min] | MS [M + H] | NMR |
|---|---|---|---|---|
| 177 | 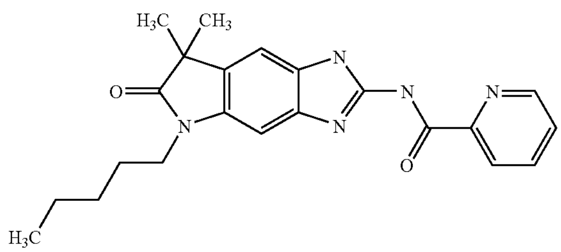 | 4.06 | 392 | (DMSO) d=0.86 (t, 3H), 1.29 (m, 10H), 1.65 (m, 2H), 3.70 (t, 2H), 7.12 (s, 1H), 7.48 (s, 1H), 7.72 (m, 1H), 8.11 (m, 1H), 8.22 (d, 1H), 8.78 (m, 1H) |
| 178 | 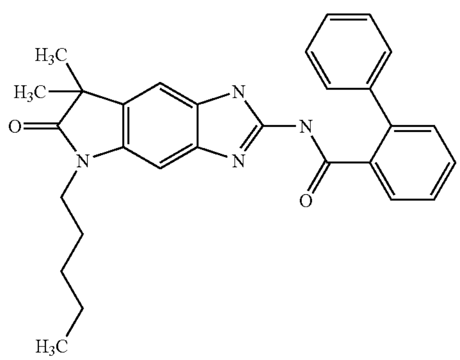 | 3.27 | 467 | (DMSO) d=0.77-0.92 (m, 3H), 1.19-1.39 (m, 10H), 1.50-1.67 (m, 2H), 3.58-3.73 (m, 2H), 6.88-7.07 (m, 1H), 7.22-7.34 (m, 2H), 7.34-7.40 (m, 2H), 7.39-7.45 (m, 2H), 7.45-7.55 (m, 2H), 7.56-7.62 (m, 1H), 7.62-7.67 (m, 1H), 11.85-12.15 (m, 2H) |
| 179 | 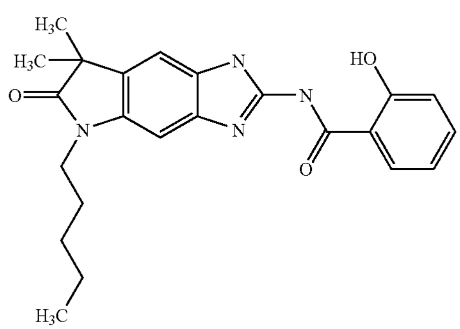 | 3.23 | 407 | (DMSO) d=0.80-0.90 (m, 3H), 1.20-1.39 (m, 10H), 1.56-1.68 (m, 2H), 3.63-3.76 (m, 2H), 6.82-6.90 (m, 2H), 7.09-7.13 (s, 1H), 7.32-7.39 (m, 1H), 7.44 (s, 1H), 7.92-8.02 (m, 1H), 11.70-14.65 (br m, 2H) [OH not visible] |
| 180 | 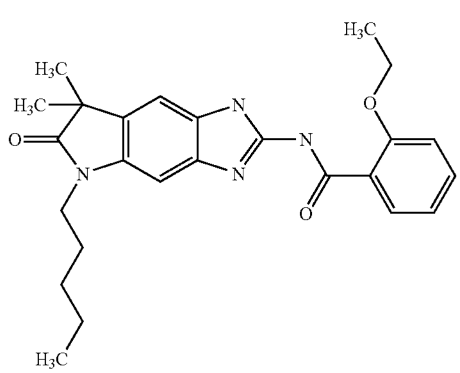 | 3.37 | 435 | (DMSO) d=0.81-0.90 (m, 3H), 1.22-1.38 (m, 10H), 1.39-1.50 (m, 3H), 1.59-1.70 (m, 2H), 3.70-3.77 (m, 2H), 4.32-4.41 (m, 2H), 7.13-7.20 (m, 1H), 7.24-7.33 (m, 2H), 7.61-7.70 (m, 2H), 7.87-7.94 (m, 1H), 12.10 (br s, 1H) [1 NH not visible] |

-continued

| # | Structure | HPLC Rt [min] | MS [M + H] | NMR |
|---|---|---|---|---|
| 181 | 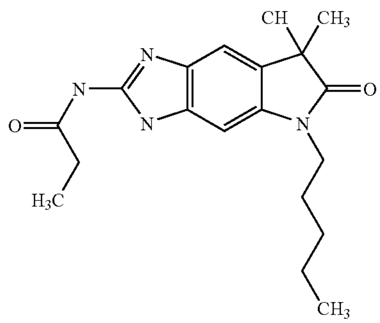 | 2.68 | 343 | (DMSO) d=0.78-0.91 (m, 3H), 1.05-1.15 (m, 3H), 1.18-1.37 (m, 10H), 1.49-1.68 (m, 2H), 2.40-2.48 (m, 2H), 3.61-3.73 (m, 2H), 6.99-7.11 (m, 1H), 7.38 (s, 1H), 11.38 (s, 1H), 11.85-12.02 (m, 1H) |
| 182 | 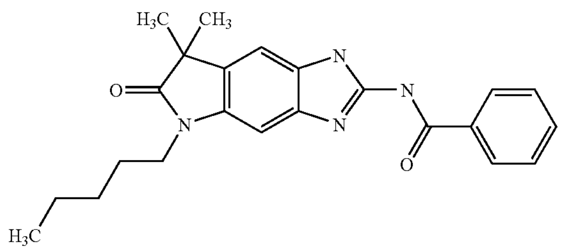 | 4.26 | 391 | (DMSO) d=0.86 (t, 3H), 1.22-1.39 (m, 10H), 1.64 (m, 2H), 3.70 (t, 2H), 7.10 (s, 1H), 7.41 (s, 1H), 7.54 (t, 2H), 7.61 (t, 1H), 8.14 (d, 2H) |
| 183 | 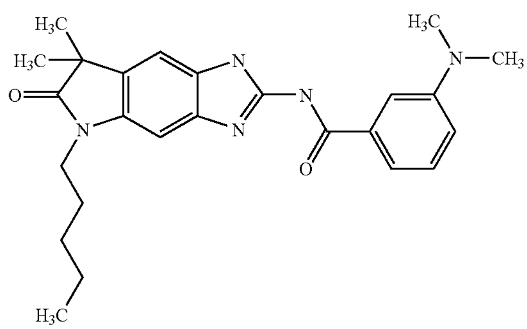 | 3.15 | 434 | (DMSO)=0.80-0.90 (m, 3H), 1.21-1.37 (m, 10H), 1.59-1.69 (m, 2H), 2.98 (s, 6H), 3.67-3.73 (m, 2H), 6.94-6.98 (m, 1H), 7.08-7.11 (m, 1H), 7.31-7.47 (m, 4H), 12.13 (br s, 2H, tautomere) |
| 184 | 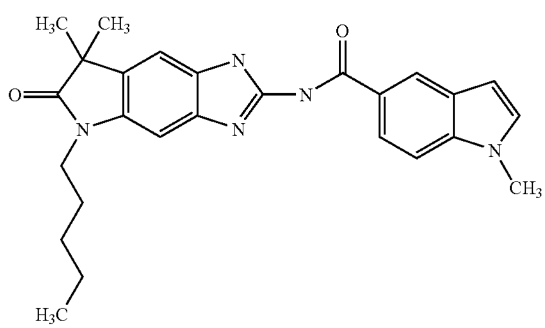 | 4.23 | 444 | (DMSO) d=0.86 (t, 3H), 1.30 (m, 10H), 1.65 (m, 2H), 3.70 (t, 2H), 3.85 (s, 3H), 6.61 (m, 1H), 7.11 (m, 1H), 7.45 (m, 2H), 7.58 (d, 1H), 7.99 (d, 1H), 8.48 (s, 1H), 12.20 (br s, NH) |
| 185 | 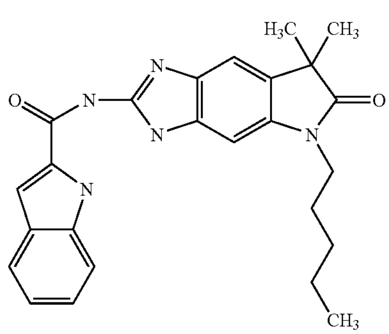 | 4.39 | 430 | (DMSO) d=0.86 (t, 3H), 1.30 (m, 10H), 1.65 (m, 2H), 3.70 (t, 2H), 7.09 (t, 1H), 7.11 (s, 1H), 7.25 (t, 1H), 7.45 (s, 1H), 7.51 (d, 1H), 7.59 (br s, 1H), 7.68 (d, 1H), 11.72 (br s, NH), 12.10 (br s, NH) |

-continued

| # | Structure | HPLC Rt [min] | MS [M + H] | NMR |
|---|---|---|---|---|
| 186 | 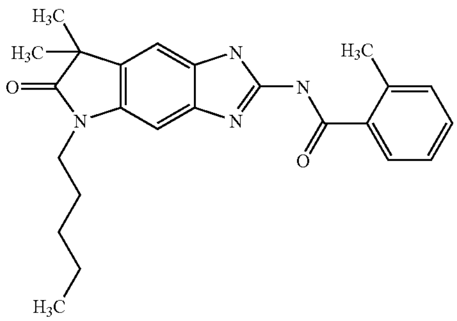 | 3.13 | 405 | (DMSO) d=0.74-0.91 (m, 3H), 1.13-1.44 (m, 10H), 1.50-1.76 (m, 2H), 2.46 (s, 3H), 3.59-3.77 (m, 2H), 7.09 (s, 1H), 7.22-7.36 (m, 2H), 7.37-7.47 (m, 2H), 7.53-7.65 (m, 1H), 12.07 (br s, 2H) |
| 187 | 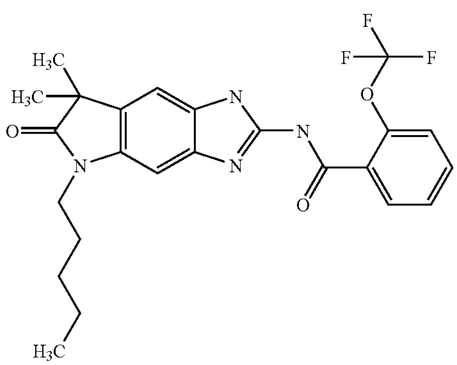 | 3.29 | 475 | (DMSO) d=0.84-0.88 (m, 3H), 1.24-1.37 (m, 10 H), 1.60-1.68 (m, 2H), 3.66-3.73 (m, 2H), 7.09 (s 1H), 7.42 (s, 1H), 7.47-7.56 (m, 2H), 7.64-7.69 (m, 1H), 7.80-7.84 (m, 1H), 12.21 (br s, 2H) |
| 188 | 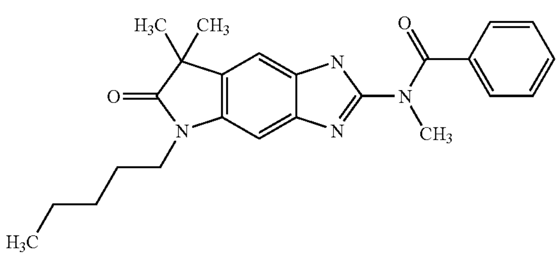 | 4.13 | 405 | (DMSO) d=0.85 (t, 3H), 1.12-1.38 (m, 10H), 1.65 (m, 2H), 3.39 (s, 3H), 3.75 (t, 2H), 7.28 (m, 2H), 7.42 (m, 2H), 7.58 (m, 2H), 7.76 (m, 1H) |
| 189 | 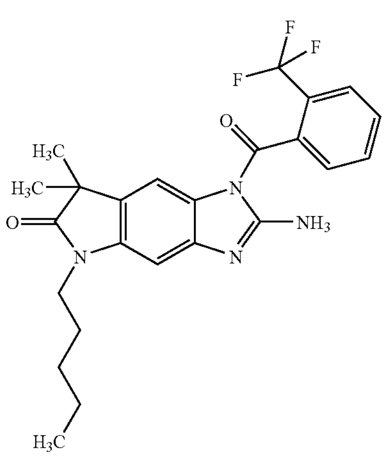 | 3.26 | 459 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |

-continued

| # | Structure | HPLC Rt [min] | MS [M + H] | NMR |
|---|---|---|---|---|
| 190 | 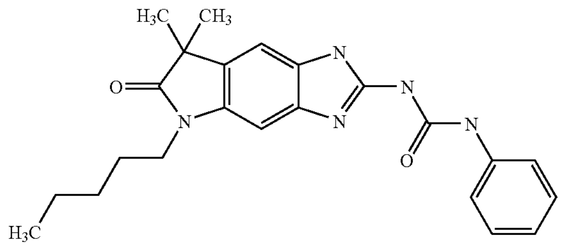 | 3.94 | 406 | (DMSO) d=0.85 (t, 3H), 1.21-1.39 (m, 10H), 1.64 (m, 2H), 3.69 (t, 2H), 7.03 (t, 1H), 7.04 (s, 1H), 7.32 (m, 2H), 7.35 (s, 1H), 7.54 (d, 2H), 9.68 (br s, NH), 10.95 (br s, NH) |
| 191 | 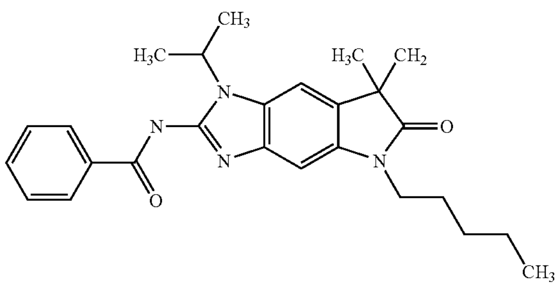 | 5.64 | 433 | (DMSO) d=0.86 (t, 3H), 1.31 (m, 10H), 1.60 (m, 2H), 1.64 (d, 6H), 3.68 (m, 2H), 5.25 (m, 1H), 7.23 (s, 1H), 7.50 (m, 1H), 7.61 (t, 1H), 7.75 (s, 1H), 7.88 (m, 1H), 7.95 (d, 1H), 8.21 (m, 1H), 12.79 (br s, NH) |
| 192 | 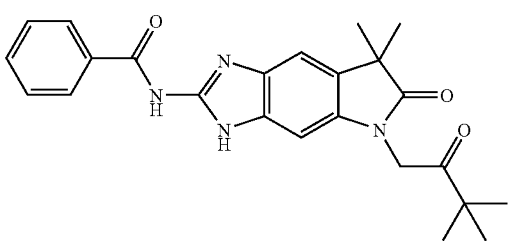 | 3.55 | 410 | |
| 193 | 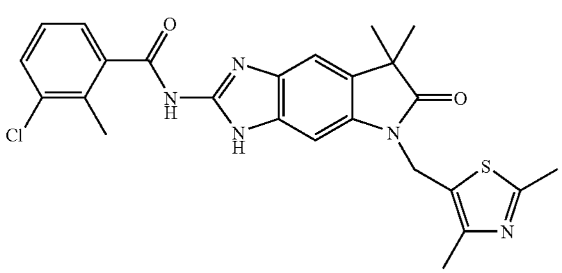 | 1.83 | 494 | |
| 194 | 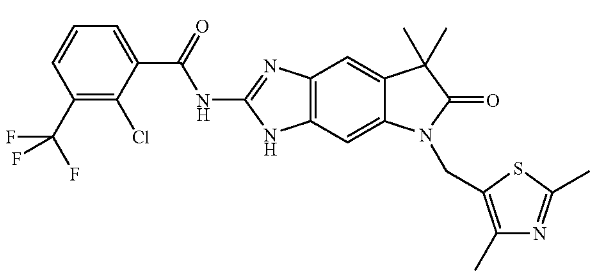 | 1.92 | 548 | |

-continued

| # | Structure | HPLC Rt [min] | MS [M + H] | NMR |
|---|---|---|---|---|
| 195 | 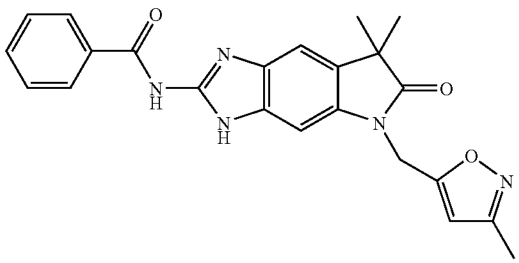 | 3.24 | 416 | |
| 196 | 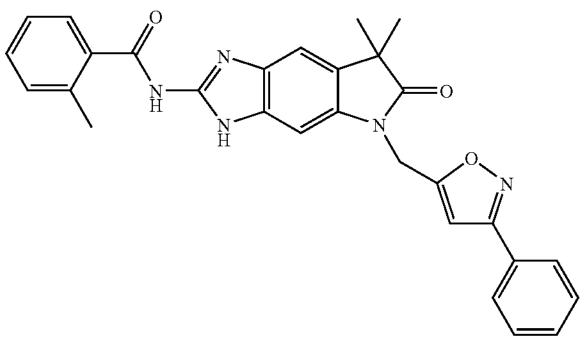 | 3.75 | 478 | |
| 197 | 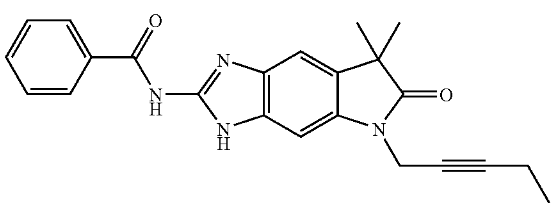 | 3.63 | 387 | |
| 198 | 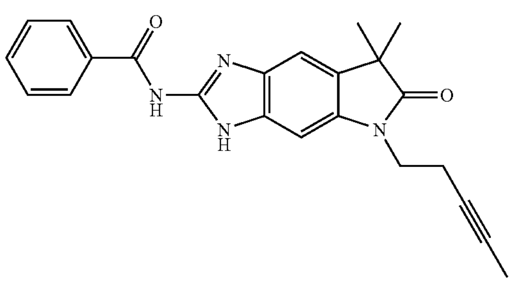 | 4.05 | 387 | |
| 199 | 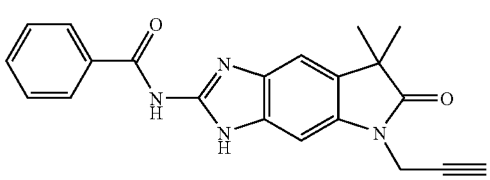 | 3.26 | 359 | |
| 200 | 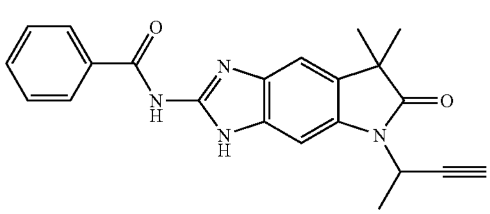 | 3.40 | 373 | |

| # | Structure | HPLC Rt [min] | MS [M + H] | NMR |
|---|---|---|---|---|
| 201 | 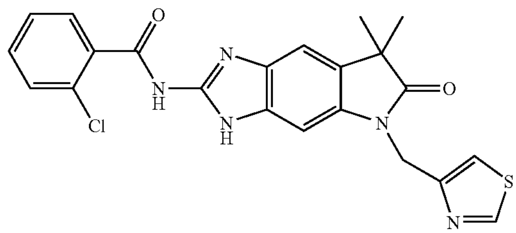 | 3.32 | 452 | |
| 202 | 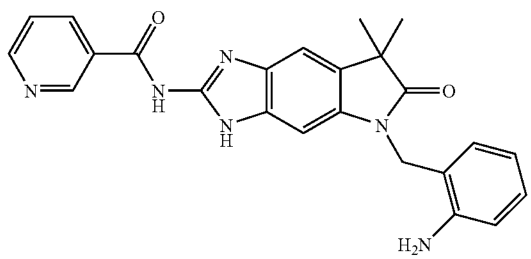 | 3.02 | 427 | |
| 203 | 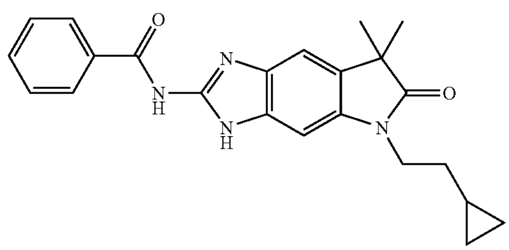 | 3.49 | 389 | |
| 204 | 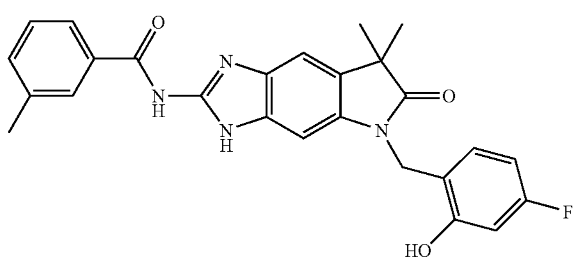 | 3.35 | 459 | |

Synthesis of Building Block E1

(E1) 2-Hydroxymethyl-7,7-dimethyl-5-pentyl-5,7-dihydro-1H-imidazo[4,5-f]indol-6-one

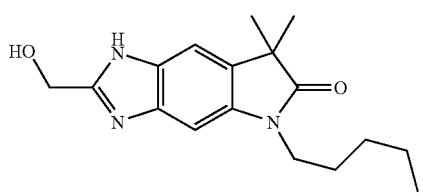

B3 (4.5 g) and hydroxyl acetic acid (4.4 g; 57.9 mmol) are dissolved in hydrochloric acid (6 N; 90 ml) and refluxed for 20 h. After completion of the reaction the mixture is cooled to RT, made alkaline with NaOH solution (8 N) and extracted with EtOAc (4 times; 100 ml each). The combined organic layer is washed with saturated NaHCO$_3$ solution and brine, dried over MgSO$_4$ and evaporated to give the desired compound (4.36 g).

Example 205 a) 2-Chloromethyl-7,7-dimethyl-5-pentyl-5,7-dihydro-1H-imidazo[4,5-f]indol-6-one E1 (330 mg) is dissolved in CHCl$_3$ (5 ml), thionyl chloride (1.2 ml) is added and the mixture is stirred at 60° C. for 15 h. The reaction mixture is concentrated in vacuo to give the compound.

b) 7,7-Dimethyl-5-pentyl-2-phenoxymethyl-5 7-dihydro-1H-imidazo[4,5-f]indol-6-one To a solution of phenol (107 mg) in CH$_2$Cl$_2$ (4 ml) is added NaH (50 mg; 1.25 mmol) and the resulting suspension is stirred for 5 min at RT. Then freshly prepared 2-chloromethyl-7,7-dimethyl-5-pentyl-5,7-dihydro-1H-imidazo[4,5-A]indol-6-one dissolved in CH$_2$Cl$_2$ (5 ml) is added and the mixture is stirred at 40° C. for 2 h. After completion of the reaction the mixture is concentrated in vacuo, adsorbed on silica gel and subjected to flash chromatography eluting with cyclohexane/EtOAc to give the desired title compound (113 mg).

Examples 206-211 are Prepared Analogously from E1 and the Corresponding Nucleophile (Phenol, Thiophenol or Amine, Respectively) as described in Example 205

Example 212

2-Benzenesulfinylmethyl-7,7-dimethyl-5-pentyl-5,7-dihydro-1H-imidazo[4,5-f]indol-6-one To a solution of thiophenol (70 μl) in CH$_2$Cl$_2$ (4 ml) is added NaH (43 mg; 1.08 mmol) and the resulting suspension is stirred for 5 min at RT. Then freshly prepared 2-chloromethyl-7,7-dimethyl-5-pentyl-5,7-dihydro-1H-imidazo[4,5-f]indol-6-one (265 mg) dissolved in CH$_2$Cl$_2$ (5 ml) is added and the mixture is stirred at 40° C. for 20 h. After cooling to 0° C. 3-chloro-benzenecarboperoxoic acid (186 mg; 0.83 mmol) is added and stirring is continued for another 3 h. After completion of the reaction the mixture is concentrated in vacuo and purified by NP-HPLC eluting with CH$_2$Cl$_2$/MeOH to give the desired compound (5.8 mg).

Example 213

2-Benzenesulfonylmethyl-7,7-dimethyl-5-pentyl-5 7-dihydro-1H-imidazo[4,5-f]indol-6-one (22 mg) is synthesized from freshly prepared 2-chloromethyl-7,7-dimethyl-5-pentyl-5,7-dihydro-1H-imidazo[4,5-f]indol-6-one (265 mg), thiophenol (70 μl) and 3-chloro-benzenecarboperoxoic acid (372 mg; 1.66 mmol) as described in Example 212.

Synthesis of Building Block F1

(F1) 2-Chloro-7,7-dimethyl-5-pentyl-5,7-dihydro-1H-imidazo[4,5-f]indol-6-one

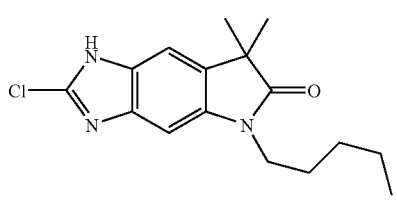

a) 7,7-Dimethyl-5-pentyl-5,7-dihydro-1H,3H-imidazo[4,5-f]indole-2,6-dione

B3 (4.5 g) is dissolved in dry THF (100 ml) and carbonyldiimidazole (3.4 g; 21 mmol) is added. The mixture is stirred at RT for 18 h. After evaporation the residue is taken-up in EtOAc, washed with saturated KHSO$_4$ solution and brine, dried over MgSO$_4$ and evaporated again to give the compound (4.28 g).

b) 2-Chloro-7,7-dimethyl-5-pentyl-5,7-dihydro-1H-imidazo[4,5-f]indol-6-one (F1)

7,7-Dimethyl-5-pentyl-5,7-dihydro-1H,3H-imidazo[4,5-f]indole-2,6-dione (3.80 g) is suspended in phosphoryl chloride (39 ml) and heated under reflux for 5 h. After re-cooling to RT the dark reaction mixture is poured into ice-water (1 l) and heavily stirred. The aqueous phase is made alkaline and extracted with CH$_2$Cl$_2$. The combined organic layer is washed with brine, dried over MgSO$_4$ and evaporated to give F1 (2.85 g) as a dark oil.

Example 214

2-Benzylamino-7,7-dimethyl-5-pentyl-5,7-dihydro-1H-imidazo[4,5-f]indol-6-one

A mixture of F1 (100 mg) and benzylamine (1.5 ml; 13.6 mmol) is stirred in a microwave apparatus at 200° C. for 8 min. After re-cooling the mixture is concentrated in vacuo and purified by RP-MPLC (Polygoprep 100-50 C18) eluting with a water/MeCN gradient to give the desired compound (13 mg).

Examples 215-216 are prepared analogously from F1 and the corresponding amine as described in Example 214.

Synthesis of Building Block G1

(G1) 2-(2-Amino-ethyl)-7,7-dimethyl-5-pentyl-5,7-dihydro-1H-imidazo[4,5-f]indol-6-one

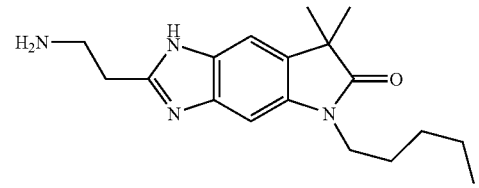

B3 (2 g) and 3-(tert-butyloxycarbonylamino)-propanal (1,33 g; 7.65 mmol) are dissolved in dry N,N-dimethylformamide (30 ml) and stirred for 72 h at RT. After evaporation the crude material is purified by RP-MPLC, eluted with a water/MeCN gradient to give [2-(7,7-dimethyl-6-oxo-5-pentyl-1,5,6,7-tetrahydro-imidazo[4,5-f]indol-2-yl)-ethyl]-carbamic acid tert-butyl ester (1.17 g). The resulting compound is treated with hydrochloric acid (in 1,4-dioxane) to remove the boc-group to obtain the desired compound as the hydrochloride (1,31 g).

Example 217

Pyridine-2-carboxylic acid [2-(7,7-dimethyl-6-oxo-5-pentyl-1,5,6,7-tetrahydro-imidazo[4,5-f]indol-2-yl)-ethyl]-amide To a solution of G1 (140 mg) in THF (6 ml) is added NEt$_3$ (0.1 ml) and pyridine-2-carbonyl chloride (126 mg; 0.89 mmol) and the resulting solution is stirred at RT for 2 h. After completion of the reaction the mixture is concentrated in vacuo and the residue is taken-up in water and extracted with EtOAc. The combined organic layer is washed with saturated NaHCO₃ solution and brine, dried over MgSO₄ and concentrated in vacuo. The crude material is dissolved in MeOH (3 ml) and piperidine (1 ml) and stirred at RT for 2 h to cleave the labile acyl group of the undesired bis-acylated by-product. After completion of the reaction the solvents are evaporated and the crude mixture is purified by RP-MPLC eluting with a water/MeCN gradient. Lyophilization yields the desired compound (82 mg) as a yellowish solid.

Example 218

N-[2-(7,7-Dimethyl-6-oxo-5-pentyl-1,5,6,7-tetrahydro-imidazo[4,5-f]indol-2-yl)-ethyl]-3-methoxy-benzamide (108 mg) is prepared from G1 (100 mg) and 3-methoxy-benzoyl chloride (109 mg) as described in Example 217.

Synthesis of Building Block H1

(H1) 2-Aminomethyl-7,7-dimethyl-5-pentyl-5,7-dihydro-1H-imidazo[4,5-f]indol-6-one

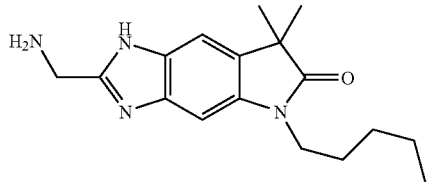

B3 (1.51 g) and 2-(tert-butyloxycarbonylamino)-ethanal (0.92 g; 5,78 mmol) are dissolved in dry N,N-dimethylformamide (30 ml) and stirred for 72 h at RT. After evaporation the crude material is purified by RP-MPLC eluted with a water/MeCN gradient to give (7,7-dimethyl-6-oxo-5-pentyl-1,5,6,7-tetrahydro-imidazo[4,5-f]indol-2-ylmethyl)-carbamic acid tert-butyl ester (1.08 g; 2.70 mmol). The boc-protected compound is treated with hydrochloric acid (in 1,4-dioxane) to remove the protecting group to give the desired compound as hydrochloride (0.91 g).

Example 219

N-(7,7-Dimethyl-6-oxo-5-pentyl-1,5,6,7-tetrahydro-imidazo[4,5-f]indol-2-ylmethyl)-3-methoxy-benzenesulfonamide (74 mg) is prepared from H1 (100 mg) and 3-methoxy-benzenesulfonyl chloride (138 mg; 0.67 mmol) as described in Example 217.

Example 220

N-(7,7-Dimethyl-6-oxo-5-pentyl-1,5,6,7-tetrahydro-imidazo[4,5-f]indol-2-ylmethyl)-3-methoxy-benzamide (101 mg) is prepared from H1 (100 mg) and 3-methoxy-benzoyl chloride (114 mg; 0.67 mmol) as described in Example 217.

Examples 205-220

| # | Structure | HPLC Rt [min] | MS [M + H]⁺ | NMR |
|---|-----------|---------------|-------------|-----|
| 205 | 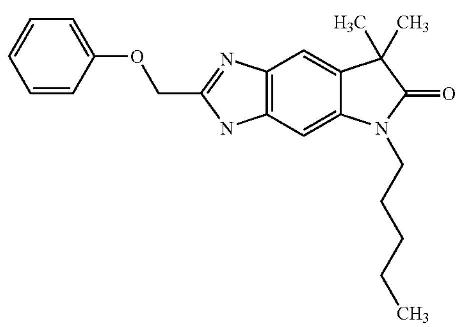 | 3.03 | 378 | (DMSO) d=0.8 1-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 206 | 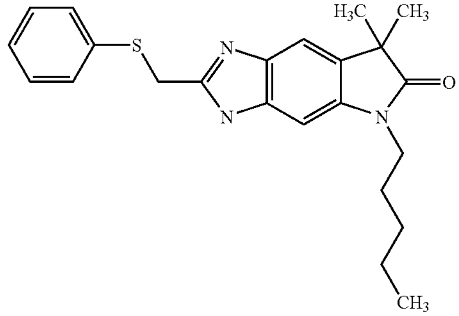 | 2.99 | 394 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |

-continued

| # | Structure | HPLC Rt [min] | MS [M + H]⁺ | NMR |
|---|---|---|---|---|
| 207 | 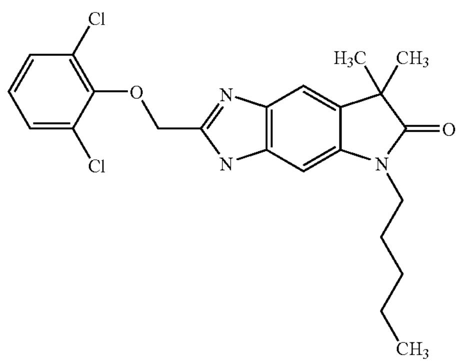 | 3.18 | 446/448 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 208 | 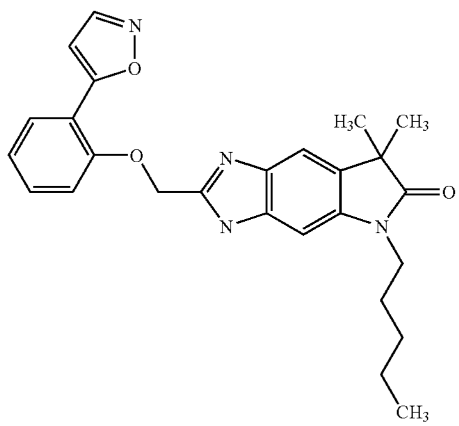 | 4.7 | 445 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 209 | 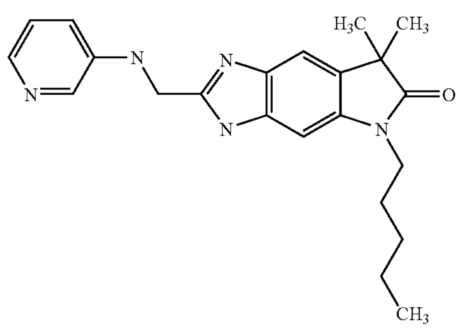 | 2.23 | 378 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 210 | 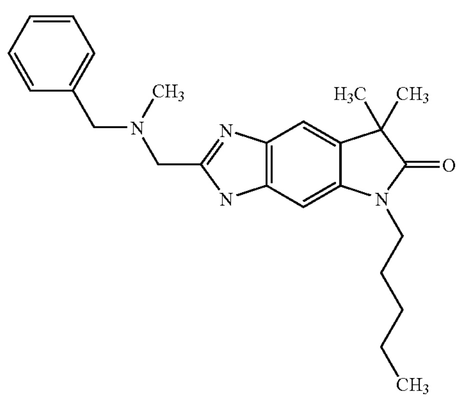 | 2.79 | 405 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |

-continued

| # | Structure | HPLC Rt [min] | MS [M + H]+ | NMR |
|---|---|---|---|---|
| 211 | 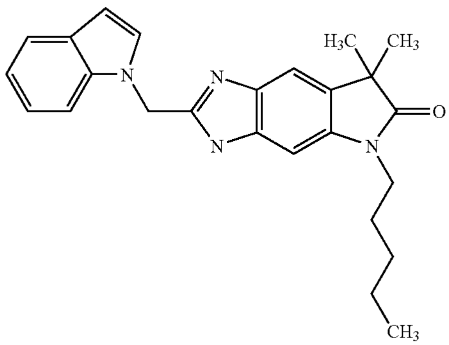 | 2.91 | 401 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 212 | 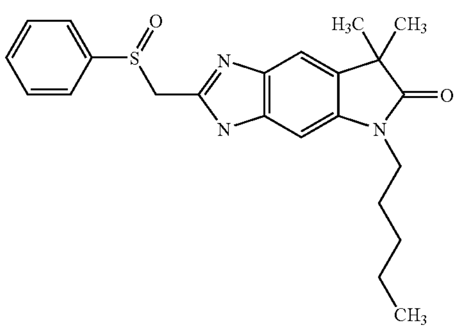 | 2.88 | 410 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 213 | 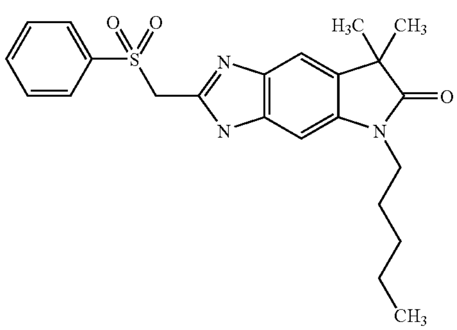 | 3.06 | 426 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 214 | 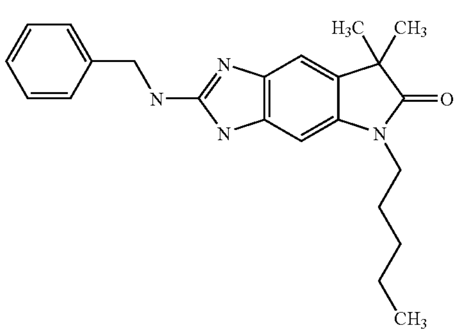 | 2.76 | 377 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |

| # | Structure | HPLC Rt [min] | MS [M + H]⁺ | NMR |
|---|---|---|---|---|
| 215 | 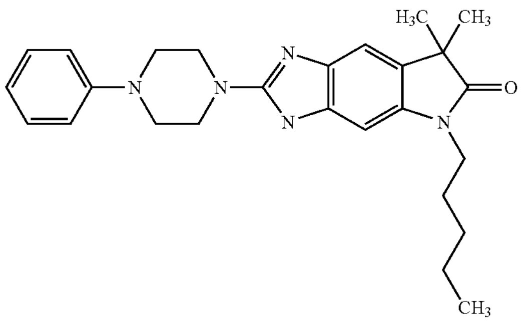 | 2.87 | 431 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 216 | 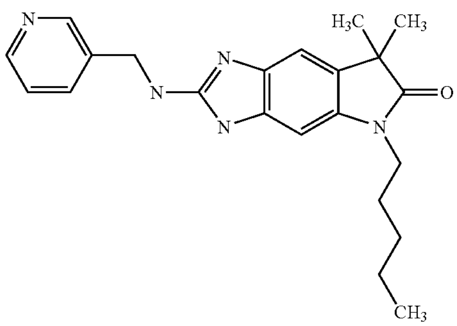 | 3.8 | 378 | (DMSO) d=0.81-0.84 (m, 3H), 0.91 (s, 6H), 1.19-1.25 (m, 2H), 1.25-1.31 (m, 2H), 1.52-1.58 (m, 2H), 3.60-3.64 (m, 2H), 5.09 (s, 1H), 6.91 (s, 1H), 7.51 (s, 2H), 7.89-7.91 (m, 1H), 7.95-8.00 (m, 2H), 8.09-8.11 (m, 1H) |
| 217 | 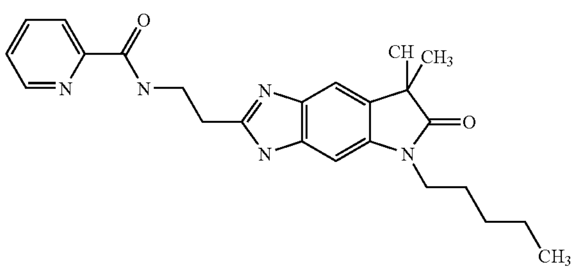 | 2.55 | 420 | (DMSO) d=0.77-0.89 (m, 3H), 1.21-1.36 (m, 10H), 1.58-1.67 (m, 2H), 3.04-3.12 (m, 2H), 3.66-3.74 (m, 2H), 3.75-3.82 (m, 2H), 7.07 (s, 1H), 7.39-7.52 (m, 1H), 7.56-7.63 (m, 1H), 7.96-8.02 (M, 1H), 8.03-8.09 (m, 1H), 8.60-8.66 (m, 1H), 8.94-9.06 (m, 1H), 12.20 (br s, 1H, tautomere) |
| 218 | 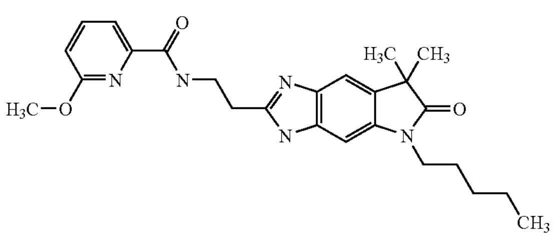 | 2.74 | 449 | (DMSO) d=0.80-0.89 (m, 3H), 1.21-1.35 (m, 10H), 1.57-1.66 (m, 2H), 3.01-3.10 (m, 2H), 3.63-3.74 (m, 4H), 3.78 (s, 3H), 6.91-7.18 (m, 2H), 7.33-7.57 (m, 4H), 11.99-12.47 (m, 1H, tautomere) |
| 219 | 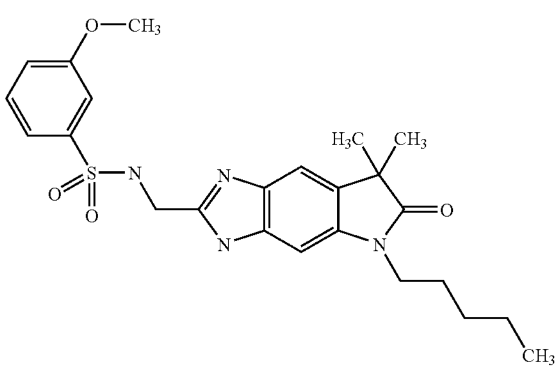 | 2.71 | 471 | (DMSO) d=0.79-0.87 (m, 3H), 1.21-1.36 (m, 10H), 1.57-1.67 (m, 2H), 3.66-3.74 (m 2H), 3.78 (s, 3H), 4.14 (s, 2H), 7.02 (s, 1H), 7.10-7.17 (m, 1H), 7.28-7.34 (m, 1H), 7.36-7.51 (m, 3H), 8.29 (br s, 1H), 12.20 (br s, 1H, tautomere) |

-continued

| # | Structure | HPLC Rt [min] | MS [M + H]+ | NMR |
|---|---|---|---|---|
| 220 | (structure) | 2.68 | 435 | (DMSO) d=0.76-0.90 (m, 3H), 1.17-1.36 (m, 10H), 1.48-1.66 (m, 2H), 3.64-3.75 (m, 2H), 3.81 (s, 3H9, 4.61-4.69 (m, 2H), 7.00-7.16 (m, 2H), 7.34-7.57 (m, 4H), 9.14-9.24 (m, 1H) |

Biological Experiments

The compounds of the invention are useful in binding to tubulin and thereby inhibiting the activity of tubulin. In doing so, these compounds are useful in blocking disease processes by binding to tubulin. Accordingly, the compounds of the present invention are useful in treating cancer or other abnormal proliferative diseases. Cancers are classified in two ways: by the type of tissue in which the cancer originates (histological type) and by primary site, or the location in the body where the cancer first developed. The most common sites in which cancer develops include the skin, lungs, female breasts, prostate, colon and rectum, cervix and uterus.

The compounds are thus useful in the treatment of a variety of cancers, including but not limited to the following:

AIDS-related cancer such as Kaposi's sarcoma; bone related cancer such as Ewing's family of tumors and osteosarcoma; brain related cancer such as adult brain tumor, childhood brain stem glioma, childhood cerebellar astrocytoma, childhood cerebral astrocytoma/malignant glioma, childhood ependymoma, childhood medulloblastoma, childhood supratentorial primitive neuroectodermal tumors, childhood visual pathway and hypothalamic glioma and other childhood brain tumors; breast cancer; digestive/gastrointestinal related cancer such as anal cancer, extrahepatic bile duct cancer, gastrointestinal carcinoid tumor, colon cancer, esophageal cancer, gallbladder cancer, adult primary liver cancer, childhood liver cancer, pancreatic cancer, rectal cancer, small intestine cancer and stomach (gastric) cancer; endocrine related cancer such as adrenocortical arcinoma, gastrointestinal carcinoid tumor, islet cell carcinoma (endocrine pancreas), parathyroid cancer, pheochromocytoma, pituitary tumor and thyroid cancer; eye related cancer such as intraocular melanoma, and retinoblastoma; genitourinary related cancer such as bladder cancer, kidney (renal cell) cancer, penile cancer, prostate cancer, transitional cell renal pelvis and ureter cancer, testicular cancer, urethral cancer, Wilms' tumor and other childhood kidney tumors; germ cell related cancer such as childhood extracranial germ cell tumor, extragonadal germ cell tumor, ovarian germ cell tumor and testicular cancer; gynecologic related cancer such as cervical cancer, endometrial cancer, gestational trophoblastic tumor, ovarian epithelial cancer, ovarian germ cell tumor, ovarian low malignant potential tumor, uterine sarcoma, vaginal cancer and vulvar cancer; head and neck related cancer such as hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, parathyroid cancer and salivary gland cancer; hematologic/blood related cancer such as leukemias, such as adult acute lymphoblastic leukemia, childhood acute lymphoblastic leukemia, adult acute myeloid leukemia, childhood acute myeloid leukemia, chronic lymphocytic leukemia, chronic myelogenous leukemia and hairy cell leukemia; and lymphomas, such as AIDS-related lymphoma, cutaneous T-cell lymphoma, adult Hodgkin's lymphoma, childhood Hodgkin's lymphoma, Hodgkin's lymphoma during pregnancy, mycosis fungoides, adult non-Hodgkin's lymphoma, childhood non-Hodgkin's lymphoma, non-Hodgkin's lymphoma during pregnancy, primary central nervous system lymphoma, Sezary syndrome, cutaneous T-cell lymphoma and Waldenström's macroglobulinemia and other hematologic/blood related cancer such as chronic myeloproliferative disorders, multiple myeloma/plasma cell neoplasm, myelodysplastic syndromes and myelodysplastic/myeloproliferative diseases; lung related cancer such as non-small cell lung cancer and small cell lung cancer musculoskeletal related cancer such as Ewing's family of tumors, osteosarcoma, malignant fibrous histiocytoma of bone, childhood rhabdomyosarcoma, adult soft tissue sarcoma, childhood soft tissue sarcoma and uterine sarcoma; neurologic related cancer such as adult brain tumor, childhood brain tumor, brain stem glioma, cerebellar astrocytoma, cerebral astrocytoma/malignant glioma, ependmoma, medulloblastoma, supratentorial primitive neuroectodermal tumors, visual pathway and hypothalamic glioma and other brain tumors such as neuroblastoma, pituitary tumor and primary central nervous system lymphoma; respiratory/thoracic related cancer such as non-small cell lung cancer, small cell lung cancer, malignant mesothelioma, thymoma and thymic carcinoma; skin related cancer such as cutaneous T-cell lymphoma, Kaposi's sarcoma, melanoma, Merkel cell carcinoma and skin cancer.

Compounds binding to tubulin may also inhibit angiogenesis and affect abnormal cellular proliferation and can be used to treat certain forms of blindness related to retinal vascularization, arthritis, especially inflammatory arthritis, multiple sclerosis, restenosis and psoriasis and may induce apoptosis, a physiological cell death process critical for normal development and homeostasis.

The compounds of the invention are also useful for treatment of e.g. follicular lymphomas, carcinomas with p53 mutations, hormone dependent tumor of the breast, prostate and ovary and precancerous lesions such as familial adenomatous polyposis, viral infections, autoimmune diseases such as systemic lupus erythematosus, immune mediated glomerulonephritis, rheumatoid arthritis, psoriasis, inflammatory bowel diseases and autoimmune diabetes mellitus.

The compounds of the invention can be used in combination with known anticancer and cytotoxic agents and treatments including radiation, especially where the second drug acts in a different phase of the cell cycle.

Methods

The in vitro assessment of the biological activity of the inventive compounds is performed as follows:

In vitro Tubulin Polymerization Assay (TPA)

The assay is performed according to Bollag M D et al. (Epothilones, a new class of microtubule-stabilizing agents with a taxol-like mechanism of action. Cancer Research 55: 2325-2333, 1995). Tubulin heterodimers (1.6 mg/ml; 160 μg/assay), from bovine brain (Cytoskeleton), are incubated with test compounds (10 μM final concentration) in PEM (100 mM PIPES, 1 mM EGTA, and 1 mM $MgCl_2$) buffer (pH 6.6) containing 1 mM GTP in a total volume of 100 μl at 37° C. for 1 h. Samples (80 μl) are then transferred to a 96-well Millipore Multiscreen Durapore hydrophilic 0.22-μm pore size filtration plate. Microtubules are recovered on the filters and are stained with 50 μl of Amido Black solution [0.1% w/v napthol blue black (Sigma), 45% v/v methanol, and 10% v/v acetic acid] for 2 min. Vacuum is applied, and unbound dye is removed by two additions of 200 μl of destain solution (90% v/v methanol, 2% v/v acetic acid). The microtubule bound dye is eluted by incubation with 200 μl of elution solution (25 mM NaOH, 0.05 mM EDTA, and 50% v/v ethanol) for 20 min. Next, 150 μl of elution solution is transferred to a 96-well half area plate, and the absorbance is measured at 600 nm using the Wallac Victor Multilabel counter (Perkin-Elmer/Wallac, Freiburg, Germany). The assay format allows the identification of novel tubulin ligands and gives some indication as to their mechanism of action (e.g. microtubule stabilizer or destabilizer). A result of less than 50% indicates inhibition of tubulin polymerization (destabilizer). A result above 150% indicates induction of tubulin polymerization (stabilizer).

Most of the compounds have values below 50% and are therefore destabilizers.

In vitro Cytotoxicity Assay (MTS)

Cytotoxicity is assessed in HeLa human squamous cell carcinoma by MTS (3-(4,5-dimethylthiazol-2-yl)-5-(3-carboxymethoxyphenyl)-2-(4-sulfenyl)-2H-tetrazolium, inner salt) assay as reported in T. L. Riss, et. al, "Comparison of MTT, XTT and a novel tetrazolium compound MTS for in vitro proliferation and chemosensitivity assays" Mol. Biol. Cell 3 (Suppl.): 184a, 1992.

Cells are plated at 2500 cells/well in 96 well microtiter plates and 24 hours later drugs are added and serial diluted (10 μM starting concentration). The cells are incubated at 37° for 4-5 days at which time the tetrazolium dye, MTS at 333 μg/ml (final concentration), in combination with the electron coupling agent phenazine methosulfate at 25 μM (final concentration) is added. The cells are then incubated for 2-3 hours at 37°. The assay is based on the cleavage of the tetrazolium compound MTS to coloured formazan by the "succinate-tetrazolium reductase" mitochondrial enzyme, active only in living (metabolic active) cells. The presence of the electron coupling reagent PMS allows the formation of a stable solution. The amount of dye is quantitated spectrophotometrically at 492 nM. The absorbance is a function of the concentration of converted dye and directly correlates to the number of metabolically active (living) cells in the culture. The results are expressed as an IC50, which is the drug concentration required to inhibit cell proliferation to 50% of that of untreated control cells.

The IC50 values for compounds of this invention fall below 10 μM.

The compounds according to the invention may be administered by oral, transdermal or parenteral route or by inhalation. The compounds according to the invention are present as active ingredients in conventional preparations, e.g. in compositions consisting essentially of an inert pharmaceutical carrier and an effective dose of the active substance, such as for example plain or coated tablets, capsules, lozenges, powders, solutions, suspensions, emulsions, syrups, suppositories, transdermal systems, etc. An effective dose of the compounds according to the invention is between 1 and 100, preferably between 1 and 50, most preferably between 5-30 mg/dose, for oral administration, and between 0.001 and 50, preferably between 0.1 and 10 mg/dose for intravenous or intramuscular administration. For inhalation, solutions containing 0.01 to 1.0, preferably 0.1 to 0.5% of active substance are suitable according to the invention. For inhalation, the use of powders is preferred. It is also possible to use the compounds according to the invention as a solution for infusion, preferably in physiological saline or nutrient salt solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions or dispersible powders. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavoring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of preservatives such as p-hydroxybenzoates, or stabilizers such as alkali metal salt of ethylenediamine tetra-acetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 800 mg, preferably 10-300 mg, in adults.

The Examples that follow illustrate the present invention without, however, restricting its scope.

Examples of Pharmaceutical Formulations

| Tablets | per tablet |
|---|---|
| active substance of formula (I) | 100 mg |
| lactose | 140 mg |
| corn starch | 240 mg |
| polyvinylpyrrolidone | 15 mg |
| magnesium stearate | 5 mg |
|  | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| Tablets | per tablet |
|---|---|
| active substance of formula (I) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
|  | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened.

The sodiumcarboxymethyl starch and the magnesium stearate are added and mixed in and the mixture is compressed to form tablets of a suitable size.

| Coated tablets | per coated tablet |
|---|---|
| Active substance of formula (I) | 5 mg |
| Corn starch | 41.5 mg |
| Lactose | 30 mg |
| Polyvinylpyrrolidone | 3 mg |
| Magnesium stearate | 0.5 mg |
|  | 80 mg |

The active substance, corn starch, lactose and polyvinylpyrrolidone are thoroughly mixed and moistened with water. The moist mass is pushed through a screen with a 1 mm mesh size, dried at about 45. degree. C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| Capsules | per capsule |
|---|---|
| Active substance of formula (I) | 50 mg |
| Corn starch | 268.5 mg |
| Magnesium stearate | 1.5 mg |
|  | 320 mg |

The substance and corn starch are mixed and moistened with water. The moist mass is screened and dried. The dry granules are screened and mixed with magnesium stearate. The finished mixture is packed into size 1 hard gelatine capsules.

Ampoule solution active substance 50 mg sodium chloride 50 mg water for inj. 5 ml The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| Suppositories | |
|---|---|
| Active substance of formula (I) | 50 mg |
| Solid fat | 1650 mg |
|  | 1700 mg |

The hard fat is melted. At 40° C. the ground active substance is homogeneously dispersed. It is cooled to 38° C. and poured into slightly chilled suppository moulds.

LIST OF ABBREVIATIONS

AcOH—Acetic acid
Ctrl—Control
decomp.—decomposition
DBU—Diaza(1,3)bicyclo[5.4.0]undecane
DIPEA—Diisopropylethyl amine
DMF—N,N-Dimethylformamide
EGTA—Ethylene glycol-bis-(2-aminoethyl)-N,N,N', N'-tetraacetic acid
EtOAc—Ethyl acetate
GTP—Guanidine triphosphate
HPLC—High performance liquid chromatography
LC/MS—Liquid chromatography mass spectrometer
MS—Mass spectrometer
MTS—3-(4,5-Dimethylthiazol-2-yl)-5-(3-carboxymethoxyphenyl)-2-(4-sulfenyl)-2H-tetrazolium, inner salt
n.d.—not determined
NMR—Nuclear Magnetic Resonance
NP-HPLC—Normal Phase high performance liquid chromatography
PIPES—Piperazine-N,N'-bis(2-ethanesulfonic acid)
PMS—N-Methyldibenzopyrazine methyl sulfate salt
RP-HPLC—Reversed phase high performance liquid chromatography RP-MPLC—Reverse phase middle pressure liquid chromatography
rt—Retention time
RT—Room temperature
TBTU—O-(Benzotriazol-1-yl)-N,N,N',N'-tetramethyluronium tetrafluoroborate
TFA—Trifluoroacetic acid
THF—Tetrahydrofuran
TPA—Tubulin Polymerisation Assay
UV—Ultraviolet

The invention claimed is:

1. A compound of formula (I):

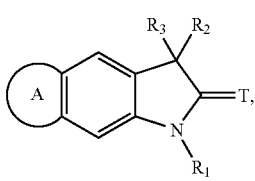

(I)

its physiologically acceptable salts or, wherein:
$R_1$ is selected from an optionally substituted group consisting of carbocyclic aryl-$(CH_2)_x$—, biaryl-$(CH_2)_x$— and cycloalkyl-$(CH_2)_x$—;
T is O or S;
$R_2$ and $R_3$ are independently selected from hydrogen or from an optionally substituted group consisting of $C_{1-4}$alkyl and cycloalkyl;
A is selected from formula (c-1) or (c-2):

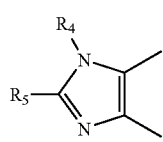

(c-1)

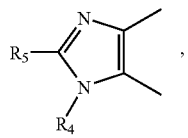

(c-2)

wherein $R_4$ is hydrogen and $R_5$ is selected from the group consisting of hydrogen, halo, hydroxy, thiol and cyano or from an optionally substituted group consisting of $C_{1-12}$alkyl, carbocyclic aryl-$(CH_2)_x$—, biaryl-$(CH_2)_x$—, and cycloalkyl-$(CH_2)_x$—;
x is 0, 1, 2, 3 or 4; and
wherein one or more hydrogens of the —$(CH_2)_x$ group may be replaced by a group selected from hydroxy, halo, cyano, alkoxy, thiol and alkylthio or from an optionally substituted group consisting of alkyl and amino;
and pharmaceutically acceptable salts thereof
with the provisio that the following compounds are excluded:
2-Cyanamino-6,7-dihydro-7,7-dimethyl-3H,5H-pyrrolo(2,3-f)benzimidazol-6-one;
2-Cyanamino-5,7,7-trimethyl-6,7-dihydro-3H-pyrrolo(2,3-f)benzimidazol-6-one; and
2-Cyanamino-6,7-dihydro-7,7-cyclopropyl-3H,5H-pyrrolo(2,3-f)benzimidazol-6-one.

2. The compound of claim 1, wherein T is O.
3. The compound of claim 1, wherein $R_2$ and $R_3$ are methyl.
4. The compound of claim 1, wherein $R_4$ is hydrogen.
5. A pharmaceutical composition containing as active ingredient one or more compounds of claim 1, or their physiologically acceptable salts, and a usual adjuvants and/or carrier.

* * * * *